(12) United States Patent
Dong et al.

(10) Patent No.: US 10,233,180 B2
(45) Date of Patent: Mar. 19, 2019

(54) SUBSTITUTED NITROGEN-CONTAINING HETEROCYCLIC DERIVATIVES, PHARMACEUTICAL COMPOSITIONS COMPRISING THE SAME AND APPLICATIONS OF ANTITUMOR THEREOF

(71) Applicants: ZHEJIANG UNIVERSITY, Zhejiang (CN); SHANGHAI INSTITUTE OF MATERIA MEDICA, CHINESE ACADEMY OF SCIENCES, Shanghai (CN)

(72) Inventors: Xiaowu Dong, Zhejiang (CN); Jia Li, Shanghai (CN); Bo Yang, Zhejiang (CN); Yongzhou Hu, Zhejiang (CN); Yubo Zhou, Shanghai (CN); Qinjie Weng, Zhejiang (CN); Wenhu Zhan, Zhejiang (CN); Lei Xu, Shanghai (CN); Tao Liu, Zhejiang (CN); Qiaojun He, Zhejiang (CN)

(73) Assignees: ZHEJIANG UNIVERSITY, Zhejiang (CN); SHANGHAI INSTITUTE OF MATERIA MEDICA, CHINESE ACADEMY OF SCIENCES, Shanghai (CN)

(*) Notice: Subject to any disclaimer, the term of this patent is extended or adjusted under 35 U.S.C. 154(b) by 0 days.

(21) Appl. No.: 15/128,298

(22) PCT Filed: Mar. 21, 2015

(86) PCT No.: PCT/CN2015/704813
§ 371 (c)(1),
(2) Date: Sep. 22, 2016

(87) PCT Pub. No.: WO2015/144021
PCT Pub. Date: Oct. 1, 2015

(65) Prior Publication Data
US 2017/0107213 A1 Apr. 20, 2017

(30) Foreign Application Priority Data

Mar. 22, 2014 (CN) .......................... 2014 1 0108818
Mar. 30, 2014 (CN) .......................... 2014 1 0124591
Mar. 8, 2015 (CN) .......................... 2015 1 0101220

(51) Int. Cl.
*C07D 401/12* (2006.01)
*C07D 401/14* (2006.01)
*C07D 405/14* (2006.01)
*C07D 409/14* (2006.01)
*C07D 413/14* (2006.01)
*C07D 417/14* (2006.01)

(52) U.S. Cl.
CPC ......... *C07D 417/14* (2013.01); *C07D 401/12* (2013.01); *C07D 401/14* (2013.01); *C07D 405/14* (2013.01); *C07D 409/14* (2013.01); *C07D 413/14* (2013.01)

(58) Field of Classification Search
None
See application file for complete search history.

(56) References Cited

U.S. PATENT DOCUMENTS

2006/0264430 A1* 11/2006 Kubota ................ C07D 231/12
514/230.5
2013/0231378 A1 9/2013 Seefeld et al.

FOREIGN PATENT DOCUMENTS

| CN | 1922172 A | 2/2007 |
|---|---|---|
| CN | 101921268 A | 12/2010 |
| CN | 102459187 A | 5/2012 |
| JP | 2012513437 A | 6/2012 |
| JP | 2013500306 A | 1/2013 |
| WO | 2010093885 A1 | 8/2010 |
| WO | 2013177168 A1 | 11/2013 |
| WO | 2014043608 A2 | 3/2014 |

OTHER PUBLICATIONS

STN Registry entry for CAS RN 1390295-04-1; entered STN Registry database Aug. 13, 2012.*
Ito et al. in Cancer Science 94(1), 3-8 (2003).*
International Search Report dated Jul. 3, 2015 received from International Application No. PCT/CN2015/074813.
Extended European Search Report dated Jul. 20, 2017 issued in corresponding Patent Application PCT/CN2015/074813.
Chinese Office Action dated Aug. 26, 2016 issued in corresponding Chinese Patent Application No. 201510101220.8, with English language translation.
Japanese Notice of Reasons for Rejection dated Nov. 2, 2018 received in Japanese Patent Application No. 2016-559264, with English-language translation.

* cited by examiner

*Primary Examiner* — Alicia L Otton
(74) *Attorney, Agent, or Firm* — Scully, Scott, Murphy & Presser, P.C.

(57) ABSTRACT

Disclosed are new substituted nitrogen-containing heterocyclic derivatives represented by formula (I) as AKT inhibitors, optical isomers, pharmaceutically acceptable salts or solvates thereof, wherein the definition of R1, R2, R3, R4, R5, R6, ring A, ring C, B, Q, Y, Z and m is shown in the description for details. In addition, medicaments comprising the derivatives as active components are also disclosed, which can be useful for treating proliferative diseases, such as cancer and inflammation, especially diseases relating to AKT kinase.

4 Claims, No Drawings

SUBSTITUTED NITROGEN-CONTAINING HETEROCYCLIC DERIVATIVES, PHARMACEUTICAL COMPOSITIONS COMPRISING THE SAME AND APPLICATIONS OF ANTITUMOR THEREOF

TECHNICAL FIELD

The invention relates to the medical field. Specifically, the invention relates to substituted nitrogen-containing heterocyclic derivatives used as Akt inhibitors, pharmaceutical compositions comprising the same and applications of antitumor thereof.

BACKGROUND ART

Therioma is one of the major diseases threatening human health. During 2008, there are about 12.7 million new cancer patients and 7.6 million patients died from cancer worldwide. It is estimated that by 2020, new cancer patients worldwide will increase to 15 million, and the death toll caused by cancer are also rising rapidly all over the world, which may increase to 13.2 million. The prevention and treatment of tumors has become an important research topic in the medical field among countries. Although there have been some antitumor drugs in clinical use, in general, the toxic, serve side effects and drug resistance of these drugs are often observed in clinic, which greatly limit the clinical treatment. Therefore, it is of great significance to develop novel antitumor drugs with high efficiency and low toxicity.

Suppression of cell apoptosis is closely related to the occurrence and development of tumors, which is believed to be one of the important reasons for drug resistance of cancer cells. The study of apoptosis signaling pathway provides a new idea for antitumor therapy, and also provides a new target for developing novel antitumor drugs. In 1995, Akt, also known as protein kinase B, was found as the downstream target of PI3K activated by various growth factors. Akt is at the core position in the PI3K/Akt signaling pathway, and Akt family members have three subtypes including Akt1, Akt2 and Akt3, with more than 80% sequence identity. It is found in the study that the different subtypes of Akt are highly consistent in view of structure and function, except for the expression levels in different tumors. Akt can directly phosphorylate mTOR, Bad and Caspase 9 protein, as well as control Fork Head transcription factor family and NF-κB for further controlling the significant cell biological process in the occurrence and development of tumors, such as transcription, translation, metabolism, apoptosis, angiogenesis, and so on. It is also found in the study that the phenomenon of Akt overexpression or activity disorders exists in most of tumors, and Akt abnormity is closely related to the occurrence and development of these tumors as well as the generated resistance to chemotherapy and radiotherapy. It has been proved that by vivo and in vitro pharmacological experiments that Akt inhibitors can promote programmed death of cancer cells. Therefore, Akt has attracted increasing attention as a potential antitumor target.

Akt inhibitors being in clinical research can be classified into: ATP-competitive inhibitors such as AZD5363, GSK-2110183 (afuresertib), GDC-0068 (Ipatasertib); allosteric inhibitors such as MK-2206; pH-domain binding inhibitors such as Perifosine. GSK-2110183 is an oral Akt inhibitor developed by GSK, and the single-drug thereof exhibits good safety and clinical activity against hematologic malignancies (including multiple myeloma), which is currently in phase II clinical trials. GDC-0068 is a highly selective pan-Akt inhibitor, the drug combination thereof with docetaxel or mFOLFOX-6 is well-tolerated in patients suffered from advanced solid tumors and exhibits preliminary signs of anti-tumor activity, and the dose-escalation trial thereof is still in clinical phase II. MK2206 is a 2,3-diphenyl quinoxalines derivative, which is currently in clinical phase II for the treatment of many kinds of cancer, such as gastric cancer, breast cancer etc. The clinical datas of above compounds confirm that the treatment strategy has good selectivity and improved tumor sensibility to chemotherapy and radiotherapy. Therefore, the development of novel Akt inhibitors is expected to provide clinical medicine with new therapeutic mechanism for tumor therapy.

SUMMARY OF THE INVENTION

The object of the invention is to provide a novel substituted nitrogen-containing heterocyclic derivatives, an optical isomers thereof, or pharmaceutically acceptable salts or solvate thereof, with strong antitumor effect and Akt inhibition.

Terminology Note: The term "aryl", as used herein, refers to a group of an all-carbon single ring or a polycyclic fused ring containing 5 to 12 carbon atoms with fully conjugated π electron system. Non-limiting examples of the aromatic ring include benzene ring, naphthalene ring and anthracene ring. The aromatic ring may be unsubstituted or substituted. Substituents of the aromatic ring are selected from the group consisting of halogen, nitro, amino, cyano, hydroxyl, $C_1$-$C_6$ alkyl, $C_1$-$C_6$ alkoxy, halogenated $C_1$-$C_6$ alkyl, halogenated $C_1$-$C_6$ alkoxy, $C_3$-$C_6$ cycloalkyl, halogenated $C_3$-$C_6$ cycloalkyl.

The term "heterocyclic aryl", as used herein, refers to a group of unsaturated carbon ring containing 5 to 12 annular atoms, wherein one or more carbon atoms are replaced by heteroatom such as oxygen, nitrogen or sulfur. The heterocyclic aromatic ring can be a single ring or a dual ring fused by two rings. Special heterocyclic aryl may be: pyridinyl, pyrimidinyl, pyrazinyl, isoxazolyl, isothiazolyl, pyrazolyl, thiazolyl, oxazolyl, imidazolyl, and the like. The heterocyclic aryl may be unsubstituted or substituted. Substituents of the heterocyclic aryl are selected from the group consisting of halogen, nitro, amino, cyano, hydroxyl, $C_1$-$C_6$ alkyl, $C_1$-$C_6$ alkoxy, halogenated $C_1$-$C_6$ alkyl, halogenated $C_1$-$C_6$ alkoxy, $C_3$-$C_6$ cycloalkyl, halogenated $C_3$-$C_6$ cycloalkyl.

The term "heterocyclic alkyl", as used herein, refers to a group of a single ring or a polycyclic fused ring with 5 to 9 annular atoms in its ring, wherein one or two annular atoms is heteroatom selected from the group consisting of N, O or $S(O)_m$ (wherein m is an integer from 0 to 2) and other annular atoms are carbon atoms. These rings may have one or more double bonds, but does not have fully conjugated π electron system. The unsubstituted heterocyclic alkyl may be pyrrolidinyl, piperidyl, piperazinyl, morpholinyl, thiomorpholinyl, homopiperazinyl, and the like. The heterocyclic ring may be unsubstituted or substituted. Substituents of the heterocyclic ring are selected from the group consisting of halogen, nitro, amino, cyano, hydroxyl, $C_1$-$C_6$ alkyl, $C_1$-$C_6$ alkoxy, halogenated $C_1$-$C_6$ alkyl, halogenated $C_1$-$C_6$ alkoxy, $C_3$-$C_6$ cycloalkyl, halogenated $C_3$-$C_6$ cycloalkyl.

The term "cycloalkyl", as used herein, refers to a group of a saturated single carbon ring with 3 to 6 carbon atoms, unless different number of atoms is specified. "Cycloalkyl" includes, for example, cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of alkoxy, halogen, and haloalkyl (e.g., perfluoroalkyl).

The term "alkoxy", as used herein, refers to the —O-alkyl group, wherein alkyl is defined as above. Examples of "alkoxy" as used herein include, but are not limited to, methoxyl, ethoxyl, n-propoxyl, isopropoxyl, n-butoxyl and t-butoxyl. "Alkoxy" also includes substituted alkoxy. The alkoxy groups may be optionally substituted with halogen for one or more times.

The term "halogen", as used herein, refers to fluorine, chlorine, bromine or iodine, preferably, fluorine or chlorine.

The term "pharmaceutically acceptable derivatives" refers to salts and solvates of the selected compound.

The term "solvate", as used herein, refers to a complex of variable stoichiometry formed by solute (e.g., compounds of formulas (I) to (XII) of this invention) and solvent. In view of the purpose of the invention, solvents do not interfere the biological activity of the solute. Examples of suitable solvent include, but are not limited to, water, methanol, ethanol and acetic acid. Preferably the solvent used is a pharmaceutically acceptable solvent. Examples of suitable pharmaceutically acceptable solvent include, but are not limited to, water, ethanol and acetic acid. More preferably, the solvent used is water.

This invention adopts the technical schemes as follows:

This invention provides substituted nitrogen-containing heterocyclic derivatives with the structure of general formula (I):

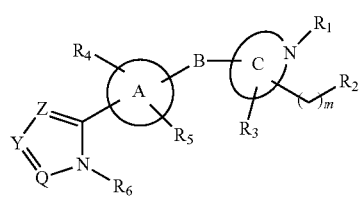

I and optical isomers thereof, or pharmaceutically acceptable salts or solvate thereof, wherein:

Ring A is selected from the group consisting of unsubstituted or substituted 5- or 6-membered aryl, 5- or 6-membered heterocyclic aryl containing 1 to 4 heteroatoms selected from O, N and S; that is, ring A may be a unsubstituted or substituted 5-membered aryl; ring A may also be a unsubstituted or substituted 6-membered aryl.

B is selected from the group consisting of

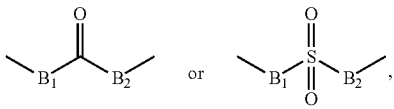

wherein B1 and B2 are same or different; B1 and B2 are each independently selected from the group consisting of O, $N(R_a)$, $C(R_b)(R_c)$ or are absent, wherein $R_a$, $R_b$ and $R_c$ are each independently selected from the group consisting of H, $C_1$-$C_4$ alkyl, halogenated $C_1$-$C_4$ alkyl, $C_1$-$C_4$ alkoxy, halogenated $C_1$-$C_4$ alkoxy;

Ring C is selected from the group consisting of 5-8 membered saturated or unsaturated aliphatic nitrogen-containing heterocyclic ring which is unsubstituted or substituted; that is, ring C may be a 5-8 membered saturated aliphatic nitrogen-containing heterocyclic ring without substitution, a 5-8 membered saturated aliphatic nitrogen-containing heterocyclic ring which is substituted, a 5-8 membered unsaturated fatty nitrogen-containing heterocyclic ring without substitution, a 5-8 membered unsaturated aliphatic nitrogen-containing heterocyclic ring which is substituted; preferably, ring C is the following aliphatic nitrogen-containing heterocyclic ring:

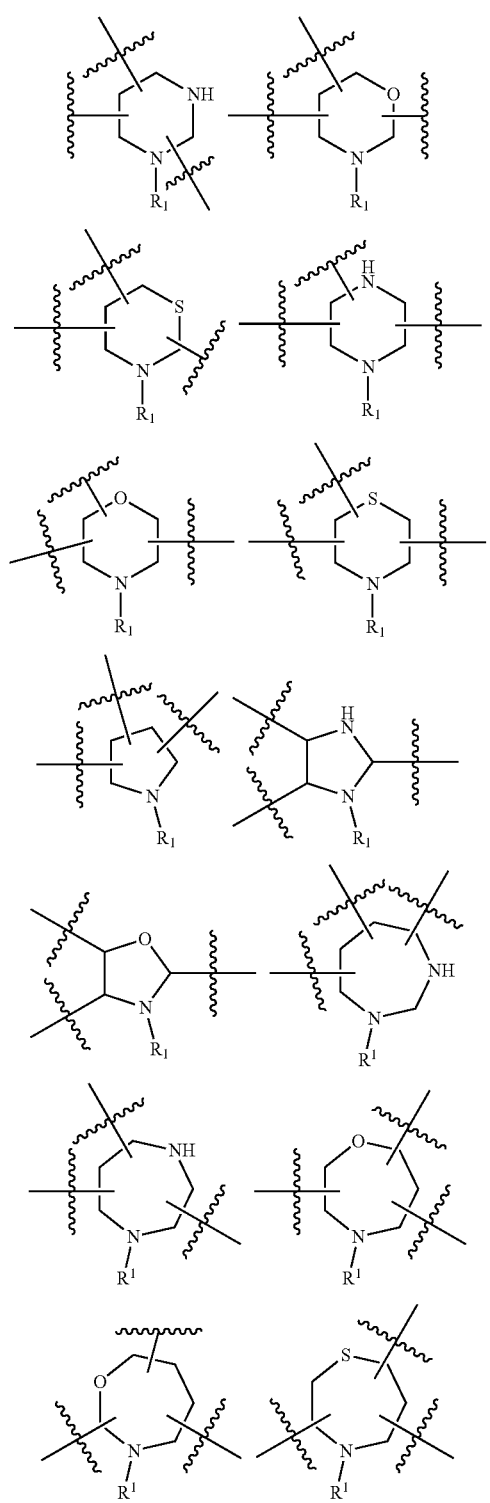

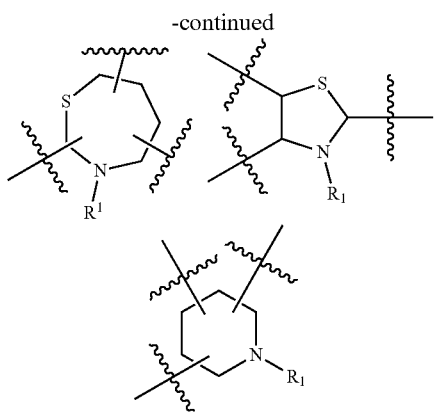

R₁ is selected from the group consisting of H, $C_1$-$C_4$ alkyl, halogenated $C_1$-$C_4$ alkyl,

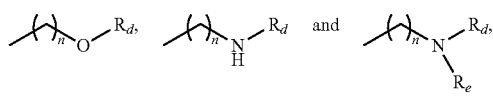

wherein n is an integer from 0 to 4, $R_d$ is selected from the group consisting of H, $C_1$-$C_4$ alkyl, halogenated $C_1$-$C_4$ alkyl, $R_e$ is selected from the group consisting of $C_1$-$C_4$ alkyl, halogenated $C_1$-$C_4$ alkyl, $C_1$-$C_4$ alkoxy, halogenated $C_1$-$C_4$ alkoxy;

$R_2$ is selected from the group consisting of unsubstituted or substituted aryl, unsubstituted or substituted heterocyclic aryl, unsubstituted or substituted cycloalkyl, unsubstituted or substituted saturated heterocyclic alkyl, unsubstituted or substituted unsaturated heterocyclic alkyl, aryl and heterocyclic aryl which is optionally fused;

m is an integer from 0 to 3;

$R_3$ is selected from the group consisting of amino, cyano, $C_1$-$C_4$ alkyl, halogenated $C_1$-$C_4$ alkyl, $C_1$-$C_4$ alkoxy, $C_1$-$C_4$ carboxyl, halogenated $C_1$-$C_4$ alkoxy,

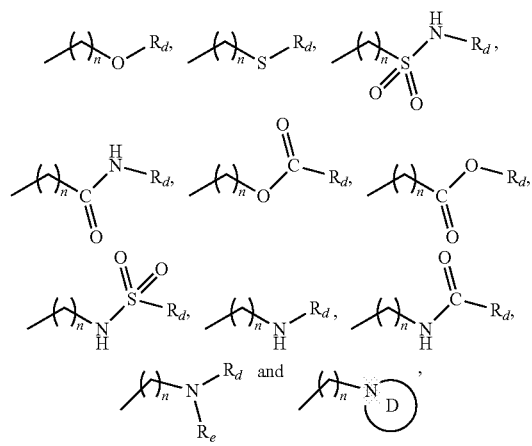

wherein n is an integer from 0 to 4, $R_d$ is selected from the group consisting of H, $C_1$-$C_4$ alkyl, halogenated $C_1$-$C_4$ alkyl, $C_1$-$C_4$ alkoxy, halogenated $C_1$-$C_4$ alkoxy, $R_e$ is selected from the group consisting of $C_1$-$C_4$ alkyl, halogenated $C_1$-$C_4$ alkyl, $C_1$-$C_4$ alkoxy, halogenated $C_1$-$C_4$ alkoxy; ring D is selected from saturated or unsaturated 5-8 membered aliphatic nitrogen-containing heterocyclic ring; that is, ring D may be a 5-8 membered saturated aliphatic nitrogen-containing heterocyclic ring without substitution, a substituted 5-8 membered saturated aliphatic nitrogen-containing heterocyclic ring, a 5-8 membered unsaturated aliphatic nitrogen-containing heterocyclic ring without substitution, a substituted 5-8 membered unsaturated aliphatic nitrogen-containing heterocyclic ring; preferably, ring D is the following aliphatic nitrogen-containing heterocyclic ring:

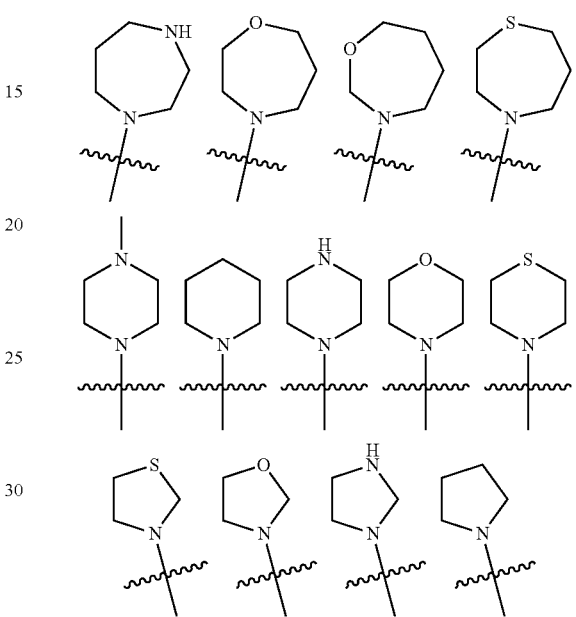

$R_4$, $R_5$ are each independently selected from the group consisting of H, halogen, nitro, amino, cyano, hydroxyl, $C_1$-$C_4$ alkyl, halogenated $C_1$-$C_4$ alkyl, $C_1$-$C_4$ alkoxy, halogenated $C_1$-$C_4$ alkoxy, unsubstituted or substituted furanyl, thiophenyl, phenyl, pyridinyl;

$R_6$ is selected from the group consisting of H, $C_1$-$C_4$ alkyl, halogenated $C_1$-$C_4$ alkyl, $C_1$-$C_4$ alkoxy, halogenated $C_1$-$C_4$ alkoxy;

Q, Y are each independently selected from N and —C($R_f$)—; Z is selected from N and —C($R_g$)—; at least one group of Q, Y and Z is N atom and at most two groups are the same; wherein $R_f$ is selected from H, halogen; $R_g$ is selected from the group consisting of H, halogen, hydroxyl, carboxyl, hydroxymethyl, saturated or unsaturated $C_1$-$C_4$ alkyl, halogenated $C_1$-$C_4$ alkyl, $C_1$-$C_4$ alkoxy, halogenated $C_1$-$C_4$ alkoxy, unsubstituted or substituted aryl, unsubstituted or substituted heterocyclic aryl, unsubstituted saturated or partly saturated heterocyclic ring, substituted saturated or partly saturated heterocyclic ring, unsubstituted or substituted cycloalkyl;

said substituent is optionally selected from the group consisting of halogen, nitro, amino, cyano, hydroxyl, $C_1$-$C_4$ alkyl, halogenated $C_1$-$C_4$ alkyl, $C_1$-$C_4$ alkoxy, $C_1$-$C_4$ alkylamino, halogenated $C_1$-$C_4$ alkoxy, halogenated $C_1$-$C_4$ alkylamino.

Further, the preferred compounds in the invention have a structure of general formula (II):

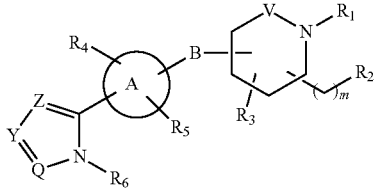

and optical isomers thereof, or pharmaceutically acceptable salts or solvate thereof, wherein: Ring A, B, $R_1$, m, $R_2$, $R_3$, $R_4$, $R_5$, Q, Y, Z and $R_6$ are as defined in the general formula (I);

V is selected from $(CH_2)_{m1}$, wherein $m_1$ is an integer from 0 to 3.

Particularly, the preferred compounds in the invention have the structure of general formula (III):

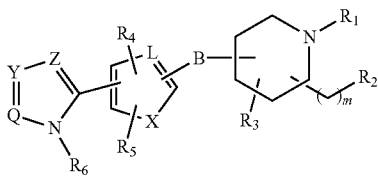

and optical isomers, or pharmaceutically acceptable salts or solvates thereof, wherein:

$R_1$, $R_2$, $R_3$, $R_4$, $R_5$, Q, Y, Z, B, m and $R_6$ are as defined in the general formula (I);

X is selected from the group consisting of O, S, $N(R_h)$, wherein $R_h$ is selected from the group consisting of H, $C_1$-$C_5$ alkyl, halogenated $C_1$-$C_5$ alkyl, $C_1$-$C_5$ alkoxy and halogenated $C_1$-$C_5$ alkoxy; L is selected from the group consisting of CH and N.

Particularly, the preferred compounds in the invention have the structure of general formula (IV):

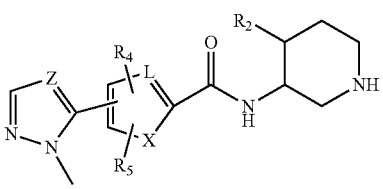

and optical isomers, or pharmaceutically acceptable salts or solvates thereof, wherein:

$R_2$, L are as defined in the general formula (III); $R_4$, $R_5$ are each independently selected from halogen and $C_1$-$C_3$ alkyl;

X is selected from the group consisting of O, S, NH and $NCH_3$; Z is selected from —$C(R_g)$—, $R_g$ is preferably selected from the group consisting of H, halogen and $C_1$-$C_3$ alkyl.

In addition, the preferred compounds in the invention have the structure of general formula (V):

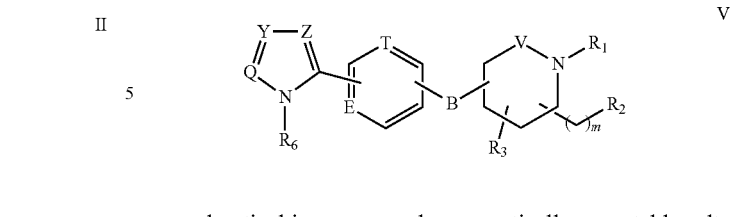

and optical isomers, or pharmaceutically acceptable salts or solvates thereof, wherein:

$R_1$, $R_2$, $R_3$, B, m, Q, Y, Z, $R_6$ are as defined in the general formula (I);

V is selected from $(CH_2)_{m1}$, wherein $m_1$ is an integer from 0 to 3;

E and T are same or different, E and T are each independently selected from N and —$C(R_i)$—, wherein $R_i$ is selected from the group consisting of H, halogen, cyano, nitro, amino, $C_1$-$C_4$ alkyl, halogenated $C_1$-$C_4$ alkyl, $C_1$-$C_4$ alkoxy, halogenated $C_1$-$C_4$ alkoxy, unsubstituted or substituted furanyl, unsubstituted or substituted thiophenyl, unsubstituted or substituted phenyl, unsubstituted or substituted pyridinyl.

Further, the preferred compounds in the invention have the structure of general formula (VI):

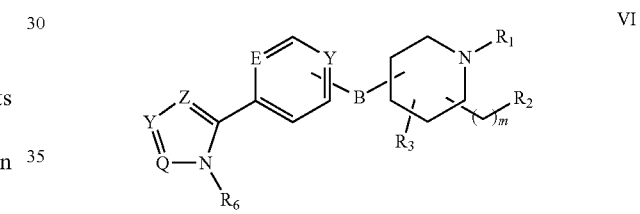

and optical isomers, or pharmaceutically acceptable salts or solvates thereof, wherein:

E, T, $R_1$, $R_2$, $R_3$, B, Q, Y, Z, m and $R_6$ are as defined in the general formula (V);

More particularly, the preferred compounds in the invention have the structure of general formula (VII):

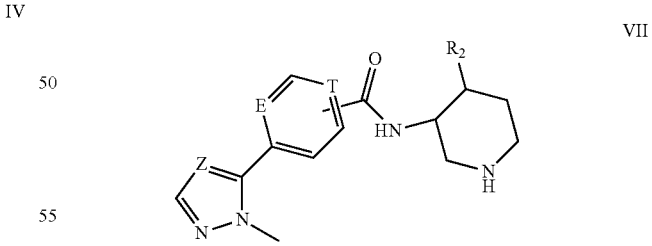

and optical isomers, or pharmaceutically acceptable salts or solvates thereof, wherein:

$R_2$ is as defined in the general formula (I); E, T are each independently selected from N and —$C(R_i)$—, wherein $R_i$ is selected from the group consisting of H, halogen and $C_1$-$C_3$ alkyl; Z is selected from —$C(R_g)$—, wherein $R_g$ is selected from the group consisting of H, halogen, $C_1$-$C_3$ alkyl.

In addition, the preferred compounds in the invention have the structure of general formula (VIII):

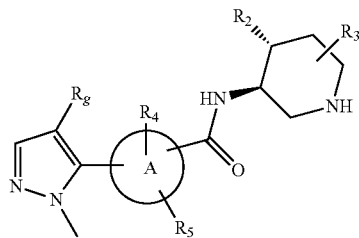

VIII and optical isomers, or pharmaceutically acceptable salts or solvates thereof, wherein:

Ring A, $R_g$, $R_2$, $R_3$, $R_4$, $R_5$ are as defined in the general formula (I).

Further, the preferred compounds in the invention have the structure of general formula (IX):

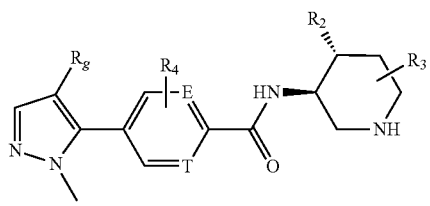

IX and optical isomers, or pharmaceutically acceptable salts or solvates thereof, wherein:

$R_g$, $R_3$ and $R_4$ are as defined in the general formula (I);

$R_2$ is preferably selected from unsubstituted or substituted aryl, unsubstituted or substituted heterocyclic aryl; said substituent is optionally selected from the group consisting of halogen, nitro, amino, cyano, hydroxyl, $C_1$-$C_4$ alkyl, halogenated $C_1$-$C_4$ alkyl, $C_1$-$C_4$ alkoxy, $C_1$-$C_4$ alkylamino, halogenated $C_1$-$C_4$ alkoxy, halogenated $C_1$-$C_4$ alkylamino;

E, T are each independently selected from N and —C($R_i$)—, wherein $R_i$ is selected from the group consisting of H, halogen, $C_1$-$C_3$ alkyl, halogenated $C_1$-$C_3$ alkyl.

Still further, the preferred compounds in the invention have the structure of general formula (X):

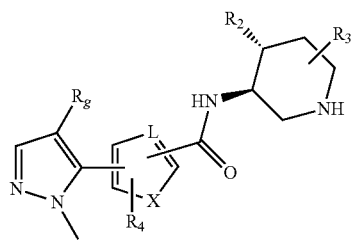

X and optical isomers, or pharmaceutically acceptable salts or solvates thereof, wherein:

$R_g$, $R_2$, $R_3$ and $R_4$ are as defined in the general formula (I); X is selected from the group consisting of O, S, NH and NCH$_3$; L is selected from CH and N.

Further, the preferred compounds in the invention have the structure of general formula (XI):

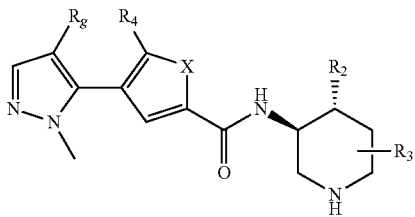

XI and optical isomers, or pharmaceutically acceptable salts or solvates thereof, wherein:

$R_g$, $R_2$, $R_3$ and $R_4$ are as defined in the general formula (I); X is selected from O, S.

Finally, the preferred compounds in the invention have the structure of general formula (XII):

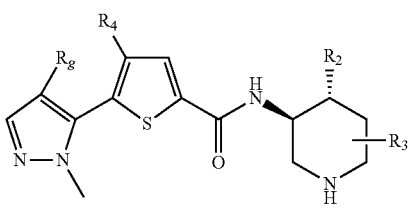

XII and optical isomers, or pharmaceutically acceptable salts or solvates thereof, wherein:

$R_g$, $R_2$, $R_3$ and $R_4$ are as defined in the general formula (I).

Specifically, according to the general formula (IV), the preferred compounds in the invention are:

4-(1-methyl-1H-pyrazol-5-yl)-N-(3,4-trans-4-phenylpiperidine-3-yl)furan-2-formamide;

5-chloro-4-(4-chloro-1-methyl-1H-pyrazol-5-yl)-N-(3,4-trans-4-(4-chlorphenyl)piperidine-3-yl) furan-2-formamide;

5-bromo-4-(1-methyl-1H-1,2,4-triazol-5-yl)-N-(3,4-trans-4-(4-trifluoromethylphenyl) piperidine-3-yl)furan-2-formamide;

5-bromo-3-ethyl-1-methyl-4-(1-methyl-1H-1,2,4-triazol-5-yl)-N-(3,4-trans-4-(3-trifluoromethylphenyl)piperidine-3-yl)-1H-pyrrole-2-formamide;

5-methyl-4-(4-chloro-1-methyl-1H-pyrazol-5-yl)-N-(3,4-trans-4-(3,4-difluorophenyl) piperidine-3-yl)thiophene-2-formamide;

5-methyl-4-(4-bromo-1-methyl-1H-pyrazol-5-yl)-N-(3,4-trans-4-(pyridine-4-yl)piperidine-3-yl)-1H-pyrrole-2-formamide;

4-chloro-5-(1-methyl-1H-1,2,4-triazol-5-yl)-N-(3,4-trans-4-(3-methylphenyl)piperidine-3-yl) furan-2-formamide;

4-chloro-5-(1-methyl-1H-1,2,4-triazol-5-yl)-N-(3,4-trans-4-(4-(1-chloroethyl)phenyl) piperidine-3-yl)thiophene-2-formamide;

5-methyl-4-(4-isopropyl-1-methyl-1H-pyrazol-5-yl)-N-(3,4-trans-4-(quinoline-3-yl)piperidine-3-yl)thiophene-2-formamide;

5-methyl-4-(1-methyl-4-bromo-1H-pyrazol-5-yl)-N-(3,4-trans-4-(3-cyanophenyl)piperidin-3-yl)-1H-pyrrole-2-formamide;

4-chloro-5-(1-methyl-1H-1,2,4-triazol-5-yl)-N-(3,4-trans-4-(3,5-dimethoxyphenyl)piperidin-3-yl)furan-2-formamide;

4-chloro-5-(1-methyl-4-bromo-1H-pyrazol-5-yl)-N-(3,4-trans-4-(1H-pyrrole-2-yl)piperidin-3-yl)furan-2-formamide;

4-methyl-5-(1-methyl-1H-1,2,4-triazol-5-yl)-N-(3,4-trans-4-(1H-indol-2-yl)piperidin-3-yl) furan-2-formamide;

5-ethyl-4-(4-isopropyl-1-methyl-1H-pyrazol-5-yl)-N-(3,4-trans-4-(7-methyl-5,6,7,8-tetrahydroquinolin-3-yl)piperidin-3-yl)thiophene-2-formamide;

5-ethyl-1-methyl-4-(4-chloro-1-methyl-1H-pyrazol-5-yl)-N-(3,4-trans-4-(3-fluorocyclopentanyl) piperidin-3-yl)-1H-pyrrole-2-formamide;

5-bromo-4-(1,4-dimethyl-1H-pyrazol-5-yl)-N-(3,4-trans-4-(4-methylcyclohexane)piperidin-3-yl)-1H-pyrrole-2-formamide;

5-ethyl-1-methyl-4-(4-ethyl-1-methyl-1H-pyrazol-5-yl)-N-(3,4-trans-4-(piperidin-3-yl) piperidin-3-yl)-1H-pyrrole-2-formamide;

5-chloro-3-methyl-4-(1-methyl-1H-1,2,4-triazol-5-yl)-N-(3,4-trans-4-(5-chloropiperidin) piperidin-3-yl)thiophene-2-formamide;

4-(1-methyl-1H-pyrazol-5-yl)-N-(3,4-trans-4-phenylpiperidin-3-yl)oxazole-2-formamide;

4-(4-chloro-1-methyl-1H-pyrazol-5-yl)-N-(3,4-trans-4-(3,4-difluorophenyl)piperidin-3-yl)-5-methylthiazole-2-formamide;

4-(1-methyl-1H-pyrazol-5-yl)-N-(3,4-trans-4-(3,4-difluorophenyl)piperidin-3-yl)furan-2-formamide;

4-(4-bromo-1-methyl-1H-pyrazol-5-yl)-N-(3,4-trans-4-phenylpiperidin-3-yl)furan-2-formamide;

4-(4-chloro-1-methyl-1H-pyrazol-5-yl)-N-(3,4-trans-4-(4-chlorphenyl)piperidin-3-yl)furan-2-formamide;

4-(4-chloro-1-methyl-1H-pyrazol-5-yl)-N-(3,4-trans-4-(4-trifluoromethylphenyl)piperidin-3-yl)furan-2-formamide;

4-(4-chloro-1-methyl-1H-pyrazol-5-yl)-N-(3,4-trans-4-(3,4-difluorophenyl)piperidin-3-yl) furan-2-formamide;

4-(4-bromo-1-methyl-1H-pyrazol-5-yl)-N-(3,4-trans-4-(4-chlorphenyl)piperidin-3-yl)furan-2-formamide;

4-(4-bromo-1-methyl-1H-pyrazol-5-yl)-N-(3,4-trans-4-(4-trifluoromethylphenyl)piperidin-3-yl)furan-2-formamide;

4-(4-bromo-1-methyl-1H-pyrazol-5-yl)-N-(3,4-trans-4-(3,4-difluorophenyl)piperidin-3-yl) furan-2-formamide;

5-chloro-4-(4-chloro-1-methyl-1H-pyrazol-5-yl)-N-(3,4-trans-4-phenylpiperidin-3-yl)furan-2-formamide;

5-chloro-4-(4-chloro-1-methyl-1H-pyrazol-5-yl)-N-(3,4-trans-4-(4-trifluoromethylphenyl) piperidin-3-yl)furan-2-formamide;

5-chloro-4-(4-chloro-1-methyl-1H-pyrazol-5-yl)-N-(3,4-trans-4-(3,4-difluorophenyl)piperidin-3-yl)furan-2-formamide;

4-(1-methyl-1H-pyrazol-5-yl)-N-(3,4-trans-4-(4-chlorphenyl)piperidin-3-yl)thiophene-2-formamide;

4-(1-methyl-1H-pyrazol-5-yl)-N-(3,4-trans-4-(3,4-difluorophenyl)piperidin-3-yl)thiophene-2-formamide;

4-(4-chloro-1-methyl-1H-pyrazol-5-yl)-N-(3,4-trans-4-phenylpiperidin-3-yl)thiophene-2-formamide;

4-(4-chloro-1-methyl-1H-pyrazol-5-yl)-N-(3,4-trans-4-(4-chlorphenyl)piperidin-3-yl) thiophene-2-formamide;

4-(4-chloro-1-methyl-1H-pyrazol-5-yl)-N-(3,4-trans-4-(3,4-difluorophenyl)piperidin-3-yl) thiophene-2-formamide;

4-(4-bromo-1-methyl-1H-pyrazol-5-yl)-N-(3,4-trans-4-(4-chlorphenyl)piperidin-3-yl) thiophene-2-formamide;

4-(4-bromo-1-methyl-1H-pyrazol-5-yl)-N-(3,4-trans-4-(3,4-difluorophenyl)piperidin-3-yl) thiophene-2-formamide;

5-chloro-4-(4-chloro-1-methyl-1H-pyrazol-5-yl)-N-((3R,4R)-4-(3,4-dichlorophenyl)piperidin-3-yl)furan-2-formamide;

5-chloro-4-(4-chloro-1-methyl-1H-pyrazol-5-yl)-N-((3S,4S)-4-(3,4-dichlorophenyl)piperidin-3-yl)furan-2-formamide;

4-(4-bromo-1-methyl-1H-pyrazol-5-yl)-N-((3R,4R)-4-(3,4-difluorophenyl)piperidin-3-yl) thiophene-2-formamide;

4-(4-bromo-1-methyl-1H-pyrazol-5-yl)-N-((3S,4S)-4-(3,4-difluorophenyl)piperidin-3-yl) thiophene-2-formamide;

5-chloro-4-(4-chloro-1-methyl-1H-pyrazol-5-yl)-N-((3R,4R)-4-(4-trifluoromethylphenyl) piperidin-3-yl)furan-2-formamide;

5-chloro-4-(4-chloro-1-methyl-1H-pyrazol-5-yl)-N-((3S,4S)-4-(4-trifluoromethylphenyl) piperidin-3-yl)furan-2-formamide;

and optical isomers of above compounds, or pharmaceutically acceptable salts or solvates thereof.

Specifically, according to the general formula (VII), the preferred compounds in the invention are:

6-methyl-4-(4-chloro-1-methyl-1H-pyrazol-5-yl)-N-(3,4-trans-4-phenylpiperidin-3-yl) pyridine-2-formamide;

4-fluoro-5-(1,4-dimethyl-1H-pyrazol-5-yl)-N-(3,4-trans-4-(3,4-difluorophenyl)piperidin-3-yl) pyridine-2-formamide;

2-methyl-6-(1-methyl-4-ethyl-1H-pyrazol-5-yl)-N-(3,4-trans-4-(4-chlorphenyl)piperidin-3-yl) pyrimidine-4-formamide;

5-(4-bromo-1-methyl-1H-pyrazol-5-yl)-N-(3,4-trans-4-(pyridin-4-yl)piperidin-3-yl)pyrazine-2-formamide;

5-ethyl-6-(4-bromo-1-methyl-1H-pyrazol-5-yl)-N-(3,4-trans-4-(4-trifluoromethylphenyl) piperidin-3-yl) pyridine-3-formamide;

4,6-dimethyl-5-(4-bromo-1-methyl-1H-pyrazol-5-yl)-N-(3,4-trans-4-(4-trifluoromethylphenyl) piperidin-3-yl)pyrimidine-2-formamide;

5-chloro-4-(4-isopropyl-1-methyl-1H-pyrazol-5-yl)-N-(3,4-trans-4-(3-fluoro cyclohexane) piperidin-3-yl)pyrimidine-2-formamide;

4-methyl-5-(4-chloro-1-methyl-1H-pyrazol-5-yl)-N-(3,4-trans-4-(3,4-difluorophenyl)piperidin-3-yl)pyrimidine-2-formamide;

2-chloro-3-(4-ethyl-1-methyl-1H-pyrazol-5-yl)-N-(3,4-trans-4-(4-chlorphenyl)piperidin-3-yl) phenyl formamide;

3-n-propyl-4-(4-bromo-1-methyl-1H-pyrazol-5-yl)-N-(3,4-trans-4-(3,5-dimethoxyphenyl) piperidin-3-yl) phenyl formamide;

4-chloro-5-(4-chloro-1-methyl-1H-pyrazol-5-yl)-N-(3,4-trans-4-(4-methylcyclohexane) piperidin-3-yl)pyrimidine-2-formamide;

5-(4-chloro-1-methyl-1H-pyrazol-5-yl)-N-(3,4-trans-4-(3-chlorocyclohexane)piperidin-3-yl)-4-methylpyridine-2-formamide;

2,5-dimethyl-4-(4-bromo-1-methyl-1H-pyrazol-5-yl)-N-(3,4-trans-4-(3-methylphenyl) piperidin-3-yl) phenyl formamide;

6-methyl-5-(4-bromo-1-methyl-1H-pyrazol-5-yl)-N-(3,4-trans-4-(pyridin-4-yl)piperidin-3-yl)pyridine-2-formamide;

6-methyl-5-(4-bromo-1-methyl-1H-pyrazol-5-yl)-N-(3,4-trans-4-(piperidin-3-yl)piperidin-3-yl)pyridine-2-formamide;

4-methyl-5-(1,4-dimethyl-1-methyl-1H-pyrazol-5-yl)-N-(3,4-trans-4-(pyrrole-2-yl)piperidin-3-yl)pyrimidine-2-formamide;

4-fluoro-5-(1,4-dimethyl-1H-pyrazol-5-yl)-N-((3R,4R)-4-(3,4-difluorophenyl)piperidin-3-yl) pyridine-2-formamide;

4-fluoro-5-(1,4-dimethyl-1H-pyrazol-5-yl)-N-((3S,4S)-4-(3,4-difluorophenyl)piperidin-3-yl) pyridine-2-formamide;

5-ethyl-6-(4-bromo-1-methyl-1H-pyrazol-5-yl)-N-((3R,4R)-4-(4-trifluoromethylphenyl) piperidin-3-yl)pyridine-3-formamide;

5-ethyl-6-(4-bromo-1-methyl-1H-pyrazol-5-yl)-N-((3S,4S)-4-(4-trifluoromethylphenyl) piperidin-3-yl)pyridine-3-formamide;

4-(1-methyl-1H-pyrazol-5-yl)-N-(3,4-trans-4-(3,4-difluorophenyl)pyrrolidin-3-yl)furan-2-formamide;

5-chloro-4-(4-chloro-1-methyl-1H-pyrazol-5-yl)-N-(3,4-trans-4-(3,4-difluorophenyl) pyrrolidin-3-yl)furan-2-formamide;

4-(4-bromo-1-methyl-1H-pyrazol-5-yl)-N-(3,4-trans-4-(4-trifluoromethylphenyl)pyrrolidin-3-yl)furan-2-formamide;

4-(4-bromo-1-methyl-1H-pyrazol-5-yl)-N-(3,4-trans-4-(3,4-difluorophenyl)pyrrolidin-3-yl) furan-2-formamide;

5-chloro-4-(4-chloro-1-methyl-1H-pyrazol-5-yl)-N-(3,4-trans-4-(4-trifluoromethylphenyl) pyrrolidin-3-yl)furan-2-formamide;

4-fluoro-5-(1,4-dimethyl-1H-pyrazol-5-yl)-N-(3,4-trans-4-(3,4-difluorophenyl)pyrrolidin-3-yl) pyridine-2-formamide;

4-fluoro-5-(1,4-dimethyl-1H-pyrazol-5-yl)-N-(3,4-trans-4-(4-trifluoromethylphenyl)pyrrolidin-3-yl)pyridine-2-formamide;

and optical isomers of above compounds, or pharmaceutically acceptable salts or solvates thereof.

Specifically, according to the general formula (IX), the preferred compounds in the invention are:

4-(4-bromo-1-methyl-1H-pyrazol-5-yl)-N-((3S,4S)-4-(4-chlorphenyl)piperidin-3-yl) benzamide;

4-(4-chloro-1-methyl-1H-pyrazol-5-yl)-N-((3S,4S)-4-(3-fluorophenyl)piperidin-3-yl) benzamide;

4-(4-chloro-1-methyl-1H-pyrazol-5-yl)-N-((3S,4S)-4-(4-chloro-3-(trifluoromethyl)phenyl) piperidin-3-yl)-3-methyl benzamide;

N-((3S,4S)-4-(4-chloro-3-(trifluoromethyl)phenyl)piperidin-3-yl)-4-(4-ethyl-1-methyl-1H-pyrazol-5-yl)-2,6-difluoro benzamide;

4-(4-chloro-1-methyl-1H-pyrazol-5-yl)-N-((3S,4S)-4-(4-chlorphenyl)piperidin-3-yl)-3-cyano benzamide;

N-((3S,4S)-4-(3,4-difluorophenyl)piperidin-3-yl)-4-(1-methyl-1H-pyrazol-5-yl)benzamide;

3-chloro-4-(4-chloro-1-methyl-1H-pyrazol-5-yl)-N-((3S,4S)-4-(3,4-difluorophenyl)piperidin-3-yl)benzamide;

3-amido-4-(4-chloro-1-methyl-1H-pyrazol-5-yl)-N-((3S,4S)-4-(3-fluorophenyl)piperidin-3-yl) benzamide;

4-(4-chloro-1-methyl-1H-pyrazol-5-yl)-N-((3S,4S)-4-(4-chlorphenyl)piperidin-3-yl)-2-(trifluoromethyl)benzamide;

4-(4-bromo-1-methyl-1H-pyrazol-5-yl)-N-((3S,4S)-4-(3,4,5-trifluorophenyl)piperidin-3-yl) benzamide;

4-(4-chloro-1-methyl-1H-pyrazol-5-yl)-N-((3S,4S)-4-(3,4-difluorophenyl)piperidin-3-yl)-3-fluoro benzamide;

4-(4-chloro-1-methyl-1H-pyrazol-5-yl)-N-((3S,4S)-4-(3-fluorophenyl)piperidin-3-yl)-3-methoxybenzamide;

4-(4-chloro-1-methyl-1H-pyrazol-5-yl)-N-((3S,4S)-4-(4-chloro-3-(trifluoromethyl)phenyl) piperidin-3-yl)-2-fluoro benzamide;

4-(4-chloro-1-methyl-1H-pyrazol-5-yl)-N-((3S,4S)-4-(3-fluorophenyl)piperidin-3-yl)-3-(trifluoromethoxy)benzamide;

3-chloro-4-(4-chloro-1-methyl-1H-pyrazol-5-yl)-N-((3S,4S)-4-(3-fluorophenyl)piperidin-3-yl) benzamide;

4-(4-chloro-1-methyl-1H-pyrazol-5-yl)-N-((3S,4S)-4-(3,4-difluorophenyl)piperidin-3-yl)-3-(furan-3-yl)benzamide;

4-(4-chloro-1-methyl-1H-pyrazol-5-yl)-N-((3S,4S)-4-(3-fluorophenyl)piperidin-3-yl)-2-(2-methylfuran-3-yl)benzamide;

N-((3S,4S)-4-(1H-indol-3-yl)piperidin-3-yl)-3-chloro-4-(4-chloro-1-methyl-1H-pyrazol-5-yl) benzamide;

4-(4-chloro-1-methyl-1H-pyrazol-5-yl)-2-(5-chlorothiophene-3-yl)-N-((3S,4S)-4-(3,4-difluorophenyl)piperidin-3-yl)benzamide;

N-((3S,4S)-4-(1H-indol-4-yl)piperidin-3-yl)-3-chloro-4-(4-chloro-1-methyl-1H-pyrazol-5-yl) benzamide;

4-chloro-5-(4-chloro-1-methyl-1H-pyrazol-5-yl)-N-((3S,4S)-4-(3-fluorophenyl)piperidin-3-yl) picolinamide;

5-(4-chloro-1-methyl-1H-pyrazol-5-yl)-N-((3S,4S)-4-(3,4-difluorophenyl)piperidin-3-yl) pyrimidine-2-formamide;

5-(4-chloro-1-methyl-1H-pyrazol-5-yl)-N-((3S,4S)-4-(3,4-difluorophenyl)piperidin-3-yl)-4-methyl picolinamide;

4-chloro-5-(4-chloro-1-methyl-1H-pyrazol-5-yl)-N-((3S,4S)-4-(4-chloro-3-(trifluoromethyl) phenyl)piperidin-3-yl)picolinamide;

5-(4-chloro-1-methyl-1H-pyrazol-5-yl)-N-((3S,4S)-4-(4-chloro-3-(trifluoromethyl)phenyl) piperidin-3-yl)picolinamide;

5-(4-chloro-1-methyl-1H-pyrazol-5-yl)-N-((3S,4S)-4-(3,4-difluorophenyl)piperidin-3-yl)-3-fluoro picolinamide;

4-(4-chloro-1-methyl-1H-pyrazol-5-yl)-N-((3S,4S)-4-(3,4-difluorophenyl)-6-(2-(methylamino)-2-oxoethyl)piperidin-3-yl)benzamide;

3-chloro-4-(4-chloro-1-methyl-1H-pyrazol-5-yl)-N-((3S,4S)-4-(3,4-difluorophenyl)-6-(2-(methylamino)-2-oxoethyl)piperidin-3-yl)benzamide;

4-(4-chloro-1-methyl-1H-pyrazol-5-yl)-N-((3S,4S)-4-(3,4-difluorophenyl)-6-(2-hydroxyethyl) piperidin-3-yl)benzamide;

4-(4-chloro-1-methyl-1H-pyrazol-5-yl)-N-((3S,4S)-4-(3,4-difluorophenyl)-6-((N-methylamino sulfonyl)methyl)piperidin-3-yl)-3-fluoro benzamide;

4-(4-chloro-1-methyl-1H-pyrazol-5-yl)-N-((3S,4S)-4-(3,4-difluorophenyl)-6-(2-(piperidin-1-yl)ethyl)piperidin-3-yl)-3-methyl benzamide;

3-chloro-4-(4-chloro-1-methyl-1H-pyrazol-5-yl)-N-((3S,4S)-4-(3-fluorophenyl)-6-(2-(methylsulfamideo)ethyl)piperidin-3-yl)benzamide;

and optical isomers of the above compounds, or pharmaceutically acceptable salts or solvates thereof.

Specifically, according to the general formula (XI), the preferred compounds in the invention are:

5-chloro-4-(4-chloro-1-methyl-1H-pyrazol-5-yl)-N-((3S,4S)-4-(3,4-difluorophenyl)-6-(2-(methylamine)-2-oxoethyl)piperidin-3-yl)thiophene-2-formamide;

5-chloro-4-(4-chloro-1-methyl-1H-pyrazol-5-yl)-N-((3S,4S)-4-(3,4-difluorophenyl)-6-(2-(methylamine)-2-oxoethyl)piperidin-3-yl)furan-2-formamide;

N-((3S,4S)-6-allyl-4-(3,4-dichlorophenyl)piperidin-3-yl)-5-chloro-4-(4-chloro-1-methyl-1H-pyrazol-5-yl)furan-2-formamide;

5-chloro-4-(4-chloro-1-methyl-1H-pyrazol-5-yl)-N-((3S,4S)-4-(3,4-dichlorophenyl)-6-(2-(dimethylamino)ethyl) piperidin-3-yl)furan-2-formamide;

5-chloro-4-(4-chloro-1-methyl-1H-pyrazol-5-yl)-N-((3S,4S)-4-(3,4-dichlorophenyl)-6-(2-(piperidin-1-yl)ethyl)piperidin-3-yl)furan-2-formamide;

5-chloro-4-(4-chloro-1-methyl-1H-pyrazol-5-yl)-N-((3S,4S)-4-(3,4-dichlorophenyl)-6-(2-(morpholin-1-yl)ethyl) piperidin-3-yl)furan-2-formamide;

5-chloro-4-(4-chloro-1-methyl-1H-pyrazol-5-yl)-N-((3S, 4S)-4-(3,4-dichlorophenyl)-6-(2-(pyrrolidin-1-yl)ethyl) piperidin-3-yl)furan-2-formamide;

5-chloro-4-(4-chloro-1-methyl-1H-pyrazol-5-yl)-N-((3S, 4S)-4-(3,4-dichlorophenyl)-6-(3-hydroxypropyl)piperidin-3-yl)furan-2-formamide;

5-chloro-4-(4-chloro-1-methyl-1H-pyrazol-5-yl)-N-((3S, 4S)-4-(3,4-dichlorophenyl)-6-(2,3-dihydroxypropyl)piperidin-3-yl)furan-2-formamide;

5-chloro-4-(4-chloro-1-methyl-1H-pyrazol-5-yl)-N-((3S, 4S)-4-(3,4-dichlorophenyl)-6-(2-hydroxyethyl)piperidin-3-yl)furan-2-formamide;

5-chloro-4-(4-chloro-1-methyl-1H-pyrazol-5-yl)-N-((3S, 4S)-4-(3,4-dichlorophenyl)-6-(2-(4-hydroxypiperidin-1-yl)ethyl)piperidin-3-yl)furan-2-formamide;

5-chloro-4-(4-chloro-1-methyl-1H-pyrazol-5-yl)-N-((3S, 4S)-4-(3,4-dichlorophenyl)-6-(2-(3-hydroxypiperidin-1-yl)ethyl)piperidin-3-yl)furan-2-formamide;

2-((4S,5S)-5-(5-chloro-4-(4-chloro-1-methyl-1H-pyrazol-5-yl)furan-2-carboxamido)-4-(3,4-dichlorophenyl)piperidin-2-yl) acetic acid;

N-((3S,4S)-6-(2-amine-2-oxoethyl)-4-(3,4-dichlorophenyl) piperidin-3-yl)-5-chloro-4-(4-chloro-1-methyl-1H-pyrazol-5-yl)furan-2-formamide;

5-chloro-4-(4-chloro-1-methyl-1H-pyrazol-5-yl)-N-((3S, 4S)-4-(3,4-dichlorophenyl)-6-(2-(methylamine)-2-oxoethyl)piperidin-3-yl)furan-2-formamide;

5-chloro-4-(4-chloro-1-methyl-1H-pyrazol-5-yl)-N-((3S, 4S)-6-(2-(cyclopropyl amine)-2-oxoethyl)-4-(3,4-dichlorophenyl)piperidin-3-yl)furan-2-formamide;

5-chloro-4-(4-chloro-1-methyl-1H-pyrazol-5-yl)-N-((3S, 4S)-6-(2-(cyclobutylamine)-2-oxoethyl)-4-(3,4-dichlorophenyl)piperidin-3-yl)furan-2-formamide;

5-chloro-4-(4-chloro-1-methyl-1H-pyrazol-5-yl)-N-((3S, 4S)-4-(3,4-dichlorophenyl)-6-(2-((2,3-dihydroxypropyl) amine)-2-oxoethyl)piperidin-3-yl)furan-2-formamide;

N-((3S,4S)-6-(2-(1H-1,2,4-triazol-1-yl)ethyl)-4-(3,4-dichlorophenyl)piperidin-3-yl)-5-chloro-4-(4-chloro-1-methyl-1H-pyrazol-5-yl)furan-2-formamide;

5-chloro-4-(4-chloro-1-methyl-1H-pyrazol-5-yl)-N-((3S, 4S)-4-(3,4-dichlorophenyl)-6-(2-((2,3-dihydroxypropyl) amine)ethyl)piperidin-3-yl)furan-2-formamide;

5-chloro-4-(4-chloro-1-methyl-1H-pyrazol-5-yl)-N-((3S, 4S)-4-(3,4-dichlorophenyl)-6-(2-methoxyethyl)piperidin-3-yl)furan-2-formamide;

5-chloro-4-(4-chloro-1-methyl-1H-pyrazol-5-yl)-N-((3S, 4S)-4-(3,4-dichlorophenyl)-6-(2-((2-hydroxyethyl) amine)-2-oxoethyl)piperidin-3-yl)furan-2-formamide;

N-((3S,4S)-6-(2-acetaminoethyl)-4-(3,4-difluorophenyl)piperidin-3-yl)-5-chloro-4-(4-chloro-1-methyl-1H-pyrazol-5-yl)furan-2-formamide;

5-chloro-4-(4-chloro-1-methyl-1H-pyrazol-5-yl)-N-((3S, 4S)-4-(3,4-difluorophenyl)-6-(2-(methylsulfonamido) ethyl)piperidin-3-yl)furan-2-formamide;

5-chloro-4-(4-chloro-1-methyl-1H-pyrazol-5-yl)-N-((3S, 4S)-4-(3,4-difluorophenyl)-6-(2,3-dihydroxypropyl)piperidin-3-yl)furan-2-formamide;

5-chloro-4-(4-chloro-1-methyl-1H-pyrazol-5-yl)-N-((3S, 4S)-4-(3,4-difluorophenyl)-6-(2-hydroxyethyl)piperidin-3-yl)furan-2-formamide;

5-chloro-4-(4-chloro-1-methyl-1H-pyrazol-5-yl)-N-((3S, 4S)-4-(3,4-dichlorophenyl)-6-propylpiperidin-3-yl)furan-2-formamide;

2-((4S,5S)-5-(5-chloro-4-(4-chloro-1-methyl-1H-pyrazol-5-yl)furan-2-carboxamido)-4-(3,4-difluorophenyl)piperidin-2-yl)ethyl acetate;

2-((4S,5S)-5-(5-chloro-4-(4-chloro-1-methyl-1H-pyrazol-5-yl)furan-2-carboxamido)-4-(3,4-difluorophenyl)piperidin-2-yl)ethyl 2,2,2-trifluoroacetate;

4-(4-chloro-1-methyl-1H-pyrazol-5-yl)-N-((3S,4S)-4-(3,4-difluorophenyl)-6-(2-(methylamine)-2-oxoethyl)piperidin-3-yl)thiophene-2-formamide;

5-chloro-4-(4-chloro-1-methyl-1H-pyrazol-5-yl)-N-((3S, 4S,5R)-4-(3-fluorophenyl)-5-propylpiperidin-3-yl)thiophene-2-formamide;

5-chloro-4-(4-chloro-1-methyl-1H-pyrazol-5-yl)-N-((3S, 4S,5R)-4-(3-fluorophenyl)-5-methylpiperidin-3-yl)thiophene-2-formamide;

5-chloro-4-(4-chloro-1-methyl-1H-pyrazol-5-yl)-N-((3S, 4S,5R)-4-(3-fluorophenyl)-5-methylpiperidin-3-yl)furan-2-formamide;

5-chloro-4-(4-chloro-1-methyl-1H-pyrazol-5-yl)-N-((3S, 4S,5R)-4-(3-fluorophenyl)-5-propylpiperidin-3-yl)furan-2-formamide;

and optical isomers of the above compounds, or pharmaceutically acceptable salts or solvates thereof.

Specifically, according to the general formula (XII), the preferred compounds in the invention are:

5-(4-chloro-1-methyl-1H-pyrazol-5-yl)-N-((3S,4S)-4-(3-fluorophenyl)piperidin-3-yl) thiophene-2-formamide;

4-chloro-5-(4-chloro-1-methyl-1H-pyrazol-5-yl)-N-((3S, 4S)-4-(3-fluorophenyl)piperidin-3-yl) thiophene-2-formamide;

N-((3S,4S)-4-(3-fluorophenyl)piperidin-3-yl)-5-(1-methyl-4-(pyridinyl-4-yl)-1H-pyrazol-5-yl) thiophene-2-formamide;

N-((3S,4S)-4-(3-fluorophenyl)piperidin-3-yl)-5-(4-(hydroxymethyl)-1-methyl-1H-pyrazol-5-yl)thiophene-2-formamide;

5-(5-(((3S,4S)-4-(3-fluorophenyl)piperidin-3-yl)carboxamido)thiophene-2-yl)-1-methyl-1H-pyrazol-4-formic acid;

N-((3S,4S)-4-(3-fluorophenyl)piperidin-3-yl)-5-(4-(1-hydroxyethyl)-1-methyl-1H-pyrazol-5-yl)thiophene-2-formamide;

N-((3S,4S)-4-(3-fluorophenyl)piperidin-3-yl)-5-(1-methyl-4-vinyl-1H-pyrazol-5-yl)thiophene-2-formamide;

5-(4-ethyl-1-methyl-1H-pyrazol-5-yl)-N-((3S,4S)-4-(3-fluorophenyl)piperidin-3-yl)thiophene-2-formamide;

N-((3S,4S)-4-(3-fluorophenyl)piperidin-3-yl)-5-(1-methyl-1H-pyrazol-5-yl)thiophene-2-formamide;

5-(4-bromo-1-methyl-1H-pyrazol-5-yl)-N-((3S,4S)-4-(3-fluorophenyl)piperidin-3-yl) thiophene-2-formamide;

N-((3S,4S)-4-(3,4-difluorophenyl)piperidin-3-yl)-5-(1-methyl-4-phenyl-1H-pyrazol-5-yl) thiophene-2-formamide;

4-chloro-5-(4-chloro-1-methyl-1H-pyrazol-5-yl)-N-((3S, 4S)-4-(3-fluorophenyl)-6-(2-(methyl amine)-2-oxoethyl) piperidin-3-yl)thiophene-2-formamide;

5-(4-chloro-1-methyl-1H-pyrazol-5-yl)-N-((3S,4S,5R)-4-(3-fluorophenyl)-5-methylpiperidin-3-yl)thiophene-2-formamide;

5-(4-chloro-1-methyl-1H-pyrazol-5-yl)-N-((3S,4S,5R)-4-(3-fluorophenyl)-5-propylpiperidin-3-yl)thiophene-2-formamide;

5-(4-chloro-1-methyl-1H-pyrazol-5-yl)-N-((3S,4S)-4-(3,4-difluorophenyl)-6-(2-(methylamine)-2-oxoethyl)piperidin-3-yl)thiophene-2-formamide;

and optical isomers of the above compounds, or pharmaceutically acceptable salts or solvates thereof.

The invention adopts the methods well-known to one skilled in the art for preparing the salts of the substituted nitrogen-containing heterocyclic compounds. Said salts may be salts of organic acid, salts of inorganic acid, and the like. Said salts of organic acid comprise citrate, fumarate, oxalate, malate, lactate, camphorsulfonate, p-toluenesulfonate, mesylate, and the like; said salts of inorganic acid comprise hydrohaloride, sulfate, phosphate, nitrate, and the like. For example, mesylate or trifluoromethanesulfonate may be formed with a lower alkyl sulfonic acid, such as methanesulfonic acid, trifluoromethanesulfonic acid, and so on; p-toluenesulfonate or benzene sulfonate may be formed with an aryl sulphonic acid, such as benzenesulfonic acid, p-toluenesulfonic acid, and so on; the corresponding salts may be formed with an organic carboxylic acid, such as acetic acid, fumaric acid, tartaric acid, oxalic acid, maleic acid, malic acid, succinic acid or citric acid and the like; glutamate or aspartate may be formed with an amino acid, such as glutamic acid or aspartic acid, and so on. The corresponding salts may be formed with an inorganic acid, such as haloid acid (such as hydrofluoric acid, hydrobromic acid, hydroiodic acid, hydrochloric acid), nitric acid, carbonic acid, sulfuric acid, or phosphoric acid, and the like.

The second object of the invention is to provide a pharmaceutical composition, comprising at least one active component and one or more pharmaceutically acceptable carriers or excipients, wherein said one active component may be any one or more selected from the group consisting of the substituted nitrogen-containing heterocyclic compounds with the structure of general formula (I) to (XII) in the invention and preferred compounds thereof, optical isomers of said compounds, pharmaceutically acceptable salts of the said compounds or the optical isomers thereof, solvates of the said compounds or the optical isomers thereof.

The carriers comprise conventional diluents, excipients, fillers, binders, humectants, disintegrants, absorption enhancers, surfactants, adsorption carries, lubricants, and the like in the pharmaceutical field, if needed, odorants, edulcorants and the like may also be added. The pharmaceutical composition in the present invention may be made into various forms such as tablets, powders, granules, capsules, oral liquid and drug for injection, and the like, and all the above dosage form can be prepared according to the conventional methods in the pharmaceutical field.

The invention also provides the use of compounds of general formula (I) to (XII) and optical isomers thereof, or pharmaceutically acceptable salts or solvates thereof for preparing antitumor drugs. Said tumor is breast cancer, sarcoma, lung cancer, prostate cancer, colon cancer, rectal cancer, kidney cancer, pancreatic cancer, leukemia, neuroblastoma, glioma, head cancer, neck cancer, thyroid cancer, liver cancer, ovarian cancer, vulvar cancer, cervical cancer, endometrial cancer, testicular cancer, bladder cancer, esophageal cancer, gastric cancer, nasopharyngeal carcinoma, buccal cancer, oral cancer, gastrointestinal stromal tumor, skin cancer and multiple myeloma.

Each compound of general formula (I) may be conveniently prepared by separately preparing three constituents of said compound, followed by synthesizing the compound of the general formula (I) with those constituents. For convenience, said three constituents are referred to herein as the head, the core, and the tail. When used individually, the head, core, and tail used throughout refer to each constituent, and also refer to the corresponding moiety when present in form of combination of head/core, tail/core, and/or head/core/tail hereins.

The head component of the compounds of general formula (I) in the present invention is a substituted nitrogen-containing heterocyclic borate or boronic acid compound represented by head (XIII); the core component is a compound with the structure of 5- or 6-membered aryl sulfonyl chloride or aryl formic acid or arylamine substituted with bromine or iodine or the like represented by the core of general formula (XIV), the tail component is a compound with the structure of substituted 5-8 membered saturated or unsaturated aliphatic nitrogen-containing heterocyclic formic acid or nitrogen-containing amino heterocyclic ring or the like represented by the tail of general formula (XV), as shown below:

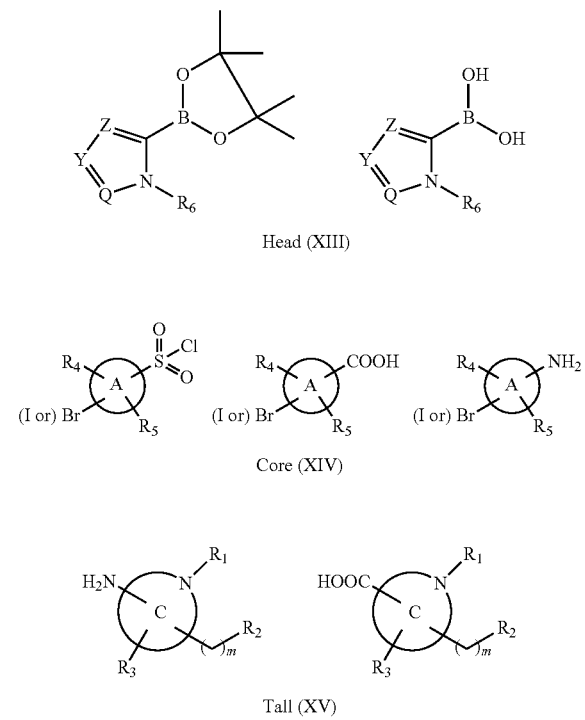

The head (XIII), core (XIV), and tail (XV) of the compounds form the general formula (I) by the synthetic route as shown below:

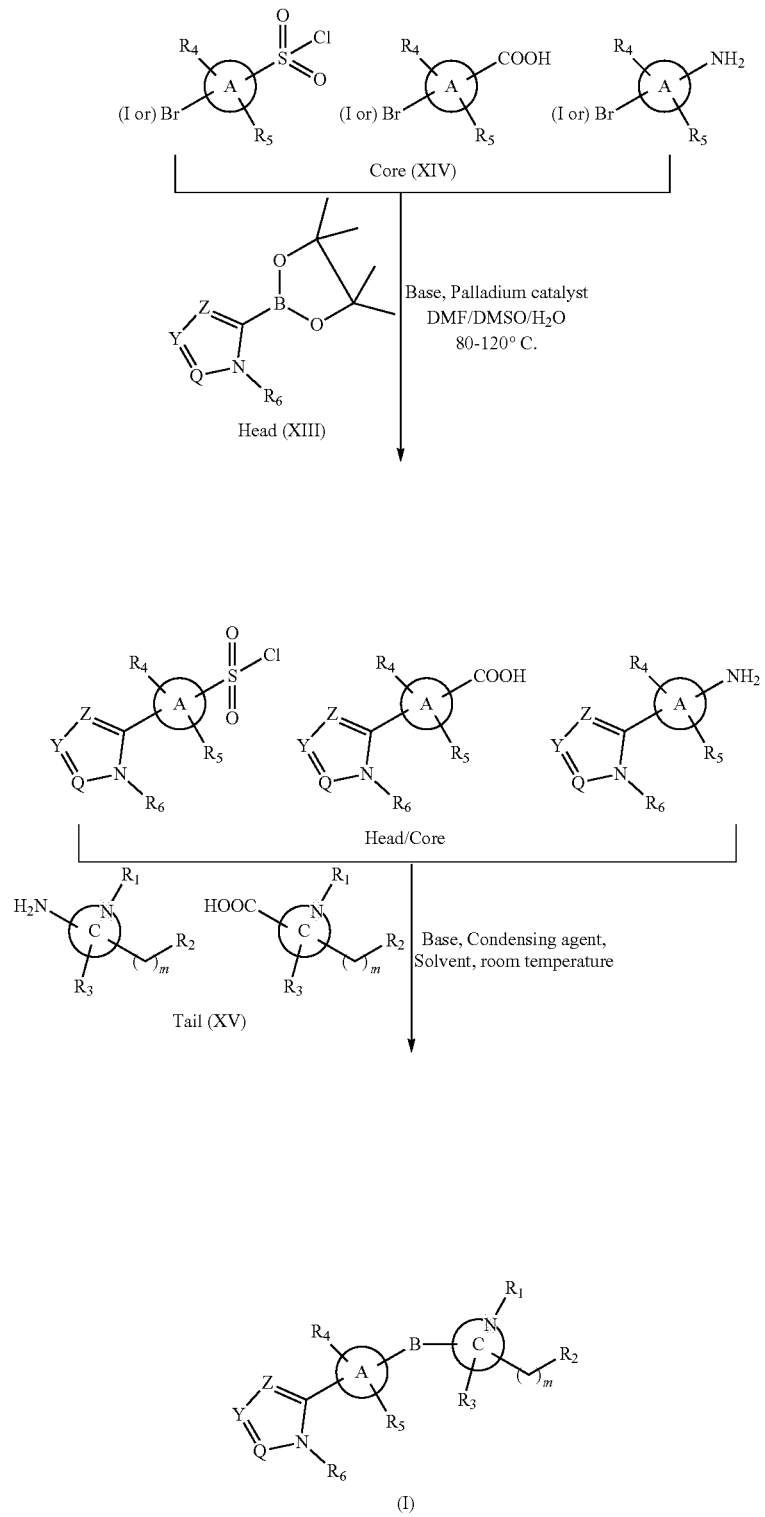

Specifically, the compounds of the general formula (VIII) in the present invention may be obtained by constituted with the synthetic route as shown below, by using N-methyl pyrazole borate or boronic acid compound represented by the head (XIII-1), 5- or 6-membered aryl formic acid compound substituted by bromine or iodine represented by the core (XIV-1), piperidine compound substituted by protecting groups represented by the tail (XV).

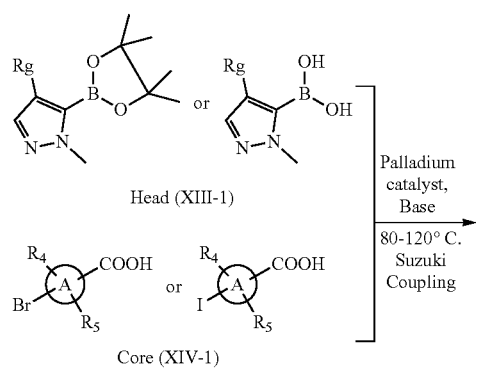

Head (XIII-1)

Core (XIV-1)

Palladium catalyst, Base
80-120° C.
Suzuki Coupling

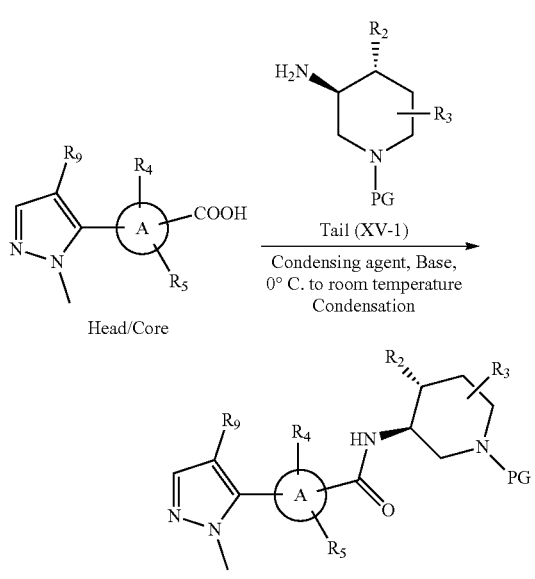

Head/Core

Tail (XV-1)
Condensing agent, Base,
0° C. to room temperature
Condensation

Head/Core/Tail

Deprotecting

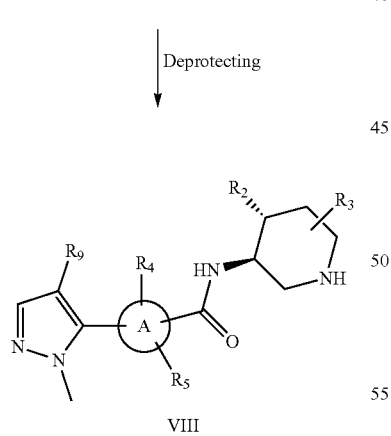

VIII

Wherein, PG is a common amino protective group, such as: Boc (t-butyloxycarboryl), Cbz (carboxybenzyl), Ac (acetyl) and the like.

More specifically, it is illustrated as represented by the compounds of the general formula (IX) and (X).

The head component of the general formula (IX) and (X) in the present invention is a pyrazol boric acid pinacol ester compound represented by the head (i):

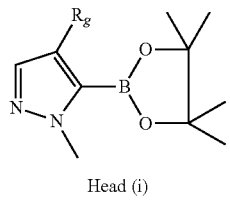

Head (i)

Wherein $R_g$ is as defined in the general formula (I), i.e., $R_g$ is selected from the group consisting of H, halogen, hydroxyl, carboxyl, hydroxymethyl, saturated or unsaturated $C_1$-$C_4$ alkyl, halogenated $C_1$-$C_4$ alkyl, $C_1$-$C_4$ alkoxy, halogenated $C_1$-$C_4$ alkoxy, unsubstituted or substituted aryl, unsubstituted or substituted heterocyclic aryl, saturated or partly saturated heterocyclic ring which is unsubstituted or substituted, unsubstituted or substituted cycloalkyl.

The core component of the general formula (IX) and (X) in the present invention is a 6- or 5-membered aryl formic acid compound substituted by bromine represented by the core of the general formula (ii-1) and (ii-2):

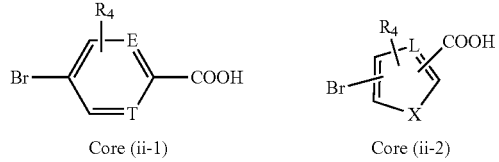

Core (ii-1)   Core (ii-2)

Wherein E, T are as defined in the general formula (IX), i.e., E, T are each independently selected from N and —C($R_i$)—, wherein $R_i$ is selected from the group consisting of H, halogen, $C_1$-$C_3$ alkyl or halogenated $C_1$-$C_3$ alkyl;

Wherein L, X are as defined in the general formula (X), i.e., X is selected from the group consisting of O, S, NH and $NCH_3$; L is selected from CH and N;

The substituent $R_4$ is as defined in the general formula (I), i.e., $R_4$ is selected from the group consisting of H, halogen, nitro, amino, cyano, $C_1$-$C_4$ alkyl, halogenated $C_1$-$C_4$ alkyl, $C_1$-$C_4$ alkoxy, halogenated $C_1$-$C_4$ alkoxy, unsubstituted or substituted furan, thiophene, phenyl, pyridinyl;

The tail component of the compounds in the present invention is a substituted piperidine compound protected by a Boc, which is represented by the tail of the general formula (iii):

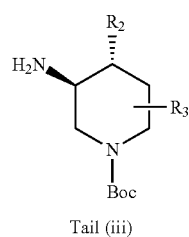

Tail (iii)

wherein the substituent $R_2$, $R_3$ are as defined in the general formula (I), i.e., $R_2$ is selected from the group consisting of unsubstituted or substituted aryl, unsubstituted or substituted heterocyclic aryl, unsubstituted or substituted cycloalkyl, saturated or unsaturated heterocyclic alkyl which is unsubstituted or substituted, aryl which is optionally fused, heterocyclic aryl; $R_3$ is selected from the group consisting of amino, cyano, $C_1$-$C_4$ alkyl, halogenated $C_1$-$C_4$ alkyl, $C_1$-$C_4$ alkoxy, $C_1$-$C_4$ carboxyl, halogenated $C_1$-$C_4$ alkoxy,

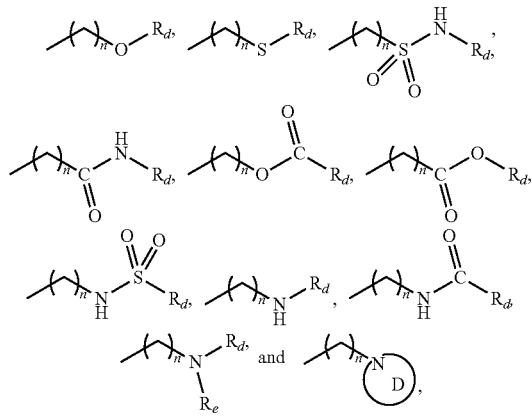

wherein n is an integer from 0 to 4, $R_d$ is selected from the group consisting of H, $C_1$-$C_4$ alkyl, halogenated $C_1$-$C_4$ alkyl, $C_1$-$C_4$ alkoxy, halogenated $C_1$-$C_4$ alkoxy, $R_e$ is selected from the group consisting of $C_1$-$C_4$ alkyl, halogenated $C_1$-$C_4$ alkyl, $C_1$-$C_4$ alkoxy, halogenated $C_1$-$C_4$ alkoxy, ring D is selected from 5-8 membered saturated or unsaturated aliphatic nitrogen-containing heterocyclic ring which is unsubstituted or substituted; said substituent is selected from the group consisting of halogen, nitro, amino, cyano, hydroxyl, $C_1$-$C_3$ alkyl, halogenated $C_1$-$C_3$ alkyl, $C_1$-$C_3$ alkoxy, halogenated $C_1$-$C_3$ alkoxy.

Said substituent is selected from the group consisting of halogen, nitro, amino, cyano, hydroxyl, $C_1$-$C_4$ alkyl, halogenated $C_1$-$C_4$ alkyl, $C_1$-$C_4$ alkoxy, $C_1$-$C_4$ alkylamino, halogenated $C_1$-$C_4$ alkoxy, halogenated $C_1$-$C_4$ alkylamino.

The head (i), core (ii) and tail (iii) of the general formula of the compounds may be combined by the synthetic route as shown below:

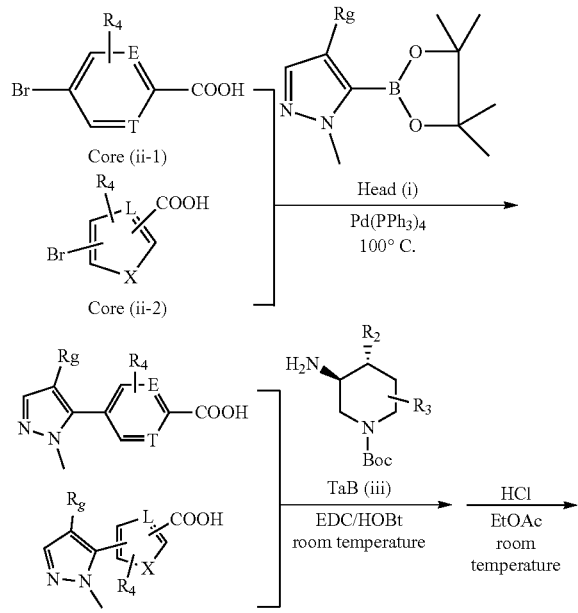

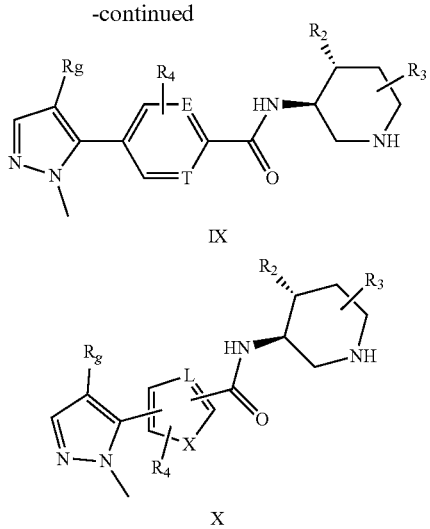

As shown in the figure, head (i) and a core (ii) of the general formula conduct Suzuki coupling reaction at heat under the condition of catalyzing by a zero valent palladium catalyst, and the obtained product is reacted with a tail (iii) under the action of condensation agent (such as EDCI), followed by that the Boc protective group of obtained product is deprotected in an acidic condition, thus obtained the compounds of the general formula (IX) and (X).

Other compounds of general formula may be prepared and obtained by referring to the preparation method of the compounds of the general formula (IX) and (X).

The present invention also provides the use of said compounds of the present invention or pharmaceutically acceptable salts thereof in the preparation of Akt inhibitors, in particular, in the preparation of medicine for treating cell proliferative diseases. Said cell proliferative diseases comprise cancer. In other words, the present invention provides the use of the substituted nitrogen-containing heterocyclic compounds or pharmaceutically acceptable salts thereof which is used alone or in combination with other drugs in the treatment of proliferative diseases (such as cancer). The antitumor drugs which may be used in combination with the compounds provided in the present invention or pharmaceutically acceptable salts thereof comprise, but are not limited to, at least one of the following group consisting of: mitotic inhibitors (such as vinblastine, vindesine, and vinorelbine); tubulin depolymerization inhibitors (such as Taxol); alkylating reagent (such as cisplatin, carboplatin and cyclophosphamide); antimetabolite (such as 5-fluorouracil, tegafur, methotrexate, cytarabine and hydroxycarbamide); insertable antibiotics (such as doxorubicin, mitomycin and bleomycin); enzymes (such as asparaginase); topoisomerase inhibitors (such as etoposide and camptothecin); biological response modifier (such as interferon); proteasome inhibitors (such asbortezomib).

It is identified by inventors of the present invention through several experiments that: the compounds of the present invention have significant inhibitory effects on Akt1, showing potent antiproliferative effects to tumor cell strains such as human ovarian cancer cell strains (OVCAR-8), colon cancer cell strains (HCT116) and the like. Therefore, the compounds of the present invention may be applied as AKT inhibitors in the drugs for treating solid tumors or leukemia in human and animals which is associated with cell proliferation.

DETAILED DESCRIPTION OF THE INVENTION

Hereinafter, the following examples are presented to illustrate the feasibility of the present invention, and it should be understood for one skilled in the art that, modifications or alternatives of the corresponding technical features according to the teaching of the prior art still be included within the scope sought to protect in the present invention.

Example 1. Preparation of Intermediate 1

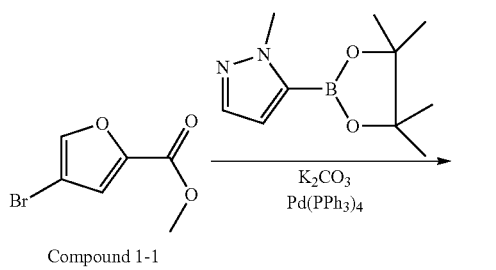

Compound 1-1

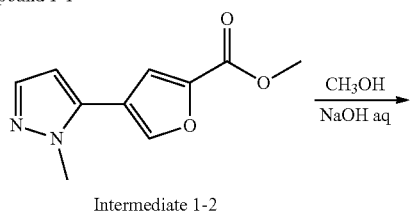

Intermediate 1-2

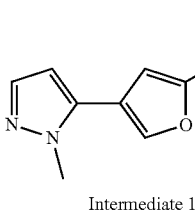

Intermediate 1

Step 1. Synthesis of 4-(1-methyl-1H-pyrazol-5-yl) furan-2-methyl formate (Intermediate 1-2)

Sequentially adding 4-bromo furan-2-methyl formate (Compound 1-1) (4.7 g, 22.9 mmol), tetra(triphenylphosphine)palladium (0.582 g, 1.145 mmol), 1-methyl-1H-pyrazol-5-boric acid pinacol ester (5.25 g, 25.2 mmol) and potassium carbonate (7.9 g, 57.25 mmol) into a 100 mL double-neck flask under the protection of $N_2$, adding 1,4-dioxane (30 mL) and water (6 mL) thereto, and reacting at 90V for 12 h. After the reaction is finished, the product is cooled to room temperature, extracting the reaction liquid with ethyl acetate for 3 times, washing the merged organic phase with saturated sodium chloride once, drying it with anhydrous sodium sulfate. Recycling the solvent under reduced pressure, and carrying out column chromatography on silica gel (eluent: petroleum ether:ethyl acetate=4:1, increasing the polarity to 1:1), 3.75 g of light yellow solid (Intermediate 1-2) is obtained and the yield is 75%.

Step 2. Synthesis of 4-(1-methyl-1H-pyrazol-5-yl) furan-2-formic acid (Intermediate 1)

Dissolving Intermediate 1-2 (1.87 g, 6.8 mmol) in methanol (10 ml), and slowly adding 11.3 ml of 6N NaOH aqueous solution at room temperature, reacting at room temperature for 12 h, monitor the reaction with TLC thin-layer chromatography for whether it is completed, and recycling the solvent under reduced pressure after the reaction. Adding 10 ml of water to the remained reaction mixture, neutralizing NaOH in the reaction liquid with 1N HCl to pH of about 3, extracting the reaction liquid with ethyl acetate for 3 times, washing the merged organic phase with saturated sodium chloride once, and drying it with anhydrous sodium sulfate. Recycling the solvent under reduced pressure, directly obtaining 1.58 g of light yellow solid (Intermediate 1) and the yield is 89%.

Example 2. Preparation of Intermediate 2 and Intermediate 3

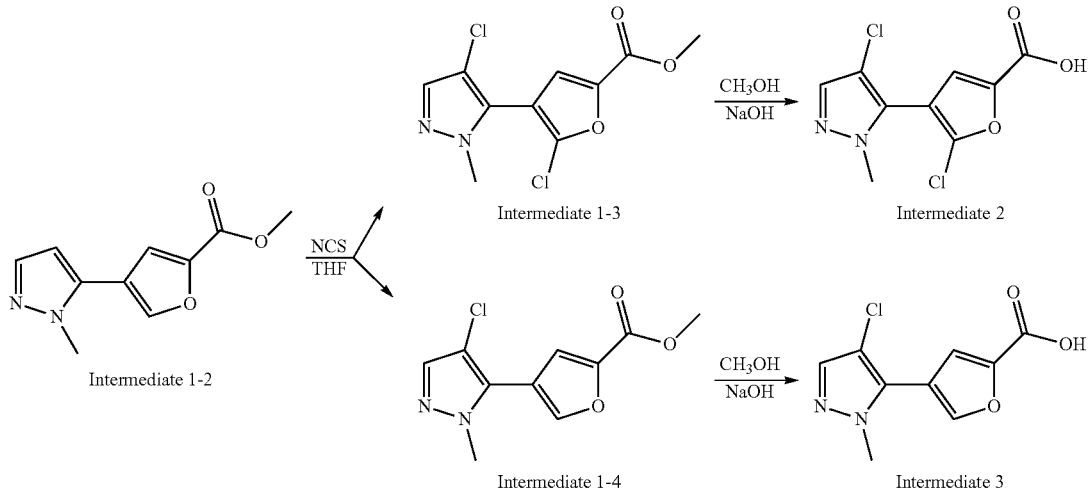

Step 1. Synthesis of 5-chloro-4-(4-chloro-1-methyl-1H-pyrazol-5-yl)furan-2-methyl formate (Intermediate 1-3) and 4-(4-chloro-1-methyl-1H-pyrazol-5-yl)furan-2-methyl formate (Intermediate 1-4)

Dissolving 4-(1-methyl-1H-pyrazol-5-yl)furan-2-methyl formate (Intermediate 1-2) (6.18 g, 30 mmol), N-chlorosuccinimide (8.01 g, 60 mmol) in the mixed solution of tetrahydrofuran (30 ml) and N,N-dimethylformamide (5 ml), raising temperature to 100° C., reacting for 5 h under seal. Monitoring the reaction with TLC thin-layer chromatography for whether it is completed, cooling the product to room temperature after the reaction is finished, recycling the solvent under reduced pressure, washing the remaining mixture with saturated NaHCO₃ aqueous solution, and extracting the reaction liquid with ethyl acetate for 3 times, washing the merged organic phase with saturated sodium chloride once, and drying it with anhydrous sodium sulfate. Recycling the solvent under reduced pressure, carrying out column chromatography on silica gel (eluent: petroleum ether:ethyl acetate=4:1), 6.18 g of light yellow solid (Intermediate 1-3) is obtained and the yield is 75%.

Dissolving 4-(1-methyl-1H-pyrazol-5-yl)furan-2-methyl formate (Intermediate 1-2) (6.18 g, 30 mmol), N-chlorosuccinimide (4.0 g, 30 mmol) in tetrahydrofuran (30 ml), raising temperature to 70° C., reacting for about 2 h. Monitoring the reaction with TLC thin-layer chromatography for whether it is completed, cooling the product to room temperature after the reaction is finished, recycling the solvent under reduced pressure, washing the remaining mixture with saturated NaHCO₃ solution, and extracting the reaction liquid with ethyl acetate for 3 times, washing the merged organic phase with saturated sodium chloride once, and drying it with anhydrous sodium sulfate. Recycling the solvent under reduced pressure, carrying out column chromatography on silica gel (eluent: petroleum ether:ethyl acetate=4:1), 3.60 g of light yellow solid (Intermediate 1-4) is obtained and the yield is 50%.

Step 2. Synthesis of 5-chloro-4-(4-chloro-1-methyl-1H-pyrazol-5-yl)furan-2-formic acid (Intermediate 2) and 4-(4-chloro-1-methyl-1H-pyrazol-5-yl)furan-2-formic acid (Intermediate 3)

The synthesis steps refer to step 2 of Example 1. Intermediate 2 (2.3 g, yield of 88%) and Intermediate 3 (2.1 g, yield of 87%) are prepared from 5-chloro-4-(4-chloro-1-methyl-1H-pyrazol-5-yl)furan-2-methyl formate (Intermediate 1-3) (2.75 g, 10.0 mmol) and 4-(4-chloro-1-methyl-1H-pyrazol-5-yl)furan-2-methyl formate (Intermediate 1-4) (2.40 g, 10.0 mmol) by the similar synthesis methods as that of Intermediate 1, respectively.

Example 3. Preparation of Intermediate 4

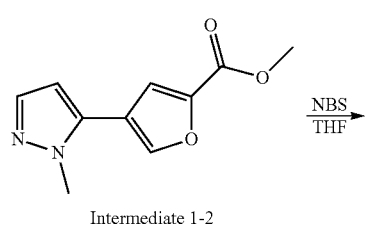

Intermediate 1-2

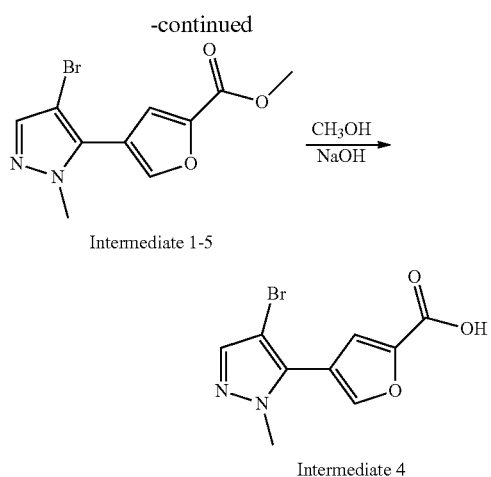

Step 1. Synthesis of 4-(4-bromo-1-methyl-1H-pyrazol-5-yl)furan-2-methyl formate (Intermediate 1-5)

Dissolving 4-(1-methyl-1H-pyrazol-5-yl)furan-2-methyl formate (Intermediate 1-2) (6.18 g, 30 mmol), N-chlorosuccinimide (5.34 g, 30 mmol) in tetrahydrofuran (40 ml), raising temperature to 65° C., reacting for about 2 h. Monitoring the reaction with TLC thin-layer chromatography for whether it is completed, cooling the product to room temperature after the reaction is finished, recycling the solvent under reduced pressure, washing the remaining mixture with saturated NaHCO₃ solution, extracting the reaction liquid with ethyl acetate for 3 times, washing the merged organic phase with saturated sodium chloride once, and drying it with anhydrous sodium sulfate. Recycling the solvent under reduced pressure, carrying out column chromatography on silica gel (eluent: petroleum ether:ethyl acetate=4:1), 10.60 g of light yellow solid (Intermediate 1-5) is obtained and the yield is 62%.

Step 2. Synthesis of 4-(4-bromo-1-methyl-1H-pyrazol-5-yl)furan-2-formic acid (Intermediate 4)

The synthesis steps refer to Step 2 of Example 1. Intermediate 4 (2.4 g, yield of 89%) is prepared from 4-(4-bromo-1-methyl-1H-pyrazol-5-yl)furan-2-methyl formate (Intermediate 1-5) (2.85 g, 10.0 mmol) by the similar synthesis method as that of Intermediate 1.

Example 4. Preparation of Intermediate 5

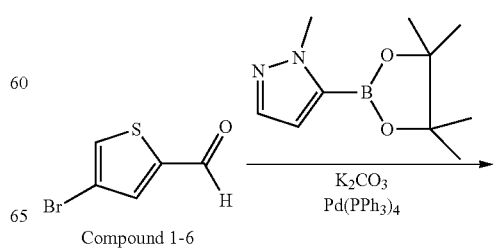

Compound 1-6

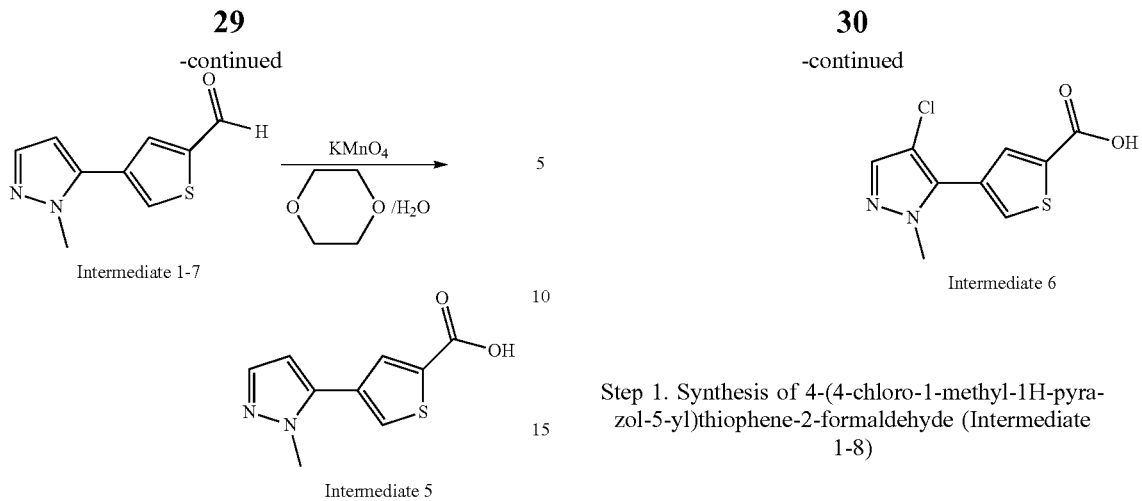

Step 1. Synthesis of 4-(1-methyl-1H-pyrazol-5-yl)thiophene-2-formaldehyde (Intermediate 1-7)

The synthesis steps refer to Step 1 of Example 1. Intermediate 1-7 (1.3 g, yield of 67%) is prepared from 4-bromothiophene formaldehyde (Compound 1-6) (1.91 g, 10.0 mmol) by the similar synthesis method as that of Intermediate 1-2.

Step 2. Synthesis of 4-(1-methyl-1H-pyrazol-5-yl)thiophene-2-formic acid (Intermediate 5)

Dissolving 4-(1-methyl-1H-pyrazol-5-yl)thiophene-2-formaldehyde (Intermediate 1-7) (0.24 g, 1.25 mmol) in methanol (5 ml), then slowly adding the aqueous solution (5 ml) dissolved with $KMnO_4$ (0.196 g, 1.25 mmol) and $Na_2HPO_4$ (0.178 g, 1.25 mmol), stirring for 2 h at room temperature. Monitoring the reaction with TLC thin-layer chromatography for whether it is completed, after the reaction, adding 1N HCl solution dissolved with $Na_2SO_3$ (0.2 g) and saturated NaCl into reaction liquid. Vacuum filtrating the above mixed solution, extracting the reaction liquid with ethyl acetate for 3 times, washing the merged organic phase with saturated sodium chloride once, and drying it with anhydrous sodium sulfate. Recycling the solvent under reduced pressure, 0.20 g of white solid (Intermediate 5) is obtained and the yield is 77%.

Example 5. Preparation of Intermediate 6

Step 1. Synthesis of 4-(4-chloro-1-methyl-1H-pyrazol-5-yl)thiophene-2-formaldehyde (Intermediate 1-8)

Dissolving 4-(1-methyl-1H-pyrazol-5-yl)thiophene-2-formaldehyde (Intermediate 1-7) (191 mg, 1 mmol), N-chlorosuccinimide (266 mg, 2 mmol) in tetrahydrofuran (10 ml), raising temperature to 80° C. and reacting for about 2 h. Monitoring the reaction with TLC thin-layer chromatography for whether it is completed, cooling the product to room temperature after the reaction, recycling tetrahydrofuran under reduced pressure, then extracting the reaction liquid with ethyl acetate for 3 times, washing the merged organic phase with saturated sodium chloride once, and drying it with anhydrous sodium sulfate. Recycling the solvent under reduced pressure, carrying out column chromatography on silica gel (eluent: petroleum ether:ethyl acetate=4:1), 130 mg of light yellow solid (Intermediate 1-8) is obtained and the yield is 58%.

Step 2. Synthesis of 4-(4-chloro-1-methyl-1H-pyrazol-5-yl)thiophene-2-formic acid (Intermediate 6)

The synthesis steps refer to Step 1 of Example 3. Intermediate 6 (1.9 g, yield of 78%) is prepared from 4-(4-chloro-1-methyl-1H-pyrazol-5-yl)thiophene-2-formaldehyde (Intermediate 1-8) (2.26 g, 10.0 mmol) with the similar synthesis method as that of Intermediate 5.

Example 6. Preparation of Intermediate 7

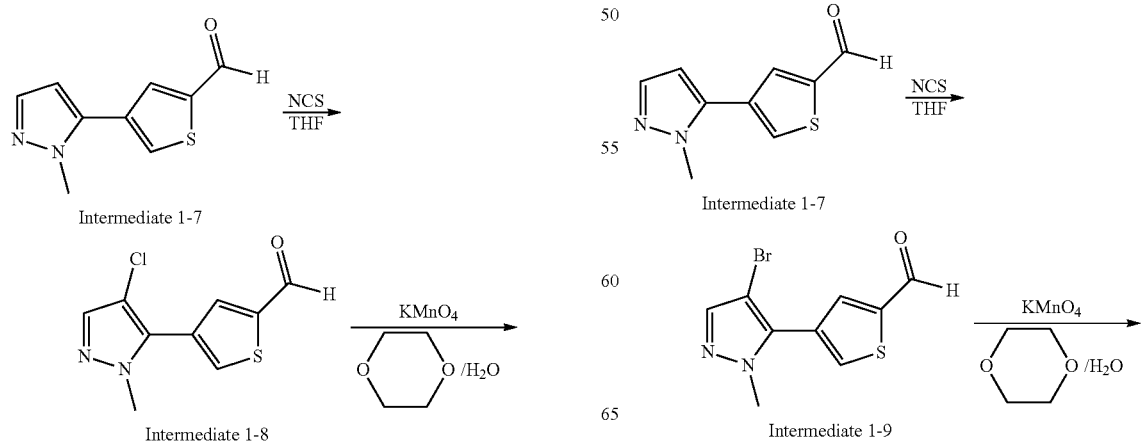

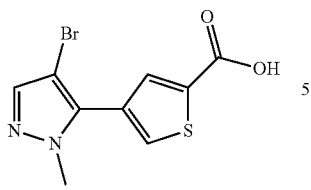

Intermediate 7

Step 1. Synthesis of 4-(4-bromo-1-methyl-1H-pyrazol-5-yl)thiophene-2-formaldehyde (Intermediate 1-9)

The synthesis steps refer to Step 1 of Example 3. Intermediate 1-9 (2.5 g, yield of 92%) is prepared from 4-(1-methyl-1H-pyrazol-5-yl)thiophene-2-formaldehyde (Intermediate 1-7) (1.92 g, 10.0 mmol) with the similar synthesis method as that of Compound 1-5.

Step 2. Synthesis of 4-(4-bromo-1-methyl-1H-pyrazol-5-yl)thiophene-2-formic acid (Intermediate 7)

The synthesis steps refer to Step 2 of Example 4. Intermediate 7 (2.6 g, yield of 91%) is prepared from 4-(4-bromo-1-methyl-1H-pyrazol-5-yl)thiophene-2-formaldehyde (Intermediate 1-9) (2.71 g, 10.0 mmol) with the similar synthesis method as that of Intermediate 5.

Example 7. Preparation of Intermediate 8

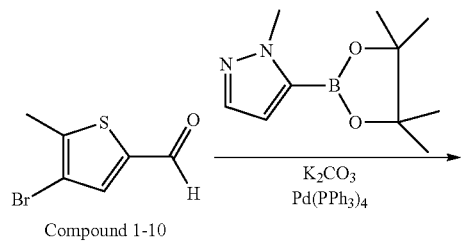
Compound 1-10

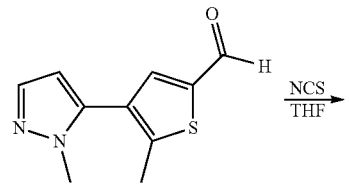
Intermediate 1-11

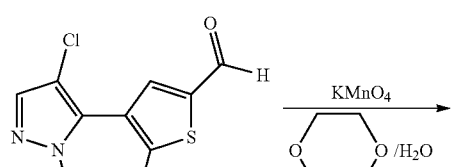
Intermediate 1-12

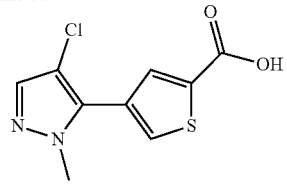

Intermediate 8

Step 1. Synthesis of 5-methyl-4-(1-methyl-1H-pyrazol-5-yl)thiophene-2-formaldehyde (Intermediate 1-11)

The synthesis steps refer to Step 1 of Example 1. Intermediate 1-11 (1.8 g, yield of 88%) is prepared from 5-methyl-4-bromothiophene-2-formaldehyde (Compound 1-10) (2.05 g, 10.0 mmol) with the similar synthesis method as that of Intermediate 1-2.

Step 2. Synthesis of 5-methyl-4-(4-chloro-1-methyl-1H-pyrazol-5-yl)thiophene-2-formaldehyde (Intermediate 1-12)

The synthesis steps refer to Step 1 of Example 5. Intermediate 1-12 (2.0 g, yield of 83%) is prepared from 5-methyl-4-(1-methyl-1H-pyrazol-5-yl)thiophene-2-formaldehyde (Intermediate 1-11) (2.06 g, 10.0 mmol) with the similar synthesis method as that of Intermediate 1-8.

Step 3. Synthesis of 5-methyl-4-(4-chloro-1-methyl-1H-pyrazol-5-yl)thiophene-2-formic acid (Intermediate 8)

The synthesis steps refer to Step 2 of Example 4. Intermediate 8 (2.13 g, yield of 83%) is prepared from 5-methyl-4-(4-chloro-1-methyl-1H-pyrazol-5-yl)thiophene-2-formaldehyde (Intermediate 1-12) (2.41 g, 10.0 mmol) with the similar synthesis method as that of Intermediate 5.

Example 8. Preparation of Intermediate 9

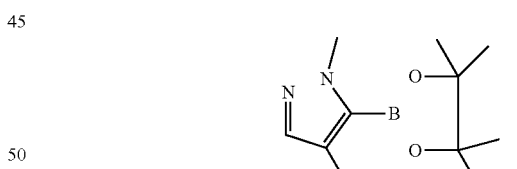
Compound 1-13

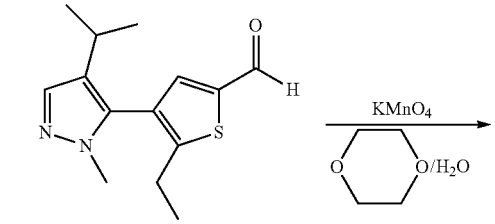
Intermediate 1-14

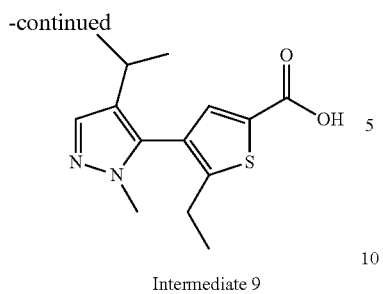

Intermediate 9

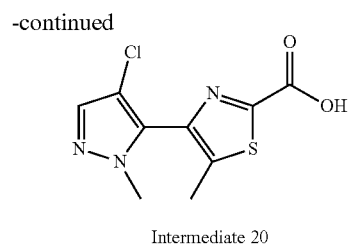

Intermediate 20

Step 1. Synthesis of 5-ethyl-4-(4-isopropyl-1-methyl-1H-pyrazol-5-yl)thiophene-2-formaldehyde (Intermediate 1-14)

The synthesis steps refer to Step 1 of Example 1. Intermediate 1-14 (2.12 g, yield of 81%) is prepared from 5-ethyl-4-bromothiophene-2-formaldehyde (Compound 1-13) (2.19 g, 10.0 mmol) with the similar synthesis method as that of Intermediate 1-2.

Step 2. Synthesis of 5-ethyl-4-(4-isopropyl-1-methyl-1H-pyrazol-5-yl)thiophene-2-formic acid (Intermediate 9)

The synthesis steps refer to Step 2 in Example 4. Intermediate 9 (2.19 g, yield of 79%) is prepared from 5-ethyl-4-(4-isopropyl-1-methyl-1H-pyrazol-5-yl)thiophene-2-formaldehyde (Intermediate 1-14) (2.6 g, 10.0 mmol) with the similar synthesis method as that of Intermediate 5.

Step 1. Synthesis of 5-methyl-4-(1-methyl-1H-pyrazol-5-yl)thiazole-2-formaldehyde (Intermediate 1-16)

The synthesis steps refer to Step 1 in Example 1. Intermediate 1-16 (1.72 g, yield of 83%) is prepared from 5-methyl-4-bromothiazole-2-formaldehyde (Compound 1-15) (2.06 g, 10.0 mmol) with the similar synthesis method as that of Intermediate 1-2.

Step 2. Synthesis of 5-methyl-4-(4-chloro-1-methyl-1H-pyrazol-5-yl)thiazole-2-formaldehyde (Intermediate 1-17)

The synthesis steps refer to Step 1 of Example 5. Intermediate 1-17 (2.23 g, yield of 92%) is prepared from 5-methyl-4-(1-methyl-1H-pyrazol-5-yl)thiazole-2-formaldehyde (Intermediate 1-16) (2.07 g, 10.0 mmol) with the similar synthesis method as that of Intermediate 1-8.

Step 3. Synthesis of 5-methyl-4-(4-chloro-1-methyl-1H-pyrazol-5-yl)thiazole-2-formic acid (Intermediate 10)

The synthesis steps refer to Step 2 of Example 4. Intermediate 10 (2.2 g, yield of 85%) is prepared from 5-methyl-4-(4-chloro-1-methyl-1H-pyrazol-5-yl)thiazole-2-formaldehyde (Intermediate 1-17) (2.4 g, 10.0 mmol) with the similar synthesis method as that of Intermediate 5.

Example 9. Preparation of Intermediate 10

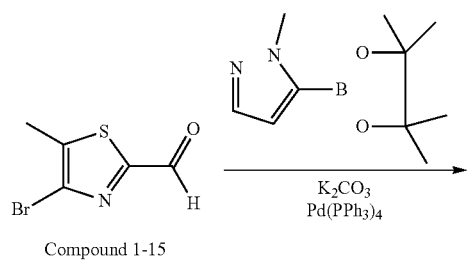

Compound 1-15

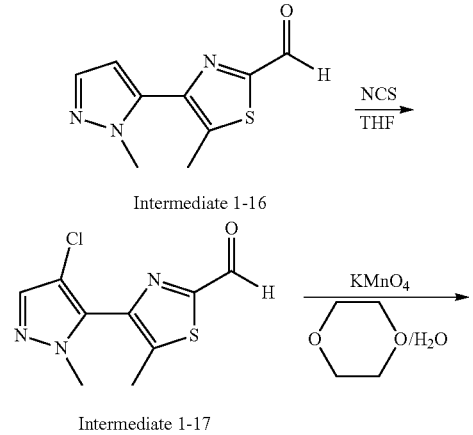

Intermediate 1-16

Intermediate 1-17

Example 10. Preparation of Intermediate 11

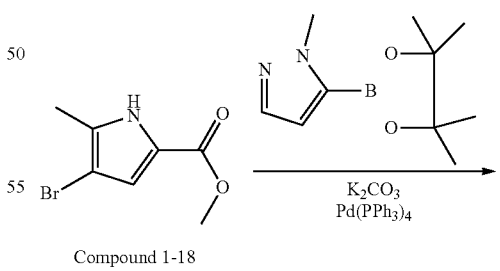

Compound 1-18

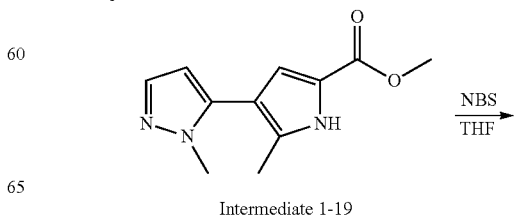

Intermediate 1-19

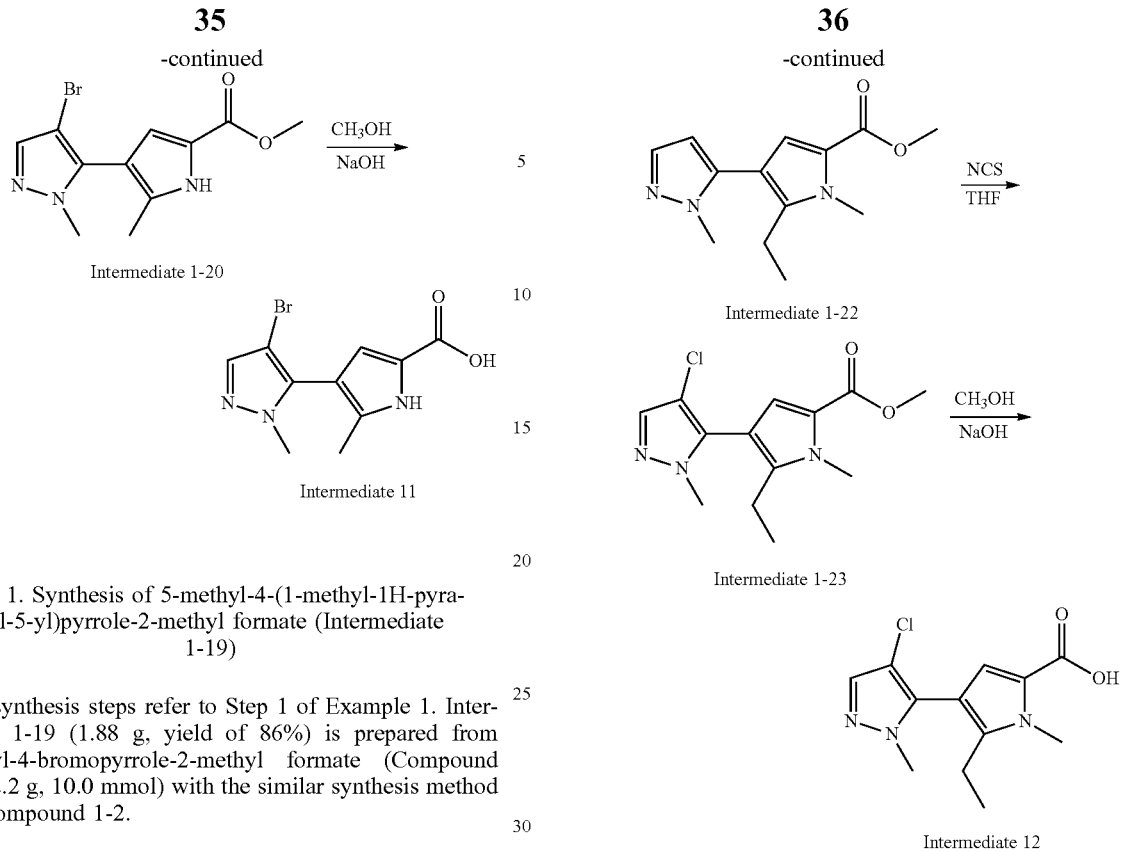

Intermediate 1-20

Intermediate 11

Step 1. Synthesis of 5-methyl-4-(1-methyl-1H-pyrazol-5-yl)pyrrole-2-methyl formate (Intermediate 1-19)

The synthesis steps refer to Step 1 of Example 1. Intermediate 1-19 (1.88 g, yield of 86%) is prepared from 5-methyl-4-bromopyrrole-2-methyl formate (Compound 1-18) (2.2 g, 10.0 mmol) with the similar synthesis method as of Compound 1-2.

Step 2. Synthesis of 5-methyl-4-(4-bromo-1-methyl-1H-pyrazol-5-yl)pyrrole-2-methyl formate (Intermediate 1-20)

The synthesis steps refer to Step 1 of Example 3. Intermediate 1-20 (2.37 g, yield of 79%) is prepared from 5-methyl-4-(1-methyl-1H-pyrazol-5-yl)pyrrole-2-methyl formate (Intermediate 1-19) (2.19 g, 10.0 mmol) with the similar synthesis method as that of Intermediate 1-5.

Step 3. Synthesis of 5-methyl-4-(4-bromo-1-methyl-1H-pyrazol-5-yl)pyrrole-2-formic acid (Intermediate 11)

The synthesis steps refer to Step 2 of Example 1. Intermediate 11 (2.57 g, yield of 86%) is prepared from 5-methyl-4-(4-bromo-1-methyl-1H-pyrazol-5-yl)pyrrole-2-methyl formate (Intermediate 1-20) (2.98 g, 10.0 mmol) with the similar synthesis method as that of Intermediate 1.

Example 11. Preparation of Intermediate 12

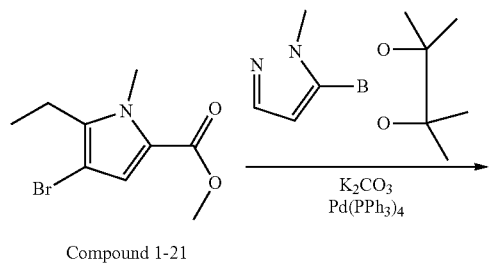

Compound 1-21

Intermediate 1-22

Intermediate 1-23

Intermediate 12

Step 1. Synthesis of 1-methyl-5-ethyl-4-(1-methyl-1H-pyrazol-5-yl)pyrrole-2-methyl formate (Intermediate 1-22)

The synthesis steps refer to Step 1 of Example 1. Intermediate 1-22 (1.9 g, yield of 77%) is prepared from 1-methyl-5-ethyl-4-bromopyrrole-2-methyl formate (Compound 1-21) (2.5 g, 10.1 mmol) with the similar synthesis methods as that of Intermediate 1-2.

Step 2. Synthesis of 1-methyl-5-ethyl-4-(4-chloro-1-methyl-1H-pyrazol-5-yl)pyrrole-2-methyl formate (Intermediate 1-23)

The synthesis steps refer to Step 1 of Example 5. Intermediate 1-23 (2.45 g, yield of 87%) is prepared from 1-methyl-5-ethyl-4-(1-methyl-1H-pyrazol-5-yl)pyrrole-2-methyl formate (Intermediate 1-22) (2.5 g, 10.2 mmol) with the similar synthesis method as that of Intermediate 1-8.

Step 3. Synthesis of 1-methyl-5-ethyl-4-(4-chloro-1-methyl-1H-pyrazol-5-yl)pyrrole-2-formic acid (Intermediate 12)

The synthesis steps refer to Step 2 of Example 1. Intermediate 12 (2.44 g, yield of 93%) is prepared from 1-methyl-5-ethyl-4-(4-chloro-1-methyl-1H-pyrazol-5-yl) pyrrole-2-methyl formate (Intermediate 1-23) (2.8 g, 10.0 mmol) with the similar synthesis method as that of Intermediate 1.

Example 12. Preparation of Intermediate 13

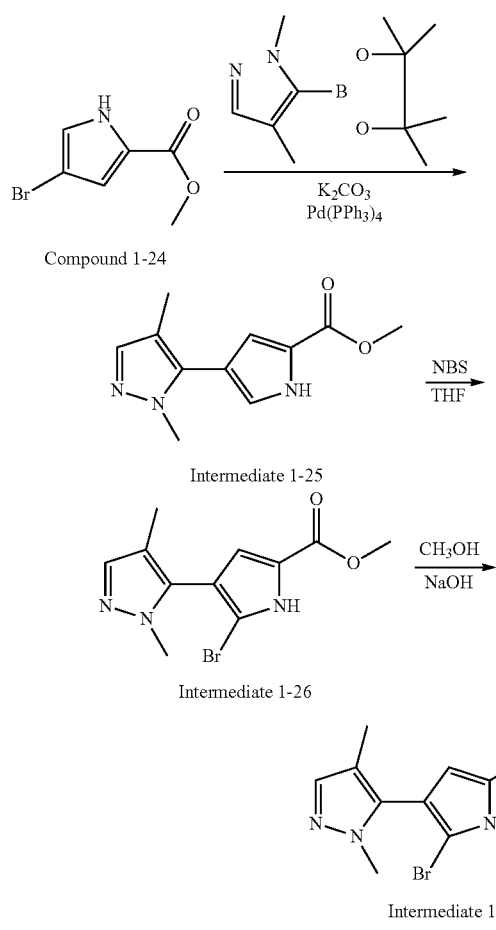

Compound 1-24

Intermediate 1-25

Intermediate 1-26

Intermediate 13

Step 1. Synthesis of 4-(1,4-dimethyl-1H-pyrazol-5-yl)pyrrole-2-methyl formate (Intermediate 1-25)

The synthesis steps refer to Step 1 of Example 1. Intermediate 1-25 (1.92 g, yield of 87%) is prepared from 4-bromopyrrole-2-methyl formate (Compound 1-24) (2.0 g, 9.9 mmol) with the similar synthesis method as that of Intermediate 1-2.

Step 2. Synthesis of 5-bromo-4-(1,4-dimethyl-1H-pyrazol-5-yl)pyrrole-2-methyl formate (Intermediate 1-26)

The synthesis steps refer to Step 1 in Example 3. Intermediate 1-26 (2.57 g, yield of 86%) is prepared from 4-(1,4-dimethyl-1H-pyrazol-5-yl)pyrrole-2-methyl formate (Intermediate 1-25) (2.19 g, 10.0 mmol) with the similar synthesis method as that of Intermediate 1-5.

Step 3. Synthesis of 5-bromo-4-(1,4-dimethyl-1H-pyrazol-5-yl)pyrrole-2-formic acid (Intermediate 13)

The synthesis steps refer to Step 2 of Example 1. Intermediate 13 (2.6 g, yield of 91%) is prepared from 5-bromo-4-(1,4-dimethyl-1H-pyrazol-5-yl)pyrrole-2-methyl formate (Intermediate 1-26) (2.99 g, 10.0 mmol) with the similar synthesis method as that of Intermediate 1.

Example 13. Preparation of Intermediate 14

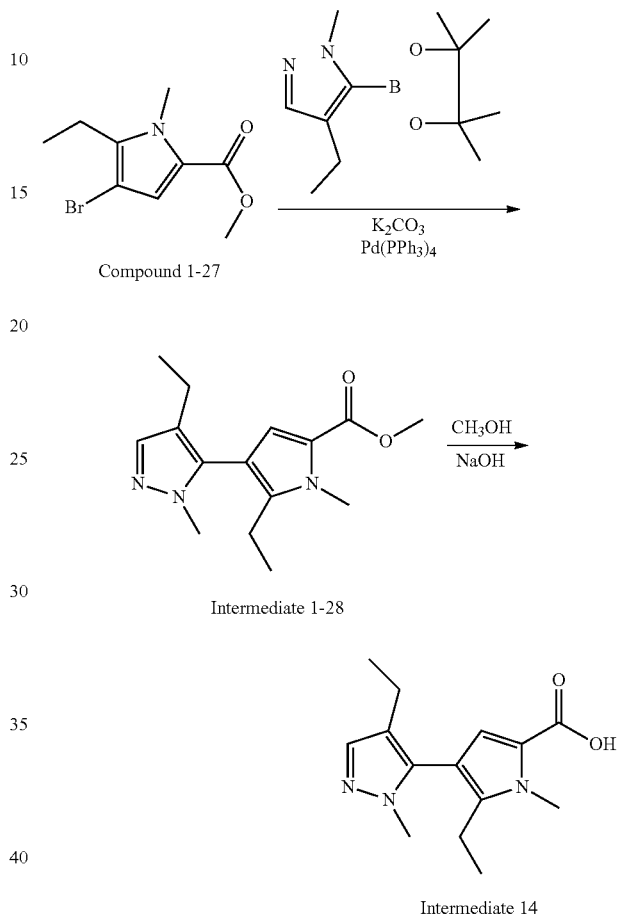

Compound 1-27

Intermediate 1-28

Intermediate 14

Step 1. Synthesis of 1-methyl-5-ethyl-4-(4-ethyl-1-methyl-1H-pyrazol-5-yl)pyrrole-2-methyl formate (Intermediate 1-28)

The synthesis steps refer to Step of in Example 1. Intermediate 1-28 (2.54 g, yield of 92%) is prepared from 1-methyl-5-ethyl-4-bromopyrrole-2-methyl formate (Compound 1-27) (2.3 g, 9.9 mmol) with the similar synthesis method as that of Intermediate 1-2.

Step 2. Synthesis of 1-methyl-5-ethyl-4-(4-ethyl-1-methyl-1H-pyrazol-5-yl)pyrrole-2-formic acid (Intermediate 14)

The synthesis steps refer to Step 2 of Example 1. Intermediate 14 (2.25 g, yield of 86%) is prepared from 1-methyl-5-ethyl-4-(4-ethyl-1-methyl-1H-pyrazol-5-yl)pyrrole-2-methyl formate (Intermediate 1-28) (2.8 g, 10.2 mmol) with the similar synthesis method as that of Intermediate 1.

Example 14. Preparation of Intermediate 15

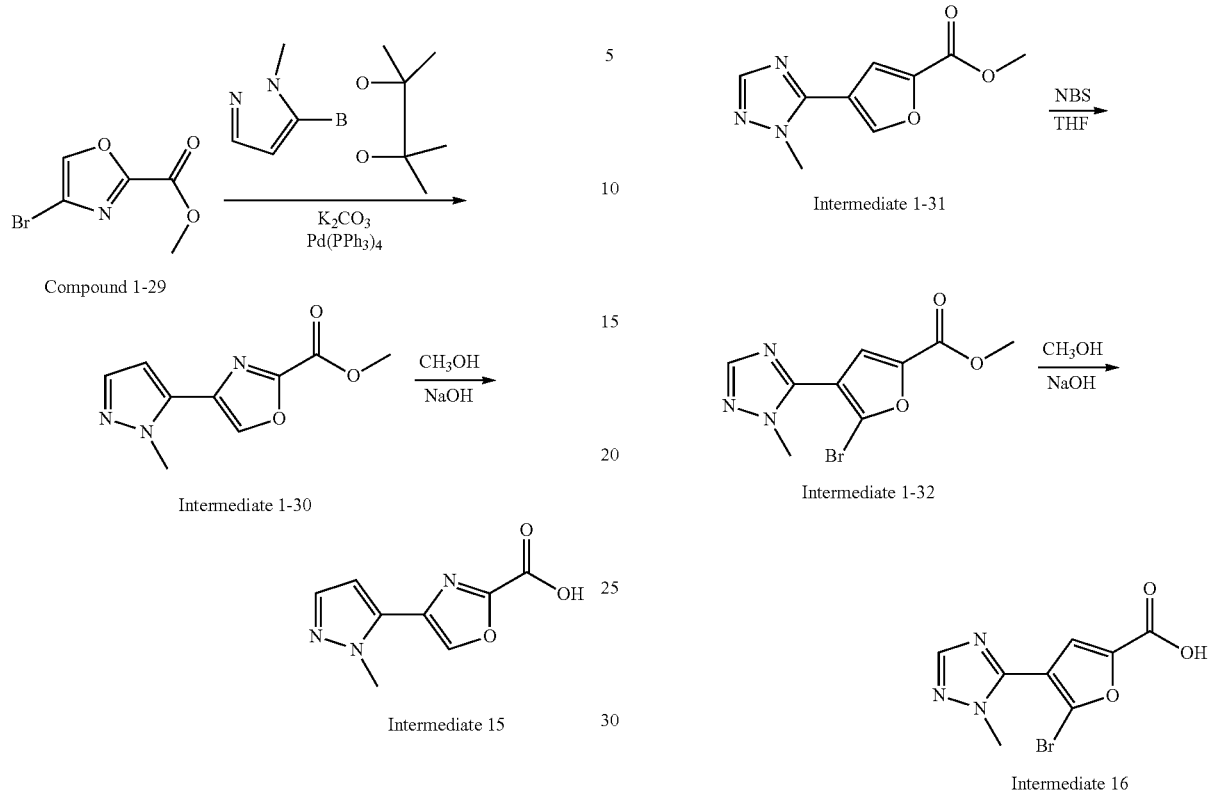

Step 1. Synthesis of 4-(1-methyl-1H-pyrazol-5-yl)oxazole-2-methyl formate (Intermediate 1-30)

The synthesis steps refer to Step 1 of Example 1. Intermediate 1-30 (1.76 g, yield of 85%) is prepared from 4-bromo-oxazole-2-methyl formate (Compound 1-29) (2.03 g, 9.9 mmol) with the similar synthesis method as that of Intermediate 1-2.

Step 2. Synthesis of 4-(1-methyl-1H-pyrazol-5-yl)oxazole-2-formic acid (Intermediate 15)

The synthesis steps refer to Step 2 in Example 1. Intermediate 15 (1.85 g, yield of 95%) is prepared from 4-(1-methyl-1H-pyrazol-5-yl)oxazole-2-methyl formate (Intermediate 1-30) (2.09 g, 10.2 mmol) with the similar synthesis method as that of Intermediate 1.

Example 15. Preparation of Intermediate 16

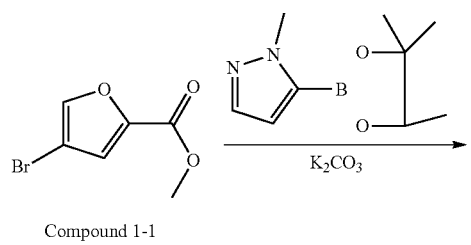

Step 1. Synthesis of 4-(1-methyl-1H-1,2,4-triazol-5-yl)furan-2-methyl formate (Intermediate 1-31)

The synthesis steps refer to Step 1 of Example 1. Intermediate 1-31 (1.8 g, yield of 87%) is prepared from 4-bromofuran-2-methyl formate (Compound 1-1) (2.08 g, 10.3 mmol) with the similar synthesis methods as that of Intermediate 1-2.

Step 2. Synthesis of 5-bromo-4-(1-methyl-1H-1,2,4-triazol-5-yl)furan-2-methyl formate (Intermediate 1-32)

The synthesis steps refer to Step 1 of Example 3. Intermediate 1-32 (2.43 g, yield of 85%) is prepared from 4-(1-methyl-1H-1,2,4-triazol-5-yl)furan-2-methyl formate (Intermediate 1-31) (2.1 g, 10.1 mmol) with the similar synthesis method as that of Intermediate 1-5.

Step 3. Synthesis of 5-bromo-4-(1-methyl-1H-1,2,4-triazol-5-yl)furan-2-formic acid (Intermediate 16)

The synthesis steps refer to Step 2 of Example 1. Intermediate 16 (2.54 g, yield of 93%) is prepared from 5-bromo-4-(1-methyl-1H-1,2,4-triazol-5-yl)furan-2-methyl formate (Intermediate 1-32) (2.90 g, 10.2 mmol) with the similar synthesis method as that of Intermediate 1.

Example 16. Preparation of Intermediate 17

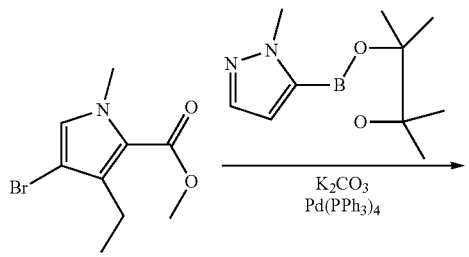

Compound 1-33

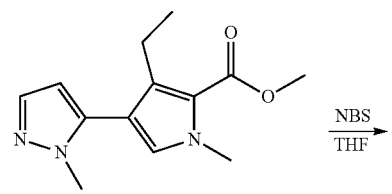

Intermediate 1-34

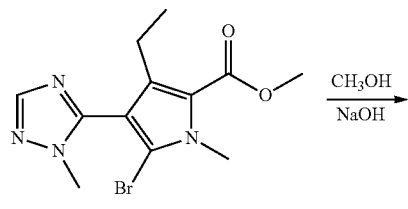

Intermediate 1-35

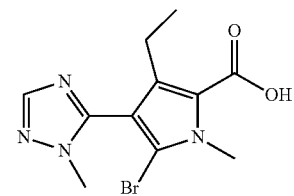

Intermediate 17

Step 1. Synthesis of 1-methyl-3-ethyl-4-(1-methyl-1H-1,2,4-triazol-5-yl)pyrrole-2-methyl formate (Intermediate 1-34)

The synthesis steps refer to Step 1 of Example 1. Intermediate 1-34 (2.12 g, yield of 85%) is prepared from 1-methyl-3-ethyl-5-bromo-4-bromofuran-2-methyl formate (Compound 1-33) (2.5 g, 10.2 mmol) with the similar synthesis method as that of Intermediate 1-2.

Step 2. Synthesis of 1-methyl-3-ethyl-5-bromo-4-(1-methyl-1H-1,2,4-triazol-5-yl)pyrrole-2-methyl formate (Intermediate 1-35)

The synthesis steps refer to Step 1 of Example 3. Intermediate 1-35 (3.03 g, yield of 93%) is prepared from 1-methyl-3-ethyl-4-(1-methyl-1H-1,2,4-triazol-5-yl)pyrrole-2-methyl formate (Intermediate 1-34) (2.5 g, 10.1 mmol) with the similar synthesis method as that of Intermediate 1-5.

Step 3. Synthesis of 1-methyl-3-ethyl-5-bromo-4-(1-methyl-1H-1,2,4-triazol-5-yl)pyrrole-2-formic acid (Intermediate 17)

The synthesis steps refer to Step 2 of Example 1. Intermediate 17 (2.99 g, yield of 96%) is prepared from 1-methyl-3-ethyl-5-bromo-4-(1-methyl-1H-1,2,4-triazol-5-yl)pyrrole-2-methyl formate (Intermediate 1-35) (3.3 g, 10.2 mmol) with the similar synthesis method as that of Intermediate 1.

Example 17. Preparation of Intermediate 18

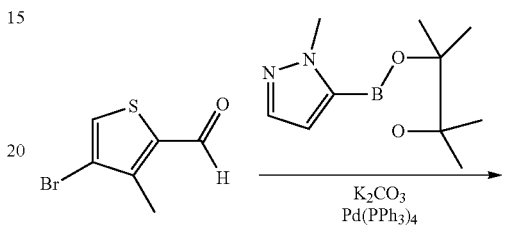

Compound 1-36

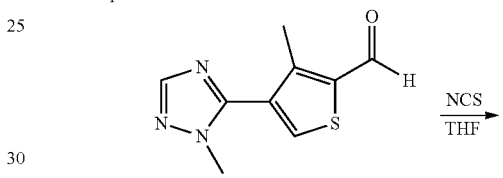

Intermediate 1-37

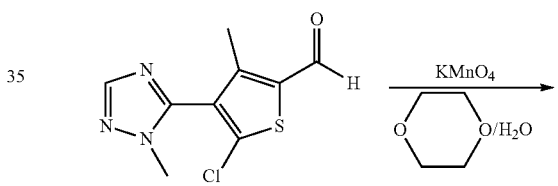

Intermediate 1-38

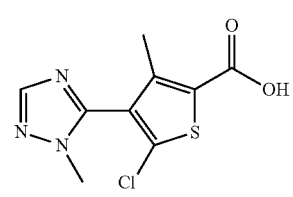

Intermediate 18

Step 1. Synthesis of 3-methyl-4-(1-methyl-1H-1,2,4-triazol-5-yl)thiophene-2-formaldehyde (Intermediate 1-37)

The synthesis steps refer to Step 1 of Example 1. Intermediate 1-37 (1.7 g, yield of 82%) is prepared from 3-methyl-4-bromofuran-2-formaldehyde (Compound 1-36) (2.2 g, 10.2 mmol) with the similar synthesis methods as that of Intermediate 1-2.

Step 2. Synthesis of 3-methyl-5-chloro-4-(1-methyl-1H-1,2,4-triazol-5-yl)thiophene-2-formaldehyde (Intermediate 1-38)

The synthesis steps refer to Step 1 of Example 5. Intermediate 1-38 (2.13 g, yield of 88%) is prepared from 3-methyl-4-(1-methyl-1H-1,2,4-triazol-5-yl)thiophene-2-formaldehyde (Intermediate 1-37) (2.1 g, 10.2 mmol) with the similar synthesis method as that of Compound 1-8.

Step 3. Synthesis of 3-methyl-5-chloro-4-(1-methyl-1H-1,2,4-triazol-5-yl)thiophene-2-formic acid (Intermediate 18)

The synthesis steps refer to Step 2 of Example 4. Intermediate 18 (2.37 g, yield of 92%) is prepared from 3-methyl-5-chloro-4-(1-methyl-1H-1,2,4-triazol-5-yl)thiophene-2-formaldehyde (Intermediate 1-38) (2.4 g, 10.0 mmol) with the similar synthesis method as that of Intermediate 5.

Example 18. Preparation of Intermediate 19

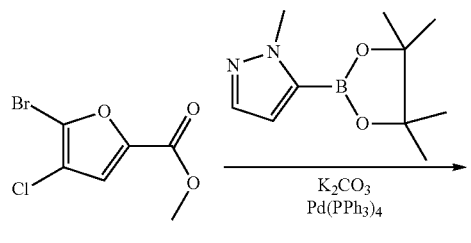

Compound 1-39

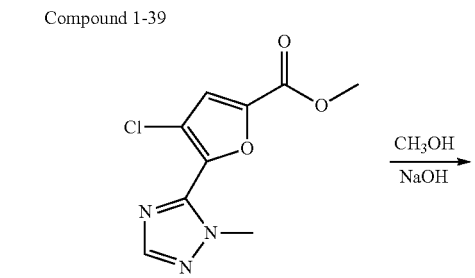

Intermediate 1-40

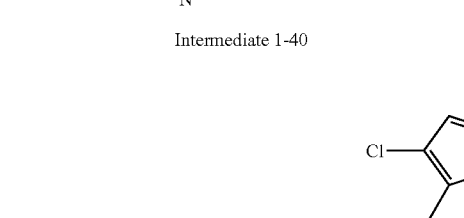

Intermediate 19

Step 1. Synthesis of 4-chloro-5-(1-methyl-1H-1,2,4-triazol-5-yl)furan-2-methyl formate (Intermediate 1-40)

The synthesis steps refer to Step 1 of Example 1. Intermediate 1-40 (1.82 g, yield of 76%) is prepared from 4-chloro-5-bromofuran-2-methyl formate (Compound 1-39) (2.43 g, 10.4 mmol) with the similar synthesis method as that of Intermediate 1-2.

Step 2. Synthesis of 4-chloro-5-(1-methyl-1H-1,2,4-triazol-5-yl)furan-2-formic acid (Intermediate 19)

The synthesis steps refer to Step 2 of Example 1. Intermediate 19 (2.01 g, yield of 88%) is prepared from 4-chloro-5-(1-methyl-1H-1,2,4-triazol-5-yl)furan-2-methyl formate (Intermediate 1-40) (2.49 g, 10.2 mmol) with the similar synthesis method as that of Intermediate 1.

Example 19. Preparation of Intermediate 20

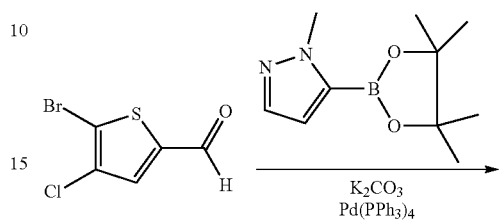

Compound 1-42

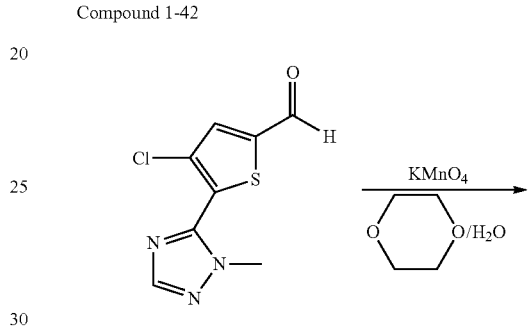

Intermediate 1-43

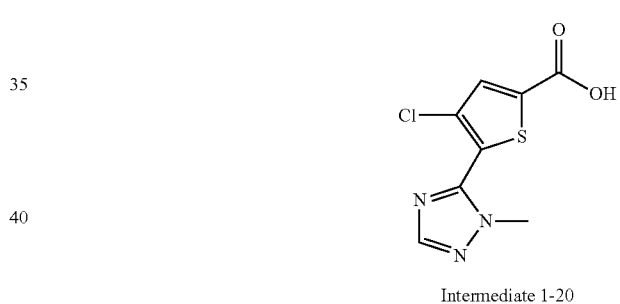

Intermediate 1-20

Step 1. Synthesis of 4-chloro-5-(1-methyl-1H-1,2,4-triazol-5-yl)thiophene-2-formaldehyde (Intermediate 1-43)

The synthesis steps refer to Step 1 of Example 1. Intermediate 1-43 (1.89 g, yield of 83%) is prepared from 4-chloro-5-bromothiophene-2-formaldehyde (Compound 1-42) (2.3 g, 10.4 mmol) with the similar synthesis method as that of Intermediate 1-2.

Step 2. Synthesis of 4-chloro-5-(1-methyl-1H-1,2,4-triazol-5-yl)thiophene-2-formic acid (Intermediate 20)

The synthesis steps refer to Step 2 of Example 4. Intermediate 20 (2.27 g, yield of 93%) is prepared from 4-chloro-5-(1-methyl-1H-1,2,4-triazol-5-yl)thiophene-2-formaldehyde (Intermediate 1-43) (2.3 g, 10.2 mmol) with the similar synthesis method as that of Intermediate 5.

Example 20. Preparation of Intermediate 21

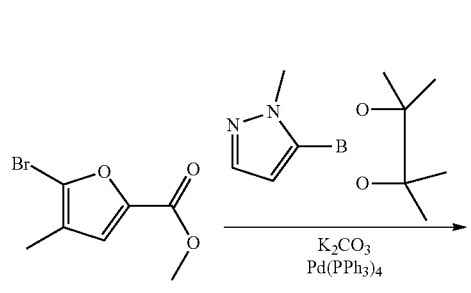

Compound 1-44

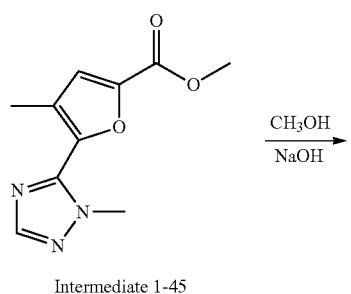

Intermediate 1-45

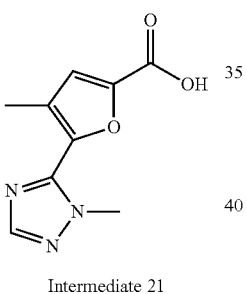

Intermediate 21

Step 1. Synthesis of 4-methyl-5-(1-methyl-1H-1,2,4-triazol-5-yl)furan-2-methyl formate (Intermediate 1-45)

The synthesis steps refer to Step 1 of Example 1. Intermediate 1-45 (1.69 g, yield of 74%) is prepared from 4-methyl-5-bromothiophene-2-formaldehyde (Compound 1-44) (2.1 g, 10.4 mmol) with the similar synthesis method as that of Intermediate 1-2.

Step 2. Synthesis of 4-methyl-5-(1-methyl-1H-1,2,4-triazol-5-yl)furan-2-formic acid (Intermediate 21)

The synthesis steps refer to Step 2 of Example 1. Intermediate 21 (2.01 g, yield of 88%) is prepared from 4-methyl-5-(1-methyl-1H-1,2,4-triazol-5-yl) furan-2-methyl formate (Intermediate 1-45) (2.49 g, 10.2 mmol) with the similar synthesis method as that of Intermediate 1.

Example 21. Preparation of Intermediate 22

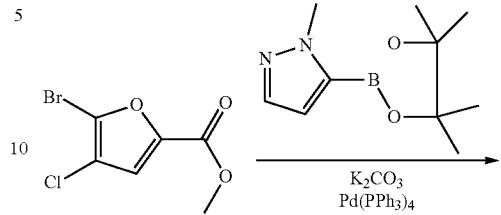

Compound 1-39

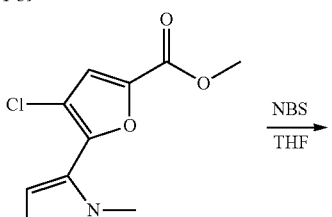

Intermediate 1-46

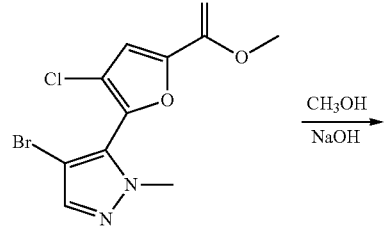

Intermediate 1-47

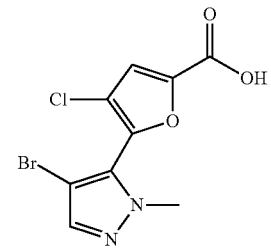

Intermediate 22

Step 1. Synthesis of 4-chloro-5-(1-methyl-1H-pyrazol-5-yl)furan-2-methyl formate (Intermediate 1-46)

The synthesis steps refer to Step 1 of Example 1. Intermediate 1-46 (1.9 g, yield of 79%) is prepared from 4-chloro-5-bromofuran-2-methyl formate (Compound 1-39) (2.5 g, 10.4 mmol) with the similar synthesis method as that of Intermediate 1-2.

Step 2. Synthesis of 4-chloro-5-(4-bromo-1-methyl-1H-pyrazol-5-yl)furan-2-methyl formate (Intermediate 1-47)

The synthesis steps refer to Step 1 of Example 3. Intermediate 1-47 (2.87 g, yield of 90%) is prepared from 4-chloro-5-(1-methyl-1H-pyrazol-5-yl)furan-2-methyl formate (Intermediate 1-46) (2.48 g, 10.1 mmol) with the similar synthesis method as that of Intermediate 1-5.

Step 3. Synthesis of 4-chloro-5-(4-bromo-1-methyl-1H-pyrazol-5-yl)furan-2-formic acid (Intermediate 22)

The synthesis steps refer to Step 2 of Example 1. Intermediate 22 (2.68 g, yield of 88%) is prepared from 4-chloro-5-(4-bromo-1-methyl-1H-pyrazol-5-yl) furan-2-methyl formate (Intermediate 1-47) (3.22 g, 10.2 mmol) with the similar synthesis method as that of Intermediate 1.

Example 22. Preparation of Intermediate 23-40

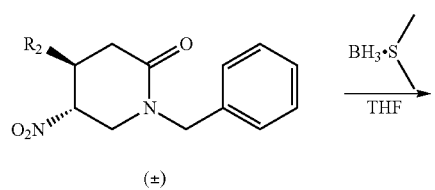

2-1a: R$_2$ = phenyl
2-1b: R$_2$ = 4-chlorphenyl
2-1c: R$_2$ = 4-trifluoromethylphenyl
2-1d: R$_2$ = 3-trifluoromethylphenyl
2-1e: R$_2$ = 3,4-difluorophenyl
2-1f: R$_2$ = 3-methylphenyl
2-1g: R$_2$ = 3-cyanophenyl
2-1h: R$_2$ = 3,5-dimethoxyphenyl
2-1i: R$_2$ = 4-(1-chloroethyl)phenyl
2-1j: R$_2$ = 4-pyridinyl
2-1k: R$_2$ = 3-quinolinyl

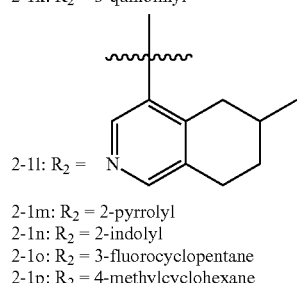

2-1l: R$_2$ =

2-1m: R$_2$ = 2-pyrrolyl
2-1n: R$_2$ = 2-indolyl
2-1o: R$_2$ = 3-fluorocyclopentane
2-1p: R$_2$ = 4-methylcyclohexane

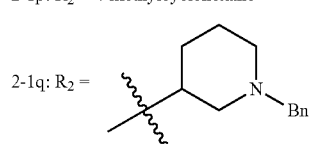

2-1q: R$_2$ =

2-1r: R$_2$ = 3-chlorocyclohexane

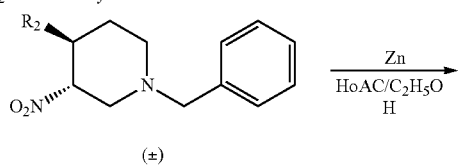

2-2a: R$_2$ = phenyl
2-2b: R$_2$ = 4-chlorphenyl
2-2c: R$_2$ = 4-trifluoromethylphenyl
2-2d: R$_2$ = 3-trifluoromethylphenyl
2-2e: R$_2$ = 3,4-difluorophenyl
2-2f: R$_2$ = 3-methylphenyl
2-2g: R$_2$ = 3-cyanophenyl
2-2h: R$_2$ = 3,5-dimethoxyphenyl
2-2i: R$_2$ = 4-(1-chloroethyl)phenyl
2-2j: R$_2$ = 4-pyridinyl
2-2k: R$_2$ = 3-quinolinyl

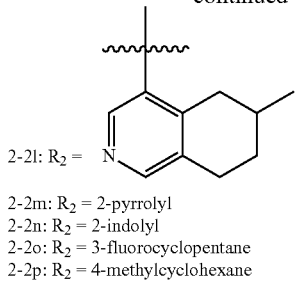

2-2l: R$_2$ =

2-2m: R$_2$ = 2-pyrrolyl
2-2n: R$_2$ = 2-indolyl
2-2o: R$_2$ = 3-fluorocyclopentane
2-2p: R$_2$ = 4-methylcyclohexane

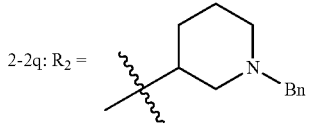

2-2q: R$_2$ =

2-2r: R$_2$ = 3-chlorocyclohexane

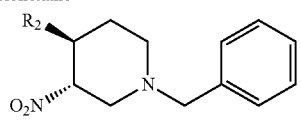

Intermediate 23: R$_2$ = phenyl
Intermediate 24: R$_2$ = 4-chlorphenyl
Intermediate 25: R$_2$ = 4-trifluoromethylphenyl
Intermediate 26: R$_2$ = 3-trifluoromethylphenyl
Intermediate 27: R$_2$ = 3,4-difluorophenyl
Intermediate 28: R$_2$ = 3-methylphenyl
Intermediate 29: R$_2$ = 3-cyanophenyl
Intermediate 30: R$_2$ = 3,5-dimethoxyphenyl
Intermediate 31: R$_2$ = 4-(1-chloroethyl)phenyl
Intermediate: 32: R$_2$ = 4-pyridinyl
Intermediate: 33: R$_2$ = 3-quinolinyl Intermediate: 34: R$_2$ =

Intermediate: 35: R$_2$ = 2-pyrrolyl
Intermediate: 36: R$_2$ = 2-indolyl
Intermediate: 37: R$_2$ = 3-fluorocyclopentane
Intermediate 38: R$_2$ = 4-methylcyclohexane Intermediate: 39: R$_2$ =

Intermediate: 40: R$_2$ = 3-chlorocyclohexane

Step 1. Synthesis of Intermediate 2-2b (Synthesis Methods of Intermediate 2-2a to 2-2i are Shown in Table 2)

Dissolving Compound 2-1b (2.96 g, 11.62 mmol) in anhydrous tetrahydrofuran (20 ml), under the protection of N$_2$, slowly dropwise adding 2N borane dimethyl sulfide solution within tetrahydrofuran (3.29 ml, 34.88 mmol) thereto under an ice bath, stirring for about 3 h at room temperature. Monitoring the reaction with TLC thin-layer chromatography for whether it is completed, after the reaction, under the ice bath, slowly dropwise adding methanol into the reaction liquid until no air bubbles. Then adding about 3 ml of 1N HCl solution into the reaction liquid, stirring for 10 min at room temperature, recycling the solvent under reduced pressure, and washing with saturated NaHCO$_3$ solution, followed by extracting the reaction liquid with ethyl acetate 3 times, washing the merged organic phase with saturated sodium chloride once, and drying it with anhydrous sodium sulfate. Recycling the solvent under reduced pressure, 2.10 g of light yellow oily liquid (Intermediate 2-2b) is obtained and the yield is 75%.

TABLE 2

Synthesis methods of Intermediate 2-2a to 2-2i

| Reactant | Amount of the reactant | Synthesis method | Product | Yield |
| --- | --- | --- | --- | --- |
| 2-1a | 2.38 g, 7.67 mmol | Similar to the synthesis method of Compound 2-2b | 2-2a | 2.08 g, 91% |
| 2-1c | 3.78 g, 10.0 mmol | Similar to the synthesis method of Compound 2-2b | 2-2c | 3.47 g, 92% |
| 2-1d | 3.78 g, 10.0 mmol | Similar to the synthesis method of Compound 2-2b | 2-2d | 3.28 g, 90% |
| 2-1e | 3.25 g, 9.3 mmol | Similar to the synthesis method of Compound 2-2b | 2-2e | 2.89 g, 92% |
| 2-1f | 2.34 g, 7.2 mmol | Similar to the synthesis method of Compound 2-2b | 2-2f | 2.0 g, 89% |
| 2-1g | 3.12 g, 9.3 mmol | Similar to the synthesis method of Compound 2-2b | 2-2g | 2.56 g, 86% |
| 2-1h | 3.08 g, 8.3 mmol | Similar to the synthesis method of Compound 2-2b | 2-2h | 2.76 g, 93% |
| 2-1i | 2.54 g, 6.8 mmol | Similar to the synthesis method of Compound 2-2b | 2-2i | 2.17 g, 89% |
| 2-1j | 3.52 g, 9.1 mmol | Similar to the synthesis method of Compound 2-2b | 2-2j | 3.07 g, 91% |
| 2-1k | 2.77 g, 6.3 mmol | Similar to the synthesis method of Compound 2-2b | 2-2k | 2.24 g, 83% |
| 2-1l | 3.09 g, 6.8 mmol | Similar to the synthesis method of Compound 2-2b | 2-2l | 2.56 g, 86% |
| 2-1m | 2.34 g, 6.2 mmol | Similar to the synthesis method of Compound 2-2b | 2-2m | 2.08 g, 92% |
| 2-1n | 2.89 g, 6.8 mmol | Similar to the synthesis method of Compound 2-2b | 2-2n | 2.32 g, 83% |
| 2-1o | 2.65 g, 6.7 mmol | Similar to the synthesis method of Compound 2-2b | 2-2o | 2.25 g, 88% |
| 2-1p | 3.66 g, 9.0 mmol | Similar to the synthesis method of Compound 2-2b | 2-2p | 3.15 g, 89% |
| 2-1q | 3.10 g, 7.9 mmol | Similar to the synthesis method of Compound 2-2b | 2-2q | 2.65 g, 89% |
| 2-1r | 2.11 g, 4.9 mmol | Similar to the synthesis method of Compound 2-2b | 2-2r | 1.81 g, 89% |

Step 2. Synthesis of Intermediate 24 (Synthesis Methods of Intermediate 23-31 are Shown in Table 3)

Dissolving Intermediate 2-2b (2.10 g, 6.36 mmol) into the mixed solution of anhydrous ethanol (10 ml) and glacial acetic acid (10 ml), adding zinc powder (1.65 g, 25.44 mmol) thereto under an ice bath, and stirring overnight at room temperature under the protection of N$_2$. After the reaction is completed, suction filtrating the reaction mixture, neutralizing the glacial acetic acid in the filtrate with saturated Na$_2$CO$_3$ to a pH of greater than 7, extracting the reaction liquid with ethyl acetate 3 times, washing with saturated sodium chloride once, and drying it with anhydrous sodium sulfate. Recycling the solvent under reduced pressure, 1.55 g of oily liquid (Intermediate 24) is obtained and the yield is 81%.

TABLE 3

Synthesis methods of Intermediate 23-31

| Reactant | Amount of the reactant | Synthesis method | Product | Yield |
| --- | --- | --- | --- | --- |
| 2-2a | 2.08 g, 7.02 mmol | Similar to the synthesis method of Intermediate 24 | Intermediate 23 | 1.62 g, 87% |
| 2-2c | 3.47 g, 9.2 mmol | Similar to the synthesis method of Intermediate 24 | Intermediate 25 | 2.84 g, 92% |
| 2-2d | 3.28 g, 9.0 mmol | Similar to the synthesis method of Intermediate 24 | Intermediate 26 | 2.65 g, 88% |
| 2-2e | 2.89 g, 8.7 mmol | Similar to the synthesis method of Intermediate 24 | Intermediate 27 | 2.32 g, 89% |
| 2-2f | 2.0 g, 6.4 mmol | Similar to the synthesis method of Intermediate 24 | Intermediate 28 | 1.43 g, 80% |
| 2-2g | 2.56 g, 7.9 mmol | Similar to the synthesis method of Intermediate 24 | Intermediate 29 | 2.1 g, 90% |
| 2-2h | 2.76 g, 7.7 mmol | Similar to the synthesis method of Intermediate 24 | Intermediate 30 | 2.17 g, 85% |
| 2-2i | 2.17 g, 6.1 mmol | Similar to the synthesis method of Intermediate 24 | Intermediate 31 | 1.67 g, 84% |
| 2-2j | 3.07 g, 8.2 mmol | Similar to the synthesis methods of Intermediate 24 | Intermediate 32 | 2.53 g, 89% |
| 2-2k | 2.24 g, 5.2 mmol | Similar to the synthesis method of Intermediate 24 | Intermediate 33 | 1.68 g, 81% |
| 2-2l | 2.56 g, 5.8 mmol | Similar to the synthesis method of Intermediate 24 | Intermediate 34 | 2.09 g, 88% |
| 2-2m | 2.08 g, 5.8 mmol | Similar to the synthesis method of Intermediate 24 | Intermediate 35 | 1.64 g, 85% |
| 2-2n | 2.32 g, 5.6 mmol | Similar to the synthesis method of Intermediate 24 | Intermediate 36 | 1.86 g, 86% |
| 2-2o | 2.25 g, 5.9 mmol | Similar to the synthesis method of Intermediate 24 | Intermediate 37 | 1.75 g, 84% |
| 2-2p | 3.15 g, 8.0 mmol | Similar to the synthesis method of Intermediate 24 | Intermediate 38 | 2.18 g, 75% |
| 2-2q | 2.65 g, 7.0 mmol | Similar to the synthesis method of Intermediate 24 | Intermediate 39 | 2.16 g, 88% |
| 2-2r | 1.81 g, 4.4 mmol | Similar to the synthesis method of Intermediate 24 | Intermediate 40 | 1.42 g, 85% |

Example 23. Preparation of Intermediate 41

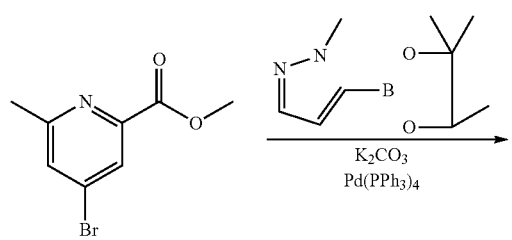

Compound 3-1

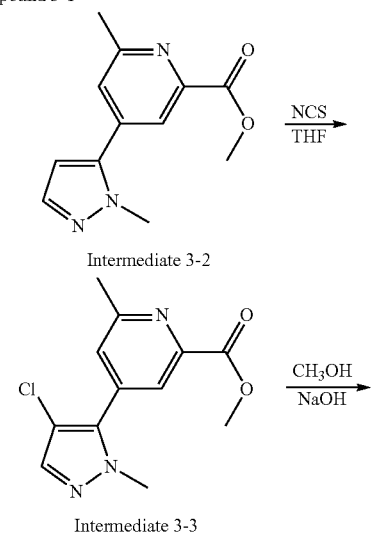

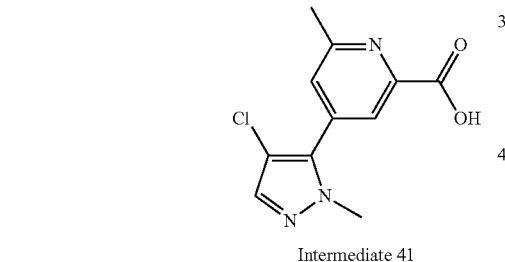

Intermediate 41

Step 1. Synthesis of 6-methyl-4-(1-methyl-1H-pyrazol-5-yl)pyridinyl-2-methyl formate (Intermediate 3-2)

The synthesis steps refer to Step 1 of Example 1. Intermediate 3-2 (1.98 g, yield of 85%) is prepared from 6-methyl-4-bromopyridinyl-2-methyl formate (Compound 3-1) (2.2 g, 9.9 mmol) with the similar synthesis method as that of Intermediate 1-2.

Step 2. Synthesis of 6-methyl-4-(4-chloro-1-methyl-1H-pyrazol-5-yl)pyridinyl-2-methyl formate (Intermediate 3-3)

The synthesis steps refer to Step 1 of Example 5. Intermediate 3-3 (1.89 g, yield of 83%) is prepared from 6-methyl-4-(1-methyl-1H-pyrazol-5-yl)pyridinyl-2-methyl formate (Intermediate 3-2) (1.98 g, 8.6 mmol) with the similar synthesis method as that of Intermediate 1-8.

Step 3. Synthesis of 6-methyl-4-(4-chloro-1-methyl-1H-pyrazol-5-yl)pyridinyl-2-formic acid (Intermediate 41)

The synthesis steps refer to Step 2 of Example 1. Intermediate 41 (1.48 g, yield of 82%) is prepared from 6-methyl-4-(4-chloro-1-methyl-1H-pyrazol-5-yl)pyridinyl-2-methyl formate (Intermediate 3-3) (1.89 g, 7.1 mmol) with the similar synthesis method as that of Intermediate 1.

Example 24. Preparation of Intermediate 42

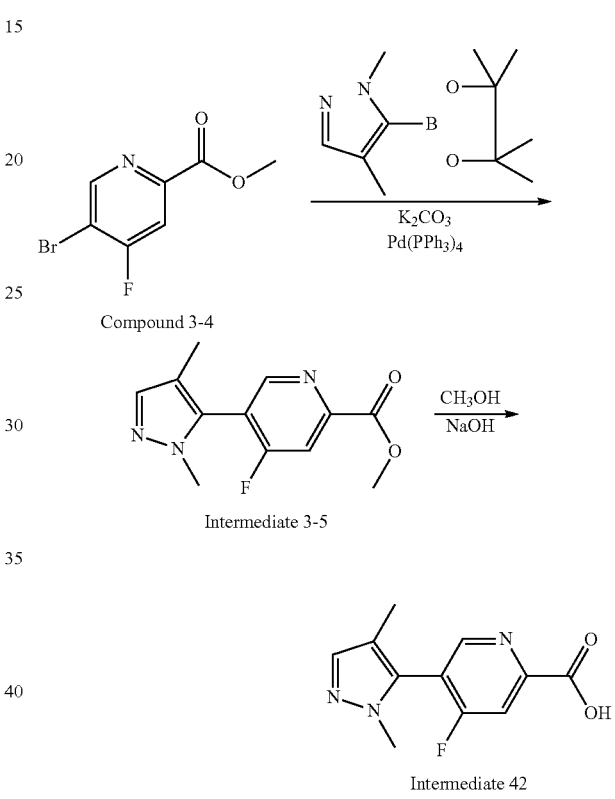

Step 1. Synthesis of 4-fluoro-5-(1,4-dimethyl-1H-pyrazol-5-yl)pyridinyl-2-methyl formate (Intermediate 3-5)

The synthesis steps refer to Step 1 of Example 1. Intermediate 3-5 (2.58 g, yield of 86%) is prepared from 4-fluoro-5-bromopyridinyl-2-methyl formate (Compound 3-4) (2.8 g, 11.9 mmol) with the similar synthesis method as that of Intermediate 1-2.

Step 2. Synthesis of 4-fluoro-5-(1,4-dimethyl-1H-pyrazol-5-yl)pyridinyl-2-formic acid (Intermediate 42)

The synthesis steps refer to Step 2 of Example 1. Intermediate 42 (2.08 g, yield of 86%) is prepared from 4-fluoro-5-(1,4-dimethyl-1H-pyrazol-5-yl)pyridinyl-2-methyl formate (Intermediate 3-5) (2.58 g, 10.4 mmol) with the similar synthesis method as that of Intermediate 1.

Example 25. Preparation of Intermediate 43

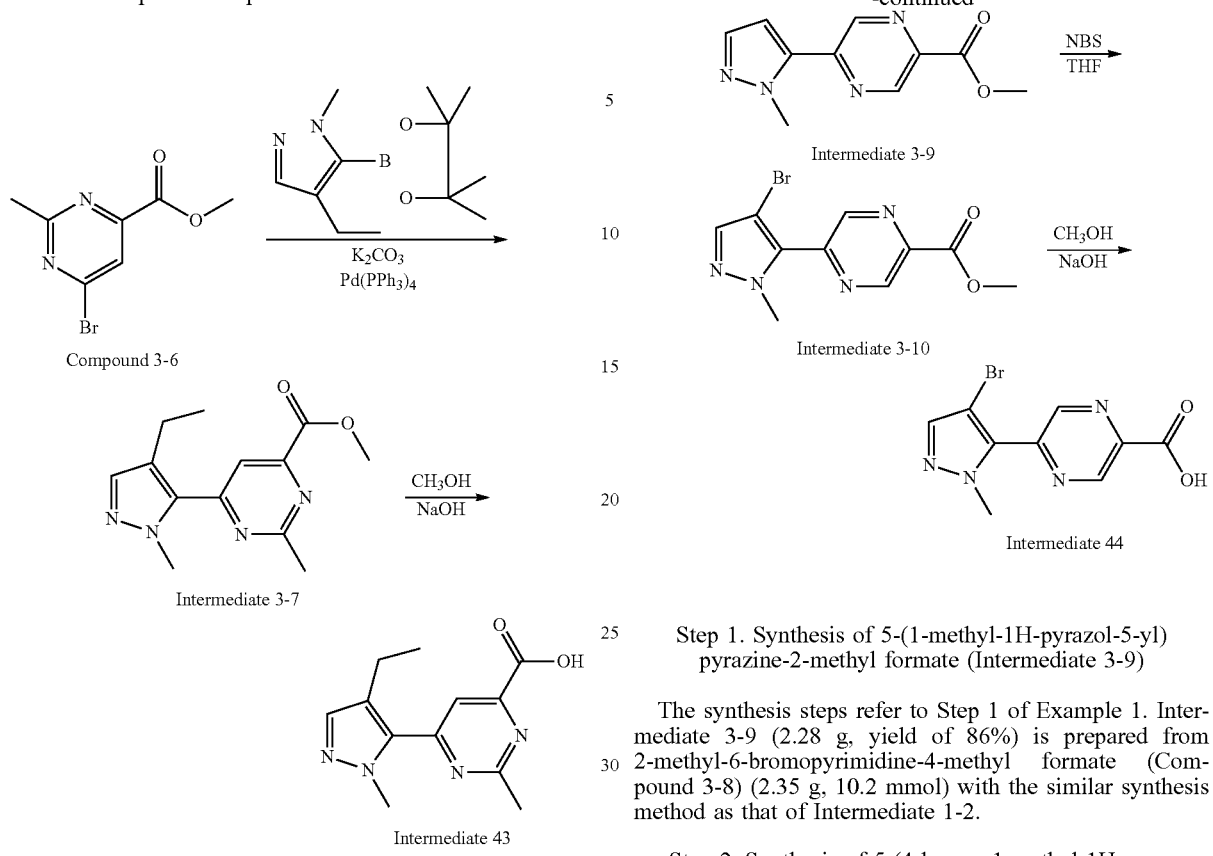

Step 1. Synthesis of 2-methyl-6-(1-methyl-4-ethyl-1H-pyrazol-5-yl)pyrimidine-4-methyl formate (Intermediate 3-7)

The synthesis steps refer to Step 1 of Example 1. Intermediate 3-7 (2.28 g, yield of 86%) is prepared from 2-methyl-6-bromopyrimidine-4-methyl formate (Compound 3-6) (2.35 g, 10.2 mmol) with the similar synthesis method as that of Intermediate 1-2.

Step 2. Synthesis of 2-methyl-6-(1-methyl-4-ethyl-1H-pyrazol-5-yl)pyrimidine-4-formic acid (Intermediate 43)

The synthesis steps refer to Step 2 of Example 1. Intermediate 43 (1.88 g, yield of 87%) is prepared from 2-methyl-6-(1-methyl-4-ethyl-1H-pyrazol-5-yl)pyrimidine-4-methyl formate (Intermediate 3-7) (2.28 g, 8.76 mmol) with the similar synthesis method as that of Intermediate 1.

Example 26. Preparation of Intermediate 44

Step 1. Synthesis of 5-(1-methyl-1H-pyrazol-5-yl)pyrazine-2-methyl formate (Intermediate 3-9)

The synthesis steps refer to Step 1 of Example 1. Intermediate 3-9 (2.28 g, yield of 86%) is prepared from 2-methyl-6-bromopyrimidine-4-methyl formate (Compound 3-8) (2.35 g, 10.2 mmol) with the similar synthesis method as that of Intermediate 1-2.

Step 2. Synthesis of 5-(4-bromo-1-methyl-1H-pyrazol-5-yl)pyrazine-2-methyl formate (Intermediate 3-10)

The synthesis steps refer to Step 1 of Example 3. Intermediate 3-10 (2.57 g, yield of 86%) is prepared from 5-(1-methyl-1H-pyrazol-5-yl)pyrazine-2-methyl formate (Compound 3-9) (2.19 g, 10.0 mmol) with the similar synthesis method as that of Intermediate 1-5.

Step 3. Synthesis of 5-(4-bromo-1-methyl-1H-pyrazol-5-yl)pyrazine-2-formic acid (Intermediate 44)

The synthesis steps refer to Step 2 of Example 1. Intermediate 44 (1.88 g, yield of 87%) is prepared from 5-(4-bromo-1-methyl-1H-pyrazol-5-yl)pyrazine-2-methyl formate (Intermediate 3-10) (2.28 g, 8.76 mmol) with the similar synthesis method as that of Intermediate 1.

Example 27. Preparation of Intermediate 45

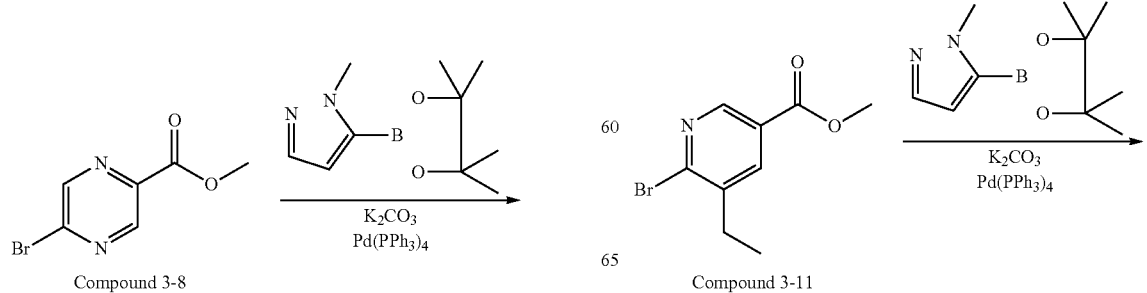

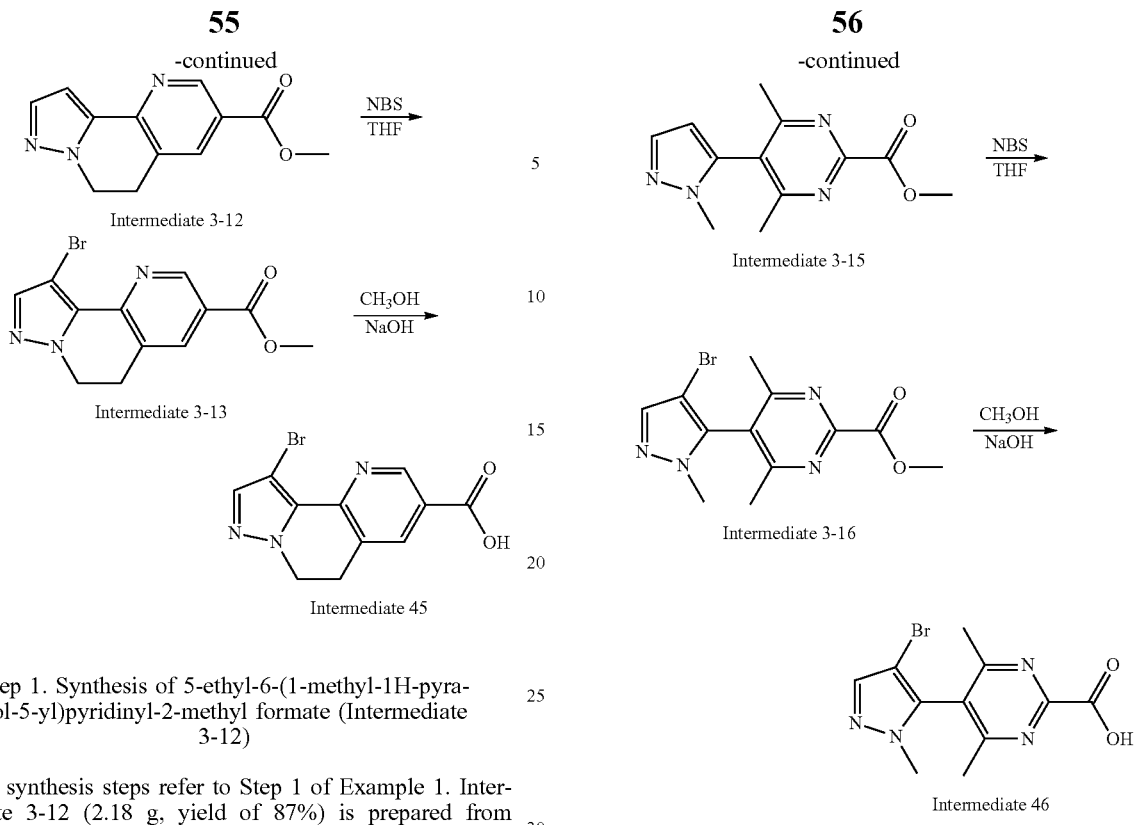

Step 1. Synthesis of 5-ethyl-6-(1-methyl-1H-pyrazol-5-yl)pyridinyl-2-methyl formate (Intermediate 3-12)

The synthesis steps refer to Step 1 of Example 1. Intermediate 3-12 (2.18 g, yield of 87%) is prepared from 5-ethyl-6-bromopyridinyl-2-methyl formate (Compound 3-11) (2.49 g, 10.2 mmol) with the similar synthesis method as that of Intermediate 1-2.

Step 2. Synthesis of 5-ethyl-6-(4-bromo-1-methyl-1H-pyrazol-5-yl)pyridinyl-2-methyl formate (Intermediate 3-13)

The synthesis steps refer to Step 1 of Example 3. Intermediate 3-13 (2.46 g, yield of 85%) is prepared from 5-ethyl-6-(1-methyl-1H-pyrazol-5-yl)pyridinyl-2-methyl formate (Intermediate 3-12) (2.18 g, 8.9 mmol) with the similar synthesis method as that of Intermediate 1-5.

Step 3. Synthesis of 5-ethyl-6-(4-bromo-1-methyl-1H-pyrazol-5-yl)pyridinyl-2-formic acid (Intermediate 45)

The synthesis steps refer to Step 2 of Example 1. Intermediate 45 (1.98 g, yield of 84%) is prepared from 5-ethyl-6-(4-bromo-1-methyl-1H-pyrazol-5-yl)pyridinyl-2-methyl formate (Intermediate 3-13) (2.46 g, 7.6 mmol) with the similar synthesis method as that of Intermediate 1.

Example 28. Preparation of Intermediate 46

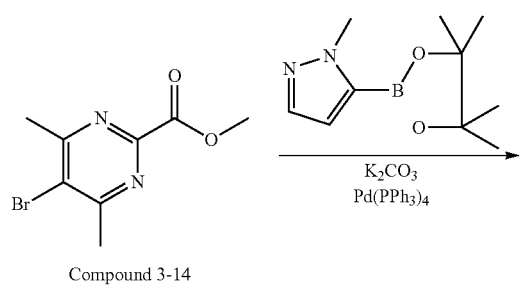

Step 1. Synthesis of 4,6-dimethyl-5-(1-methyl-1H-pyrazol-5-yl)pyrimidine-2-methyl formate (Intermediate 3-15)

The synthesis steps refer to Step 1 of Example 1. Intermediate 3-15 (2.17 g, yield of 87%) is prepared from 4,6-dimethyl-5-bromopyrimidine-2-methyl formate (Compound 3-14) (2.49 g, 10.2 mmol) with the similar synthesis method as that of Intermediate 1-2.

Step 2. Synthesis of 4,6-dimethyl-5-(4-bromo-1-methyl-1H-pyrazol-5-yl)pyrimidine-2-methyl formate (Intermediate 3-16)

The synthesis steps refer to Step 1 of Example 3. Intermediate 3-16 (2.46 g, yield of 85%) is prepared from 4,6-dimethyl-5-(1-methyl-1H-pyrazol-5-yl)pyrimidine-2-methyl formate (Intermediate 3-15) (2.17 g, 8.9 mmol) with the similar synthesis method as that of Intermediate 1-5.

Step 3. Synthesis of 4,6-dimethyl-5-(4-bromo-1-methyl-1H-pyrazol-5-yl)pyrimidine-2-formic acid (Intermediate 46)

The synthesis steps refer to Step 2 of Example 1. Intermediate 46 (1.98 g, yield of 84%) is prepared from 4,6-dimethyl-5-(4-bromo-1-methyl-1H-pyrazol-5-yl)pyrimidine-2-methyl formate (Intermediate 3-16) (2.46 g, 7.6 mmol) with the similar synthesis method as that of Intermediate 1.

Example 29. Preparation of Intermediate 47

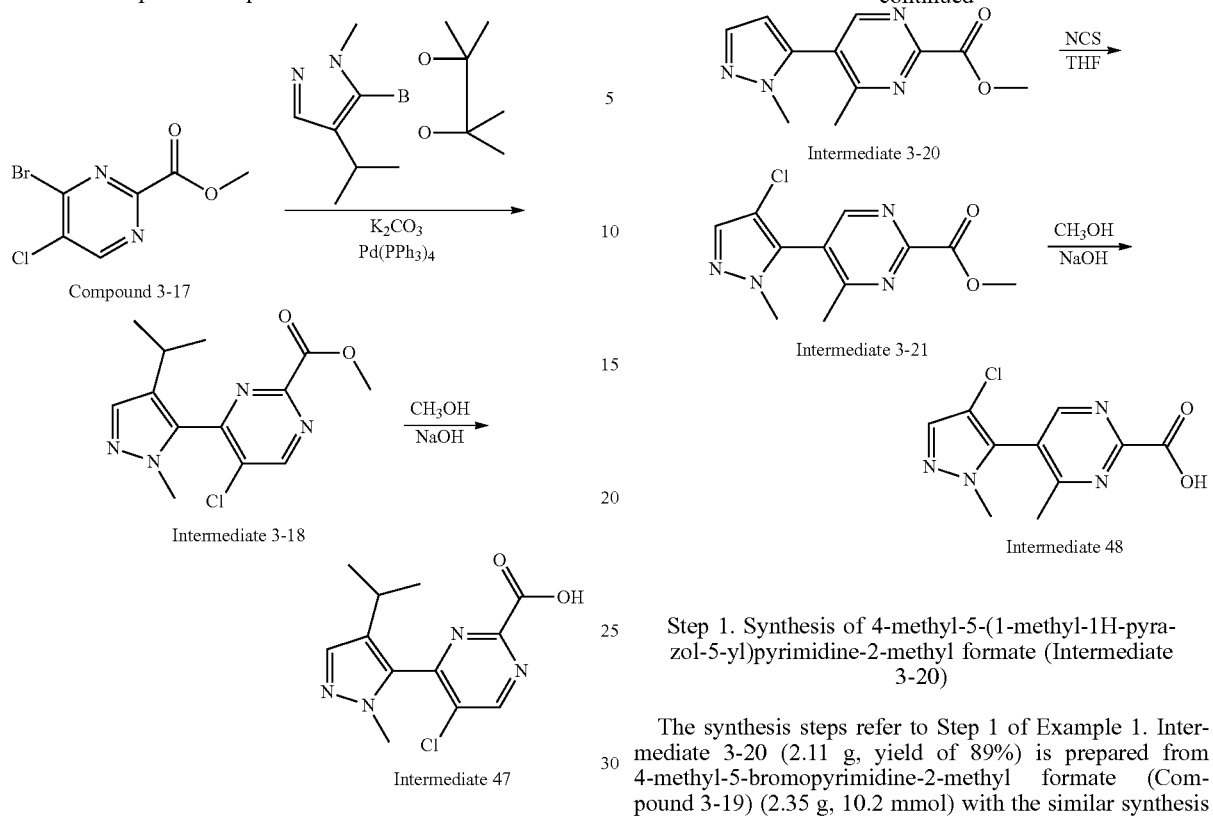

Step 1. Synthesis of 5-chloro-4-(4-isopropyl-1-methyl-1H-pyrazol-5-yl)pyrimidine-2-methyl formate (Intermediate 3-18)

The synthesis steps refer to Step 1 of Example 1. Intermediate 3-18 (2.67 g, yield of 89%) is prepared from 5-chloro-4-bromopyrimidine-2-methyl formate (Compound 3-17) (2.57 g, 10.2 mmol) with the similar synthesis method as that of Intermediate 1-2.

Step 2. Synthesis of 5-chloro-4-(4-isopropyl-1-methyl-1H-pyrazol-5-yl)pyrimidine-2-formic acid (Intermediate 47)

The synthesis steps refer to Step 2 of Example 1. Intermediate 47 (2.33 g, yield of 92%) is prepared from 5-chloro-4-(4-isopropyl-1-methyl-1H-pyrazol-5-yl)pyrimidine-2-methyl formate (Intermediate 3-18) (2.67 g, 9.1 mmol) with the similar synthesis method as that of Intermediate 1.

Example 30. Preparation of Intermediate 48

Step 1. Synthesis of 4-methyl-5-(1-methyl-1H-pyrazol-5-yl)pyrimidine-2-methyl formate (Intermediate 3-20)

The synthesis steps refer to Step 1 of Example 1. Intermediate 3-20 (2.11 g, yield of 89%) is prepared from 4-methyl-5-bromopyrimidine-2-methyl formate (Compound 3-19) (2.35 g, 10.2 mmol) with the similar synthesis method as that of Intermediate 1-2.

Step 2. Synthesis of 4-methyl-5-(4-chloro-1-methyl-1H-pyrazol-5-yl)pyrimidine-2-methyl formate (Intermediate 3-21)

The synthesis steps refer to Step 1 of Example 5. Intermediate 3-21 (2.17 g, yield of 90%) is prepared from 4-methyl-5-(1-methyl-1H-pyrazol-5-yl)pyrimidine-2-methyl formate (Intermediate 3-20) (2.11 g, 9.0 mmol) with the similar synthesis method as that of Intermediate 1-8.

Step 3. Synthesis of 4-methyl-5-(4-chloro-1-methyl-1H-pyrazol-5-yl)pyrimidine-2-formic acid (Intermediate 48)

The synthesis steps refer to Step 2 of Example 1. Intermediate 48 (1.76 g, yield of 86%) is prepared from 4-methyl-5-(4-chloro-1-methyl-1H-pyrazol-5-yl)pyrimidine-2-methyl formate (Intermediate 3-21) (2.17 g, 8.1 mmol) with the similar synthesis method as that of Intermediate 1.

Example 31. Preparation of Intermediate 49

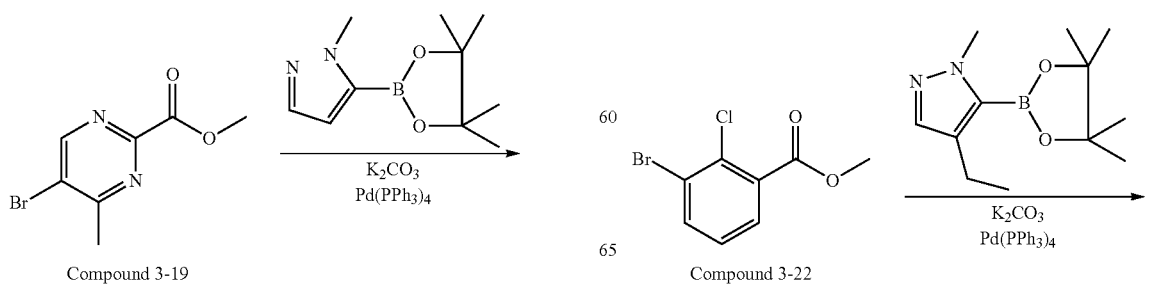

-continued

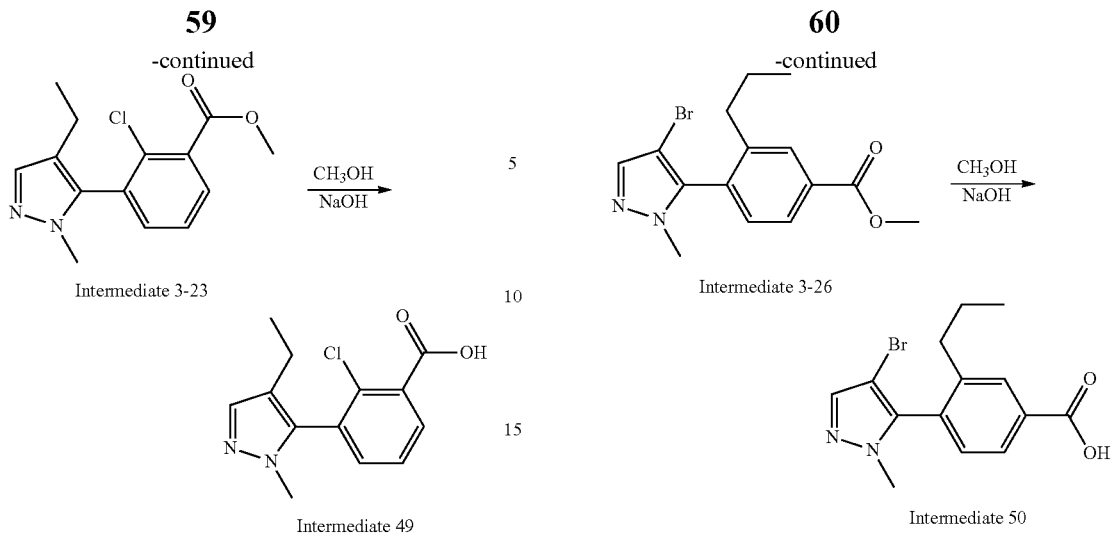

Step 1. Synthesis of 2-chloro-3-(4-ethyl-1-methyl-1H-pyrazol-5-yl)phenyl methyl formate (Intermediate 3-23)

The synthesis steps refer to Step 1 of Example 1. Intermediate 3-23 (2.54 g, yield of 90%) is prepared from 2-chloro-3-bromophenyl methyl formate (Compound 3-22) (2.53 g, 10.2 mmol) with the similar synthesis method as that of Intermediate 1-2.

Step 2. Synthesis of 2-chloro-3-(4-ethyl-1-methyl-1H-pyrazol-5-yl)phenyl formic acid (Intermediate 49)

The synthesis steps refer to Step 2 of Example 1. Intermediate 49 (2.23 g, yield of 92%) is prepared from 2-chloro-3-(4-ethyl-1-methyl-1H-pyrazol-5-yl)phenyl methyl formate (Intermediate 3-23) (2.54 g, 9.1 mmol) with the similar synthesis method as that of Intermediate 1.

Example 32. Preparation of Intermediate 50

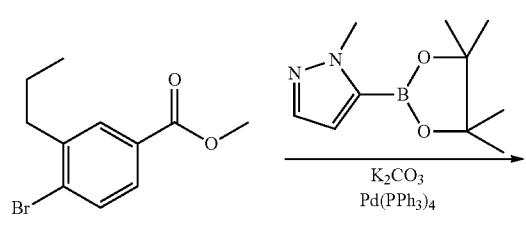

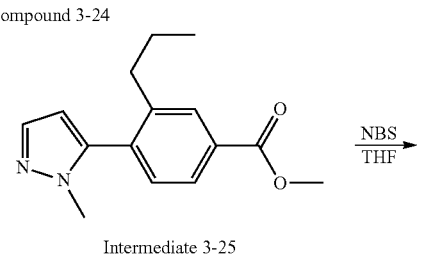

Step 1. Synthesis of 3-n-propyl-4-(1-methyl-1H-pyrazol-5-yl)phenyl methyl formate (Intermediate 3-25)

The synthesis steps refer to Step 1 of Example 1. Intermediate 3-25 (2.38 g, yield of 79%) is prepared from 3-n-propyl-4-bromophenyl methyl formate (Compound 3-24) (3.0 g, 11.7 mmol) with the similar synthesis method as that of Intermediate 1-2.

Step 2. Synthesis of 3-n-propyl-4-(4-bromo-1-methyl-1H-pyrazol-5-yl)phenyl methyl formate (Intermediate 3-26)

The synthesis steps refer to Step 1 of Example 3. Intermediate 3-26 (2.67 g, yield of 88%) is prepared from 3-n-propyl-4-(1-methyl-1H-pyrazol-5-yl)phenyl methyl formate (Intermediate 3-25) (2.38 g, 9.22 mmol) with the similar synthesis method as that of Intermediate 1-5.

Step 3. Synthesis of 3-n-propyl-4-(4-bromo-1-methyl-1H-pyrazol-5-yl)phenyl formic acid (Intermediate 50)

The synthesis steps refer to Step 2 of Example 1. Intermediate 50 (2.34 g, yield of 92%) is prepared from 3-n-propyl-4-(4-bromo-1-methyl-1H-pyrazol-5-yl)phenyl methyl formate (Intermediate 3-26) (2.67 g, 7.9 mmol) with the similar synthesis method as that of Intermediate 1.

Example 33. Preparation of Intermediate 51

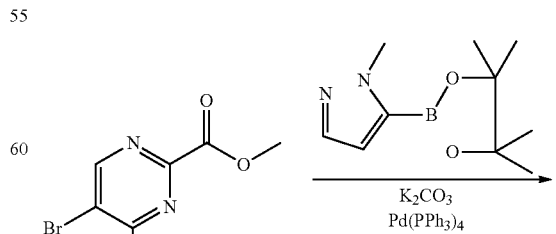

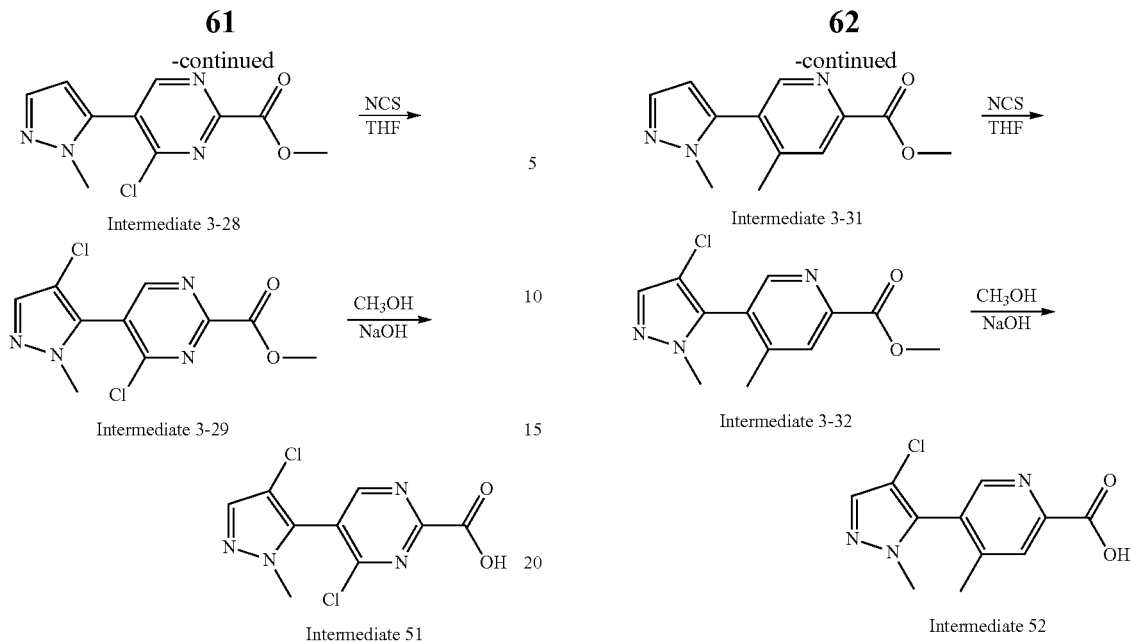

Step 1. Synthesis of 4-chloro-5-(1H-pyrazol-5-yl) pyrimidine-2-methyl formate (Intermediate 3-28)

The synthesis steps refer to Step 1 of Example 1. Intermediate 3-28 (2.2 g, yield of 88%) is prepared from 4-chloro-5-bromopyrimidine-2-methyl formate (Compound 3-27) (2.5 g, 9.9 mmol) with the similar synthesis method as that of Compound 1-2.

Step 2. Synthesis of 4-chloro-5-(4-chloro-1H-pyrazol-5-yl)pyrimidine-2-methyl formate (Intermediate 3-29)

The synthesis steps refer to Step 1 of Example 5. Intermediate 3-29 (2.14 g, yield of 85%) is prepared from 4-chloro-5-(1H-pyrazol-5-yl)pyrimidine-2-methyl formate (Intermediate 3-28) (2.2 g, 8.7 mmol) with the similar synthesis method as that of Intermediate 1-8.

Step 3. Synthesis of 4-chloro-5-(4-chloro-1H-pyrazol-5-yl)pyrimidine-2-formic acid (Intermediate 51)

The synthesis steps refer to Step 2 of Example 1. Intermediate 51 (1.89 g, yield of 93%) is prepared from 4-chloro-5-(4-ch*/6loro-1H-pyrazol-5-yl)pyrimidine-2-methyl formate (Intermediate 3-29) (2.14 g, 7.4 mmol) with the similar synthesis method as that of Intermediate 1.

Example 34. Preparation of Intermediate 52

Step 1. Synthesis of 4-methyl-5-(1H-pyrazol-5-yl) pyridinyl-2-methyl formate (Intermediate 3-31)

The synthesis steps refer to Step 1 of Example 1. Intermediate 3-31 (1.47 g, yield of 81%) is prepared from 4-methyl-5-bromopyridinyl-2-methyl formate (Compound 3-30) (1.8 g, 7.8 mmol) with the similar synthesis method as that of Intermediate 1-2.

Step 2. Synthesis of 4-methyl-5-(4-chloro-1H-pyrazol-5-yl)pyridinyl-2-methyl formate (Intermediate 3-32)

The synthesis steps refer to Step 1 of Example 5. Intermediate 3-32 (1.3 g, yield of 77%) is prepared from 4-methyl-5-(1H-pyrazol-5-yl)pyridinyl-2-methyl formate (Intermediate 3-31) (1.47 g, 6.3 mmol) with the similar synthesis method as that of Intermediate 1-8.

Step 3. Synthesis of 4-methyl-5-(4-chloro-1H-pyrazol-5-yl)pyridinyl-2-formic acid (Intermediate 52)

The synthesis steps refer to Step 2 of Example 1. Intermediate 52 (0.9 g, yield of 73%) is prepared from 4-methyl-5-(4-chloro-1H-pyrazol-5-yl)pyridinyl-2-methyl formate (Intermediate 3-32) (1.3 g, 4.9 mmol) with the similar synthesis method as that of Intermediate 1.

Example 35. Preparation of Intermediate 53

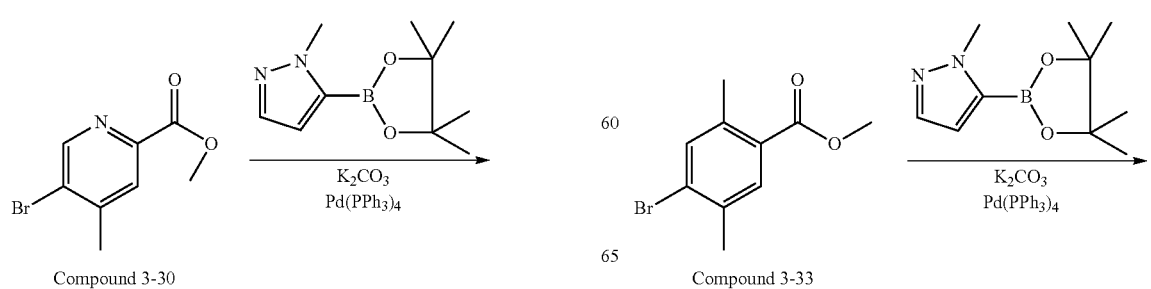

63

-continued

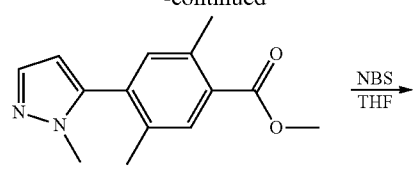

Intermediate 3-34

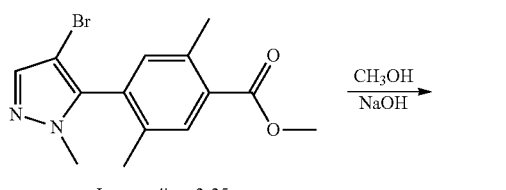

Intermediate 3-35

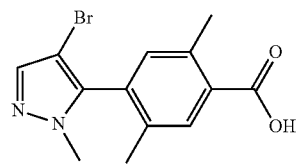

Intermediate 53

Step 1. Synthesis of 2,5-dimethyl-4-(1-methyl-1H-pyrazol-5-yl)phenyl methyl formate (Intermediate 3-34)

The synthesis steps refer to Step 1 of Example 1. Intermediate 3-34 (2.8 g, yield of 90%) is prepared from 2,5-dimethyl-4-bromophenyl methyl formate (Compound 3-33) (3.1 g, 12.7 mmol) with the similar synthesis method as that of Intermediate 1-2.

Step 2. Synthesis of 2,5-dimethyl-4-(4-bromo-1-methyl-1H-pyrazol-5-yl)phenyl methyl formate (Intermediate 3-35)

The synthesis steps refer to Step 1 of Example 3. Intermediate 3-35 (3.18 g, yield of 86%) is prepared from 2,5-dimethyl-4-(1-methyl-1H-pyrazol-5-yl)phenyl methyl formate (Intermediate 3-34) (2.8 g, 11.5 mmol) with the similar synthesis method as that of Intermediate 1-5.

Step 3. Synthesis of 2,5-dimethyl-4-(4-bromo-1-methyl-1H-pyrazol-5-yl)phenyl formic acid (Intermediate 53)

The synthesis steps refer to Step 2 of Example 1. Intermediate 53 (2.7 g, yield of 87%) is prepared from 2,5-dimethyl-4-(4-bromo-1-methyl-1H-pyrazol-5-yl)phenyl methyl formate (Intermediate 3-35) (3.18 g, 9.8 mmol) with the similar synthesis method as that of Intermediate 1.

64

Example 36. Preparation of Intermediate 54

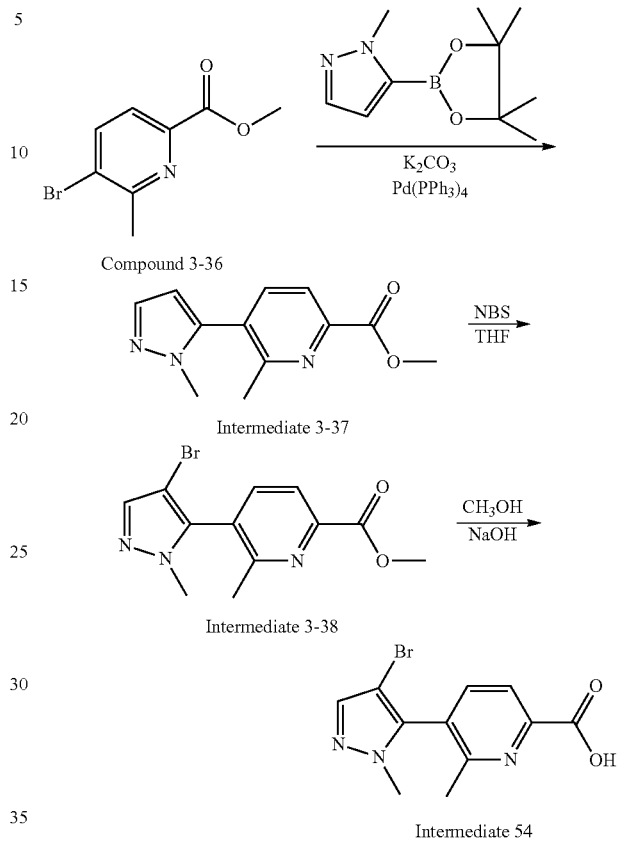

Step 1. Synthesis of 6-methyl-5-(1-methyl-1H-pyrazol-5-yl)pyridinyl-2-methyl formate (Intermediate 3-37)

The synthesis steps refer to Step 1 of Example 1. Intermediate 3-37 (2.1 g, yield of 84%) is prepared from 6-methyl-5-bromopyridinyl-2-methyl formate (Compound 3-36) (2.5 g, 10.8 mmol) with the similar synthesis method as that of Intermediate 1-2.

Step 2. Synthesis of 6-methyl-5-(4-bromo-1-methyl-1H-pyrazol-5-yl)pyridinyl-2-methyl formate (Intermediate 3-38)

The synthesis steps refer to Step 1 of Example 3. Intermediate 3-38 (2.27 g, yield of 81%) is prepared from 6-methyl-5-(1-methyl-1H-pyrazol-5-yl)pyridinyl-2-methyl formate (Intermediate 3-37) (2.1 g, 9.1 mmol) with the similar synthesis method as that of Intermediate 1-5.

Step 3. Synthesis of 6-methyl-5-(4-bromo-1-methyl-1H-pyrazol-5-yl)pyridinyl-2-formic acid (Intermediate 54)

The synthesis steps refer to Step 2 of Example 1. Intermediate 54 (1.9 g, yield of 88%) is prepared from 6-methyl-5-(4-bromo-1-methyl-1H-pyrazol-5-yl)pyridinyl-2-methyl formate (Intermediate 3-38) (2.27 g, 7.3 mmol) with the similar synthesis method as that of Intermediate 1.

Example 37. Preparation of Intermediate 55

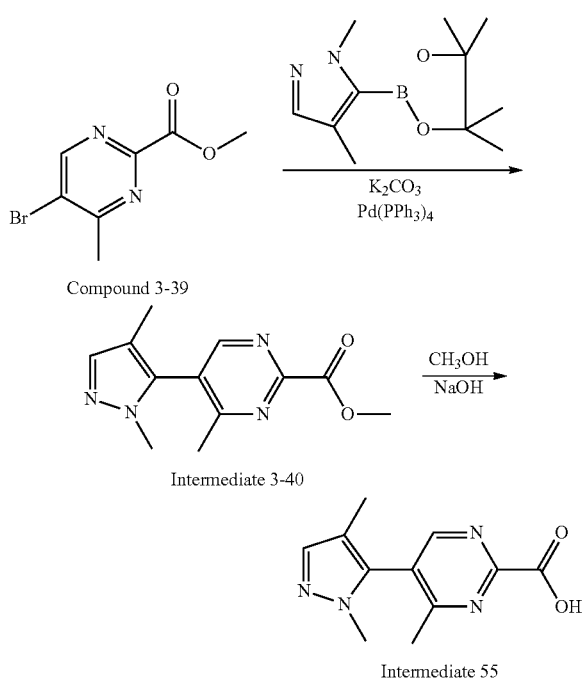

Step 1. Synthesis of 4-methyl-5-(1,4-dimethyl-1H-pyrazol-5-yl)pyrimidine-2-methyl formate (Intermediate 3-40)

The synthesis steps refer to Step 1 of Example 1. Intermediate 3-40 (2.0 g, yield of 89%) is prepared from 4-methyl-5-bromopyrimidine-2-methyl formate (Compound 3-39) (2.1 g, 9.1 mmol) with the similar synthesis method as that of Intermediate 1-2.

Step 2. Synthesis of 4-methyl-5-(1,4-dimethyl-1H-pyrazol-5-yl)pyrimidine-2-formic acid (Intermediate 55)

The synthesis steps refer to Step 2 of Example 1. Intermediate 55 (1.4 g, yield of 74%) is prepared from 4-methyl-5-(1,4-dimethyl-1H-pyrazol-5-yl)pyrimidine-2-methyl formate (Intermediate 3-40) (2.0 g, 8.1 mmol) with the similar synthesis method as that of Intermediate 1.

Example 38. Preparation of Intermediate 56-61

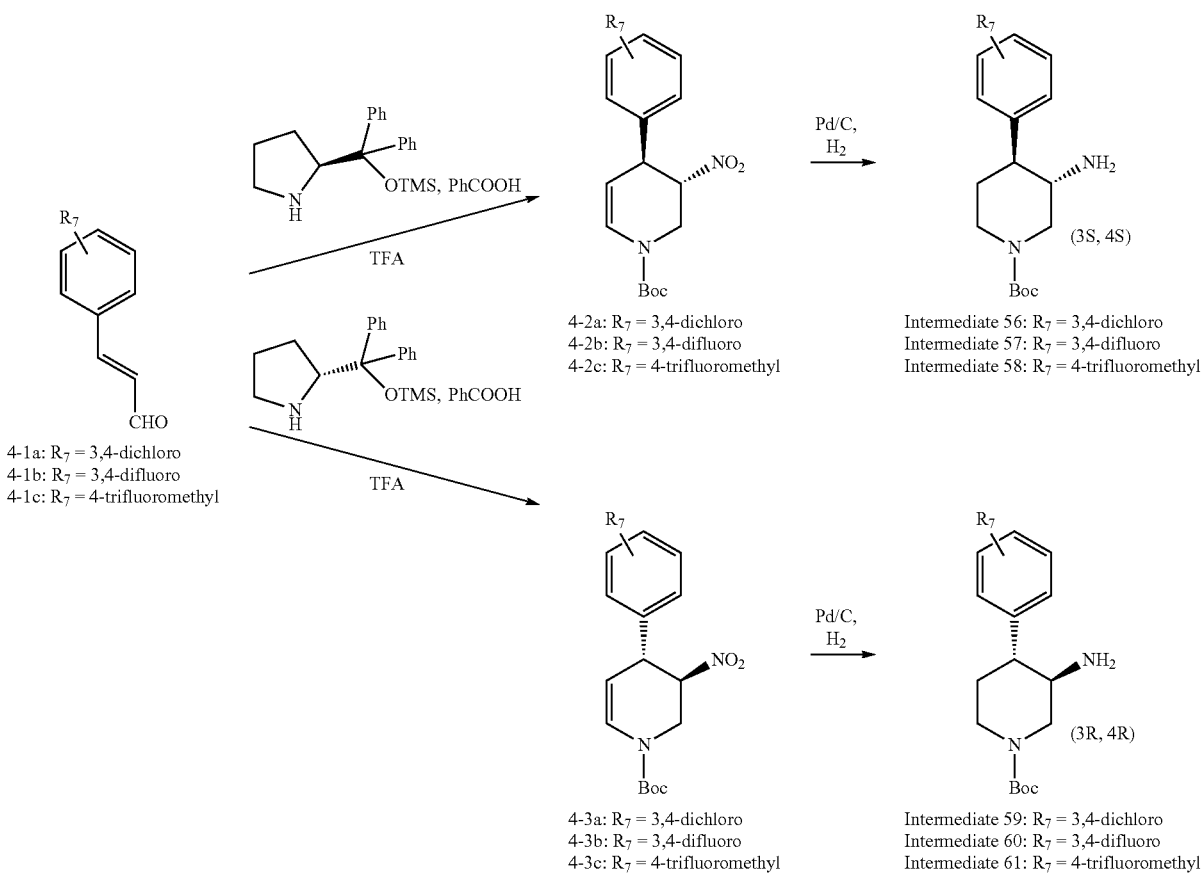

Step 1. Synthesis of Compound 4-2a (Synthesis Methods of Intermediate 4-2b to 4-2c, 4-3a to 4-3c are Shown in Table 4)

Dissolving 2-nitroethyl tert-butyl carbamate (Compound 6-5, 380 mg, 2 mmol), ((S)-(−)-α,α-diphenyl-2-pyrrylmethyl)trimethylsilyl ether (33 mg, 0.1 mmol), and benzoic acid (25 mg, 0.2 mmol) into anhydrous dichloromethane (2 ml), slowly adding Intermediate 4-1a (201 mg, 1 mmol) thereto in an ice bath under the protection of $N_2$, stirring for about 24 h at room temperature, diluting the reaction system with dichloromethane to 10 ml, slowly dropwise adding 200 μl of trifluoroacetic acid into the reaction liquid in an ice bath, and reacting for 5 h at room temperature. Then adding about 10 ml of 1N $NaHCO_3$ solution into the reaction liquid, stirring for 10 min at room temperature, followed by extracting the reaction liquid with ethyl acetate 3 times, washing the merged organic phase with saturated sodium chloride once, drying it with anhydrous sodium sulfate, and purifying by column chromatograph, 270 mg of light yellow oily liquid (Intermediate 4-2a) is obtained and the yield is 72%.

TABLE 4

Synthesis methods of Intermediate 4-2b to 4-2c, 4-3a to 4-3c

| Reactant | Amount of the reactant | Synthesis method | Product | Yield |
|---|---|---|---|---|
| 4-1a | 14.3 g, 71 mmol | Similar to the synthesis method of Intermediate 4-2a | 4-3a | 16.6 g, 63% |
| 4-1b | 12.7 g, 76 mmol | Similar to the synthesis method of Intermediate 4-2a | 4-2b | 15.7 g, 61% |
| 4-1b | 11.8 g, 70 mmol | Similar to the synthesis method of Intermediate 4-2a | 4-3b | 12.9 g, 54% |
| 4-1c | 8.7 g, 43 mmol | Similar to the synthesis method of Intermediate 4-2a | 4-2c | 11.8 g, 73% |
| 4-1c | 6.9 g, 34 mmol | Similar to the synthesis method of Intermediate 4-2a | 4-3c | 9.0 g, 70% |

Step 2. Synthesis of Intermediate 56 (Synthesis Methods of Intermediate 56-61 are Shown in Table 5)

Dissolving Intermediate 4-2a (186 mg, 0.5 mmol) into methanol (10 ml), adding 30 mg of 10% Pd/C thereto, and hydrogenating overnight at room temperature (monitoring the reaction with TLC thin-layer chromatography for whether is completed). After the reaction is completed, filtering to remove black insoluble substance from the reaction mixture, and spin drying under reduced pressure, 120 mg of oily liquid (Intermediate 56) is obtained and the yield is 70%.

TABLE 5

Synthesis methods of Intermediate 56-61

| Reactant | Amount of the reactant | Synthesis method | Product | Yield |
|---|---|---|---|---|
| 4-2b | 16.6 g, 44.5 mmol | Similar to the synthesis method of Intermediate 56 | Intermediate 57 | 13.8 g, 90% |
| 4-2c | 15.7 g, 46.2 mmol | Similar to the synthesis method of Intermediate 56 | Intermediate 58 | 11.8 g, 82% |
| 4-3a | 12.9 g, 37.9 mmol | Similar to the synthesis method of Intermediate 56 | Intermediate 59 | 8.9 g, 75% |
| 4-3b | 11.8 g, 32 mmol | Similar to the synthesis method of Intermediate 56 | Intermediate 60 | 9.5 g, 86% |
| 4-3c | 9.0 g, 24 mmol | Similar to the synthesis method of Intermediate 56 | Intermediate 61 | 6.5 g, 79% |

Example 39. Preparation of Intermediate 62 and Intermediate 63

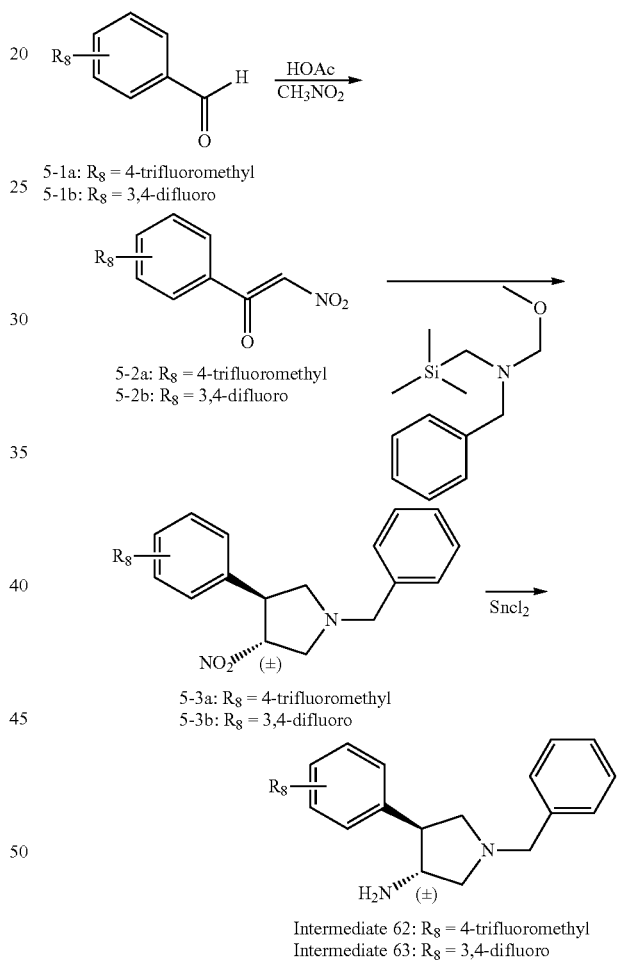

5-1a: $R_8$ = 4-trifluoromethyl
5-1b: $R_8$ = 3,4-difluoro 5-2a: $R_8$ = 4-trifluoromethyl
5-2b: $R_8$ = 3,4-difluoro 5-3a: $R_8$ = 4-trifluoromethyl
5-3b: $R_8$ = 3,4-difluoro Intermediate 62: $R_8$ = 4-trifluoromethyl
Intermediate 63: $R_8$ = 3,4-difluoro

Step 1. Synthesis of Intermediate 5-2b and Compound 5-2a

Dissolving Compound 5-1b of 3,4-difluorobenzaldehyde (5.5 ml, 50 mmol), nitromethane (22.5 ml, 420 mmol), and ammonium acetate (9.85 g, 128 mmol) in glacial acetic acid (70 ml), heating to 90° C. and reacting for 3 h, monitoring the reaction with TLC thin-layer chromatography for whether it is completed. Adding water (20 ml) into the reaction liquid after the reaction is completed, neutralizing glacial acetic acid in the reaction liquid with $Na_2CO_3$ to a pH of about 7, extracting the reaction liquid with ethyl acetate 3 times, washing the merged organic phase with saturated sodium chloride once, and drying it with anhydrous sodium sulfate. Recycling the solvent under reduced pressure. Carrying out column chromatography on silica gel (eluent: petroleum ether:ethyl acetate=10:1), 7.0 g of yellow solid (Intermediate 5-2b) is obtained. The yield is 85%.

Synthesis steps of Intermediate 5-2a (21 g, yield of 80%) refer to the synthesis method of Compound 5-2b in Step 1 of Example 39, in which Intermediate 5-2a is prepared from 4-trifluoromethylbenzaldehyde (Compound 5-1a) (20 g, 114.9 mmol).

Step 2. Synthesis of Intermediate 5-3b, 5-3a

Dissolving Intermediate 5-2b (501 mg, 2.71 mmol) and trifluoroacetic acid (0.02 mL, 0.271 mmmol) into dichloromethane (10 ml), slowly dropwise adding dichloromethane solution (10 ml) dissolved with N-methoxymethyl-N-(trimethylsilane methyl)benzylamine (1.0 ml, 5.42 mmol) thereto at 0° C. under the protection of $N_2$, and stirring overnight at room temperature. After the reaction is completed, adding 10 ml of water to the reaction liquid, extracting the reaction liquid with ethyl acetate 3 times, washing the merged organic phase with saturated sodium chloride once, and drying it with anhydrous sodium sulfate. Recycling the solvent under reduced pressure. Purifying by column chromatography on silica gel (eluent: petroleum ether:ethyl acetate=9:1), 603 mg of yellow-green semi-solid (Intermediate 5-3b) is obtained. The yield is 81%.

Synthesis steps of Intermediate 5-3a refer to that of Compound 5-3b in Step 2 of Example 39, in which Intermediate 5-3a (14.5 g, yield of 44%) is prepared from Intermediate 5-2a (21 g, 90.5 mmol).

Step 3. Synthesis of Intermediate 63 and Intermediate 62

Dissolving Intermediate 5-3b (302 mg, 0.95 mmol) and anhydrous stannous chloride (1.07 mg, 4.75 mmmol) into ethyl acetate (10 ml), raising temperature to 50° C. and reacting for 2 h. After the reaction is completed, adding saturated $NaHCO_3$ solution (10 ml) to the reaction liquid, extracting the reaction liquid with ethyl acetate 3 times, washing the merged organic phase with saturated sodium chloride once, and drying it with anhydrous sodium sulfate. Recycling the solvent under reduced pressure. Purifying by column chromatography on silica gel (eluent: petroleum ether:ethyl acetate=9:1, and then increase the polarity to ethyl acetate:methanol=20:1), 123 mg of oily liquid (Intermediate 63) is obtained and the yield is 61%.

Synthesis steps of Intermediate 62 refer to that of Intermediate 63 in Step 3 of Example 39, in which Intermediate 62 (8.6 g, yield of 68%) is prepared from Intermediate 5-3a (14.5 g, 39.7 mmol).

Example 40. Preparation of Intermediate 64-70

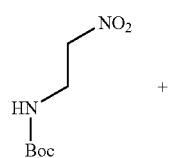

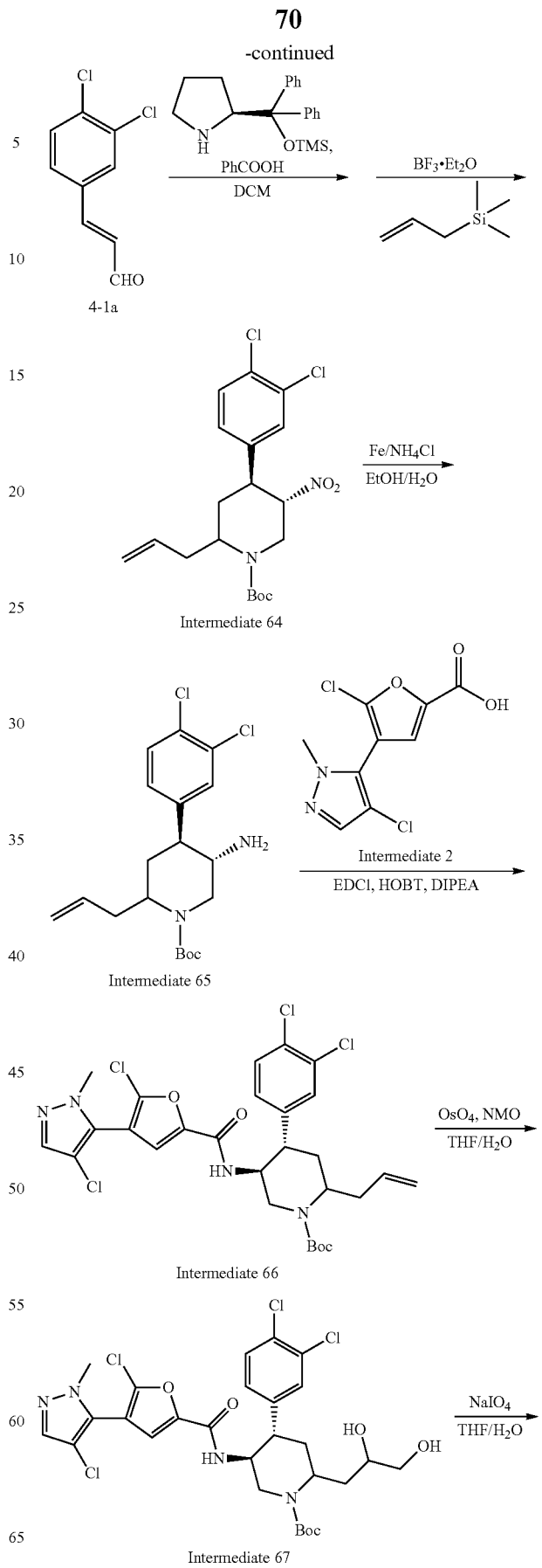

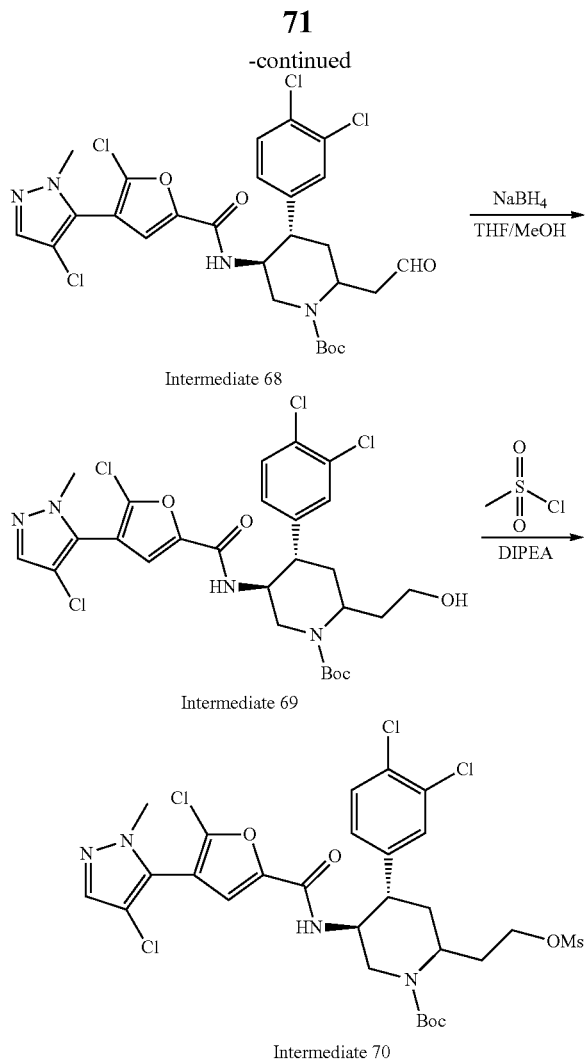

Intermediate 68

Intermediate 69

Intermediate 70

Step 1. Synthesis of Intermediate 64

Dissolving 2-nitroethyl tert-butyl carbamate (Compound 6-5, 2.85 g, 15 mmol), ((S)-(−)-α,α-diphenyl-2-pyrrylmethyl)trimethylsilyl ether (0.36 g, 1.1 mmol), and benzoic acid (0.25 g, 2 mmol) in anhydrous dichloromethane (15 ml), slowly adding Compound 4-1a (2.01 g, 10 mmol) in an ice bath under the protection of $N_2$, stirring for about 18 h at room temperature, and diluting the reaction system with dichloromethane to 100 ml. Adding allyltrimethylsilane (5 ml, 30 mmol) into the reaction liquid in an ice bath, decreasing the temperature of the reaction system to −78° C., slowly dropwise adding 2.5 ml of aether boron trifluoride, continue to react for 10 h. Adding about 100 ml of 1N $NaHCO_3$ solution into the reaction liquid, stirring for 10 min at room temperature, and then extracting the reaction liquid with ethyl acetate 3 times, washing the merged organic phase with saturated sodium chloride once, and drying it with anhydrous sodium sulfate. Passing through silica gel column, 2.1 g of white solid (Intermediate 64) is obtained and the yield is 50.9%; $^1$H NMR (500 MHz, CDCl$_3$) δ7.39 (d, J=8.3 Hz, 1H), 7.29 (d, J=1.7 Hz, 1H), 7.04 (dd, J=8.3, 1.7 Hz, 1H), 5.81-5.67 (m, 1H), 5.16 (d, J=17.1 Hz, 1H), 5.10 (d, J=9.9 Hz, 1H), 4.77-4.35 (m, 3H), 3.46 (dd, J=17.1, 11.2 Hz, 1H), 3.38-3.20 (m, 1H), 2.63-2.51 (m, 1H), 2.46-2.31 (m, 1H), 1.96-1.82 (m, 2H), 1.48 (s, 9H).

Step 2. Synthesis of Intermediate 65

Dissolving Intermediate 64 (2.10 g, 5 mmol) into the mixed solution of anhydrous ethanol (40 ml) and water (10 ml), adding iron powder (2.3 g, 40 mmol), and ammonium chloride (0.8, 15 mmol) thereto, after the protection of $N_2$, reacting for 2 h under heating reflux with mechanical stirring, performing suction filtration and spin dry, adding 60 ml of saturated $Na_2CO_3$ solution, washing with ethyl acetate 3 times and then with saturated sodium chloride once, and drying it with anhydrous sodium sulfate. Recycling the solvent under reduced pressure, 1.6 g of light yellow solid (Intermediate 65) is obtained and the yield is 83.1%.

Step 3. Synthesis of Intermediate 66

Dissolving Intermediate 65 (0.82 g, 3.14 mmol), 1-hydroxybenzotriazole (HOBT) (0.76 g, 5.65 mmol) and 1-ethyl-(3-dimethylaminopropyl)carbodiimide hydrochloride EDC.HCl (1.1 g, 5.65 mmol) in anhydrous dichloromethane (50 ml), after stirring for 10 min in an ice bath, adding diisopropylethylamine (1.4 ml, 7.85 mmol), continue stirring for 30 min in an ice bath, slowly adding dichloromethane solution (10 ml) dissolved with Intermediate 3 (1.2 g, 3.14 mmol), and stirring overnight at room temperature. Pouring the reaction liquid to 100 ml of saturated $Na_2CO_3$ solution, extracting the reaction liquid with dichloromethane 3 times, washing the merged organic phase with saturated sodium chloride once, drying it with anhydrous sodium sulfate, recycling the solvent under reduced pressure, carrying out column chromatography on silica gel, 1.43 g of white powder (Intermediate 66) is obtained and the yield is 73.2%; $^1$H NMR (500 MHz, CDCl$_3$) δ7.48 (s, 1H), 7.38 (d, J=8.2 Hz, 1H), 7.34 (d, J=1.8 Hz, 1H), 7.12 (d, J=8.2 Hz, 2H), 6.04 (s, 1H), 5.84-5.71 (m, 1H), 5.14 (d, J=17.0 Hz, 1H), 5.08 (d, J=10.1 Hz, 1H), 4.57-4.27 (m, 2H), 4.26-4.16 (m, 1H), 3.76 (s, 3H), 3.12-2.94 (m, 1H), 2.89 (t, J=12.0 Hz, 1H), 2.58-2.47 (m, 1H), 2.45-2.30 (m, 1H), 1.94-1.79 (m, 2H), 1.48 (s, 9H).

Step 4. Synthesis of Intermediate 67

Dissolving Intermediate 66 (280 mg, 0.45 mmol) in the mixed solution of tetrahydrofuran (12 ml) and water (4 ml), adding N-methylmorpholine nitrogen oxide (105 mg, 9 mmol) and osmium tetroxide (6 mg, 0.02 mmol) thereto, stirring overnight at room temperature, pouring the reaction liquid into 30 ml of saturated sodium thiosulfate solution, extracting the reaction liquid with ethyl acetate 3 times, washing with saturated sodium chloride once, drying it with anhydrous sodium sulfate, 288.1 mg of white solid (Intermediate 67) is obtained by spin drying and the yield is 98.2%; $^1$H NMR (500 MHz, CDCl$_3$) δ7.49 (s, 1H), 7.40 (d, J=8.2 Hz, 1H), 7.35 (s, 1H), 7.16-7.10 (m, 2H), 6.00 (d, J=6.9 Hz, 1H), 4.68-4.61 (m, 1H), 4.41-4.33 (m, 1H), 4.30-4.20 (m, 1H), 3.77 (s, 3H), 3.67-3.47 (m, 3H), 3.04-2.94 (m, 1H), 2.86-2.76 (m, 1H), 2.11-2.00 (m, 2H), 1.83 (d, J=13.6 Hz, 2H), 1.50 (s, 9H).

Step 5. Synthesis of Intermediate 68

Dissolving Intermediate 67 (288 mg, 0.43 mmol) in the mixed solution of tetrahydrofuran (6 ml) and water (2 ml), adding sodium periodate (171 mg, 0.8 mmol) thereto, stirring for 2 h at room temperature, adding 10 ml of saturated sodium chloride solution into the reaction liquid for diluting, extracting the reaction liquid with ethyl acetate 3 times, merging the organic layer, and drying it with anhydrous sodium sulfate, 257 mg of white solid (Intermediate 68) is obtained after spin drying, and the yield is 93.5%; $^1$H NMR (500 MHz, CDCl$_3$) δ9.79 (s, 1H), 7.49 (s, 1H), 7.39 (d, J=8.0 Hz, 1H), 7.34 (d, J=1.8 Hz, 1H), 7.15-7.10 (m, 2H), 6.11 (s, 1H), 5.13-4.86 (m, 1H), 4.54-4.28 (m, 1H), 4.27-4.15 (m, 1H), 3.76 (s, 3H), 3.11-2.86 (m, 3H), 2.75-2.69 (m, 1H), 2.03-1.97 (m, 1H), 1.88-1.85 (m, 1H), 1.48 (s, 9H).

Step 6. Synthesis of Intermediate 69

Dissolving Intermediate 68 (200 mg, 0.32 mmol) in the mixed solution of tetrahydrofuran (5 ml) and water (0.5 ml), slowly adding sodium borohydride (24 mg, 0.64 mmol) under an ice bath, reacting for 2 h at room temperature, slowly dropwise adding 6 ml of saturated ammonium chloride solution to the reaction liquid, extracting the reaction liquid with ethyl acetate 3 times, merging the organic layer, washing with saturated sodium chloride twice, and drying it with anhydrous sodium sulfate, 183 mg of white solid (Intermediate 69) is obtained after spin drying, and the yield is 92.6%; $^1$H NMR (500 MHz, CDCl$_3$) δ7.49 (s, 1H), 7.40 (d, J=8.3 Hz, 1H), 7.36 (d, J=1.6 Hz, 1H), 7.16-7.11 (m, 2H), 6.01 (d, J=8.0 Hz, 1H), 4.66-4.58 (m, 1H), 4.40-4.32 (m, 1H), 4.28-4.17 (m, 1H), 3.76 (s, 3H), 3.69 (d, J=11.3 Hz, 1H), 3.41 (t, J=11.3 Hz, 1H), 2.99 (t, J=11.0 Hz, 1H), 2.81 (t, J=12.1 Hz, 1H), 2.11-2.00 (m, 3H), 1.84 (d, J=12.1 Hz, 1H), 1.71 (d, J=12.1 Hz, 1H), 1.50 (s, 9H).

Step 7. Synthesis of Intermediate 70

Dissolving Intermediate 69 (100 mg, 0.16 mmol) in anhydrous dichloromethane (5 ml), adding diisopropylethylamine (0.083 ml, 0.48 mmol) and methylsulfonyl chloride (0.031 ml, 0.40 mmol) under an ice bath, and reacting for 2 h at room temperature. Adding 15 ml of saturated NaHCO$_3$ solution to the reaction liquid, extracting thereof with dichloromethane twice, merging the organic layer, washing with saturated sodium chloride twice, and drying it with anhydrous sodium sulfate, 92 mg of white solid (Intermediate 70) is obtained after spin drying and carrying out column chromatography, and the yield is 81.2%; $^1$H NMR (500 MHz, CDCl$_3$) δ7.49 (s, 1H), 7.39 (d, J=8.3 Hz, 1H), 7.36 (d, J=1.9 Hz, 1H), 7.15-7.12 (m, 2H), 6.06 (s, 1H), 4.67-4.33 (m, 2H), 4.33-4.22 (m, 2H), 4.22-4.12 (m, 1H), 3.77 (s, 3H), 3.14-2.96 (m, 4H), 2.91 (t, J=12.2 Hz, 1H), 2.41-2.30 (m, 1H), 2.02-1.91 (m, 2H), 1.85 (d, J=12.6 Hz, 1H), 1.50 (s, 9H).

Example 41. Preparation of 4-(1-methyl-1H-pyrazol-5-yl)-N-(3,4-trans-4-phenylpiperidin-3-yl)furan-2-formamide (Compound 1)

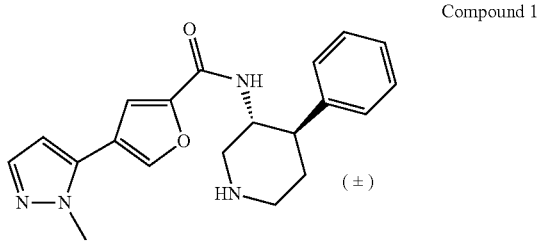 [SMILES: Cn1nccc1-c1coc(C(=O)N[C@H]2CNCC[C@@H]2c2ccccc2)c1]

Compound 1

Dissolving 4-(1-methyl-1H-pyrazol-5-yl)furan-2-formic acid (Intermediate 1, 66.2 mg, 0.345 mmol), 1-hydroxybenzotriazole (HOBT) (78.62 mg, 0.517 mmol) and 1-ethyl-(3-dimethylaminopropyl)carbodiimide hydrochloride (EDC.HCl, 98.8 mg, 0.517 mmol) in anhydrous dichloromethane (4 ml), after stirring for 10 min in an ice bath, adding diisopropylethylamine (0.115 ml, 1.21 mmol), continue stirring for 30 min in an ice bath, and slowly adding dichloromethane solution (4 ml) dissolved with 3,4-trans-1-benzyl-4-phenyl-3-amino piperidine (Intermediate 23, 82.8 mg, 0.31 mmol). Stirring overnight at room temperature overnight, monitor the reaction with TLC thin-layer chromatography for whether it is completed. After the reaction is completed, extracting the reaction liquid with dichloromethane 3 times, washing the merged organic phase with saturated sodium chloride once, drying it with anhydrous sodium sulfate, and recycling the solvent under reduced pressure. Dissolving the above recovered mixture into 1,2-dichloroethane (5 ml), slowly adding chloroethyl chloroformate (196 mg, 1.38 mmol) thereto, refluxing for 4 h, monitor the reaction with TLC thin-layer chromatography for whether it is completed, after the reaction is completed, recycling the solvent, adding 5 ml of methanol, and refluxing for 2 h. Recycling methanol, wash with saturated NaHCO$_3$ solution once, extracting the reaction liquid with ethyl acetate twice, merging the organic phase, and drying it with anhydrous sodium sulfate. Carrying out column chromatography on silica gel (ethyl acetate:methanol:triethylamine=10:1:0.1), 32 mg of light yellow oily liquid (Compound 1) is obtained and the yield is 21.5%; $^1$H NMR (500 MHz, d-DMSO) δ 8.51-8.54 (d, J=11.35 Hz, 1H), 8.17 (s, 1H), 7.40 (s, 1H), 7.17-7.33 (m, 6H), 6.45 (s, 1H), 4.55 (m, 1H), 4.21 (s, 2H), 3.87 (s, 3H), 3.38 (m, 2H), 2.93-3.07 (m, 3H), 1.96 (m, 2H); ESI (M+H)$^+$=351.

Example 42. Preparation of 5-chloro-4-(4-chloro-1-methyl-1H-pyrazol-5-yl)-N-(3,4-trans-4-(4-chlorphenyl)piperidin-3-yl)furan-2-formamide (Compound 2)

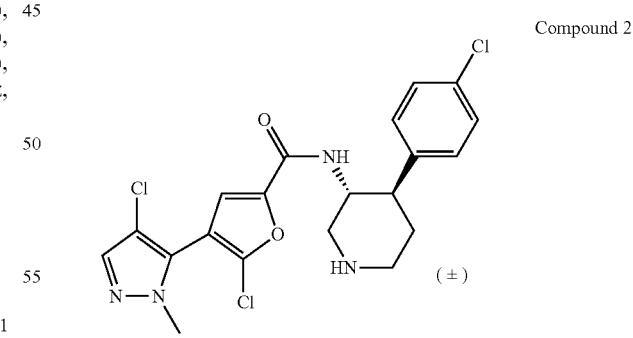

Compound 2

By using Intermediate 2 and Intermediate 24 as raw materials, the target product is synthesized and obtained according to the synthesis methods as in Example 41, the yield is 26.6%; $^1$H NMR (500 MHz, d-DMSO) δ 8.75-8.77 (d, J=10.90 Hz, 1H), 7.68 (s, 1H), 7.46 (s, 1H), 7.35-7.37 (d, J=10.25 Hz, 2H), 7.28-7.30 (d, J=10.25 Hz, 2H), 4.54 (m, 1H), 4.22 (s, 2H), 3.74 (s, 3H), 3.39 (m, 2H), 3.08 (m, 2H), 2.96 (m, 1H), 1.96 (m, 2H); ESI (M+H)$^+$=453.

Example 43. 5-bromo-4-(1-methyl-1H-1,2,4-triazol-5-yl)-N-(3,4-trans-4-(4-trifluoromethylphenyl)piperidin-3-yl)furan-2-formamide (Compound 3)

Compound 3

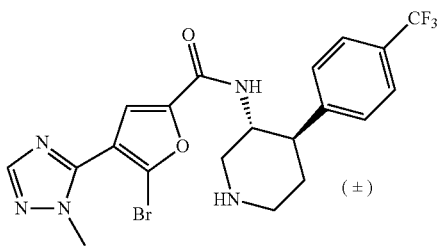

By using Intermediate 16 and Intermediate 25 as raw materials, the target product is prepared and obtained according to the methods as in Example 41; the yield is 29.1%; ESI (M+H)$^+$=498.

Example 44. 5-bromo-3-ethyl-1-methyl-4-(1-methyl-1H-1,2,4-triazol-5-yl)-N-(3,4-trans-4-(3-trifluoromethylphenyl)piperidin-3-yl)-1H-pyrrole-2-formamide (Compound 4)

Compound 4

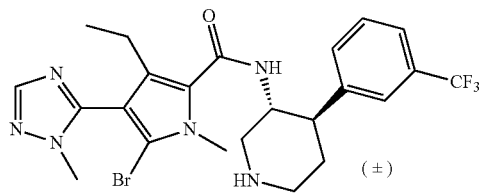

By using Intermediate 17 and Intermediate 26 as raw materials, the target product is prepared and obtained according to the methods as in Example 41; the yield is 35.5%; ESI (M+H)$^+$=539.

Example 45. 5-methyl-4-(4-chloro-1-methyl-1H-pyrazol-5-yl)-N-(3,4-trans-4-(3,4-difluorophenyl)piperidin-3-yl)thiophene-2-formamide (Compound 5)

Compound 5

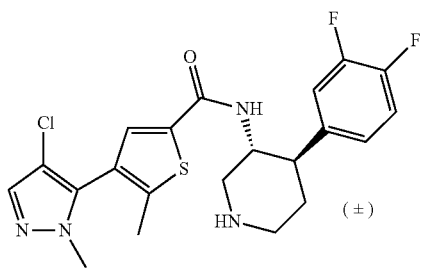

By using Intermediate 8 and Intermediate 27 as raw materials, the target product is prepared and obtained according to the methods as in Example 41; the yield is 29.2%; ESI (M+H)$^+$=451.

Example 46. 5-methyl-4-(4-bromo-1-methyl-1H-pyrazol-5-yl)-N-(3,4-trans-4-(pyridin-4-yl)piperidin-3-yl)-1H-pyrrole-2-formamide (Compound 6)

Compound 6

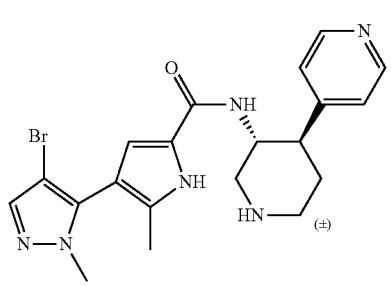

By using Intermediate 11 and Intermediate 32 as raw materials, the target product is prepared and obtained according to the methods as in Example 41; the yield is 33.1%; ESI (M+H)$^+$=443.

Example 47. 4-chloro-5-(1-methyl-1H-1,2,4-triazol-5-yl)-N-(3,4-trans-4-(3-methylphenyl) piperidin-3-yl)furan-2-formamide (Compound 7)

Compound 7

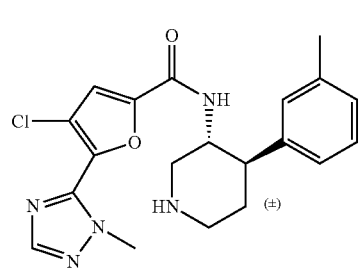

By using Intermediate 19 and Intermediate 28 as raw materials, the target product is prepared and obtained according to the methods as in Example 41; the yield is 34.1%; ESI (M+H)$^+$=400.

Example 48. 4-chloro-5-(1-methyl-1H-1,2,4-triazol-5-yl)-N-(3,4-trans-4-(4-(1-chloroethyl) phenyl)piperidin-3-yl)thiophene-2-formamide (Compound 8)

Compound 8

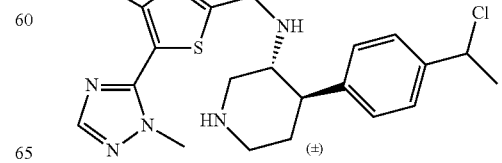

By using Intermediate 20 and Intermediate 31 as raw materials, the target product is prepared and obtained according to the methods as in Example 41; the yield is 38.2%; ESI (M+H)$^+$=464.

Example 49. 5-methyl-4-(4-isopropyl-1-methyl-1H-pyrazol-5-yl)-N-(3,4-trans-4-(quinolin-3-yl)piperidin-3-yl)thiophene-2-formamide (Compound 9)

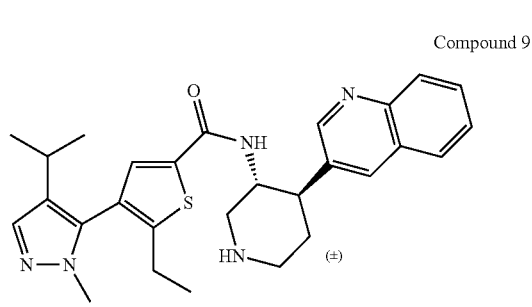 [SMILES: CCc1sc(C(=O)N[C@H]2CNCC[C@@H]2c2cnc3ccccc3c2)cc1-c1c(C(C)C)cnn1C]

Compound 9

By using Intermediate 9 and Intermediate 33 as raw materials, the target product is prepared and obtained according to the methods as in Example 41; the yield is 36.8%; ESI (M+H)$^+$=488.

Example 50. 5-methyl-4-(1-methyl-4-bromo-1H-pyrazol-5-yl)-N-(3,4-trans-4-(3-cyanophenyl)piperidin-3-yl)-1H-pyrrole-2-formamide (Compound 10)

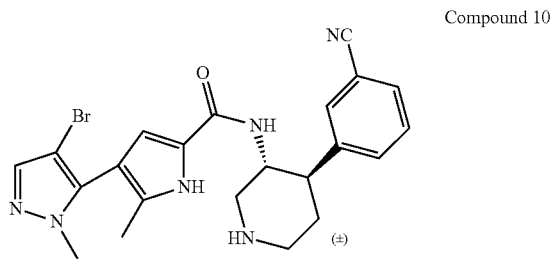 [SMILES: Cc1[nH]c(C(=O)N[C@H]2CNCC[C@@H]2c2cccc(C#N)c2)cc1-c1c(Br)cnn1C]

Compound 10

By using Intermediate 11 and Intermediate 29 as raw materials, the target product is prepared and obtained according to the methods as in Example 41; the yield is 33.6%; ESI (M+H)$^+$=467.

Example 51. 4-chloro-5-(1-methyl-1H-1,2,4-triazol-5-yl)-N-(3,4-trans-4-(3,5-dimethoxyphenyl)piperidin-3-yl)furan-2-formamide (Compound 11)

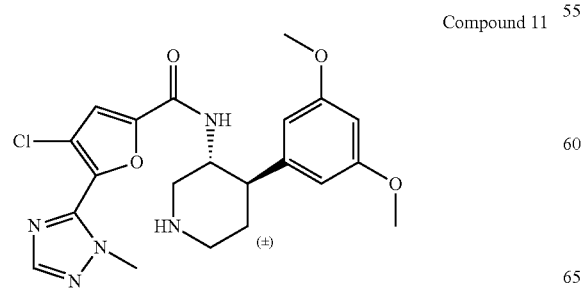

Compound 11

By using Intermediate 19 and Intermediate 30 as raw materials, the target product is prepared and obtained according to the methods as in Example 41; the yield is 37.2%; ESI (M+H)$^+$=446.

Example 52. 4-chloro-5-(1-methyl-4-bromo-1H-pyrazol-5-yl)-N-(3,4-trans-4-(1H-pyrrol-2-yl)piperidin-3-yl)furan-2-formamide (Compound 12)

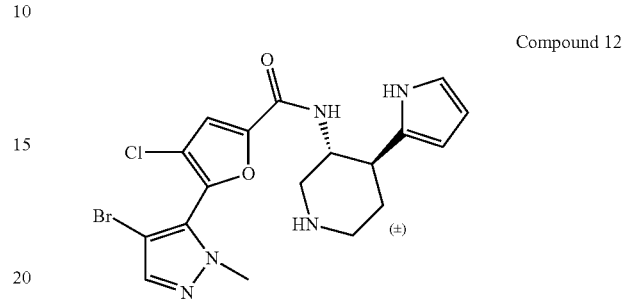

Compound 12

By using Intermediate 21 and Intermediate 35 as raw materials, the target product is prepared and obtained according to the methods as in Example 41; the yield is 28.4%; ESI (M+H)$^+$=452.

Example 53. 4-methyl-5-(1-methyl-1H-1,2,4-triazol-5-yl)-N-(3,4-trans-4-(1H-indol-2-yl) piperidin-3-yl) furan-2-formamide (Compound 13)

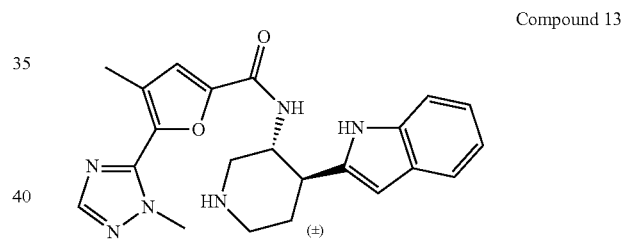

Compound 13

By using Intermediate 20 and Intermediate 36 as raw materials, the target product is prepared and obtained according to the methods as in Example 41; the yield is 35.1%; ESI (M+H)$^+$=405.

Example 54. 5-ethyl-4-(4-isopropyl-1-methyl-1H-pyrazol-5-yl)-N-(3,4-trans-4-(7-methyl-5,6,7,8-tetrahydroquinolin-3-yl)piperidin-3-yl)thiophene-2-formamide (Compound 14)

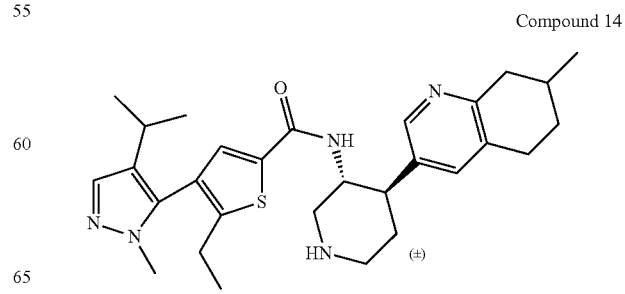

Compound 14

By using Intermediate 9 and Intermediate 34 as raw materials, the target product is prepared and obtained according to the methods as in Example 41; the yield is 32.9%; ESI (M+H)$^+$=506.

Example 55. 5-ethyl-1-methyl-4-(4-chloro-1-methyl-1H-pyrazol-5-yl)-N-(3,4-trans-4-(3-fluorocyclopentanyl)piperidin-3-yl)-1H-pyrrole-2-formamide (Compound 15)

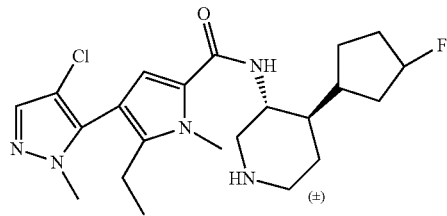

Compound 15

By using Intermediate 12 and Intermediate 37 as raw materials, the target product is prepared and obtained according to the methods as in Example 41; the yield is 39.0%; ESI (M+H)$^+$=436.

Example 56. 5-bromo-4-(1,4-dimethyl-1H-pyrazol-5-yl)-N-(3,4-trans-4-(4-methylcyclohexane)piperidin-3-yl)-1H-pyrrole-2-formamide (Compound 16)

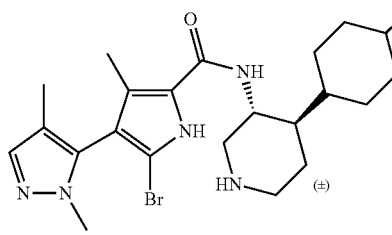

Compound 16

By using Intermediate 13 and Intermediate 38 as raw materials, the target product is prepared and obtained according to the methods as in Example 41; the yield is 28.1%; ESI (M+H)$^+$=540.

Example 57. 5-ethyl-1-methyl-4-(4-ethyl-1-methyl-1H-pyrazol-5-yl)-N-(3,4-trans-4-(piperidin-3-yl) piperidin-3-yl)-1H-pyrrole-2-formamide (Compound 17)

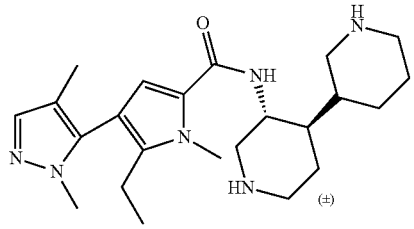

Compound 17

By using Intermediate 14 and Intermediate 39 as raw materials, the target product is prepared and obtained according to the methods as in Example 41; the yield is 27.6%; ESI (M+H)$^+$=427.

Example 58. 5-chloro-3-methyl-4-(1-methyl-1H-1,2,4-triazol-5-yl)-N-(3,4-trans-4-(5-chloropiperidin)piperidin-3-yl)thiophene-2-formamide (Compound 18)

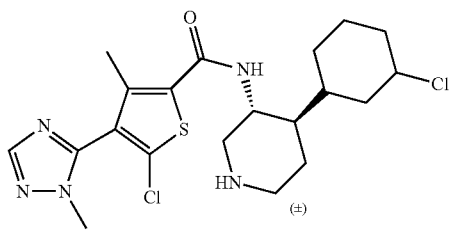

Compound 18

By using Intermediate 18 and Intermediate 40 as raw materials, the target product is prepared and obtained according to the methods as in Example 41; the yield is 24.1%; ESI (M+H)$^+$=456.

Example 59. 4-(1-methyl-1H-pyrazol-5-yl)-N-(3,4-trans-4-phenylpiperidin-3-yl)oxazole-2-formamide (Compound 19)

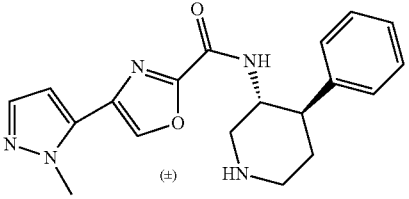

Compound 19

By using Intermediate 15 and Intermediate 23 as raw materials, the target product is prepared and obtained according to the methods as in Example 41; the yield is 34.7%; ESI (M+H)$^+$=352.

Example 60. 4-(4-chloro-1-methyl-1H-pyrazol-5-yl)-N-(3,4-trans-4-(3,4-difluorophenyl) piperidin-3-yl)-5-methylthiazole-2-formamide (Compound 20)

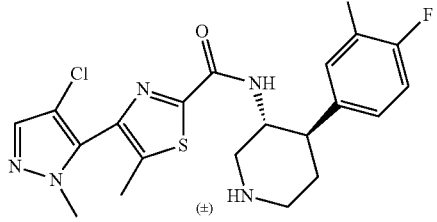

Compound 20

By using Intermediate 10 and Intermediate 27 as raw materials, the target product is prepared and obtained according to the methods as in Example 41; the yield is 26.9%; ESI (M+H)+=452.

Example 61. 4-(1-methyl-1H-pyrazol-5-yl)-N-(3,4-trans-4-(3,4-difluorophenyl)piperidin-3-yl)furan-2-formamide (Compound 21)

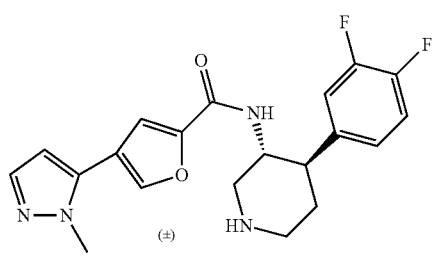

Compound 21

By using Intermediate 1 and Intermediate 27 as raw materials, the target product is prepared and obtained according to the methods as in Example 41; the yield is 31.6%; $^1$H NMR (500 MHz, d-DMSO) δ 8.61 (d, J=10.75 Hz, 1H), 8.20 (s, 1H), 7.92 (d, J=15.75 Hz, 1H), 7.21-7.41 (m, 3H), 7.11 (m, 1H), 6.48 (s, 1H), 4.49 (m, 1H), 4.18 (s, 2H), 3.88 (s, 3H), 3.35 (m, 2H), 3.08 (m, 1H), 2.94 (m, 1H), 2.85 (m, 1H), 1.97 (m, 2H); ESI (M+H)+=387.

Example 62. 4-(4-bromo-1-methyl-1H-pyrazol-5-yl)-N-(3,4-trans-4-phenylpiperidin-3-yl) furan-2-formamide (Compound 22)

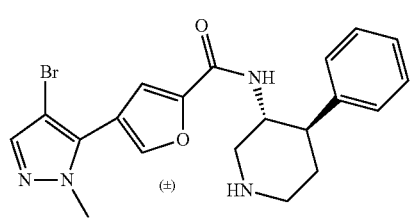

Compound 22

By using Intermediate 4 and Intermediate 23 as raw materials, the target product is prepared and obtained according to the methods as in Example 41; the yield is 26.5%; $^1$H NMR (500 MHz, d-DMSO) δ 8.54-8.56 (d, J=8.55 Hz, 1H), 8.22 (s, 1H), 7.62 (s, 1H), 7.34 (s, 1H), 7.16-7.30 (m, 6H), 4.50 (m, 1H), 4.05 (s, 2H), 3.82 (s, 3H), 3.34 (m, 2H), 3.04 (m, 1H), 2.94 (m, 1H), 2.85 (m, 1H), 1.98 (m, 1H), 1.86 (m, 1H); ESI (M+H)+=429.

Example 63. 4-(4-chloro-1-methyl-1H-pyrazol-5-yl)-N-(3,4-trans-4-(4-chlorphenyl) piperidin-3-yl)furan-2-formamide (Compound 23)

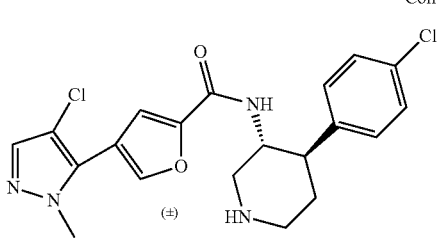

Compound 23

By using Intermediate 3 and Intermediate 24 as raw materials, the target product is prepared and obtained according to the methods as in Example 41; the yield is 29.5%; $^1$H NMR (500 MHz, d-DMSO) δ 8.62-8.64 (d, J=10.15 Hz, 1H), 8.25 (s, 1H), 7.62 (s, 1H), 7.25-7.38 (m, 5H), 4.50 (m, 1H), 4.22 (s, 2H), 3.84 (s, 3H), 3.36 (m, 2H), 2.91 (m, 3H), 1.95 (m, 2H); ESI (M+H)+=419.

Example 64. 4-(4-chloro-1-methyl-1H-pyrazol-5-yl)-N-(3,4-trans-4-(4-trifluoromethyl phenyl)piperidin-3-yl)furan-2-formamide (Compound 24)

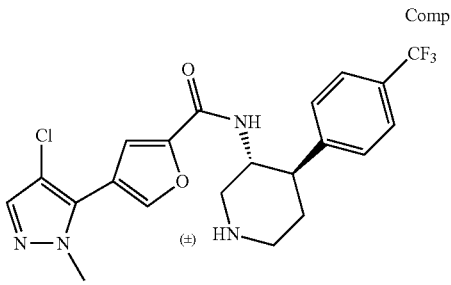

Compound 24

By using Intermediate 3 and Intermediate 25 as raw materials, the target product is prepared and obtained according to the methods as in Example 41; the yield is 28.1%; $^1$H NMR (500 MHz, d-DMSO) δ 8.71 (d, 1H), 8.22 (s, 1H), 7.67 (m, 2H), 7.60 (s, 1H), 7.51 (m, 2H), 7.39 (s, 1H), 4.59 (m, 1H), 4.19 (s, 2H), 3.82 (s, 3H), 3.38 (m, 2H), 3.23 (m, 1H), 2.96 (m, 2H), 1.99 (m, 2H); ESI (M+H)+=453.

Example 65. 4-(4-chloro-1-methyl-1H-pyrazol-5-yl)-N-(3,4-trans-4-(3,4-difluorophenyl) piperidin-3-yl)furan-2-formamide (Compound 25)

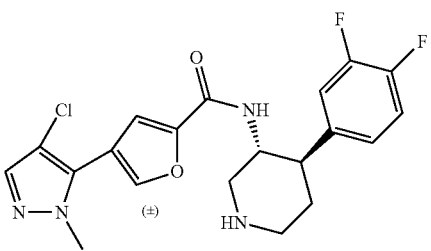

Compound 25

By using Intermediate 3 and Intermediate 27 as raw materials, the target product is prepared and obtained according to the methods as in Example 41; the yield is 26.7%; ¹H NMR (500 MHz, d-DMSO) δ 8.70-8.72 (d, J=11.05 Hz, 1H), 8.23 (s, 1H), 7.59 (s, 1H), 7.41 (s, 1H), 7.12-7.31 (m, 1H), 4.50 (m, 1H), 4.28 (s, 2H), 3.83 (s, 3H), 3.39 (m, 2H), 3.07 (m, 2H), 2.98 (m, 1H), 1.99 (m, 2H); ESI (M+H)⁺=421.

Example 66. 4-(4-bromo-1-methyl-1H-pyrazol-5-yl)-N-(3,4-trans-4-(4-chlorphenyl) piperidin-3-yl)furan-2-formamide (Compound 26)

Compound 26

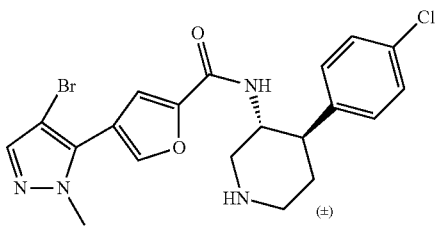

By using Intermediate 4 and Intermediate 24 as raw materials, the target product is prepared and obtained according to the methods as in Example 41; the yield is 22.2%; ¹H NMR (500 MHz, d-DMSO) δ 8.65-8.67 (d, J=11.15 Hz, 1H), 8.23 (s, 1H), 7.62 (s, 1H), 7.38 (s, 1H), 7.35-7.37 (d, J=10.25 Hz, 2H), 7.28-7.31 (d, J=10.25 Hz, 2H), 4.52 (m, 1H), 4.22 (s, 2H), 3.84 (s, 3H), 3.39 (m, 2H), 3.10 (m, 1H), 2.95 (m, 2H), 1.97 (m, 2H); ESI (M+H)⁺=463.

Example 67. 4-(4-bromo-1-methyl-1H-pyrazol-5-yl)-N-(3,4-trans-4-(4-trifluoromethyl phenyl)piperidin-3-yl)furan-2-formamide (Compound 27)

Compound 27

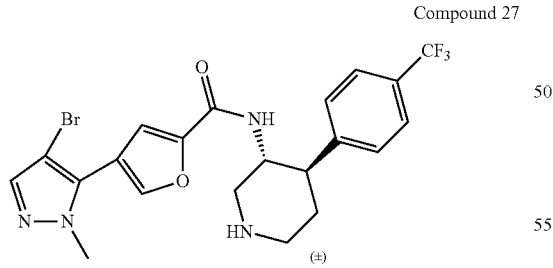

By using Intermediate 4 and Intermediate 25 as raw materials, the target product is prepared and obtained according to the methods as in Example 41; the yield is 26.8%; ¹H NMR (500 MHz, d-DMSO) δ 8.77-8.79 (d, J=10.95 Hz, 1H), 8.23 (s, 1H), 7.67-7.68 (d, J=5.4 Hz, 2H), 7.62 (s, 1H), 7.52 (d, J=5.4 Hz, 2H), 7.39 (s, 1H), 4.60 (m, 1H), 4.19 (s, 4H), 3.83 (s, 3H), 3.39 (m, 2H), 3.23 (m, 1H), 2.96 (m, 2H), 2.00 (m, 2H); ESI (M+H)⁺=497.

Example 68. 4-(4-bromo-1-methyl-1H-pyrazol-5-yl)-N-(3,4-trans-4-(3,4-difluorophenyl) piperidin-3-yl)furan-2-formamide (Compound 28)

Compound 28

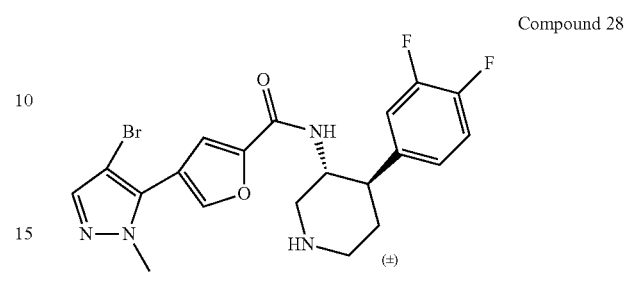

By using Intermediate 4 and Intermediate 27 as raw materials, the target product is prepared and obtained according to the methods as in Example 41; the yield is 22.5%; ¹H NMR (500 MHz, d-DMSO) δ 8.62-8.64 (d, J=10.90 Hz, 1H), 8.25 (s, 1H), 7.62 (s, 1H), 7.38 (s, 1H), 7.08-7.36 (m, 3H), 4.44 (m, 1H), 4.19 (s, 2H), 3.83 (s, 3H), 3.37 (m, 2H), 3.30 (m, 1H), 2.91 (m, 2H), 1.98 (m, 1H), 1.90 (m, 1H); ESI (M+H)⁺=465.

Example 69. 5-chloro-4-(4-chloro-1-methyl-1H-pyrazol-5-yl)-N-(3,4-trans-4-phenyl piperidin-3-yl)furan-2-formamide (Compound 29)

Compound 29

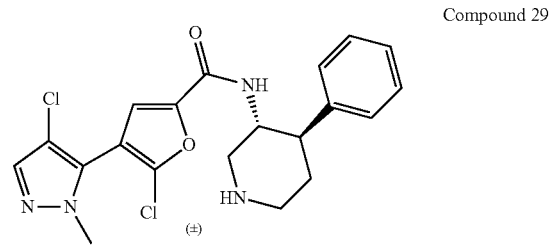 [SMILES: Cn1ncc(Cl)c1-c1cc(C(=O)N[C@H]2CNCC[C@@H]2c2ccccc2)oc1Cl]

By using Intermediate 2 and Intermediate 23 as raw materials, the target product is prepared and obtained according to the methods as in Example 41; the yield is 28.6%; ¹H NMR (500 MHz, d-DMSO) δ 8.77-8.79 (d, J=11.15 Hz, 1H), 7.71 (s, 1H), 7.46 (s, 1H), 7.24-7.33 (m, 5H), 4.59 (m, 1H), 4.26 (s, 2H), 3.77 (s, 3H), 3.42 (m, 2H), 3.12 (m, 1H), 3.00 (m, 2H), 2.01 (m, 2H); ESI (M+H)⁺=419.

Example 70. 5-chloro-4-(4-chloro-1-methyl-1H-pyrazol-5-yl)-N-(3,4-trans-4-(4-trifluoromethylphenyl)piperidin-3-yl)furan-2-formamide (Compound 30)

Compound 30

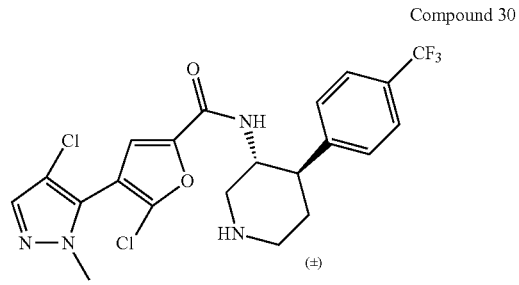 [SMILES: Cn1ncc(Cl)c1-c1cc(C(=O)N[C@H]2CNCC[C@@H]2c2ccc(C(F)(F)F)cc2)oc1Cl]

By using Intermediate 2 and Intermediate 25 as raw materials, the target product is prepared and obtained according to the methods as in Example 41; the yield is 29.9%; $^1$H NMR (500 MHz, d-DMSO) δ 8.79-8.81 (d, J=10.85 Hz, 1H), 7.68 (s, 1H), 7.49 (s, 1H), 7.13-7.38 (m, 4H), 4.49 (m, 1H), 4.21 (s, 4H), 3.74 (s, 3H), 3.36 (m, 2H), 3.10 (m, 1H), 2.95 (m, 2H), 1.98 (m, 2H); ESI (M+H)$^+$=487.

Example 71. 5-chloro-4-(4-chloro-1-methyl-1H-pyrazol-5-yl)-N-(3,4-trans-4-(3,4-difluorophenyl) piperidin-3-yl)furan-2-formamide (Compound 31)

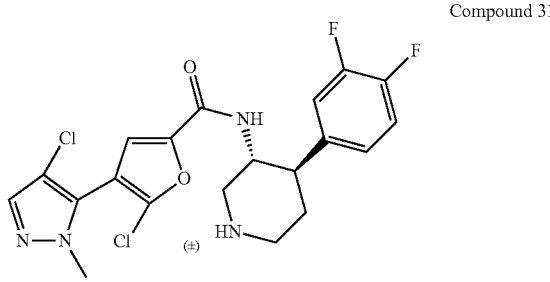 [SMILES: Cn1ncc(Cl)c1-c1cc(C(=O)N[C@H]2CNCC[C@@H]2c2ccc(F)c(F)c2)oc1Cl]

Compound 31

By using Intermediate 2 and Intermediate 25 as raw materials, the target product is prepared and obtained according to the methods as in Example 41; the yield is 33.9%; $^1$H NMR (500 MHz, d-DMSO) δ 8.63-8.65 (d, J=9.05 Hz, 1H), 8.23 (s, 1H), 7.62 (s, 1H), 7.36 (s, 1H), 7.10-7.34 (m, 3H), 4.46 (m, 1H), 4.21 (s, 2H), 3.82 (s, 3H), 3.36 (m, 3H), 2.90 (m, 2H), 2.85 (m, 1H), 1.98 (m, 1H), 1.91 (m, 1H); ESI (M+H)$^+$=455.

Example 72. 4-(1-methyl-1H-pyrazol-5-yl)-N-(3,4-trans-4-(4-chlorphenyl)piperidin-3-yl) thiophene-2-formamide (Compound 32)

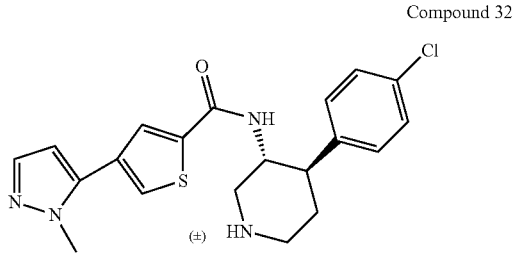 [SMILES: Cn1nccc1-c1csc(C(=O)N[C@H]2CNCC[C@@H]2c2ccc(Cl)cc2)c1]

Compound 32

By using Intermediate 5 and Intermediate 24 as raw materials, the target product is prepared and obtained according to the methods as in Example 41; the yield is 31.2%; $^1$H NMR (500 MHz, d-DMSO) δ 8.70-8.72 (d, J=10.55 Hz, 1H), 7.95 (s, 1H), 7.90 (s, 1H), 7.64 (s, 1H), 7.43 (s, 1H), 7.30-7.34 (m, 4H), 4.48 (m, 1H), 4.25 (s, 2H), 3.89 (s, 3H), 3.55 (m, 1H), 3.39 (m, 1H), 3.00 (m, 3H), 1.97 (m, 2H). ESI (M+H)$^+$=401.

Example 73. 4-(1-methyl-1H-pyrazol-5-yl)-N-(3,4-trans-4-(3,4-difluorophenyl)piperidin-3-yl)thiophene-2-formamide (Compound 33)

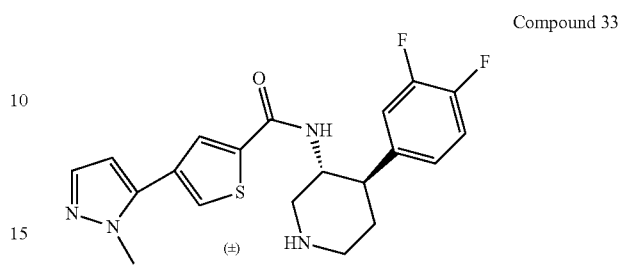

Compound 33

By using Intermediate 5 and Intermediate 27 as raw materials, the target product is prepared and obtained according to the methods as in Example 41; the yield is 32.5%; $^1$H NMR (500 MHz, d-DMSO) δ 8.78-8.80 (d, J=10.85 (Hz, 1H), 7.96 (s, 1H), 7.92 (s, 1H), 7.44 (s, 1H), 7.14-7.36 (m, 3H), 6.43 (s, 1H), 4.45 (m, 1H), 4.24 (s, 2H), 3.90 (s, 3H), 3.39 (m, 2H), 3.00 (m, 1H), 3.09 (m, 2H), 2.01 (m, 2H); ESI (M+H)$^+$=403.

Example 74. 4-(4-chloro-1-methyl-1H-pyrazol-5-yl)-N-(3,4-trans-4-phenylpiperidin-3-yl) thiophene-2-formamide (Compound 34)

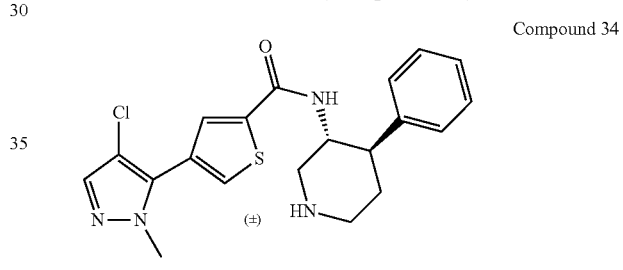

Compound 34

By using Intermediate 6 and Intermediate 23 as raw materials, the target product is prepared and obtained according to the methods as in Example 41; the yield is 23.8%; $^1$H NMR (500 MHz, d-DMSO) δ 8.64-8.66 (d, J=10.65 Hz, 1H), 7.96 (s, 1H), 7.81 (s, 1H), 7.56 (s, 1H), 7.11-7.21 (m, 5H), 4.42 (m, 1H), 4.11 (s, 2H), 3.74 (s, 3H), 3.32 (m, 2H), 2.85-2.96 (m, 3H), 1.92 (m, 2H); ESI (M+H)$^+$=401.

Example 75. 4-(4-chloro-1-methyl-1H-pyrazol-5-yl)-N-(3,4-trans-4-(4-chlorphenyl) piperidin-3-yl) thiophene-2-formamide (Compound 35)

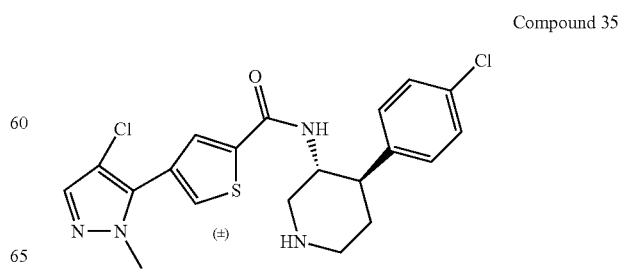

Compound 35

By using Intermediate 6 and Intermediate 24 as raw materials, the target product is prepared and obtained according to the methods as in Example 41; the yield is 28.6%; $^1$H NMR (500 MHz, d-DMSO) δ 8.76-8.78 (d, J=9.80 Hz, 1H), 8.04 (s, 1H), 7.89 (s, 1H), 7.64 (s, 1H), 7.33 (m, 4H), 4.46 (m, 1H), 4.19 (s, 2H), 3.82 (s, 3H), 3.39 (m, 2H), 2.97-3.08 (m, 3H), 1.98 (m, 2H); ESI (M+H)$^+$=435.

Example 76. 4-(4-chloro-1-methyl-1H-pyrazol-5-yl)-N-(3,4-trans-4-(3,4-difluorophenyl) piperidin-3-yl)thiophene-2-formamide (Compound 36)

Compound 36

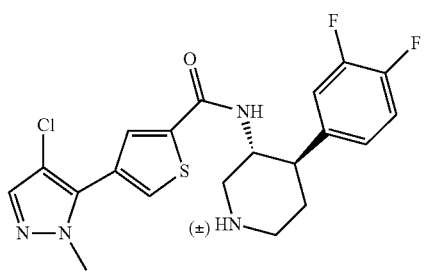

By using Intermediate 6 and Intermediate 27 as raw materials, the target product is prepared and obtained according to the methods as in Example 41; the yield is 25.1%; $^1$H NMR (500 MHz, d-DMSO) δ 8.79-8.81 (d, J=10.10 (Hz, 1H), 8.06 (s, 1H), 7.92 (s, 1H), 7.64 (s, 1H), 7.15-7.36 (m, 3H), 4.47 (m, 1H), 4.24 (s, 2H), 3.84 (s, 3H), 3.42 (m, 2H), 3.09 (m, 2H), 3.01 (m, 1H), 2.03 (m, 2H); ESI (M+H)$^+$=437.

Example 77. 4-(4-bromo-1-methyl-1H-pyrazol-5-yl)-N-(3,4-trans-4-(4-chlorphenyl) piperidin-3-yl) thiophene-2-formamide (Compound 37)

Compound 37

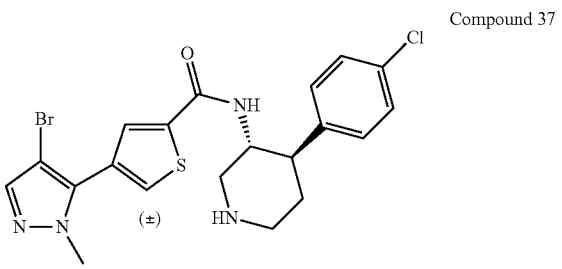 [SMILES: Cn1ncc(Br)c1-c1csc(C(=O)N[C@H]2CNCC[C@@H]2c2ccc(Cl)cc2)c1]

By using Intermediate 7 and Intermediate 24 as raw materials, the target product is prepared and obtained according to the methods as in Example 41; the yield is 27.0%; $^1$H NMR (500 MHz, d-DMSO) δ 8.66 (d, 1H), 8.04 (s, 1H), 7.83 (s, 1H), 7.64 (s, 1H), 7.34-7.36 (d, J=10.25 Hz, 2H), 7.27-7.29 (d, J=10.25 Hz, 2H), 4.43 (m, 1H), 4.22 (s, 2H), 3.80 (s, 3H), 3.40 (m, 2H), 3.08 (m, 2H), 2.89 (m, 1H), 1.97 (m, 2H); ESI (M+H)$^+$=479.

Example 78. 4-(4-bromo-1-methyl-1H-pyrazol-5-yl)-N-(3,4-trans-4-(3,4-difluorophenyl) piperidin-3-yl)thiophene-2-formamide (Compound 38)

Compound 38

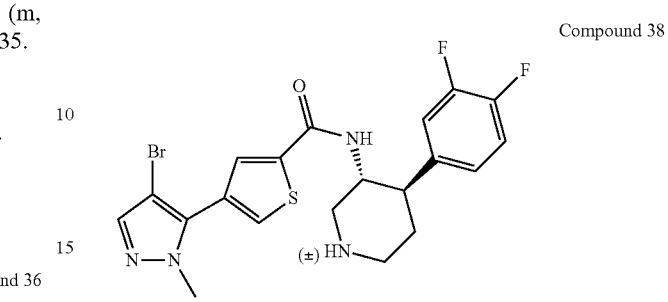

By using Intermediate 7 and Intermediate 24 as raw materials, the target product is prepared and obtained according to the methods as in Example 41; the yield is 35.3%; $^1$H NMR (500 MHz, d-DMSO) δ 8.82-8.84 (d, J=10.25 Hz, 1H), 8.05 (s, 1H), 7.91 (s, 1H), 7.65 (s, 1H), 7.16-7.36 (m, 3H), 4.51 (m, 1H), 4.31 (s, 2H), 3.84 (s, 3H), 3.45 (m, 2H), 3.01 (m, 3H), 2.05 (m, 2H); ESI (M+H)$^+$=481.

Example 79. 5-chloro-4-(4-chloro-1-methyl-1H-pyrazol-5-yl)-N-((3R,4R)-4-(3,4-dichlorophenyl) piperidin-3-yl)furan-2-formamide (Compound 39)

Compound 39

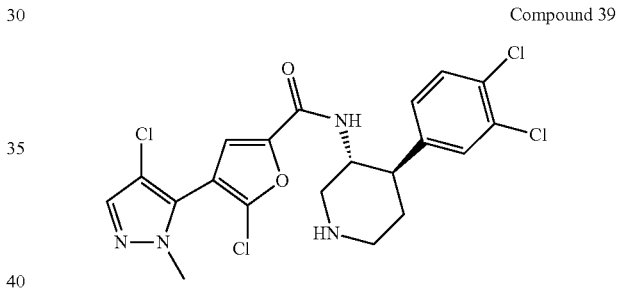

By using Intermediate 2 and Intermediate 59 as raw materials, the target product is prepared and obtained according to the methods as in Example 41; the yield is 32.1%; $^1$H NMR (500 MHz, DMSO) δ 8.79 (d, J=8.0 Hz, 1H), 7.66 (s, 1H), 7.54 (t, J=8.7 Hz, 1H), 7.49 (d, J=9.0 Hz, 1H), 7.46 (s, 1H), 7.26 (dd, J=18.3, 8.5 Hz, 1H), 4.47 (d, J=7.2 Hz, 1H), 4.10 (s, 2H), 3.71 (s, 3H), 3.35 (dd, J=13.9, 6.9 Hz, 2H), 3.13-3.00 (m, 1H), 2.90 (s, 2H), 1.91 (d, J=28.3 Hz, 2H). ESI (M+H)$^+$=488.

Example 80. 5-chloro-4-(4-chloro-1-methyl-1H-pyrazol-5-yl)-N-((3S,4S)-4-(3,4-dichlorophenyl) piperidin-3-yl)furan-2-formamide (Compound 40)

Compound 40

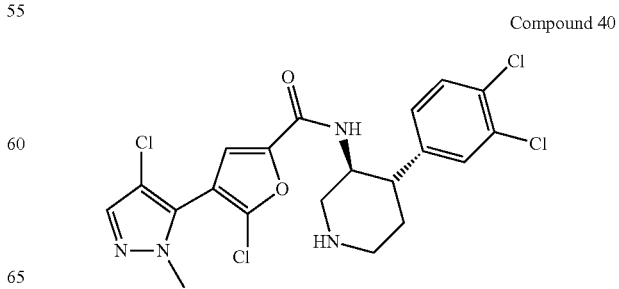

By using Intermediate 2 and Intermediate 56 as raw materials, the target product is prepared and obtained according to the methods as in Example 41; the yield is 33.5%; ESI (M+H)+=488.

Example 81. 4-(4-bromo-1-methyl-1H-pyrazol-5-yl)-N-((3R,4R)-4-(3,4-difluorophenyl) piperidin-3-yl)thiophene-2-formamide (Compound 41)

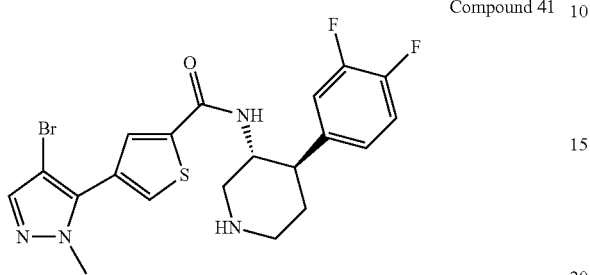

Compound 41

By using Intermediate 7 and Intermediate 60 as raw materials, the target product is prepared and obtained according to the methods as in Example 41; the yield is 37.9%; ESI (M+H)+=481.

Example 82. 4-(4-bromo-1-methyl-1H-pyrazol-5-yl)-N-((3S,4S)-4-(3,4-difluorophenyl) piperidin-3-yl)thiophene-2-formamide (Compound 42)

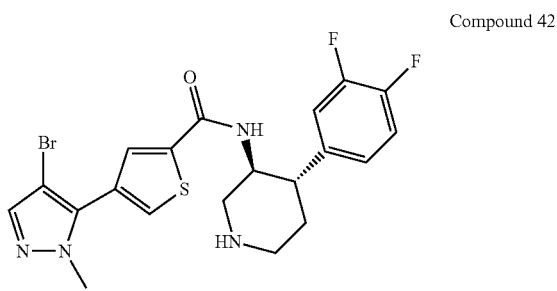 [SMILES: Cn1ncc(Br)c1-c1csc(C(=O)N[C@@H]2CNCC[C@H]2c2ccc(F)c(F)c2)c1]

Compound 42

By using Intermediate 7 and Intermediate 57 as raw materials, the target product is prepared and obtained according to the methods as in Example 41; the yield is 35.7%; ESI (M+H)+=481.

Example 83. 5-chloro-4-(4-chloro-1-methyl-1H-pyrazol-5-yl)-N-((3R,4R)-4-(4-trifluoromethylphenyl)piperidin-3-yl)furan-2-formamide (Compound 43)

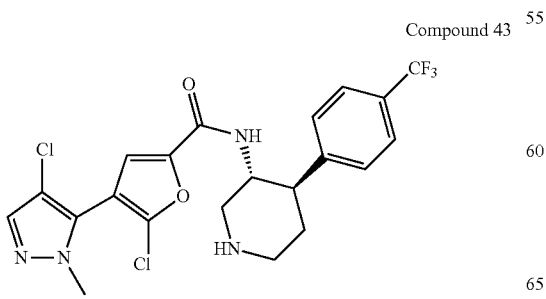

Compound 43

By using Intermediate 2 and Intermediate 61 as raw materials, the target product is prepared and obtained according to the methods as in Example 41; the yield is 39.2%; $^1$H NMR (500 MHz, d-DMSO) δ 8.79-8.81 (d, J=10.85 Hz, 1H), 7.68 (s, 1H), 7.49 (s, 1H), 7.13-7.38 (m, 4H), 4.49 (m, 1H), 4.21 (s, 4H), 3.74 (s, 3H), 3.36 (m, 2H), 3.10 (m, 1H), 2.95 (m, 2H), 1.98 (m, 2H). ESI (M+H)+=487.

Example 84. 5-chloro-4-(4-chloro-1-methyl-1H-pyrazol-5-yl)-N-((3S,4S)-4-(4-trifluoromethylphenyl)piperidin-3-yl)furan-2-formamide (Compound 44)

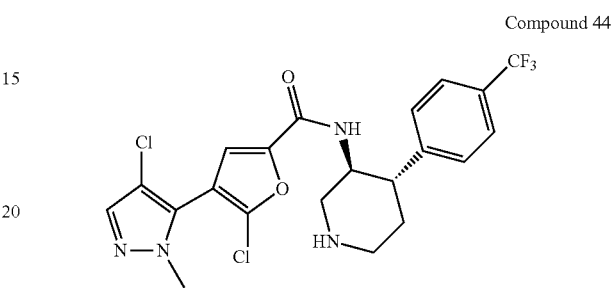

Compound 44

By using Intermediate 2 and Intermediate 58 as raw materials, the target product is prepared and obtained according to the methods as in Example 41; the yield is 28.4%; ESI (M+H)+=487.

Example 85. 6-methyl-4-(4-chloro-1-methyl-1H-pyrazol-5-yl)-N-(3,4-trans-4-phenylpiperidin-3-yl)pyridinyl-2-formamide (Compound 45)

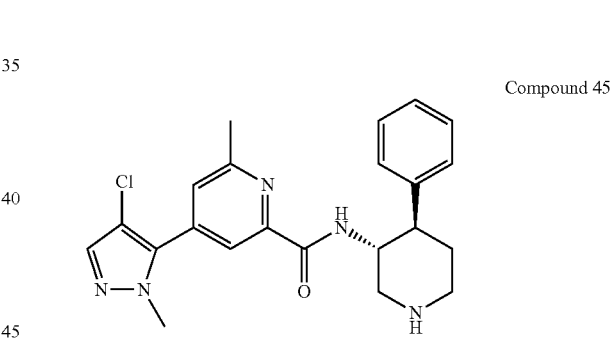

Compound 45

By using Intermediate 41 and Intermediate 23 as raw materials, the target product is prepared and obtained according to the methods as in Example 41; the yield is 38.3%; ESI (M+H)+=401.

Example 86. 4-fluoro-5-(1,4-dimethyl-1H-pyrazol-5-yl)-N-(3,4-trans-4-(3,4-difluorophenyl)piperidin-3-yl)pyridinyl-2-formamide (Compound 46)

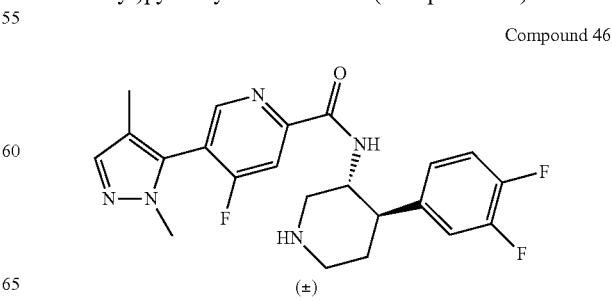

Compound 46

(±)

By using Intermediate 42 and Intermediate 27 as raw materials, the target product is prepared and obtained according to the methods as in Example 41; the yield is 39.1%; ESI (M+H)$^+$=430.

Example 87. 2-methyl-6-(1-methyl-4-ethyl-1H-pyrazol-5-yl)-N-(3,4-trans-4-(4-chlorophenyl)piperidin-3-yl)pyrimidine-4-formamide (Compound 47)

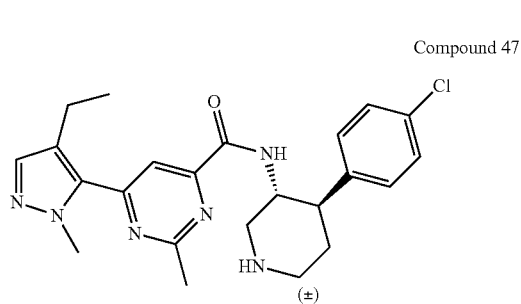 [SMILES: CCc1cnn(C)c1-c1cc(C(=O)N[C@H]2CNCC[C@@H]2c2ccc(Cl)cc2)nc(C)n1]

Compound 47

By using Intermediate 43 and Intermediate 24 as raw materials, the target product is prepared and obtained according to the methods as in Example 41; the yield is 34.9%; ESI (M+H)$^+$=439.

Example 88. 5-(4-bromo-1-methyl-1H-pyrazol-5-yl)-N-(3,4-trans-4-(pyridinyl-4-yl) piperidin-3-yl)pyrazine-2-formamide (Compound 48)

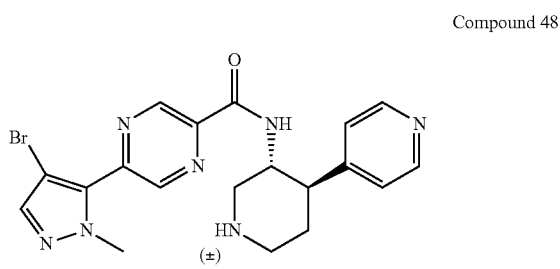 [SMILES: Cn1ncc(Br)c1-c1cnc(C(=O)N[C@H]2CNCC[C@@H]2c2ccncc2)cn1]

Compound 48

By using Intermediate 44 and Intermediate 32 as raw materials, the target product is prepared and obtained according to the methods as in Example 41; the yield is 37.4%; ESI (M+H)$^+$=442.

Example 89. 5-ethyl-6-(4-bromo-1-methyl-1H-pyrazol-5-yl)-N-(3,4-trans-4-(4-trifluoromethylphenyl)piperidin-3-yl)pyridinyl-3-formamide (Compound 49)

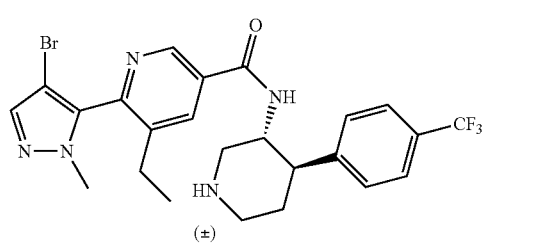

Compound 49

By using Intermediate 45 and Intermediate 25 as raw materials, the target product is prepared and obtained according to the methods as in Example 41; the yield is 39.2%; ESI (M+H)$^+$=536.

Example 90. 4,6-dimethyl-5-(4-bromo-1-methyl-1H-pyrazol-5-yl)-N-(3,4-trans-4-(4-trifluoromethylphenyl)piperidin-3-yl)pyrimidine-2-formamide (Compound 50)

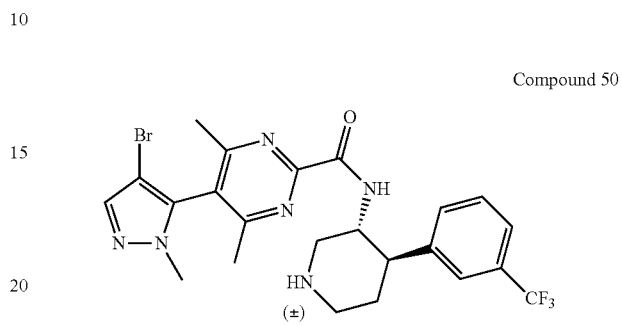

Compound 50

By using Intermediate 46 and Intermediate 26 as raw materials, the target product is prepared and obtained according to the methods as in Example 41; the yield is 32.6%; ESI (M+H)$^+$=537.

Example 91. 5-chloro-4-(4-isopropyl-1-methyl-1H-pyrazol-5-yl)-N-(3,4-trans-4-(3-fluorocyclopentane)piperidin-3-yl)pyrimidine-2-formamide (Compound 51)

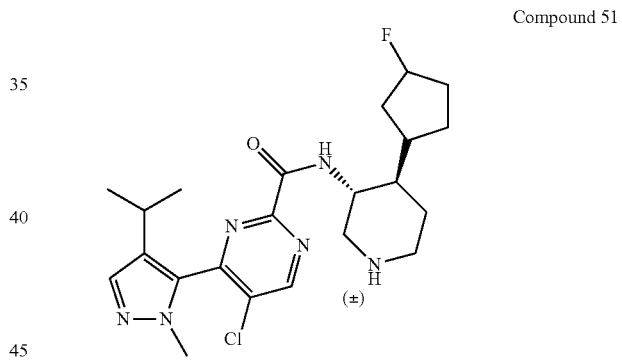

Compound 51

By using Intermediate 47 and Intermediate 37 as raw materials, the target product is prepared and obtained according to the methods as in Example 41; the yield is 45.1%; ESI (M+H)$^+$=449.

Example 92. 4-methyl-5-(4-chloro-1-methyl-1H-pyrazol-5-yl)-N-(3,4-trans-4-(3,4-difluorophenyl)piperidin-3-yl)pyrimidine-2-formamide (Compound 52)

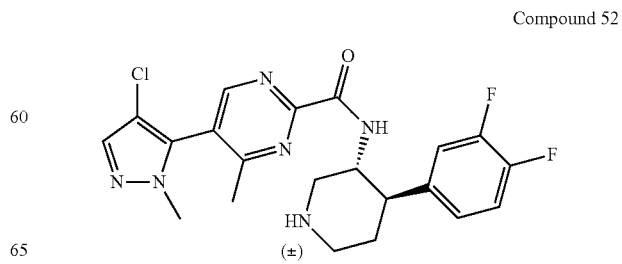

Compound 52

By using Intermediate 48 and Intermediate 27 as raw materials, the target product is prepared and obtained according to the methods as in Example 41; the yield is 35.7%; ESI (M+H)⁺=447.

Example 93. 2-chloro-3-(4-ethyl-1-methyl-1H-pyrazol-5-yl)-N-(3,4-trans-4-(4-chlorophenyl)piperidin-3-yl)phenyl formamide (Compound 53)

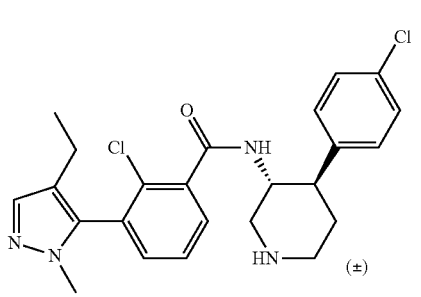

Compound 53

By using Intermediate 49 and Intermediate 24 as raw materials, the target product is prepared and obtained according to the methods as in Example 41; the yield is 39.4%; ESI (M+H)⁺=457.

Example 94. 3-n-propyl-4-(4-bromo-1-methyl-1H-pyrazol-5-yl)-N-(3,4-trans-4-(3,5-dimethoxyphenyl)piperidin-3-yl)phenyl formamide (Compound 54)

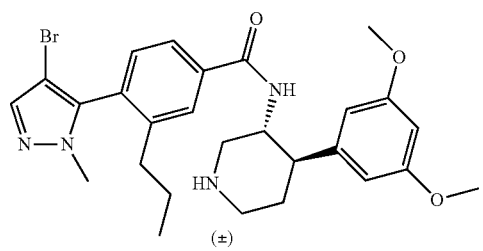

Compound 54

By using Intermediate 50 and Intermediate 30 as raw materials, the target product is prepared and obtained according to the methods as in Example 41; the yield is 37.3%; ESI (M+H)⁺=541.

Example 95. 4-chloro-5-(4-chloro-1-methyl-1H-pyrazol-5-yl)-N-(3,4-trans-4-(4-methylcyclohexane)piperidin-3-yl)pyrimidine-2-formamide (Compound 55)

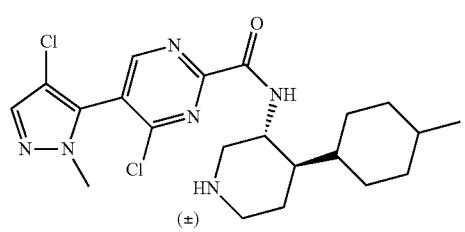

Compound 55

By using Intermediate 51 and Intermediate 38 as raw materials, the target product is prepared and obtained according to the methods as in Example 41; the yield is 42.5%; ESI (M+H)⁺=451.

Example 96. 5-(4-chloro-1-methyl-1H-pyrazol-5-yl)-N-(3,4-trans-4-(3-chloro cyclohexane)piperidin-3-yl)-4-methylpyridinyl-2-formamide (Compound 56)

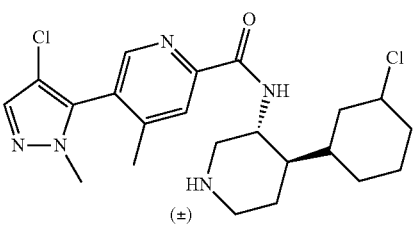

Compound 56

By using Intermediate 52 and Intermediate 37 as raw materials, the target product is prepared and obtained according to the methods as in Example 41; the yield is 48.1%; ESI (M+H)⁺=450.

Example 97. 2,5-dimethyl-4-(4-bromo-1-methyl-1H-pyrazol-5-yl)-N-(3,4-trans-4-(3-methylphenyl)piperidin-3-yl)phenyl formamide (Compound 57)

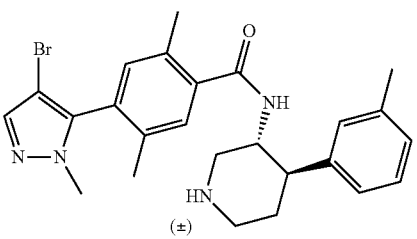

Compound 57

By using Intermediate 53 and Intermediate 28 as raw materials, the target product is prepared and obtained according to the methods as in Example 41; the yield is 44.5%; ESI (M+H)⁺=481.

Example 98. 6-methyl-5-(4-bromo-1-methyl-1H-pyrazol-5-yl)-N-(3,4-trans-4-(pyridinyl-4-yl)piperidin-3-yl)pyridinyl-2-formamide (Compound 58)

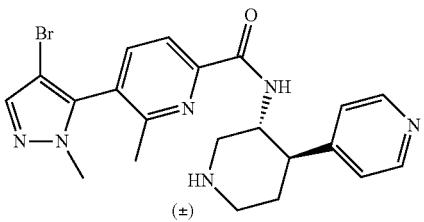

Compound 58

By using Intermediate 54 and Intermediate 32 as raw materials, the target product is prepared and obtained according to the methods as in Example 41; the yield is 47.3%; ESI (M+H)⁺=455.

Example 99. 6-methyl-5-(4-bromo-1-methyl-1H-pyrazol-5-yl)-N-(3,4-trans-4-(piperidin-3-yl)piperidin-3-yl)pyridinyl-2-formamide (Compound 59)

Compound 59

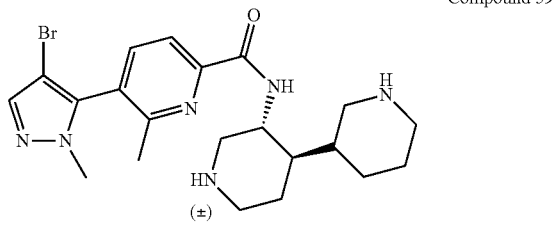

By using Intermediate 54 and Intermediate 39 as raw materials, the target product is prepared and obtained according to the methods as in Example 41; the yield is 39.7%; ESI (M+H)$^+$=461.

Example 100. 4-methyl-5-(1,4-dimethyl-1-methyl-1H-pyrazol-5-yl)-N-(3,4-trans-4-(pyrrole-2-yl)piperidins-3-yl)pyrimidine-2-formamide (Compound 60)

Compound 60

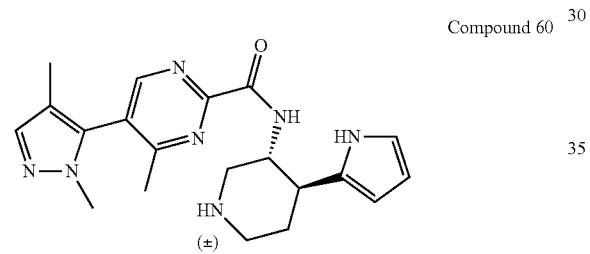

By using Intermediate 55 and Intermediate 35 as raw materials, the target product is prepared and obtained according to the methods as in Example 41; the yield is 32.9%; ESI (M+H)$^+$=380.

Example 101. 4-fluoro-5-(1,4-dimethyl-1H-pyrazol-5-yl)-N-((3R,4R)-4-(3,4-difluoro phenyl)piperidin-3-yl)pyridinyl-2-formamide (Compound 61)

Compound 61

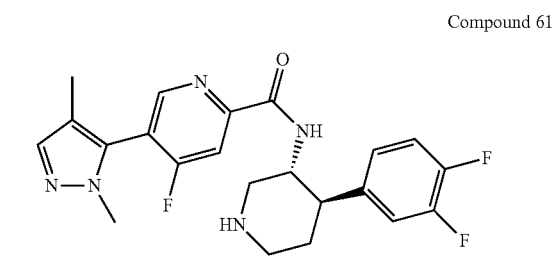 [SMILES: Cc1cnn(C)c1-c1cnc(C(=O)N[C@H]2CNCC[C@@H]2c2ccc(F)c(F)c2)cc1F]

By using Intermediate 42 and Intermediate 60 as raw materials, the target product is prepared and obtained according to the methods as in Example 41; the yield is 35.1%; ESI (M+H)$^+$=430.

Example 102. 4-fluoro-5-(1,4-dimethyl-1H-pyrazol-5-yl)-N-((3S,4S)-4-(3,4-difluoro phenyl)piperidin-3-yl)pyridinyl-2-formamide (Compound 62)

Compound 62

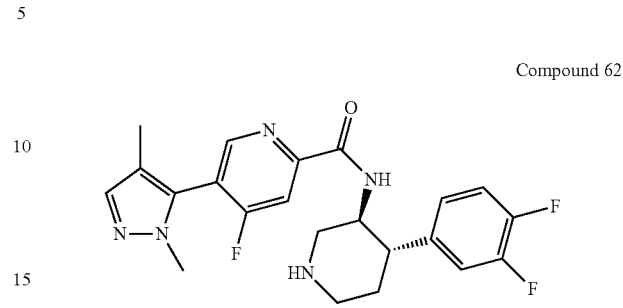

By using Intermediate 42 and Intermediate 57 as raw materials, the target product is prepared and obtained according to the methods as in Example 41; the yield is 31.2%; ESI (M+H)$^+$=430.

Example 103. 5-ethyl-6-(4-bromo-1-methyl-1H-pyrazol-5-yl)-N-((3R,4R)-4-(4-trifluoro methylphenyl)piperidin-3-yl)pyridinyl-3-formamide (Compound 63)

Compound 63

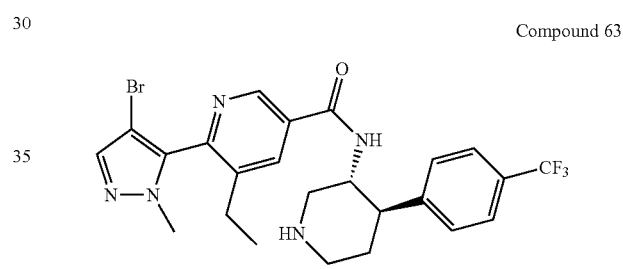

By using Intermediate 45 and Intermediate 61 as raw materials, the target product is prepared and obtained according to the methods as in Example 41; the yield is 33.9%; ESI (M+H)$^+$=537.

Example 104. 5-ethyl-6-(4-bromo-1-methyl-1H-pyrazol-5-yl)-N-((3S,4S)-4-(4-trifluoro methylphenyl)piperidin-3-yl)pyridinyl-3-formamide (Compound 64)

Compound 64

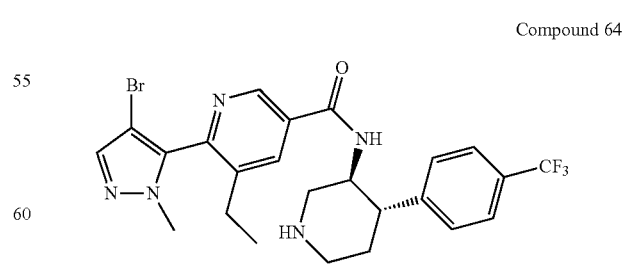

By using Intermediate 45 and Intermediate 58 as raw materials, the target product is prepared and obtained according to the methods as in Example 41; the yield is 38.2%; ESI (M+H)$^+$=537.

Example 105. 4-(1-methyl-1H-pyrazol-5-yl)-N-(3,4-trans-4-(3,4-difluorophenyl) pyrrolidin-3-yl)furan-2-formamide (Compound 65)

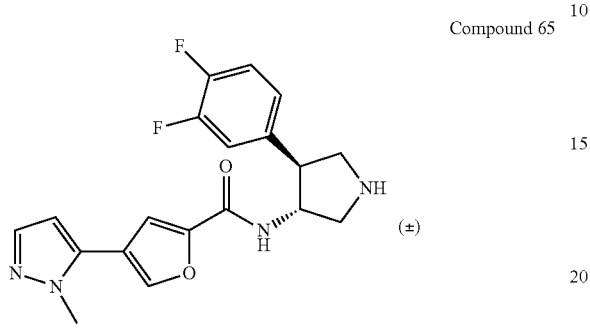

Compound 65

By using Intermediate 1 and Intermediate 63 as raw materials, the target product is prepared and obtained according to the methods as in Example 41; the yield is 23.4%; $^1$H NMR (500 MHz, CDCl$_3$) δ 7.61 (d, J=0.9 Hz, 1H), 7.47 (d, J=1.9 Hz, 1H), 7.38-7.40 (d, J=7.75 z, 1H), 7.30 (d, J=0.9 Hz, 1H), 7.09-7.20 (m, 3H), 6.32 (d, J=1.9 Hz, 1H), 4.66 (m, 1H), 3.92 (s, 3H), 3.62 (m, 1H), 3.52 (m, 1H), 3.44 (m, 1H), 3.18 (m, 2H). ESI (M+H)$^+$=373.

Example 106. 5-chloro-4-(4-chloro-1-methyl-1H-pyrazol-5-yl)-N-(3,4-trans-4-(3,4-difluorophenyl) pyrrolidin-3-yl)furan-2-formamide (Compound 66)

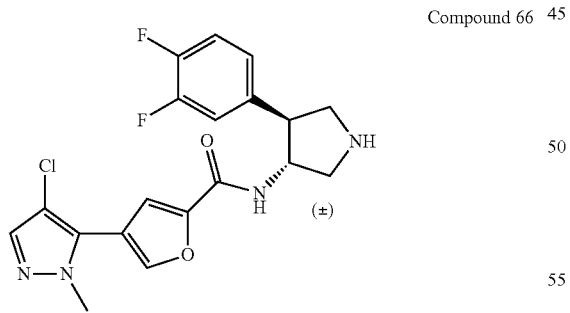

Compound 66

By using Intermediate 3 and Intermediate 63 as raw materials, the target product is prepared and obtained according to the methods as in Example 41; the yield is 33.5%; $^1$H NMR (500 MHz, CDCl$_3$) δ 7.75 (s, 1H), 7.57-7.59 (d, J=7.65 z, 1H), 7.43 (s, 1H), 7.39 (s, 1H), 7.07-7.20 (m, 3H), 4.69 (m, 1H), 3.86 (s, 3H), 3.68 (m, 1H), 3.59 (m, 1H), 3.50 (m, 1H), 3.26 (s, 1H) 3.20 (m, 1H). ESI (M+H)$^+$=407.

Example 107. 4-(4-bromo-1-methyl-1H-pyrazol-5-yl)-N-(3,4-trans-4-(4-trifluoromethyl phenyl)pyrrolidin-3-yl)furan-2-formamide (Compound 67)

Compound 67

By using Intermediate 4 and Intermediate 62 as raw materials, the target product is prepared and obtained according to the methods as in Example 41; the yield is 28.2%; $^1$HNMR (500 MHz, d-DMSO) δ 8.91 (d, J=8.2 Hz, 1H), 8.29 (s, 1H), 7.70-7.72 (d, J=8.1 Hz, 2H), 7.65 (s, 1H), 7.60-7.62 (d, J=8.1 Hz, 2H), 7.47 (s, 1H), 4.65 (m, 1H), 3.86 (s, 3H), 3.59 (m, 2H), 3.49 (m, 1H), 3.11 (m, 1H), 3.02 (m, 1H). ESI (M+H)$^+$=448.

Example 108. 4-(4-bromo-1-methyl-1H-pyrazol-5-yl)-N-(3,4-trans-4-(3,4-difluorophenyl) pyrrolidin-3-yl)furan-2-formamide (Compound 68)

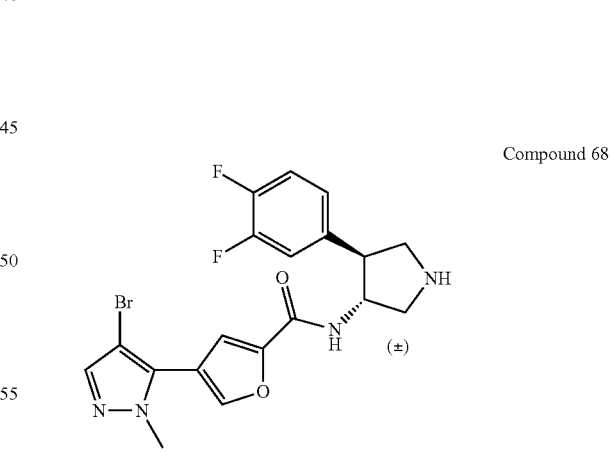

Compound 68

By using Intermediate 4 and Intermediate 63 as raw materials, the target product is prepared and obtained according to the methods as in Example 41; the yield is 36.7%; $^1$H NMR (500 MHz, CDCl$_3$) δ 7.78 (s, 1H), 7.73-7.74 (d, J=6.75 z, 1H), 7.48 (s, 1H), 7.41 (s, 1H), 7.10-7.24 (m, 3H), 4.72 (m, 1H), 3.88 (s, 3H), 3.72 (m, 1H), 3.58 (m, 2H), 3.26-3.30 (m, 2H). ESI (M+H)$^+$=415.

Example 109. 5-chloro-4-(4-chloro-1-methyl-1H-pyrazol-5-yl)-N-(3,4-trans-4-(4-trifluoro methylphenyl)pyrrolidin-3-yl)furan-2-formamide (Compound 69)

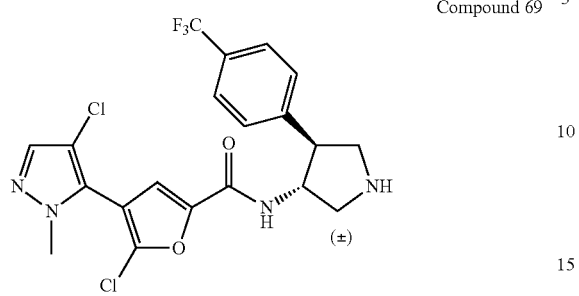

Compound 69

By using Intermediate 2 and Intermediate 62 as raw materials, the target product is prepared and obtained according to the methods as in Example 41; the yield is 39.5%; 1H NMR (500 MHz, d-DMSO) δ 9.03 (d, J=8.1 Hz, 1H), 7.71-7.72 (d, J=8.1 Hz, 2H), 7.69 (s, 1H), 7.61-7.63 (d, J=8.1 Hz, 2H), 7.53 (s, 1H), 4.71 (m, 1H), 3.74 (s, 3H), 3.65 (m, 2H), 3.52 (m, 1H), 3.19 (m, 1H), 3.09 (m, 1H). ESI $(M+H)^+$=448.

Example 110. 4-fluoro-5-(1,4-dimethyl-1H-pyrazol-5-yl)-N-(3,4-trans-4-(3,4-difluoro phenyl)pyrrolidin-3-yl)pyridinyl-2-formamide (Compound 70)

Compound 70

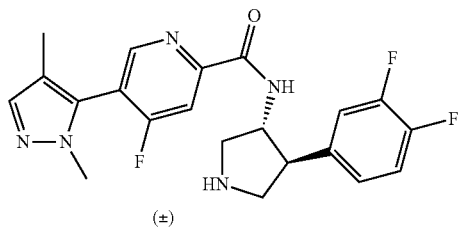

By using Intermediate 42 and Intermediate 63 as raw materials, the target product is prepared and obtained according to the methods as in Example 41; the yield is 40.5%; ESI $(M+H)^+$=473.

Example 111. 4-fluoro-5-(1,4-dimethyl-1H-pyrazol-5-yl)-N-(3,4-trans-4-(4-trifluoro methylphenyl)pyrrolidin-3-yl)pyridinyl-2-formamide (Compound 71)

Compound 71

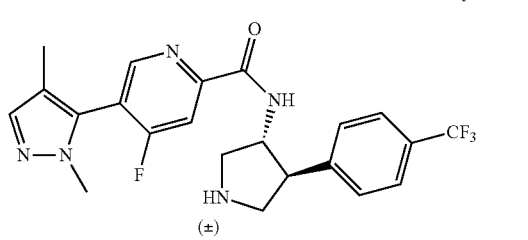

By using Intermediate 42 and Intermediate 62 as raw materials, the target product is prepared and obtained according to the methods as in Example 41; the yield is 38.2%; ESI $(M+H)^+$=473.

Example 112. 4-(4-bromo-1-methyl-1H-pyrazol-5-yl)-N-((3S,4S)-4-(4-chlorophenyl) piperidin-3-yl) benzamide (Compound 72)

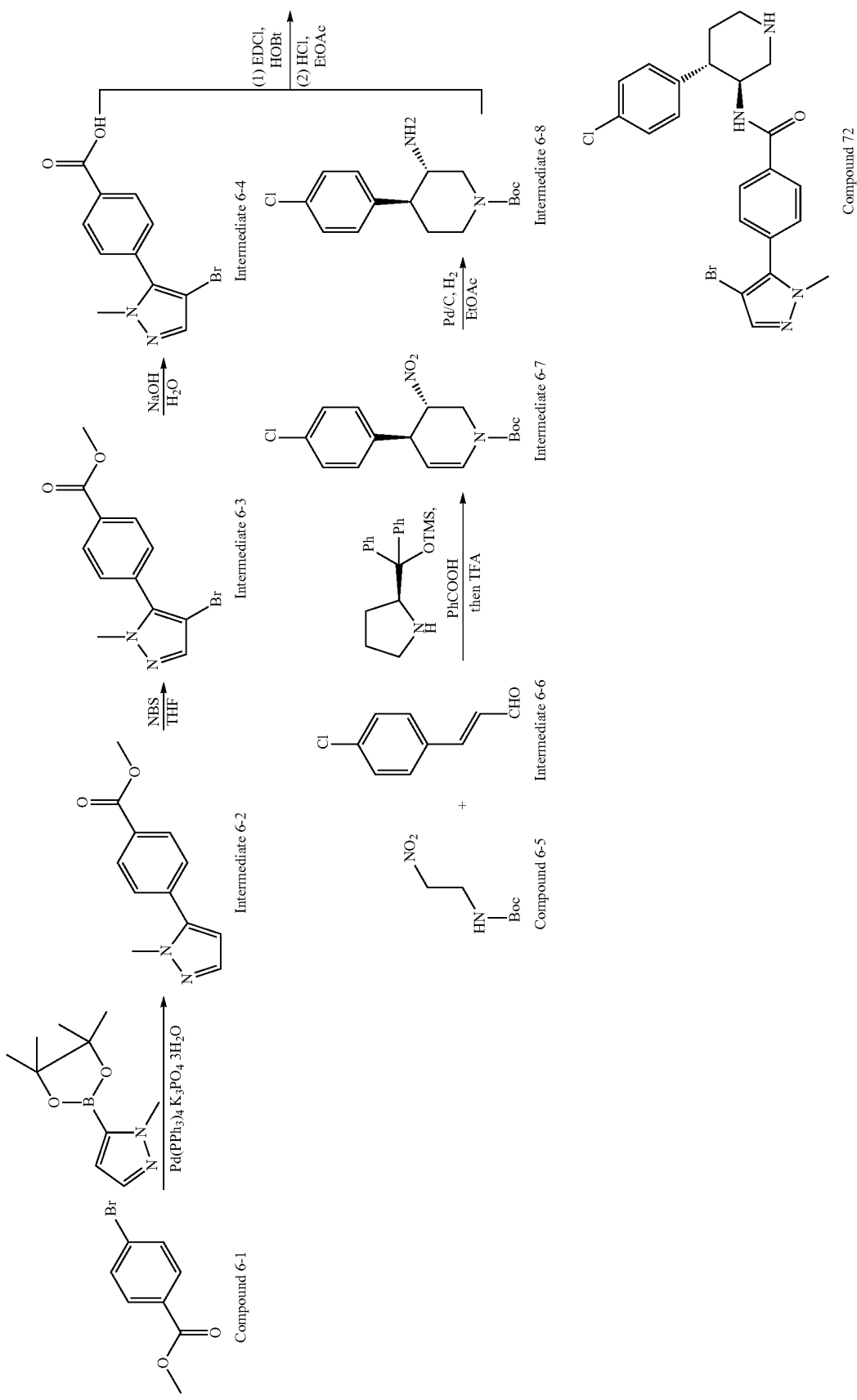

Step 1. Synthesis of 4-(1-methyl-1H-pyrazol-5-yl) methyl benzoate (Intermediate 6-2)

Sequentially adding 4-methyl bromobenzoate (Compound 6-1) (2.2 g, 10 mmol), tetra(triphenylphosphine) palladium (1.15 g, 1 mmol), 1-methyl-1H-pyrazol-5-boric acid pinacol ester (2.5 g, 12 mmol) and potassium phosphate trihydrate (4.0 g, 15 mmol) to 100 ml of three-neck flask with 50 mL of DMF under the protection of $N_2$, fully stirring the reaction system at 90° C. and reacting overnight. Cooling the product to room temperature after the reaction is completed, pouring the reaction liquid into 100 ml of water, extracting the reaction liquid with ethyl acetate 3 times, merging the organic layer, washing with saturated sodium chloride twice, drying it with anhydrous sodium sulfate, concentrating under reduced pressure, and purify the obtained primary product by column chromatography on silica gel, 1.83 g of light yellow solid (Intermediate 6-2) is obtained and the yield is 85%; $^1$H NMR (500 MHz, CDCl$_3$) δ 8.12 (d, J=8.3 Hz, 2H), 7.54 (d, J=1.9 Hz, 1H), 7.51 (d, J=8.3 Hz, 2H), 6.38 (d, J=1.9 Hz, 1H), 3.95 (s, 3H), 3.93 (s, 3H).

Step 2. Synthesis of 4-(4-bromo-1-methyl-1H-pyrazol-5-yl)benzoic acid (Intermediate 6-4)

Dissolving Intermediate 6-2 (1.1 g, 5 mmol) in 20 ml tetrahydrofuran, slowly adding NBS (1.1 g, 6 mmol), after reacting for 5 h at room temperature, adding 10 ml of 6N NaOH aqueous solution, continue reacting for 6 h at room temperature, and removing the organic solvent under reduced pressure. Adding 10 ml of water to the remaining reaction mixture, washing with dichloromethane twice, adjusting the water layer with 1N HCl solution to pH of about 3, a large amount of solid and filter is precipitated, washing the filter cake once and drying it, 1.2 g of white solid (Intermediate 6-4) is obtained and the yield is 86%; $^1$H NMR (500 MHz, CDCl$_3$) δ 8.26 (d, J=8.3 Hz, 2H), 7.59 (s, 1H), 7.56 (d, J=8.3 Hz, 2H), 3.87 (s, 3H).

Step 3. Synthesis of (3S,4S)-4-(4-chlorphenyl)-3-nitro-3,4-dihydropyridine-1(2H)-tert-butyl formate (Intermediate 6-7)

Dissolving 2-nitroethyl tert-butyl carbamate (Compound 6-5, 380 mg, 2 mmol), ((S)-(−)-α,α-diphenyl-2-pyrrylmethyl)trimethylsilyl ether (33 mg, 0.1 mmol), benzoic acid (25 mg, 0.2 mmol) in anhydrous dichloromethane (2 ml), slowly adding 4-chlorocinnamaldehyde (Intermediate 1-6, 167 mg, 1 mmol) in an ice bath, stirring for about 24 h at room temperature, diluting the reaction system with dichloromethane to 10 ml, slowly dropwise adding 200 μl of trifluoroacetic acid to the reaction liquid, reacting for 5 h at room temperature, subsequently adding about 10 ml of 1N NaHCO$_3$ solution to the reaction liquid, stirring for 10 min at room temperature, and then extracting the reaction liquid with ethyl acetate 3 times, washing the merged organic phase with saturated sodium chloride once, drying it with anhydrous sodium sulfate, and purifying by column chromatography, 260 mg of light yellow solid (Intermediate 6-7) is obtained and the yield is 77%; $^1$H NMR (500 MHz, CDCl$_3$) δ 7.32 (d, J=8.4 Hz, 2H), 7.18 (d, J=8.4 Hz, 2H), 7.16-6.96 (m, 1H), 4.94-4.78 (m, 1H), 4.61 (s, 1H), 4.21 (s, 1H), 4.09-3.91 (m, 2H), 1.52 (s, 9H).

Step 4. Synthesis of (3S,4S)-3-amido-4-(4-chlorophenyl)piperidin-1-tert-butyl formate (Intermediate 6-8)

Dissolving Intermediate 6-7 (169 mg, 0.5 mmol) in ethyl acetate (10 ml), adding 30 mg of 10% Pd/C thereto, hydrogenating overnight at room temperature, suction filtrating after the reaction is completed, and spin drying the filtrate, 110 mg of oily liquid (Intermediate 6-8) is obtained and the yield is 71%; ESI (M+H)$^+$=311.

Step 5. Synthesis of 4-(4-bromo-1-methyl-1H-pyrazol-5-yl)-N-((3S,4S)-4-(4-chlorophenyl) piperidin-3-yl)benzamide (Compound 72)

Dissolving Intermediate 6-4 (97 mg, 0.345 mmol), 1-hydroxybenzotriazole (HOBt) (78.62 mg, 0.517 mmol) and 1-ethyl-(3-dimethylaminopropyl)carbodiimide hydrochloride EDC.HCl (98.8 mg, 0.517 mmol) in anhydrous dichloromethane (4 ml), adding diisopropylethylamine (0.115 ml, 1.21 mmol) thereto, after stirring for 10 min in an ice bath, continue stirring for 15 min in an ice bath, and then slowly adding dichloromethane solution (4 ml) dissolved with Intermediate 6-8 (109 mg, 0.35 mmol), and stirring overnight at room temperature. After the reaction is completed, pouring the reaction liquid into 15 ml of water, extracting the reaction liquid with dichloromethane 3 times, merging the organic phase, washing with saturated sodium chloride twice, drying it with anhydrous sodium sulfate, and spin drying; dissolving the obtained residue to a small amount of acetate ethyl, slowly adding ethyl acetate saturated with HCl thereto in an ice bath, after reacting for 2 h at room temperature, spin dry, add saturated NaHCO$_3$ solution, extract the reaction liquid with ethyl acetate twice, merging the organic phase, drying it with anhydrous sodium sulfate, and purifying by column chromatography on silica gel, 80 mg of white powder (Compound 72) is obtained and the yield is 49%; $^1$H NMR (500 MHz, CDCl$_3$) δ 7.63 (d, J=8.4 Hz, 2H), 7.49 (s, 1H), 7.40 (d, J=8.4 Hz, 2H), 7.28 (d, J=8.5 Hz, 2H), 7.24 (d, J=8.5 Hz, 2H), 5.94 (d, J=6.5 Hz, 1H), 4.32 (m, 1H), 3.76 (s, 3H), 3.59 (m, 1H), 3.20 (d, J=12.7 Hz, 1H), 2.81-2.70 (m, 2H), 2.66-2.57 (m, 1H), 2.25-2.15 (m, 1H), 1.82; ESI (M+H)$^+$=473.

Example 113. 4-(4-chloro-1-methyl-1H-pyrazol-5-yl)-N-((3S,4S)-4-(3-fluorophenyl) piperidin-3-yl)benzamide (Compound 73)

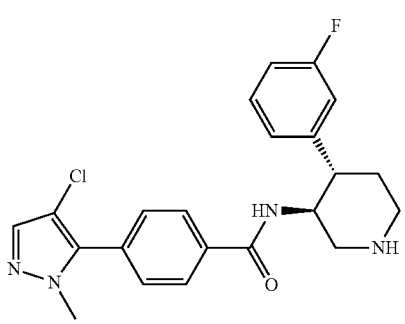

Compound 73

By using Intermediate 6-2 and 3-fluorocinnamaldehyde as raw materials, Compound 73 is prepared and obtained according to the methods as in Example 112, the yield is 34%; $^1$H NMR (500 MHz, MeOD) δ 7.77 (d, J=8.4 Hz, 2H), 7.58 (s, 1H), 7.55-7.51 (m, 2H), 7.35 (td, J=8.0, 6.1 Hz, 1H), 7.21 (d, J=7.8 Hz, 1H), 7.17-7.13 (m, 1H), 6.98 (td, J=8.3, 2.0 Hz, 1H), 4.67 (td, J=11.6, 4.4 Hz, 1H), 3.79 (s, 3H), 3.69-3.64 (m, 1H), 3.57 (d, J=12.8 Hz, 1H), 3.29-3.19 (m, 2H), 3.16 (t, J=12.0 Hz, 1H), 2.23 (dd, J=14.5, 2.3 Hz, 1H), 2.16-2.08 (m, 1H). ESI (M+H)$^+$=413.

Example 114. 4-(4-chloro-1-methyl-1H-pyrazol-5-yl)-N-((3S,4S)-4-(4-chloro-3-(trifluoro methyl)phenyl)piperidin-3-yl)-3-methylbenzamide (Compound 74)

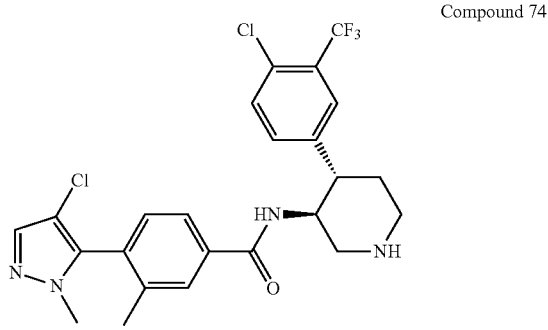 [SMILES: Cc1cc(C(=O)N[C@@H]2CNCC[C@H]2c2ccc(Cl)c(C(F)(F)F)c2)ccc1-c1c(Cl)cnn1C]

Compound 74

By using 4-bromo-3-methyl methylbenzoate and 3-trifluoromethyl-4-chlorocinnamaldehyde as raw materials, Compound 74 is prepared and obtained according to the methods as in Example 112, the yield is 39%; ESI (M+H)⁺=511.

Example 115. N-((3S,4S)-4-(4-chloro-3-(trifluoromethyl)phenyl)piperidin-3-yl)-4-(4-ethyl-1-methyl-1H-pyrazol-5-yl)-2,6-difluorobenzamide (Compound 75)

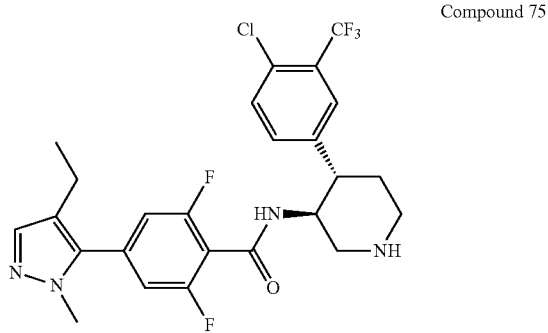 [SMILES: CCc1cnn(C)c1-c1cc(F)c(C(=O)N[C@@H]2CNCC[C@H]2c2ccc(Cl)c(C(F)(F)F)c2)c(F)c1]

Compound 75

By using 2,5-difluoro-4-bromo-methyl benzoate and 3-trifluoromethyl-4-chlorocinnamaldehyde as raw materials, Compound 75 is prepared and obtained according to the methods as in Example 112, the yield is 29%; ESI (M+H)⁺=527.

Example 116. 4-(4-chloro-1-methyl-1H-pyrazol-5-yl)-N-((3S,4S)-4-(4-chlorophenyl) piperidin-3-yl)-3-cyanobenzamide (Compound 76)

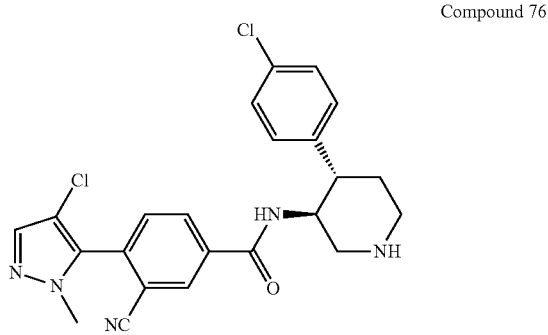 [SMILES: Cn1ncc(Cl)c1-c1ccc(C(=O)N[C@@H]2CNCC[C@H]2c2ccc(Cl)cc2)cc1C#N]

Compound 76

By using 3-cyano-4-bromo-methyl benzoate and 4-chlorocinnamaldehyde as raw materials, Compound 76 is prepared and obtained according to the methods as in Example 112, the yield is 21%; ESI (M+H)⁺=454.

Example 117. N-((3S,4S)-4-(3,4-difluorophenyl)piperidin-3-yl)-4-(1-methyl-1H-pyrazol-5-yl)benzamide (Compound 77)

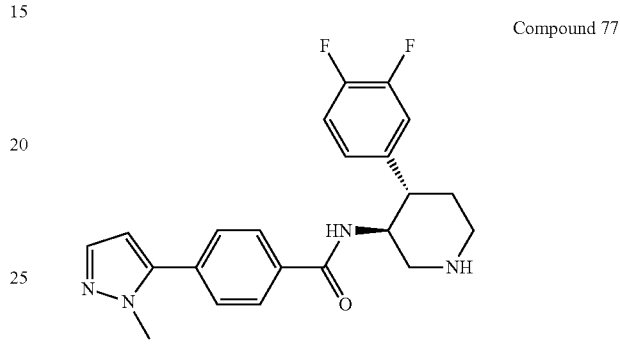

Compound 77

By using Intermediate 6-2 and 3,4-difluorocinnamaldehyde as raw materials, Compound 77 is prepared and obtained according to the methods as in Example 112, the yield is 30%; ¹H NMR (400 MHz, DMSO) δ 8.60 (d, J=8.8 Hz, 1H), 7.75 (d, J=8.3 Hz, 2H), 7.58 (d, J=8.3 Hz, 2H), 7.47 (d, J=1.9 Hz, 1H), 7.33 (tt, J=17.0, 8.4 Hz, 2H), 7.14 (s, 1H), 6.44 (d, J=1.9 Hz, 1H), 4.49 (m, 1H), 3.84 (s, 3H), 3.38 (dd, J=14.0, 7.0 Hz, 2H), 3.07 (dt, J=13.7, 8.2 Hz, 1H), 2.92 (dd, J=23.6, 12.0 Hz, 2H), 1.98 (s, 2H). ESI (M+H)⁺=397.

Example 118. 3-chloro-4-(4-chloro-1-methyl-1H-pyrazol-5-yl)-N-((3S,4S)-4-(3,4-difluoro phenyl)piperidin-3-yl)benzamide (Compound 78)

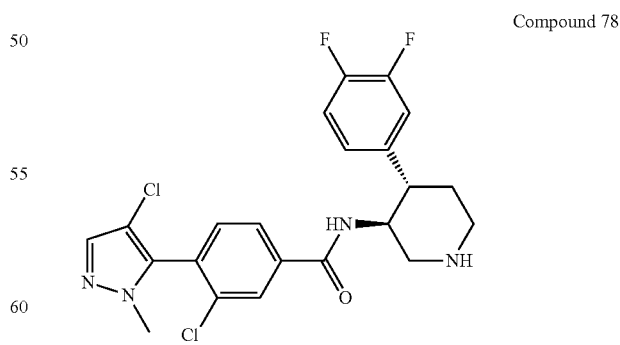

Compound 78

By using 3-chloro-4-bromo-methyl benzoate and 3,4-difluorocinnamaldehyde as raw materials, Compound 78 is prepared and obtained according to the methods as in Example 112, the yield is 39%; ESI (M+H)⁺=465.

Example 119. 3-amido-4-(4-chloro-1-methyl-1H-pyrazol-5-yl)-N-((3S,4S)-4-(3-fluoro phenyl)piperidin-3-yl)benzamide (Compound 79)

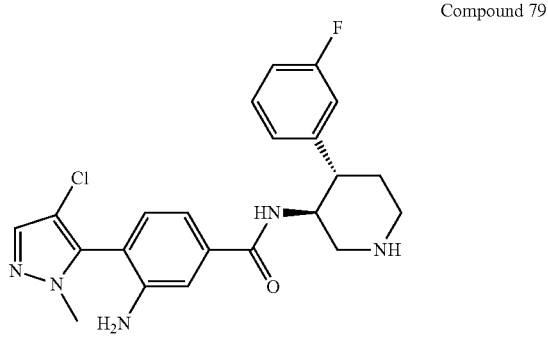 [SMILES: Cn1ncc(Cl)c1-c1ccc(C(=O)N[C@@H]2CNCC[C@H]2c2cccc(F)c2)cc1N]

Compound 79

By using 3-amido-4-bromo-methyl benzoate and 3-fluorocinnamaldehyde as raw materials, Compound 79 is prepared and obtained according to the methods as in Example 112, the yield is 32%; ESI (M+H)$^+$=428.

Example 120. 4-(4-chloro-1-methyl-1H-pyrazol-5-yl)-N-((3S,4S)-4-(4-chlorophenyl) piperidin-3-yl)-2-(trifluoromethyl)benzamide (Compound 80)

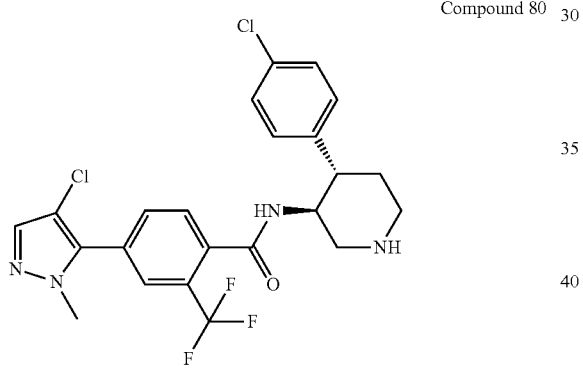

Compound 80

By using 2-trifluoromethyl-4-bromo-methyl benzoate and 4-chlorocinnamaldehyde as raw materials, Compound 80 is prepared and obtained according to the methods as in Example 112, the yield is 28%; ESI (M+H)$^+$=497.

Example 121. 4-(4-bromo-1-methyl-1H-pyrazol-5-yl)-N-((3S,4S)-4-(3,4,5-trifluorophenyl) piperidin-3-yl)benzamide (Compound 81)

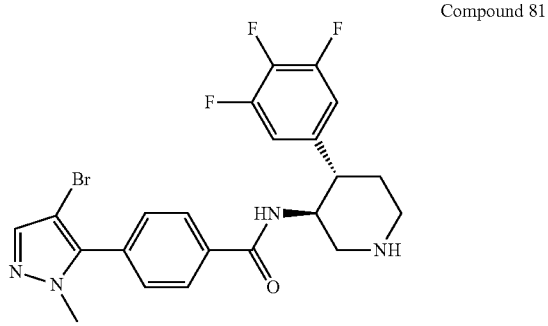 [SMILES: Cn1ncc(Br)c1-c1ccc(C(=O)N[C@@H]2CNCC[C@H]2c2cc(F)c(F)c(F)c2)cc1]

Compound 81

By using Intermediate 6-2 and 3,4,5-trifluorocinnamaldehyde as raw materials, Compound 81 is prepared and obtained according to the methods as in Example 112, the yield is 37%; ESI (M+H)$^+$=493.

Example 122. 4-(4-chloro-1-methyl-1H-pyrazol-5-yl)-N-((3S,4S)-4-(3,4-difluorophenyl) piperidin-3-yl)-3-fluorobenzamide (Compound 82)

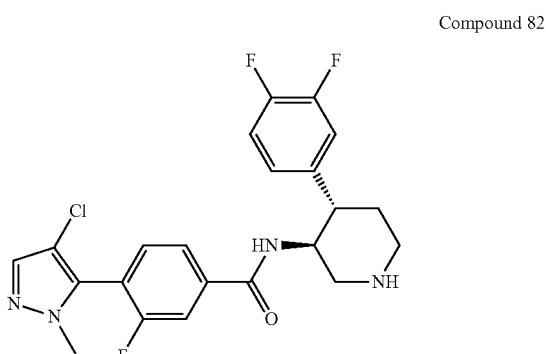

Compound 82

By using 3-fluoro-4-bromo-methyl benzoate and 3,4-difluorocinnamaldehyde as raw materials, Compound 82 is prepared and obtained according to the methods as in Example 112, the yield is 33%; ESI (M+H)$^+$=449.

Example 123. 4-(4-chloro-1-methyl-1H-pyrazol-5-yl)-N-((3S,4S)-4-(3-fluorophenyl) piperidin-3-yl)-3-methoxybenzamide (Compound 83)

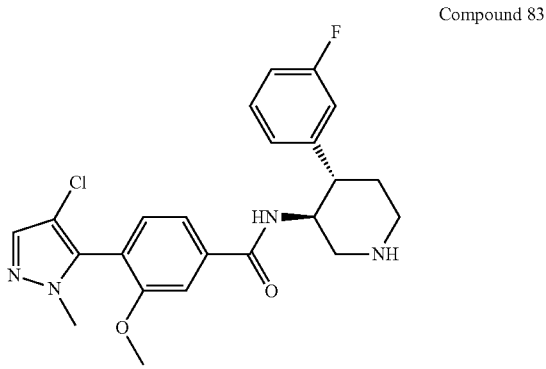 [SMILES: COc1cc(C(=O)N[C@@H]2CNCC[C@H]2c2cccc(F)c2)ccc1-c1c(Cl)cnn1C]

Compound 83

By using 3-methoxyl-4-bromo-methyl benzoate and 3-fluorocinnamaldehyde as raw materials, Compound 83 is prepared and obtained according to the methods as in Example 112, the yield is 33%; ESI (M+H)$^+$=443.

Example 124. 4-(4-chloro-1-methyl-1H-pyrazol-5-yl)-N-((3S,4S)-4-(4-chloro-3-(trifluoro methyl)phenyl)piperidin-3-yl)-2-fluorobenzamide (Compound 84)

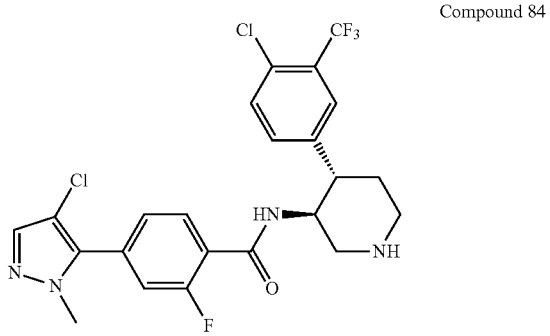 [SMILES: Cn1ncc(Cl)c1-c1ccc(C(=O)N[C@@H]2CNCC[C@H]2c2ccc(Cl)c(C(F)(F)F)c2)c(F)c1]

Compound 84

By using 2-fluoro-4-bromo-methyl benzoate and 3-trifluoromethyl-4-chlorocinnamaldehyde as raw materials, Compound 84 is prepared and obtained according to the methods as in Example 112, the yield is 27%; ESI (M+H)$^+$=515.

Example 125. 4-(4-chloro-1-methyl-1H-pyrazol-5-yl)-N-((3S,4S)-4-(3-fluorophenyl) piperidin-3-yl)-3-(trifluoromethoxy)benzamide (Compound 85)

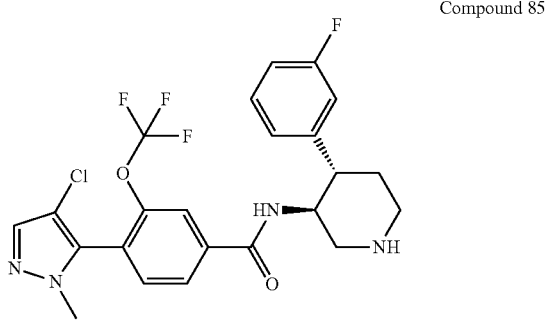 [SMILES: Cn1ncc(Cl)c1-c1ccc(C(=O)N[C@@H]2CNCC[C@H]2c2cccc(F)c2)cc1OC(F)(F)F]

Compound 85

By using 3-trifluoromethoxy-4-bromo-methyl benzoate and 3-fluorocinnamaldehyde as raw materials, Compound 85 is prepared and obtained according to the methods as in Example 112, the yield is 34%; ESI (M+H)$^+$=497.

Example 126. 3-chloro-4-(4-chloro-1-methyl-1H-pyrazol-5-yl)-N-((3S,4S)-4-(3-fluoro phenyl)piperidin-3-yl)benzamide (Compound 86)

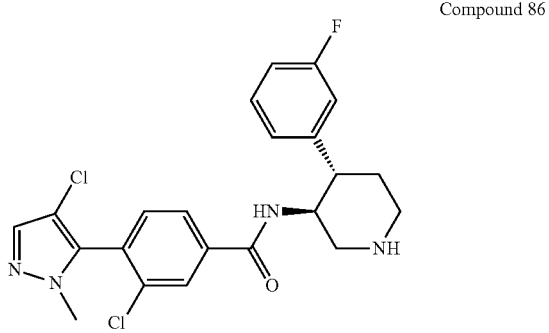 [SMILES: Cn1ncc(Cl)c1-c1ccc(C(=O)N[C@@H]2CNCC[C@H]2c2cccc(F)c2)cc1Cl]

Compound 86

By using 3-chloro-4-bromo-methyl benzoate and 3-fluorocinnamaldehyde as raw materials, Compound 86 is prepared and obtained according to the methods as in Example 112, the yield is 31%; ESI (M+H)$^+$=447.

Example 127. 4-(4-chloro-1-methyl-1H-pyrazol-5-yl)-N-((3S,4S)-4-(3,4-difluorophenyl) piperidin-3-yl)-3-(furan-3-yl)benzamide (Compound 87)

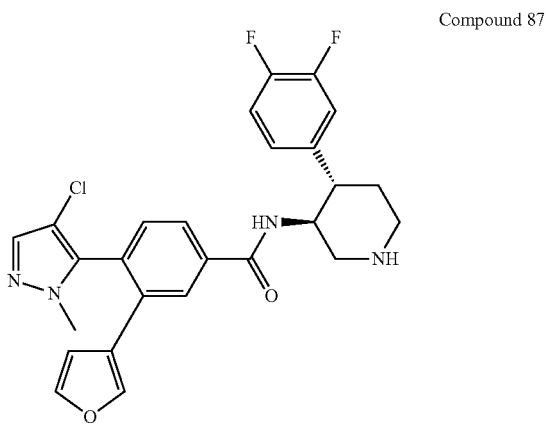 [SMILES: Cn1ncc(Cl)c1-c1ccc(C(=O)N[C@@H]2CNCC[C@H]2c2ccc(F)c(F)c2)cc1-c1ccoc1]

Compound 87

By using 3-(furan-3-yl)-4-bromo-methyl benzoate and 3,4-difluorocinnamaldehyde as raw materials, Compound 87 is prepared and obtained according to the methods as in Example 112, the yield is 26%; ESI (M+H)$^+$=497.

Example 128. 4-(4-chloro-1-methyl-1H-pyrazol-5-yl)-N-((3S,4S)-4-(3-fluorophenyl) piperidin-3-yl)-2-(2-methylfuran-3-yl)benzamide (Compound 88)

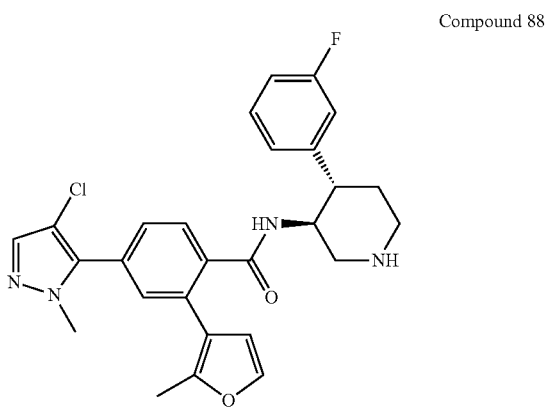 [SMILES: Cc1occc1-c1cc(-c2c(Cl)cnn2C)ccc1C(=O)N[C@@H]1CNCC[C@H]1c1cccc(F)c1]

Compound 88

By using 2-(2-methylfuran-3-yl)-4-bromo-methyl benzoate and 3-fluorocinnamaldehyde as raw materials, Compound 88 is prepared and obtained according to the methods as in Example 112, the yield is 33%; ESI (M+H)$^+$=493.

Example 129. N-((3S,4S)-4-(1H-indol-3-yl)piperidin-3-yl)-3-chloro-4-(4-chloro-1-methyl-1H-pyrazol-5-yl)benzamide (Compound 89)

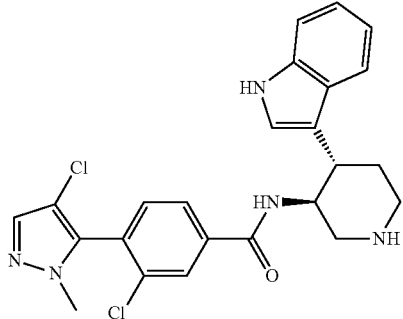

Compound 89

By using 3-chloro-4-bromo-methyl benzoate and (E)-3-(1H-indol-3-yl)acrylic aldehyde as raw materials, Compound 89 is prepared and obtained according to the methods as in Example 112, the yield is 35%; ESI (M+H)$^+$=468.

Example 130. 4-(4-chloro-1-methyl-1H-pyrazol-5-yl)-2-(5-chlorothiophene-3-yl)-N-((3S, 4S)-4-(3,4-difluorophenyl)piperidin-3-yl)benzamide (Compound 90)

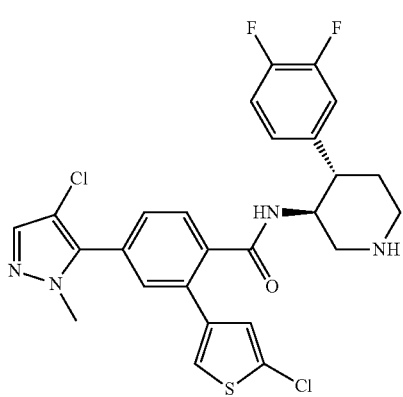

Compound 90

By using 2-(5-chlorothiophene-3-yl)-4-bromo-methyl benzoate and 3,4-difluorocinnamaldehyde as raw materials, Compound 90 is prepared and obtained according to the methods as in Example 112, the yield is 32%; ESI (M+H)$^+$=547.

Example 131. N-((3S,4S)-4-(1H-indol-4-yl)piperidin-3-yl)-3-chloro-4-(4-chloro-1-methyl-1H-pyrazol-5-yl)benzamide (Compound 91)

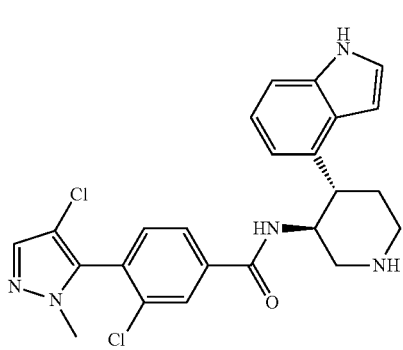

Compound 91

By using 3-chloro-4-bromo-methyl benzoate and (E)-3-(1H-indol-4-yl)acrylic aldehyde as raw materials, Compound 91 is prepared and obtained according to the methods as in Example 112, the yield is 31%; ESI (M+H)$^+$=468.

Example 92. 4-chloro-5-(4-chloro-1-methyl-1H-pyrazol-5-yl)-N-((3S,4S)-4-(3-fluoro phenyl)piperidin-3-yl)picolinamide (Compound 92)

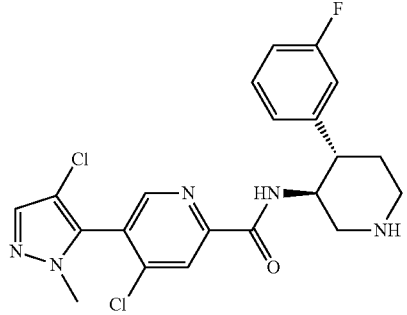

Compound 92

By using 5-bromo-4-chloropyridinyl-2-formic acid and 3-fluorocinnamaldehyde as raw materials, Compound 92 is prepared and obtained according to the methods as in Example 112, the yield is 40%; ESI (M+H)$^+$=448.

Example 133. 5-(4-chloro-1-methyl-1H-pyrazol-5-yl)-N-((3S,4S)-4-(3,4-difluorophenyl) piperidin-3-yl)pyrimidine-2-formamide (Compound 93)

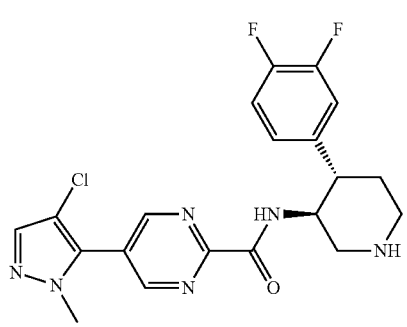

Compound 93

By using 5-bromopyrimidine-2-formic acid and 3,4-difluorocinnamaldehyde as raw materials, Compound 93 is prepared and obtained according to the methods as in Example 112, the yield is 35%; ESI (M+H)$^+$=433.

Example 134. 5-(4-chloro-1-methyl-1H-pyrazol-5-yl)-N-((3S,4S)-4-(3,4-difluorophenyl) piperidin-3-yl)-4-methylpicolinamide (Compound 94)

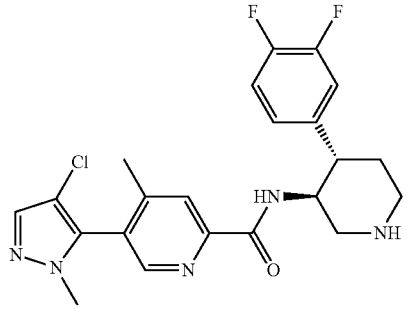

Compound 94

By using 4-methyl-5-bromo-pyridinyl-2-formic acid and 3,4-difluorocinnamaldehyde as raw materials, Compound 94 is prepared and obtained according to the methods as in Example 112, the yield is 32%; ESI (M+H)+=446.

Example 135. 4-chloro-5-(4-chloro-1-methyl-1H-pyrazol-5-yl)-N-((3S,4S)-4-(4-chloro-3-(trifluoromethyl)phenyl)piperidin-3-yl)picolinamide (Compound 95)

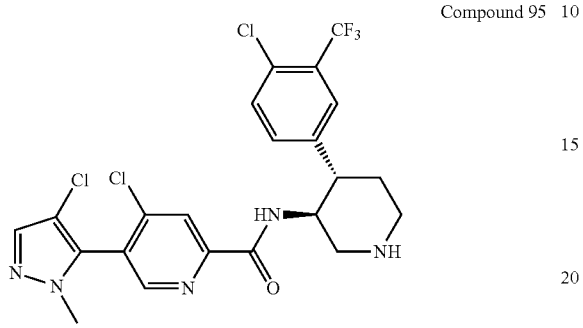

Compound 95

By using 4-chloro-5-bromo-pyridinyl-2-formic acid and 3-trifluoromethyl-4-chlorocinnamaldehyde as raw materials, Compound 95 is prepared and obtained according to the methods as in Example 112, the yield is 33%; ESI (M+H)+=532.

Example 136. 5-(4-chloro-1-methyl-1H-pyrazol-5-yl)-N-((3S,4S)-4-(4-chloro-3-(trifluoromethyl)phenyl) piperidin-3-yl)picolinamide (Compound 96)

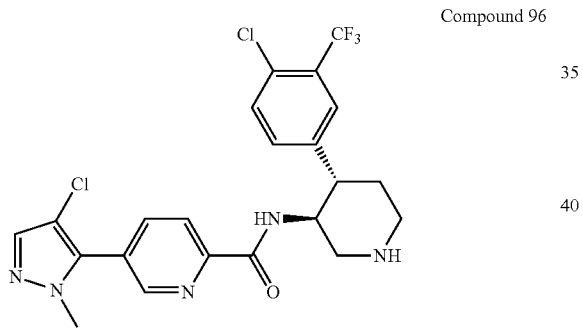

Compound 96

By using 5-bromo-pyridinyl-2-formic acid and 3-trifluoromethyl-4-chlorocinnamaldehyde as raw materials, Compound 96 is prepared and obtained according to the methods as in Example 112, the yield is 43%; ESI (M+H)+=498.

Example 137. 5-(4-chloro-1-methyl-1H-pyrazol-5-yl)-N-((3S,4S)-4-(3,4-difluorophenyl) piperidin-3-yl)-3-fluoropicolinamide (Compound 97)

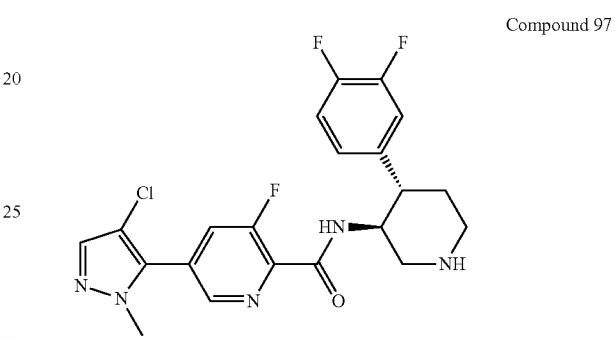

Compound 97

By using 3-fluoro-5-bromo-pyridinyl-2-formic acid and 3,4-difluorocinnamaldehyde as raw materials, Compound 97 is prepared and obtained according to the methods as in Example 112, the yield is 39%; ESI (M+H)+=450.

Example 138. 4-(4-chloro-1-methyl-1H-pyrazol-5-yl)-N-(((3S,4S)-4-(3,4-difluorophenyl)-6-(2-(methylamino)-2-oxoethyl)piperidin-3-yl)benzamide (Compound 98)

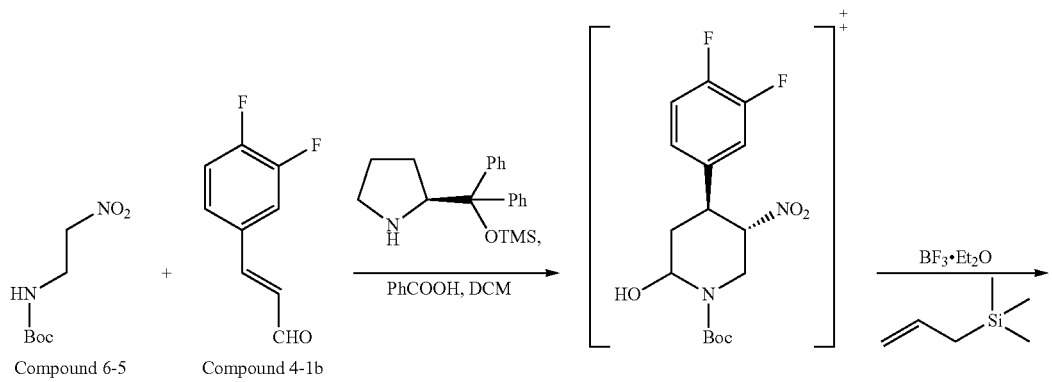

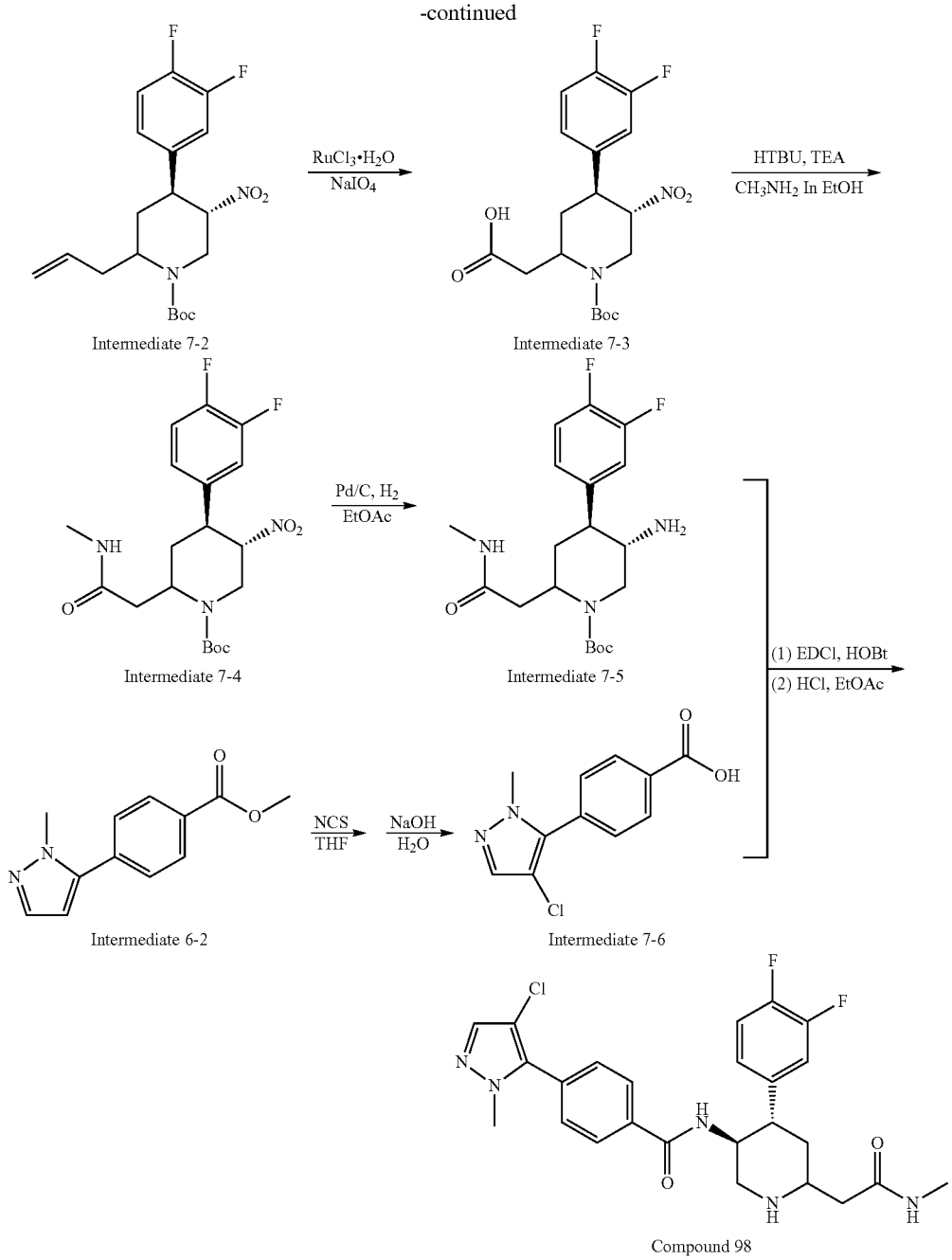

Step 1. Synthesis of (4S,5S)-2-allyl-4-(3,4-difluorophenyl)-5-nitropiperidine-1-tert-butyl formate (Intermediate 7-2)

Dissolving 2-nitroethyl tert-butyl carbamate (Intermediate 6-5, 2.85 g, 15 mmol), ((S)-(−)-α,α-diphenyl-2-pyrrylmethyl)trimethylsilyl ether (0.36 g, 1.1 mmol), and benzoic acid (0.25 g, 2 mmol) in anhydrous dichloromethane (15 ml), slowly adding 3,4-difluorocinnamaldehyde (Compound 4-1b, 1.68 g, 10 mmol) thereto in an ice bath, stirring for about 18 h at room temperature, diluting the reaction system with dichloromethane to 100 ml. Decreasing the temperature of the reaction system to −78° C., adding allyltrimethylsilane (5 ml, 30 mmol) into the reaction liquid, subsequently, slowly dropwise adding 2.5 ml of aether boron trifluoride, continue reacting for 10 h, adding about 100 ml of 1N NaHCO$_3$ solution into the reaction liquid, stirring for 10 min at room temperature, and then extracting the reaction liquid with ethyl acetate 3 times, merging the organic phase, washing with saturated sodium chloride twice, drying it with anhydrous sodium sulfate, and purifying by column chromatography on silica gel, 1.9 g of white solid (Intermediate 7-2) is obtained and the yield is 50%; $^1$H NMR (500 MHz, CDCl$_3$) δ 7.15-7.07 (m, 1H), 7.06-6.98 (m, 1H), 6.92 (d, J=8.3 Hz, 1H), 5.74 (s, 1H), 5.17 (d, J=16.3 Hz, 1H), 5.10 (d, J=9.8 Hz, 1H), 4.67-4.34 (m, 3H), 3.51-3.41 (m, 1H), 3.29 (dt, J=49.6, 12.0 Hz, 1H), 2.58 (s, 1H), 2.40 (d, J=19.3 Hz, 1H), 1.97-1.82 (m, 2H), 1.48 (s, 9H).

Step 2. Synthesis of 2-((4S,5S)-1-Boc-4-(3,4-difluorophenyl)-5-nitropiperidin-2-yl)acetic acid (Intermediate 7-3)

Dissolving Intermediate 7-2 (1.9 g, 5 mmol) in 40 ml solvent of mixed DCM/CH$_3$CN/H$_2$O (v/v/v=1/1/2), sequentially slowly adding NaIO$_4$ (5.35 g, 25 mmol) and RuCl$_3$ monohydrate (170 mg, 1 mmol) thereto in an ice bath, stirring overnight at room temperature, filtering to remove black insoluble substance, adjusting the filtrate with dilute hydrochloric acid solution to a pH of 5, extracting the reaction liquid with dichloromethane 3 times, merging the organic layer, washing with saturated sodium chloride twice, drying it with anhydrous sodium sulfate, and spin drying, 1.8 g of colorless oily matter (Intermediate 7-3) is obtained and the yield is 90%; $^1$H NMR (500 MHz, CDCl$_3$) δ 7.11 (dd, J=18.2, 8.4 Hz, 1H), 7.05-7.00 (m, 1H), 6.92 (dd, J=5.4, 3.1 Hz, 1H), 4.89 (m, 1H), 4.62 (m, 2H), 3.42 (m, 1H), 3.29 (m, 1H), 2.76 (d, J=6.7 Hz, 2H), 1.97 (s, 2H), 1.46 (s, 9H).

Step 3. Synthesis of (4S,5S)-4-(3,4-difluorophenyl)-2-(2-(1-methylamino)-2-oxoethyl)-5-nitropiperidine-1-tert-butyl formate (Intermediate 7-4)

Dissolving Intermediate 7-3 (200 mg, 0.5 mmol) in 5 ml of DMF, sequentially adding HBTU (379 mg, 1 mmol) and 0.25 ml of triethylamine thereto in an ice bath, dropwise adding ethanol solution (1 ml) with 30% methylamine to the reaction liquid after reacting for 15 min at room temperature, continue reacting for 3 h. After the reaction is finished, pouring the reaction system to 10 ml of water, extracting the reaction liquid with ethyl acetate 3 times, merging the organic phase, washing it with saturated sodium chloride twice, drying it with anhydrous sodium sulfate, and spin drying, 200 mg of white solid (Intermediate 7-4) is obtained and the yield is 97%, which is directly used for the next reaction without purification.

Step 4. Synthesis of (4S,5S)-4-(3,4-difluorophenyl)-2-(2-(1-methylamino)-2-oxoethyl)-5-amido piperidine-1-tert-butyl formate (Intermediate 7-5)

Dissolving Intermediate 7-4 (200 mg, 0.5 mmol) in ethyl acetate (10 ml), adding 30 mg of 10% Pd/C, hydrogenating overnight at room temperature, suction filtrating after the reaction is completed, and spin drying the filtrate, 180 mg of oily liquid (Intermediate 7-5) is obtained and the yield is 91%; ESI (M+H)$^+$=384.

Step 5. Synthesis of 4-(4-chloro-1-methyl-1H-pyrazol-5-yl)benzoic acid (Intermediate 7-6)

Dissolving Intermediate 6-2 (1.1 g, 5 mmol) in 20 ml of tetrahydrofuran, slowly adding NCS (0.8 g, 6 mmol), and adding 10 ml of 6N NaOH aqueous solution after reacting for 5 h at room temperature, continue reacting for 6 h at room temperature, and removing the organic solvent under the reduced pressure. Adding 10 ml of water to the remained reaction mixture, washing with dichloromethane twice, adjusting the water layer with 1N HCl solution to a pH of about 3, a large amount of solid is precipitedng and filtered, washing the filter cake once and drying it, 0.88 g of white solid (Intermediate 7-6) is obtained and the yield is 75%; $^1$H NMR (500 MHz, DMSO) δ 8.11-8.08 (m, 2H), 7.70 (s, 1H), 7.68-7.64 (m, 2H), 3.80 (s, 3H).

Step 6. Synthesis of 4-(4-chloro-1-methyl-1H-pyrazol-5-yl)-N-((3S,4S)-4-(3,4-difluorophenyl)-6-(2-(methylamino)-2-oxoethyl)piperidin-3-yl)benzamide (Compound 98)

Dissolving Intermediate 7-6 (81 mg, 0.345 mmol), 1-hydroxybenzotriazole (HOBt) (78.62 mg, 0.517 mmol) and 1-ethyl-(3-dimethylaminopropyl) carbodiimide hydrochloride EDC.HCl (98.8 mg, 0.517 mmol) in anhydrous dichloromethane (4 ml), adding diisopropylethylamine (0.115 ml, 1.21 mmol) thereto after stirring for 10 min in an ice bath, continue stirring for 15 min in an ice bath, and then slowly adding dichloromethane solution (4 ml) dissolved with Intermediate 7-5 (134 mg, 0.35 mmol), and stirring overnight at room temperature. After the reaction is completed, pouring the reaction liquid to 15 ml of water, extracting the reaction liquid with dichloromethane 3 times, merging the organic phase, washing it with saturated sodium chloride twice, drying it with anhydrous sodium sulfate, and spin drying; dissolving the obtained residue to a small amount of acetate ethyl, slowly adding ethyl acetate saturated with HCl thereto in an ice bath, spin drying after reacting for 3 h at room temperature, adding saturated NaHCO$_3$ solution, extracting the reaction liquid with ethyl acetate twice, merging the organic phase, drying it with anhydrous sodium sulfate, and purifying by column chromatography on silica gel, 97 mg of white powder (Compound 98) is obtained and the yield is 56%; 1H NMR (500 MHz, MeOD) δ 7.88-7.79 (m, 2H), 7.59-7.54 (m, 3H), 7.33 (ddd, J=11.6, 7.6, 1.9 Hz, 1H), 7.22 (ddd, J=15.6, 13.7, 8.5 Hz, 2H), 4.57 (td, J=11.5, 4.9 Hz, 1H), 4.16-4.08 (m, 1H), 3.80 (s, 3H), 3.54-3.47 (m, 1H), 3.46-3.37 (m, 2H), 3.08 (dd, J=16.3, 10.0 Hz, 1H), 2.81 (d, J=4.9 Hz, 3H), 2.77 (dd, J=16.3, 5.1 Hz, 1H), 2.31-2.22 (m, 1H), 2.13-2.06 (m, 1H). ESI (M+H)$^+$=502.

Example 139. 3-chloro-4-(4-chloro-1-methyl-1H-pyrazol-5-yl)-N-((3S,4S)-4-(3,4-difluoro phenyl)-6-(2-(methylamido)-2-oxoethyl)piperidin-3-yl)benzamide (Compound 99)

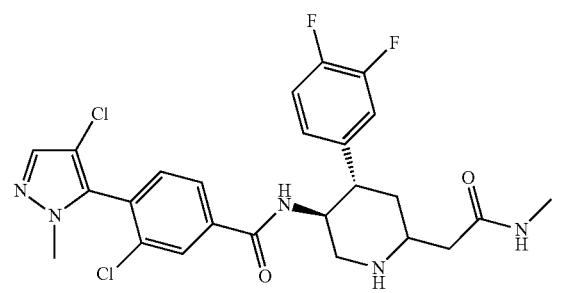

Compound 99

By using 3-chloro-4-(4-chloro-1-methyl-1H-pyrazol-5-yl)benzoic acid and Intermediate 7-5 as raw materials, Compound 99 is prepared and obtained according to the methods as in Example 138, the yield is 44%; ESI (M+H)$^+$=536.

Example 140. 4-(4-chloro-1-methyl-1H-pyrazol-5-yl)-N-((3S,4S)-4-(3,4-difluorophenyl)-6-(2-hydroxyl-ethyl)piperidin-3-yl)benzamide (Compound 100)

Compound 100

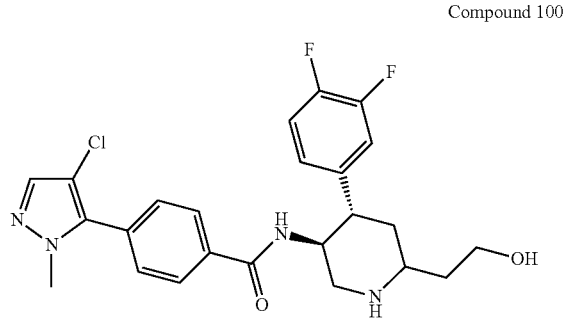 [SMILES: Cn1ncc(Cl)c1-c1ccc(C(=O)N[C@@H]2CNC(CCO)C[C@H]2c2ccc(F)c(F)c2)cc1]

By using Intermediate 7-6 and Intermediate 7-2 as raw materials, Compound 100 is prepared and obtained by condensation, oxidation, deprotection steps and the like according to the methods as in Example 138, the yield is 47%; ESI (M+H)$^+$=475.

Example 141. 4-(4-chloro-1-methyl-1H-pyrazol-5-yl)-N-((3S,4S)-4-(3,4-difluorophenyl)-6-((N-methyl-sulfamoyl)methyl)piperidin-3-yl)-3-fluorobenzamide (Compound 101)

Compound 101

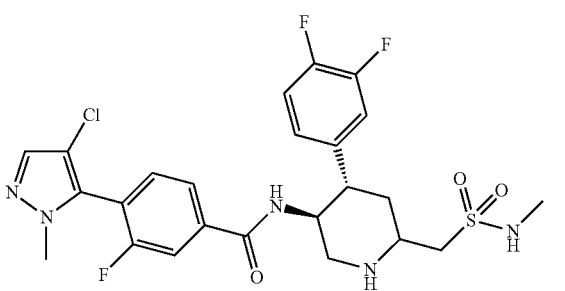

By using 3-fluoro-4-(4-chloro-1-methyl-1H-pyrazol-5-yl)benzoic acid and Intermediate 7-2 as raw materials, Compound 101 is prepared and obtained according to the methods as in Example 138, the yield is 38%; ESI (M+H)$^+$=556.

Example 142. 4-(4-chloro-1-methyl-1H-pyrazol-5-yl)-N-((3S,4S)-4-(3,4-difluorophenyl)-6-(2-(piperidin-1-yl)ethyl)piperidin-3-yl)-3-methylbenzamide (Compound 102)

Compound 102

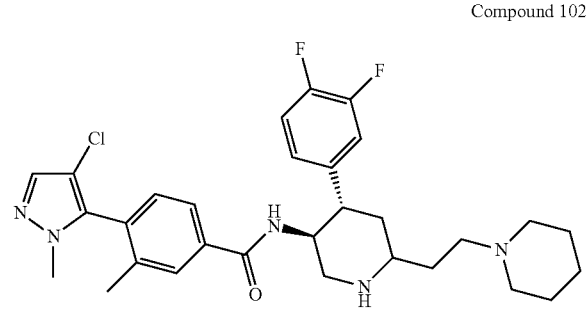 [SMILES: Cc1cc(C(=O)N[C@@H]2CNC(CCN3CCCCC3)C[C@H]2c2ccc(F)c(F)c2)ccc1-c1c(Cl)cnn1C]

By using 3-methyl-4-(4-chloro-1-methyl-1H-pyrazol-5-yl)benzoic acid and Intermediate 7-2 as raw materials, Compound 102 is prepared and obtained according to the methods as in Example 138, the yield is 19%; ESI (M+H)$^+$=556.

Example 143. 3-chloro-4-(4-chloro-1-methyl-1H-pyrazol-5-yl)-N-((3S,4S)-4-(3-fluoro phenyl)-6-(2-(methylsulfonamido)ethyl)piperidin-3-yl)benzamide (Compound 103)

Compound 103

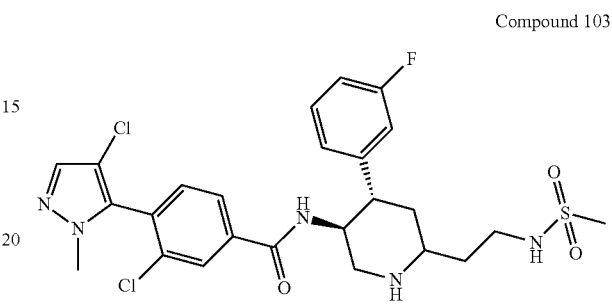

By using 3-chloro-4-(4-chloro-1-methyl-1H-pyrazol-5-yl)benzoic acid and Intermediate 7-2 as raw materials, Compound 103 is prepared and obtained according to the methods as in Example 138, the yield is 31%; ESI (M+H)$^+$=568.

Example 144. 5-chloro-4-(4-chloro-1-methyl-1H-pyrazol-5-yl)-N-((3S,4S)-4-(3,4-difluoro phenyl)-6-(2-(methylamido)-2-oxoethyl)piperidin-3-yl)thiophene-2-formamide (Compound 104)

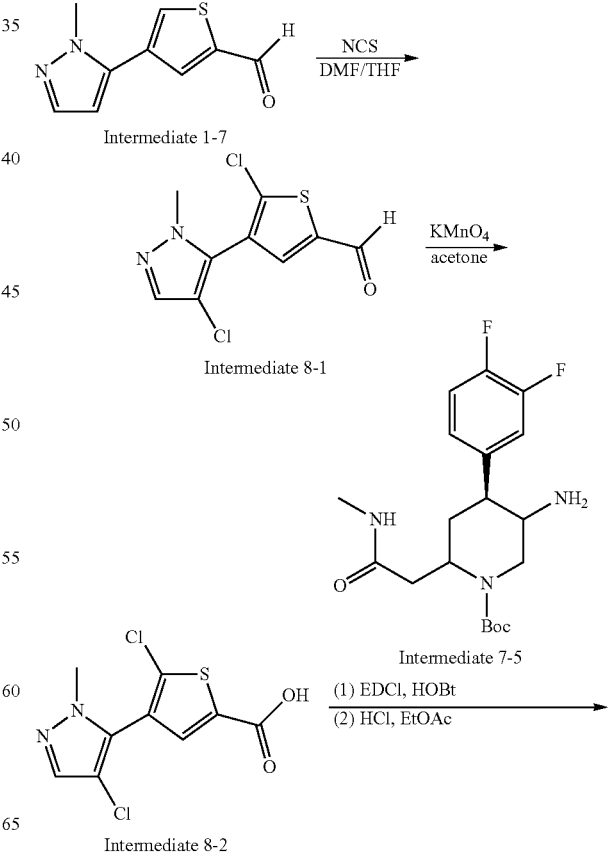

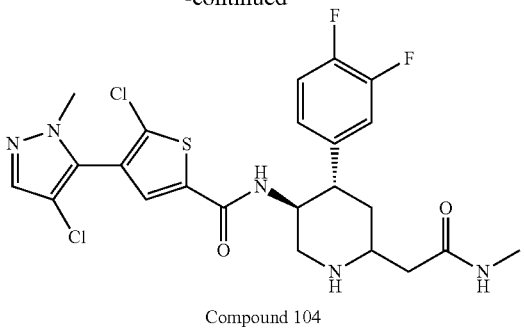

Compound 104

Step 1. Synthesis of 5-chloro-4-(4-chloro-1-methyl-1H-pyrazol-5-yl)thiophene-2-formaldehyde (Intermediate 8-1)

Dissolving Intermediate 1-7 (191 mg, 1 mmol), N-chlorosuccinimide (399 mg, 3 mmol) in DMF/THF (v/v=1:1, 10 ml), raising temperature to 80° C. and reacting for about 3 h, cooling the product to room temperature after the reaction is completed, pouring the system to water, and then extracting the reaction liquid with ethyl acetate 3 times, washing the merged organic phase with saturated sodium chloride once, and drying it with anhydrous sodium sulfate. Recycling the solvent under reduced pressure, and purifying it by column chromatography on silica gel, 160 mg of light yellow solid (Intermediate 8-1) is obtained and the yield is 61%; $^1$H NMR (500 MHz, CDCl$_3$) δ 10.00 (d, J=1.1 Hz, 1H), 7.92 (t, J=1.2 Hz, 1H), 7.91 (d, J=1.4 Hz, 1H), 3.87 (s, 3H).

Step 2. Synthesis of 5-chloro-4-(4-chloro-1-methyl-1H-pyrazol-5-yl) thiophene-2-formic acid (Intermediate 8-2)

Dissolving Intermediate 8-1 (520 mg, 2 mmol) in acetone (5 ml), then slowly adding KMnO$_4$ (380 mg, 2.4 mmol) thereto, stirring for 2 h at room temperature, suction filtrating after the reaction is completed, washing filter cake with ethyl acetate twice, concentrating the merged filtrate and recrystallizing thereof with ethyl acetate, 0.44 g of white solid (Intermediate 8-2) is obtained and the yield is 80%; $^1$H NMR (500 MHz, DMSO) δ 7.99 (s, 1H), 7.67 (s, 1H), 3.82 (s, 3H).

Step 3. Synthesis of 5-chloro-4-(4-chloro-1-methyl-1H-pyrazol-5-yl)-N-((3S,4S)-4-(3,4-difluorophenyl)-6-(2-(methylamido)-2-oxoethyl)piperidin-3-yl)thiophene-2-formamide (Compound 104)

Dissolving Intermediate 8-2 (95 mg, 0.345 mmol), 1-hydroxybenzotriazole (HOBt) (78.62 mg, 0.517 mmol) and 1-ethyl-(3-dimethylaminopropyl)carbodiimide hydrochloride EDC.HCl (98.8 mg, 0.517 mmol) in anhydrous dichloromethane (4 ml), adding diisopropylethylamine (0.115 ml, 1.21 mmol) after stirring for 10 min in an ice bath, after continue stirring for 15 min in an ice bath, slowly adding dichloromethane solution (4 ml) dissolved with Intermediate 7-5 (134 mg, 0.35 mmol), and stirring overnight at room temperature. After the reaction is completed, pouring the reaction liquid to 15 ml of water, extracting thereof with dichloromethane 3 times, washing the merged organic phase with saturated sodium chloride twice, drying it with anhydrous sodium sulfate, and spin drying; dissolving the obtained residue to a small amount of acetate ethyl, slowly adding HCl saturated ethyl acetate in an ice bath, spin drying after reacting for 3 h at room temperature, adding saturated NaHCO$_3$ solution, extracting the reaction liquid with ethyl acetate twice, merging the organic phase, drying it with anhydrous sodium sulfate, and purifying by column chromatography on silica gel, 125 mg of white powder (Compound 104) is obtained and the yield is 67%; 1H NMR (500 MHz, MeOD) δ 7.99 (dd, J=4.9, 1.5 Hz, 1H), 7.88 (d, J=1.4 Hz, 1H), 7.31 (ddd, J=11.5, 7.6, 1.9 Hz, 1H), 7.25-7.15 (m, 2H), 4.50 (td, J=11.3, 5.0 Hz, 1H), 4.15-4.09 (m, 1H), 3.85 (s, 3H), 3.50-3.45 (m, 1H), 3.44-3.37 (m, 2H), 3.06 (dd, J=16.2, 9.9 Hz, 1H), 2.80 (d, J=4.8 Hz, 3H), 2.76 (dd, J=16.3, 5.2 Hz, 1H), 2.30-2.21 (m, 1H), 2.08 (dd, J=11.3, 2.0 Hz, 1H). ESI (M+H)$^+$=542.

Example 145. 5-chloro-4-(4-chloro-1-methyl-1H-pyrazol-5-yl)-N-((3S,4S)-4-(3,4-difluoro phenyl)-6-(2-(methylamido)-2-oxoethyl)piperidin-3-yl)furan-2-formamide (Compound 105)

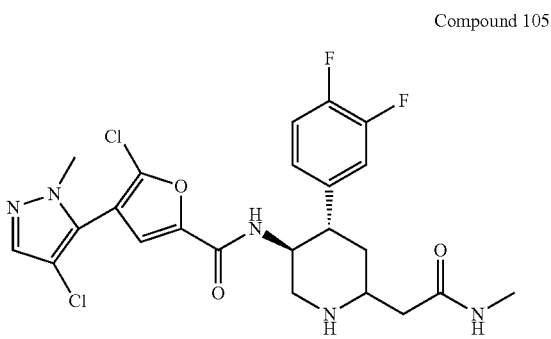 [SMILES: CNC(=O)CC1C[C@@H](c2ccc(F)c(F)c2)[C@H](NC(=O)c2cc(-c3c(Cl)cnn3C)c(Cl)o2)CN1]

Compound 105

By using 5-chloro-4-(4-chloro-1-methyl-1H-pyrazol-5-yl)furan-2-formic acid and Intermediate 7-5 as raw materials, Compound 105 is prepared and obtained according to the methods as in Example 144, the yield is 48%; $^1$H NMR (400 MHz, MeOD) δ 7.55 (s, 1H), 7.40-7.28 (m, 2H), 7.24-7.14 (m, 2H), 4.63-4.53 (m, 1H), 4.13 (d, J=3.7 Hz, 1H), 3.75 (d, J=12.0 Hz, 3H), 3.52-3.35 (m, 3H), 3.11-3.01 (m, 1H), 2.86-2.72 (m, 4H), 2.28 (td, J=14.7, 4.9 Hz, 1H), 2.13-2.02 (m, 1H). ESI (M+H)$^+$=526.

Example 146. N-((3S,4S)-6-allyl-4-(3,4-dichlorophenyl)piperidin-3-yl)-5-chloro-4-(4-chloro-1-methyl-1H-pyrazol-5-yl)furan-2-formamide (Compound 106)

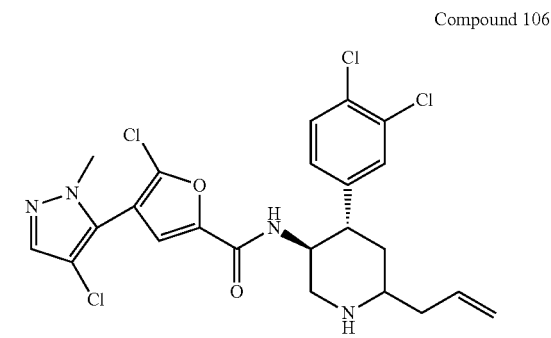 [SMILES: C=CCC1C[C@@H](c2ccc(Cl)c(Cl)c2)[C@H](NC(=O)c2cc(-c3c(Cl)cnn3C)c(Cl)o2)CN1]

Compound 106

By using 5-chloro-4-(4-chloro-1-methyl-1H-pyrazol-5-yl)furan-2-formic acid and (4S,5S)-2-allyl-4-(3,4-difluorophenyl)-5-amidopiperidine-1-tert-butyl formate as raw materials, Compound 106 is prepared and obtained according to the methods as in Example 144, the yield is 41%; $^1$H NMR (500 MHz, MeOD) δ 7.53 (s, 1H), 7.51 (d, J=2.0 Hz, 1H), 7.47-7.43 (m, 1H), 7.30 (s, 1H), 7.26 (dd, J=8.3, 2.0 Hz, 1H), 5.89-5.81 (m, 1H), 5.41 (dd, J=17.0, 1.1 Hz, 1H), 5.30 (d, J=10.3 Hz, 1H), 4.57 (td, J=11.5, 5.0 Hz, 1H), 3.82-3.76 (m, 1H), 3.76 (s, 3H), 3.43-3.31 (m, 3H), 2.81-2.68 (m, 2H), 2.20-2.07 (m, 2H). ESI (M+H)$^+$=529.

Example 147. 5-chloro-4-(4-chloro-1-methyl-1H-pyrazol-5-yl)-N-((3S,4S)-4-(3,4-dichloro phenyl)-6-(2-(dimethylamino)ethyl)piperidin-3-yl)furan-2-formamide (Compound 107)

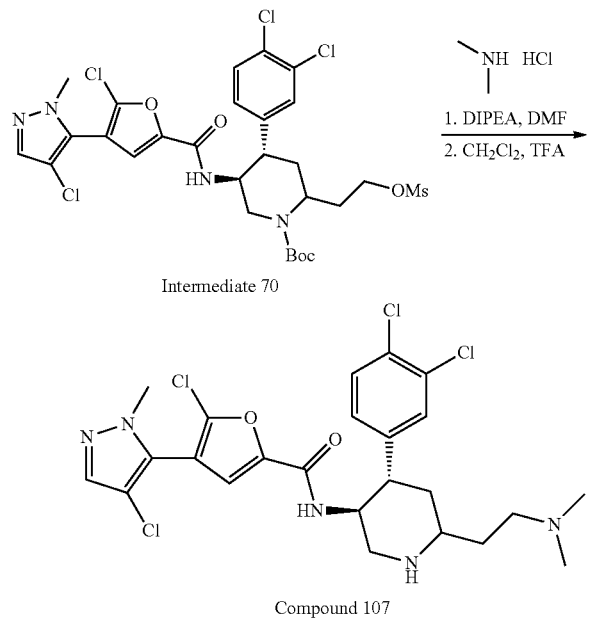

Compound 107

Dissolving Intermediate 70 (70 mg, 0.1 mmol), dimethylamine hydrochloride (81 mg, 1 mmol), diisopropylethylamine (0.26 ml, 1.5 mmol) in anhydrous DMF (10 ml), and reacting overnight at 55° C. under the protection of N$_2$. Adding 30 ml of saturated sodium chloride solution to the reaction liquid for diluting, extracting thereof with ethyl acetate 3 times, merging the organic layer, drying it with anhydrous sodium sulfate, spin drying and carrying out column chromatography, 32 mg of white solid is obtained. Dissolving the obtained white solid in dichloromethane (5 ml), slowly dropwise adding trifluoroacetic acid (0.5 ml) in an ice bath, stirring for 30 min at room temperature, and recycling the solvent under reduced pressure, 18 mg of light yellow solid (Compound 107) is directly obtained and the yield is 30.5%; $^1$H NMR (500 MHz, DMSO) δ 9.56 (d, J=9.7 Hz, 1H), 9.01 (d, J=9.2 Hz, 1H), 7.67 (s, 1H), 7.61 (s, 1H), 7.59-7.54 (m, 2H), 7.30 (dd, J=8.4, 1.9 Hz, 1H), 4.59-4.50 (m, 1H), 3.78-3.67 (m, 4H), 3.49-3.44 (m, 1H), 3.30-3.15 (m, 4H), 2.79 (d, J=4.1 Hz, 3H), 2.76 (d, J=4.1 Hz, 3H), 2.30 (dd, J=13.7, 7.3 Hz, 2H), 2.19-2.11 (m, 1H), 1.95 (d, J=14.5 Hz, 1H). ESI (M+H)$^+$=560.

Example 148. 5-chloro-4-(4-chloro-1-methyl-1H-pyrazol-5-yl)-N-((3S,4S)-4-(3,4-dichlorophenyl)-6-(2-(piperidin-1-yl)ethyl)piperidin-3-yl)furan-2-formamide (Compound 108)

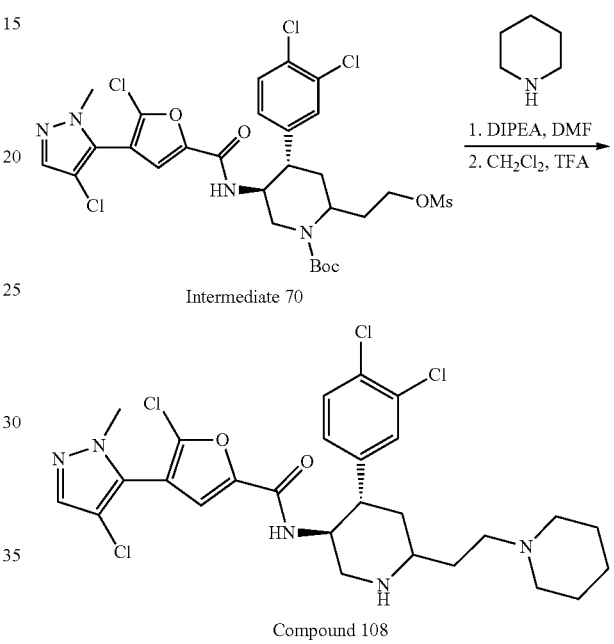

Compound 108

Dissolving Intermediate 70 (70 mg, 0.1 mmol), piperidine (86 mg, 1 mmol), and diisopropylethylamine (0.26 ml, 1.5 mmol) in anhydrous DMF (10 ml), and reacting overnight at 60° C. under the protection of N$_2$. Adding 30 ml of saturated sodium chloride solution into the reaction liquid for diluting, extracting the reaction liquid with ethyl acetate 3 times, merging the organic layer, drying it with anhydrous sodium sulfate, spin drying and carrying out column chromatography, 29 mg of white solid is obtained. Dissolve the obtained white solid in dichloromethane (5 ml), slowly dropwise adding trifluoroacetic acid (0.5 ml) thereto in an ice bath, stirring for 30 min at room temperature, and recycling the solvent under reduced pressure, 21 mg of light yellow solid (Compound 108) is directly obtained and the yield is 33.2%; $^1$H NMR (500 MHz, DMSO) δ 9.55 (s, 1H), 8.97 (d, J=5.5 Hz, 1H), 7.68 (s, 1H), 7.61 (d, J=2.0 Hz, 2H), 7.58 (d, J=8.3 Hz, 1H), 7.32 (dd, J=8.4, 2.0 Hz, 1H), 4.61-4.51 (m, 1H), 3.79-3.71 (m, 4H), 3.49 (d, J=11.7 Hz, 3H), 3.30-3.13 (m, 4H), 2.90 (dd, J=13.0, 8.2 Hz, 2H), 2.36 (dd, J=13.3, 7.5 Hz, 2H), 2.16 (t, J=12.6 Hz, 1H), 1.97 (d, J=11.9 Hz, 1H), 1.82 (s, 4H), 1.77-1.68 (m, 1H), 1.49-1.34 (m, 1H). ESI (M+H)$^+$=600.

Example 149. 5-chloro-4-(4-chloro-1-methyl-1H-pyrazol-5-yl)-N-((3S,4S)-4-(3,4-dichlorophenyl)-6-(2-(morpholin-1-yl)ethyl)piperidin-3-yl)furan-2-formamide (Compound 109)

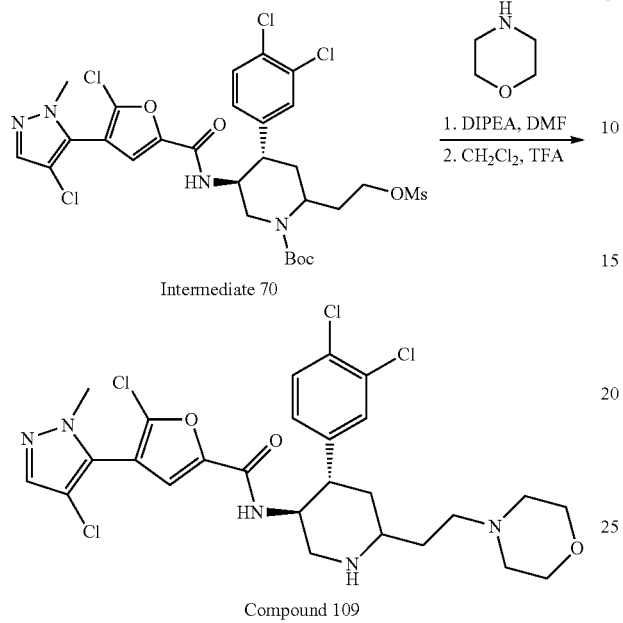

Intermediate 70

Compound 109

Dissolving Intermediate 70 (70 mg, 0.1 mmol), morpholine (88 mg, 1 mmol), diisopropylethylamine (0.26 ml, 1.5 mmol) in anhydrous DMF (12 ml), and reacting overnight at 60° C. under the protection of $N_2$. Adding 30 ml of saturated sodium chloride solution into the reaction liquid for diluting, extracting thereof with ethyl acetate 3 times, merging the organic layer, drying it with anhydrous sodium sulfate, spin drying and carry out column chromatography, 30 mg of white solid is obtained. Dissolving the obtained white solid in dichloromethane (5 ml), slowly dropwise adding trifluoroacetic acid (0.5 ml) thereto in an ice bath, stirring for 30 min at room temperature, and recycling the solvent under reduced pressure, 25 mg of yellow solid (Compound 109) is obtained; the yield is 33.1%; $^1$H NMR (500 MHz, DMSO) δ 9.50 (s, 1H), 8.94 (s, 1H), 7.68 (s, 1H), 7.62-7.57 (m, 3H), 7.32 (dd, J=8.4, 1.9 Hz, 1H), 4.61-4.51 (m, 1H), 4.04-3.96 (m, 2H), 3.91-3.85 (m, 2H), 3.80 (s, 1H), 3.74 (s, 3H), 3.53 (d, J=12.0 Hz, 1H), 3.46-3.39 (m, 2H), 3.30 (d, J=5.8 Hz, 2H), 3.21 (dd, J=16.3, 9.6 Hz, 2H), 3.16-3.05 (m, 2H), 2.38-2.28 (m, 2H), 2.15 (t, J=13.7 Hz, 1H), 2.02-1.96 (m, 1H). ESI (M+H)$^+$=602.

Example 150. 5-chloro-4-(4-chloro-1-methyl-1H-pyrazol-5-yl)-N-((3S,4S)-4-(3,4-dichlorophenyl)-6-(2-(pyrrolidin-1-yl)ethyl)piperidin-3-yl)furan-2-formamide (Compound 110)

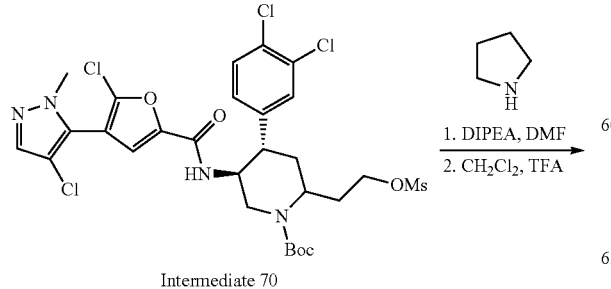

Intermediate 70

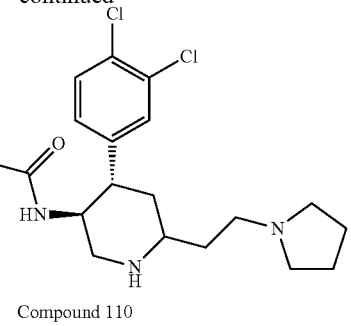

Compound 110

Dissolving Intermediate 70 (70 mg, 0.1 mmol), pyrrolidine (71 mg, 1 mmol), diisopropylethylamine (0.25 ml, 1.4 mmol) in anhydrous DMF (15 ml), and reacting overnight at 65° C. under the protection of $N_2$. Adding 30 ml of saturated sodium chloride solution into the reaction liquid for diluting, extracting thereof with ethyl acetate 3 times, merging the organic layer, drying it with anhydrous sodium sulfate, spin drying and carrying out column chromatography, 26 mg of white solid is obtained. Dissolve the obtained white solid in dichloromethane (5 ml), slowly dropwise adding trifluoroacetic acid (0.5 ml) thereto in an ice bath, stirring for 30 min at room temperature, and recycling the solvent under reduced pressure, 19 mg of white solid (Compound 110) is directly obtained; the yield is 29.9%; $^1$H NMR (500 MHz, DMSO) δ 9.53 (d, J=10.4 Hz, 1H), 8.99 (d, J=9.2 Hz, 1H), 7.68 (s, 1H), 7.62-7.56 (m, 3H), 7.31 (dd, J=8.4, 2.0 Hz, 1H), 4.60-4.50 (m, 1H), 3.81 (s, 1H), 3.74 (s, 3H), 3.48-3.26 (m, 4H), 3.25-3.12 (m, 2H), 3.06-2.99 (m, 2H), 2.33 (t, J=12.3 Hz, 2H), 2.17 (td, J=14.4, 4.5 Hz, 1H), 2.07-1.87 (m, 6H). ESI (M+H)$^+$=586.

Example 151. 5-chloro-4-(4-chloro-1-methyl-1H-pyrazol-5-yl)-N-((3S,4S)-4-(3,4-dichlorophenyl)-6-(3-hydroxypropyl)piperidin-3-yl)furan-2-formamide (Compound 111)

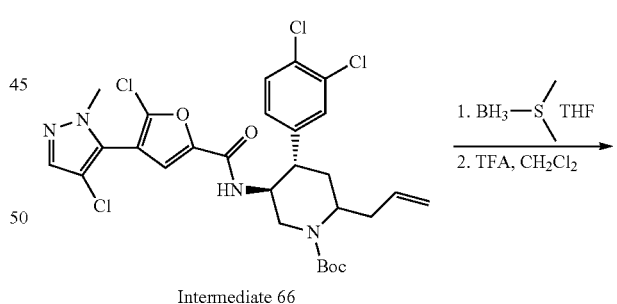

Intermediate 66

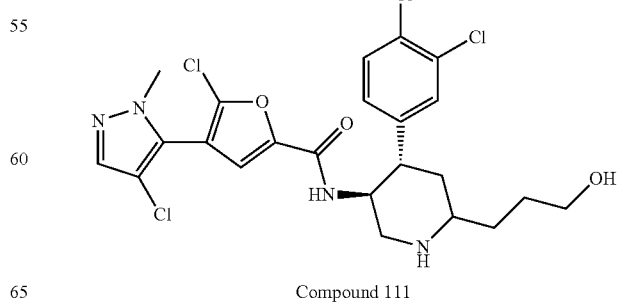

Compound 111

Dissolving Intermediate 66 (63 mg, 0.1 mmol) in anhydrous tetrahydrofuran (2 ml), slowly dropwise adding 2N borane dimethyl sulfide complex (0.15 ml, 0.3 mmol) thereto in an ice bath, after reacting for 3 h at room temperature, dropwise adding 1 ml of 10% NaOH solution and 0.5 ml of 30% hydrogen peroxide to the reaction system at 0° C., and continue to react for 1 h. Adding Dilute 5 ml of saturated sodium chloride solution into the reaction liquid for diluting, extracting thereof with ethyl acetate 3 times, merging the organic layer, drying it with anhydrous sodium sulfate, spin drying and obtaining white solid. Dissolving this solid in dichloromethane (2 ml), slowly dropwise adding 1 ml of trifluoroacetic acid thereto, reacting for 1 h at room temperature, and recycling the solvent under reduced pressure, 22.3 mg of white solid (Compound 111) is obtained; the yield is 50%; $^1$H NMR (500 MHz, CDCl$_3$) δ7.54-7.46 (m, 2H), 7.44 (s, 1H), 7.40 (d, J=8.2 Hz, 1H), 7.25-7.18 (m, 2H), 4.49-4.44 (m, 1H), 3.81-3.70 (m, 4H), 3.68-3.59 (m, 1H), 3.31-3.12 (m, 4H), 2.18-2.09 (m, 1H), 2.08-1.94 (m, 3H), 1.89-1.66 (m, 3H).

Example 152. 5-chloro-4-(4-chloro-1-methyl-1H-pyrazol-5-yl)-N-((3S,4S)-4-(3,4-dichlorophenyl)-6-(2,3-dihydroxypropyl)piperidin-3-yl)furan-2-formamide (Compound 112)

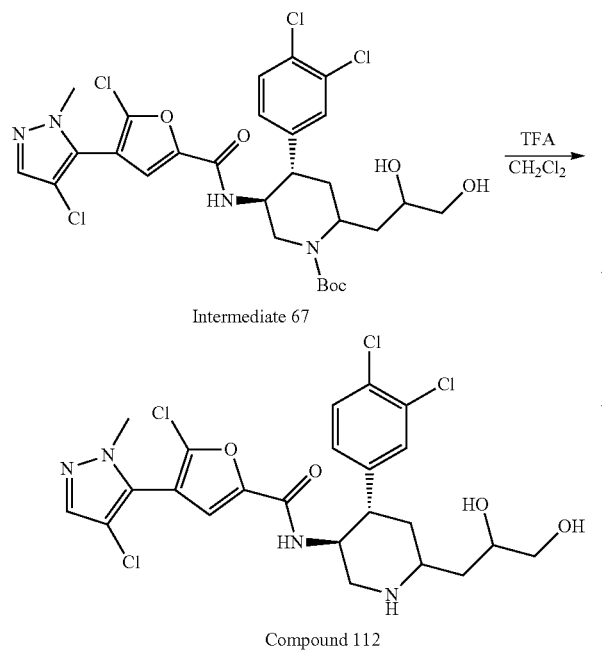

Dissolving Intermediate 67 (63 mg, 0.1 mmol) in 5 ml of dichloromethane, slowly dropwise adding 0.5 ml of trifluoroacetic acid thereto in an ice bath, reacting for 1 h under stirring at room temperature, and recycling the solvent under reduced pressure, 20.2 mg of white solid (Compound 112) is obtained; the yield is 87%; $^1$H NMR (500 MHz, MeOD) δ 7.53 (s, 1H), 7.52 (d, J=2.0 Hz, 1H), 7.46 (dd, J=8.3, 1.4 Hz, 1H), 7.27 (dd, J=5.9, 2.0 Hz, 2H), 4.55 (td, J=11.1, 5.0 Hz, 1H), 4.03-3.94 (m, 1H), 3.94-3.84 (m, 1H), 3.75 (s, 3H), 3.64-3.55 (m, 2H), 3.45-3.34 (m, 3H), 2.37-2.09 (m, 3H), 2.05-1.90 (m, 1H). ESI (M+H)$^+$=561.

Example 153. 5-chloro-4-(4-chloro-1-methyl-1H-pyrazol-5-yl)-N-((3S,4S)-4-(3,4-dichlorophenyl)-6-(2-hydroxyethyl)piperidin-3-yl)furan-2-formamide (Compound 113)

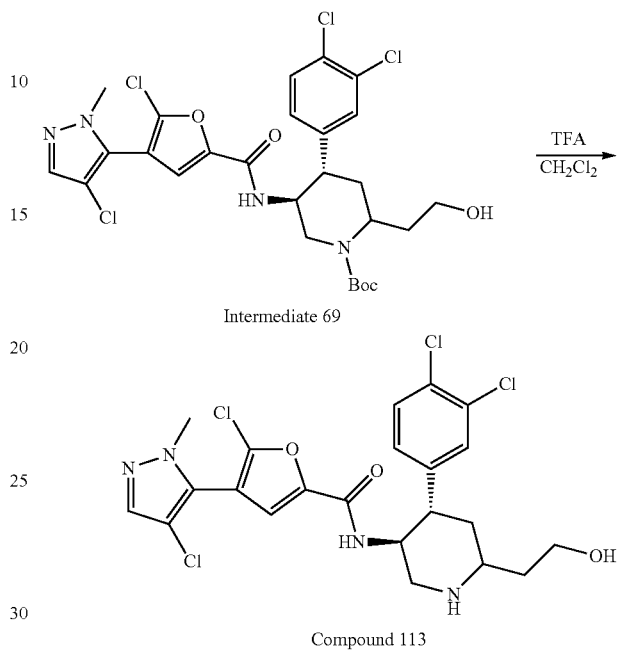

Dissolving in Intermediate 69 (66 mg, 0.1 mmol) in 5 ml of dichloromethane, slowly dropwise adding 1 ml of trifluoroacetic acid thereto in an ice bath, reacting for 1 h under stirring at room temperature, and recycling the solvent under reduced pressure, 29.2 mg of white solid (Compound 113) is obtained; the yield is 77%; $^1$H NMR (500 MHz, MeOD) δ 7.53 (s, 1H), 7.48 (dd, J=12.9, 1.9 Hz, 1H), 7.41 (t, J=7.0 Hz, 1H), 7.28-7.22 (m, 1H), 7.21 (d, J=6.2 Hz, 1H), 4.37-4.31 (m, 1H), 3.79-3.71 (m, 5H), 3.47-3.40 (m, 1H), 3.23-3.15 (m, 1H), 3.13-2.99 (m, 2H), 2.16-2.10 (m, 1H), 2.09-1.99 (m, 1H), 1.97-1.91 (m, 1H), 1.89-1.77 (m, 1H). ESI (M+H)$^+$=531.

Example 154. 5-chloro-4-(4-chloro-1-methyl-1H-pyrazol-5-yl)-N-((3S,4S)-4-(3,4-dichloro phenyl)-6-(2-(4-hydroxylpiperidin-1-yl)ethyl)piperidin-3-yl)furan-2-formamide (Compound 114)

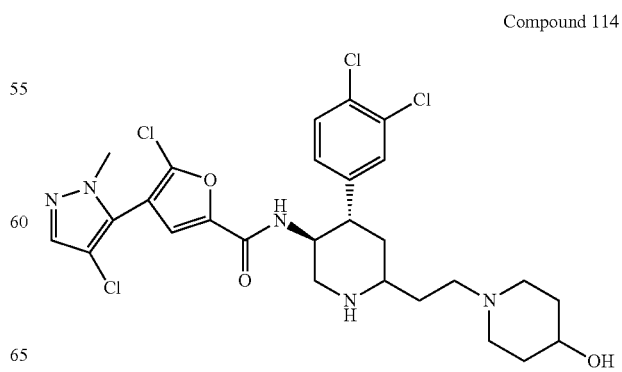

Compound 114

By using 5-chloro-4-(4-chloro-1-methyl-1H-pyrazol-5-yl)furan-2-formic acid and (4S,5S)-2-(2-(4-hydroxylpiperidin-1-yl)ethyl)-4-(3,4-dichlorophenyl)-5-amidopiperidine-1-tert-butyl formate as raw materials, Compound 114 is prepared and obtained according to the methods as in Example 144, the yield is 40%; $^1$H NMR (500 MHz, MeOD) δ 7.62 (s, 1H), 7.53 (s, 1H), 7.45 (d, J=8.3 Hz, 1H), 7.37-7.31 (m, 2H), 4.60 (s, 1H), 4.14-3.81 (m, 2H), 3.77-3.67 (m, 4H), 3.57-3.39 (m, 5H), 3.39-3.32 (m, 2H), 3.18 (d, J=21.6 Hz, 1H), 2.62 (s, 1H), 2.40 (s, 1H), 2.26-2.09 (m, 4H), 1.97 (d, J=18.8 Hz, 1H), 1.86 (dd, J=23.7, 11.2 Hz, 1H). ESI (M+H)$^+$=616.

Example 155. 5-chloro-4-(4-chloro-1-methyl-1H-pyrazol-5-yl)-N-((3S,4S)-4-(3,4-dichloro phenyl)-6-(2-(3-hydroxylpiperidin-1-yl)ethyl)piperidin-3-yl) furan-2-formamide (Compound 115)

By using 5-chloro-4-(4-chloro-1-methyl-1H-pyrazol-5-yl)furan-2-formic acid and 2-((4S,5S)-1-Boc-4-(3,4-dichlorophenyl)-5-amidopiperidin-2-yl)methyl acetate as raw materials, Compound 116 is prepared and obtained by amide condensation, alkaline hydrolysis, deprotection steps and the like according to the methods as in Example 144, the yield is 30%; $^1$H NMR (500 MHz, MeOD) δ 7.54 (s, 1H), 7.53 (d, J=1.2 Hz, 1H), 7.47-7.42 (m, 1H), 7.29 (d, J=8.2 Hz, 2H), 4.60 (d, J=6.2 Hz, 1H), 4.21-4.10 (m, 1H), 3.74 (s, 3H), 3.49-3.42 (m, 1H), 3.40-3.32 (m, 2H), 3.21-3.10 (m, 1H), 3.01-2.92 (m, 1H), 2.35-2.22 (m, 1H), 2.18-2.09 (m, 1H). ESI (M+H)$^+$=547.

Example 157. N-((3S,4S)-6-(2-amido-2-oxoethyl)-4-(3,4-dichlorophenyl)piperidin-3-yl)-5-chloro-4-(4-chloro-1-methyl-1H-pyrazol-5-yl)furan-2-formamide (Compound 117)

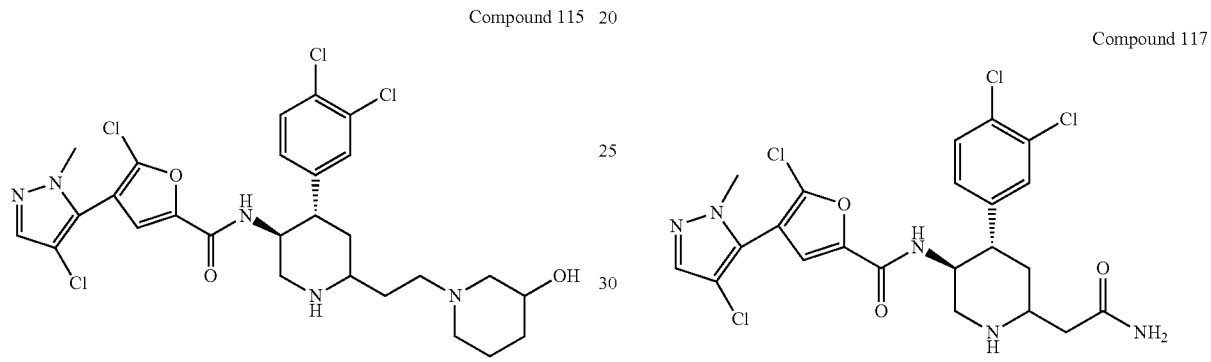

Compound 115

Compound 117

By using 5-chloro-4-(4-chloro-1-methyl-1H-pyrazol-5-yl)furan-2-formic acid and (4S,5S)-2-(2-(3-hydroxylpiperidin-1-yl)ethyl)-4-(3,4-dichlorophenyl)-5-amidopiperidine-1-tert-butyl formate as raw materials, Compound 115 is prepared and obtained according to the methods as in Example 144, the yield is 27%; $^1$H NMR (500 MHz, MeOD) δ 7.63-7.56 (m, 1H), 7.51 (s, 1H), 7.42 (d, J=8.3 Hz, 1H), 7.36-7.28 (m, 2H), 4.64-4.51 (m, 1H), 4.24-3.94 (m, 1H), 3.87-3.75 (m, 1H), 3.72 (s, 3H), 3.55-3.33 (m, 5H), 3.23-2.90 (m, 2H), 2.85-2.02 (m, 6H), 1.94-1.41 (m, 3H). ESI (M+H)$^+$=616.

Example 156. 2-((4S,5S)-5-(5-chloro-4-(4-chloro-1-methyl-1H-pyrazol-5-yl)furan-2-formamide)-4-(3,4-dichlorophenyl) piperidin-2-yl)acetic acid (Compound 116)

By using 5-chloro-4-(4-chloro-1-methyl-1H-pyrazol-5-yl)furan-2-formic acid and (4S,5S)-2-(2-amido-2-oxoethyl)-4-(3,4-dichlorophenyl)-5-amidopiperidine-1-tert-butyl formate as raw materials, Compound 117 is prepared and obtained according to the methods as in Example 144, the yield is 40%; $^1$H NMR (500 MHz, MeOD) δ 7.55 (s, 1H), 7.53 (d, J=5.4 Hz, 1H), 7.46 (d, J=7.9 Hz, 1H), 7.33-7.28 (m, 2H), 4.56 (s, 1H), 4.10 (dd, J=14.2, 7.1 Hz, 1H), 3.75 (s, 3H), 3.50-3.35 (m, 3H), 3.13-3.05 (m, 1H), 2.81 (d, J=17.0 Hz, 1H), 2.26 (t, J=12.6 Hz, 1H), 2.11-2.04 (m, 1H). ESI (M+H)$^+$=546.

Example 158. 5-chloro-4-(4-chloro-1-methyl-1H-pyrazol-5-yl)-N-((3S,4S)-4-(3,4-dichloro phenyl)-6-(2-(methylamido)-2-oxoethyl)piperidin-3-yl)furan-2-formamide (Compound 118)

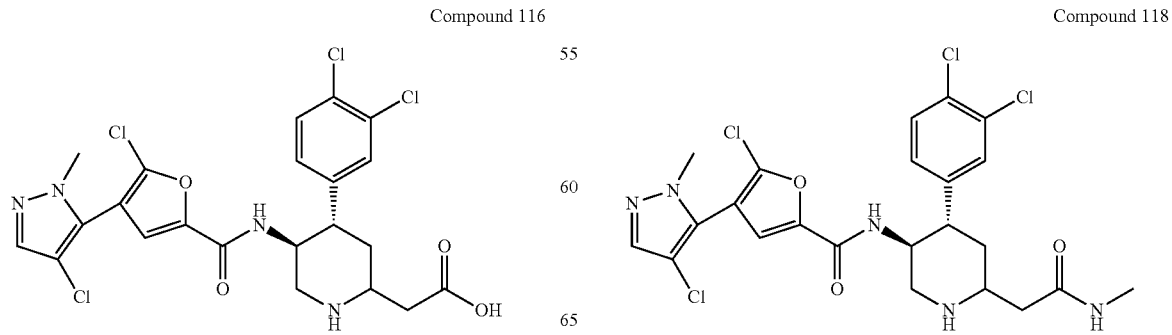

Compound 116

Compound 118

By using 5-chloro-4-(4-chloro-1-methyl-1H-pyrazol-5-yl)furan-2-formic acid and (4S,5S)-2-(2-methylamido-2-oxyethyl)-4-(3,4-dichlorophenyl)-5-amidopiperidine-1-tert-butyl formate as raw materials, Compound 118 is prepared and obtained according to the methods as in Example 144, the yield is 33%; $^1$H NMR (500 MHz, MeOD) δ 7.57 (s, 1H), 7.55 (s, 1H), 7.50-7.45 (m, 1H), 7.36-7.32 (m, 2H), 4.58 (s, 1H), 4.12 (dd, J=14.0, 6.9 Hz, 1H), 3.77 (s, 3H), 3.50-3.36 (m, 3H), 3.06 (dd, J=25.2, 15.5 Hz, 1H), 2.83-2.83 (m, 4H), 2.33-2.22 (s, 1H), 2.08 (d, J=13.3 Hz, 1H). ESI (M+H)$^+$=560.

Example 159. 5-chloro-4-(4-chloro-1-methyl-1H-pyrazol-5-yl)-N-((3S,4S)-6-(2-(cyclo propylamido)-2-oxoethyl)-4-(3,4-dichlorophenyl)piperidin-3-yl)furan-2-formamide (Compound 119)

Compound 119

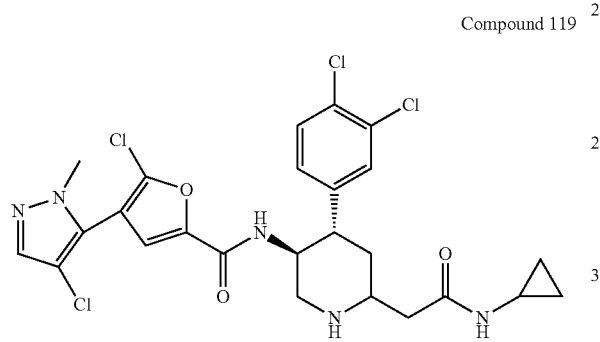

By using 5-chloro-4-(4-chloro-1-methyl-1H-pyrazol-5-yl)furan-2-formic acid and (4S,5S)-2-(2-cyclopropylamido-2-oxoethyl)-4-(3,4-dichlorophenyl)-5-amidopiperidine-1-tert-butyl formate as raw materials, Compound 119 is prepared and obtained according to the methods as in Example 144, the yield is 32%; $^1$H NMR (500 MHz, MeOD) δ 7.57-7.54 (m, 2H), 7.48 (d, J=7.1 Hz, 1H), 7.37-7.29 (m, 2H), 4.58 (s, 1H), 4.17-4.10 (m, 1H), 3.77 (s, 3H), 3.50-3.35 (m, 3H), 3.03 (dd, J=17.5, 8.3 Hz, 1H), 2.79-2.71 (m, 2H), 2.27 (t, J=13.5 Hz, 1H), 2.07 (d, J=13.3 Hz, 1H), 0.82-0.72 (m, 2H), 0.63-0.52 (m, 2H). ESI (M+H)$^+$=586.

Example 160. 5-chloro-4-(4-chloro-1-methyl-1H-pyrazol-5-yl)-N-((3S,4S)-6-(2-(cyclo butylamido)-2-oxoethyl)-4-(3,4-dichlorophenyl)piperidin-3-yl)furan-2-formamide (Compound 120)

Compound 120

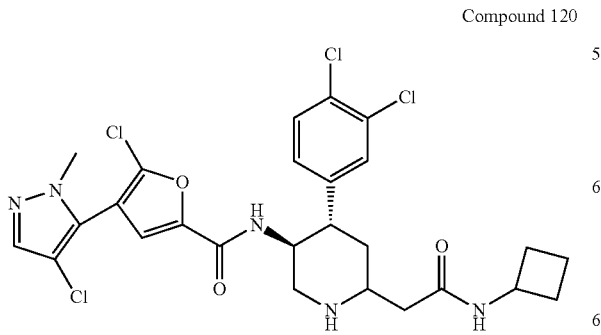

By using 5-chloro-4-(4-chloro-1-methyl-1H-pyrazol-5-yl)furan-2-formic acid and (4S,5S)-2-(2-cyclobutylamido-2-oxoethyl)-4-(3,4-dichlorophenyl)-5-amidopiperidine-1-tert-butyl formate as raw materials, Compound 120 is prepared and obtained according to the methods as in Example 144, the yield is 37%; NMR (500 MHz) δ 7.55 (s, 2H), 7.49 (d, J=8.2 Hz, 1H), 7.33 (s, 1H), 7.30 (d, J=8.3 Hz, 1H), 4.55 (s, 1H), 4.40-4.34 (m, 1H), 4.12-4.06 (m, 1H), 3.77 (s, 3H), 3.48-3.35 (m, 3H), 3.03 (dd, J=16.6, 9.5 Hz, 1H), 2.74 (d, J=14.2 Hz, 1H), 2.35-2.21 (m, 3H), 2.10-1.98 (m, 3H), 1.83-1.72 (m, 2H). ESI (M+H)$^+$=600.

Example 161. 5-chloro-4-(4-chloro-1-methyl-1H-pyrazol-5-yl)-N-((3S,4S)-4-(3,4-dichloro phenyl)-6-(2-((2,3-dihydroxypropyl)amido)-2-oxoethyl)piperidin-3-yl)furan-2-formamide (Compound 121)

Compound 121

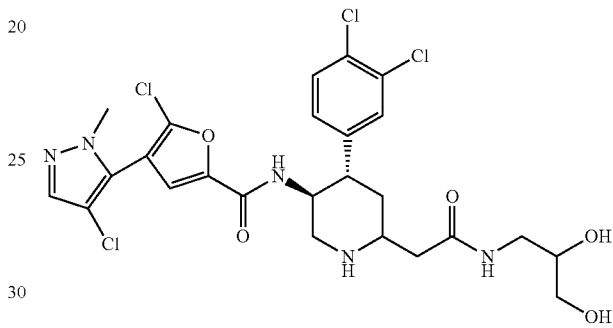

By using 5-chloro-4-(4-chloro-1-methyl-1H-pyrazol-5-yl)furan-2-formic acid and (4S,5S)-2-(2-(2,3-dihydroxypropyl)amido-2-oxoethyl)-4-(3,4-dichlorophenyl)-5-amidopiperidin-1-tert-butyl formate as raw materials, Compound 121 is prepared and obtained according to the methods as in Example 144, the yield is 21%; $^1$H NMR (500 MHz, MeOD) δ 7.56 (s, 1H), 7.52 (d, J=1.9 Hz, 1H), 7.45 (d, J=8.3 Hz, 1H), 7.28 (dd, J=8.3, 1.9 Hz, 1H), 7.24 (s, 1H), 4.31 (td, J=10.4, 4.6 Hz, 1H), 3.77 (s, 3H), 3.75-3.71 (m, 1H), 3.63 (d, J=4.9 Hz, 1H), 3.53 (d, J=5.7 Hz, 2H), 3.50-3.37 (m, 2H), 3.30-3.24 (m, 1H), 3.11-3.04 (m, 1H), 3.03-2.97 (m, 1H), 2.83 (dd, J=14.6, 8.7 Hz, 1H), 2.57 (dd, J=14.8, 6.2 Hz, 1H), 2.10-2.03 (m, 1H), 1.94-1.88 (m, 1H). ESI (M+H)$^+$=620.

Example 162. N-((3S,4S)-6-(2-(1H-1,2,4-triazol-1-yl)ethyl)-4-(3,4-dichlorophenyl) piperidin-3-yl)-5-chloro-4-(4-chloro-1-methyl-1H-pyrazol-5-yl)furan-2-formamide (Compound 122)

Compound 122

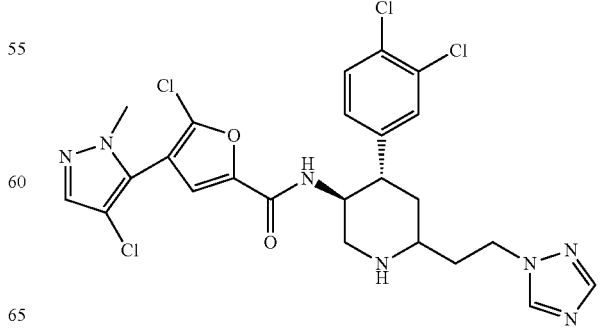

By using 5-chloro-4-(4-chloro-1-methyl-1H-pyrazol-5-yl)furan-2-formic acid and (4S,5S)-2-(2-(1H-1,2,4-triazol-1-yl)ethyl)-4-(3,4-dichlorophenyl)-5-amidopiperidine-1-tert-butyl formate as raw materials, Compound 122 is prepared and obtained according to the methods as in Example 144, the yield is 26%; ¹H NMR (500 MHz, MeOD) δ 9.53 (s, 1H), 8.65 (s, 1H), 7.61 (d, J=1.9 Hz, 1H), 7.55 (s, 1H), 7.47 (d, J=8.3 Hz, 1H), 7.36 (dd, J=8.3, 1.9 Hz, 1H), 7.34 (s, 1H), 4.73 (dt, J=13.5, 6.7 Hz, 1H), 4.67-4.57 (m, 2H), 3.95 (s, 1H), 3.77 (s, 3H), 3.53-3.40 (m, 3H), 2.79 (d, J=7.2 Hz, 1H), 2.62 (dd, J=13.7, 6.4 Hz, 1H), 2.33-2.24 (m, 1H), 2.20 (d, J=13.3 Hz, 1H). ESI (M+H)⁺=584.

Example 163. 5-chloro-4-(4-chloro-1-methyl-1H-pyrazol-5-yl)-N-((3S,4S)-4-(3,4-dichlorophenyl)-6-(2-((2,3-dihydroxypropyl)amido)ethyl)piperidin-3-yl)furan-2-formamide (Compound 123)

Compound 123

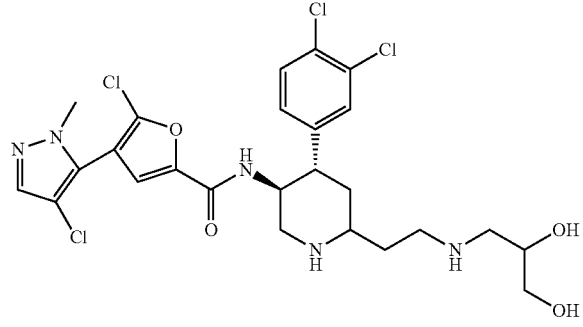

By using 5-chloro-4-(4-chloro-1-methyl-1H-pyrazol-5-yl)furan-2-formic acid and (4S,5S)-2-(2-(2,3-dihydroxypropyl)amido)ethyl)-4-(3,4-dichlorophenyl)-5-amidopiperidine-1-tert-butyl formate as raw materials, Compound 123 is prepared and obtained according to the methods as in Example 144, the yield is 36%; ESI (M+H)⁺=606.

Example 164. 5-chloro-4-(4-chloro-1-methyl-1H-pyrazol-5-yl)-N-((3S,4S)-4-(3,4-dichloro phenyl)-6-(2-methoxyethyl)piperidin-3-yl)furan-2-formamide (Compound 124)

Compound 124

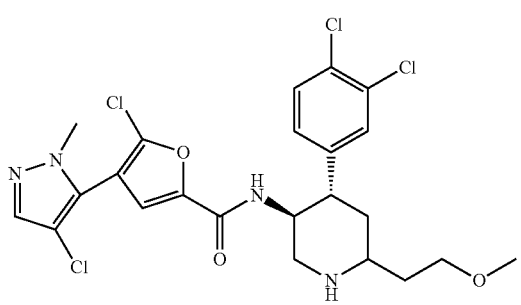

By using 5-chloro-4-(4-chloro-1-methyl-1H-pyrazol-5-yl)furan-2-formic acid and (4S,5S)-2-(2-methoxyethyl)-4-(3,4-dichlorophenyl)-5-amidopiperidine-1-tert-butyl formate as raw materials, Compound 124 is prepared and obtained according to the methods as in Example 144, the yield is 39%; ¹H NMR (500 MHz, MeOD) δ 7.54 (s, 1H), 7.51 (s, 1H), 7.47 (d, J=8.3 Hz, 1H), 7.29-7.24 (m, 2H), 4.57-4.48 (m, 1H), 3.87 (s, 1H), 3.75 (s, 3H), 3.68-3.62 (m, 2H), 3.45-3.32 (m, 6H), 2.36 (dd, J=14.1, 5.6 Hz, 1H), 2.23-2.10 (m, 2H), 2.11-2.03 (m, 1H). ESI (M+H)⁺=547.

Example 165. 5-chloro-4-(4-chloro-1-methyl-1H-pyrazol-5-yl)-N-((3S,4S)-4-(3,4-dichloro phenyl)-6-(2-((2-hydroxyethyl)amido)-2-oxoethyl)piperidin-3-yl)furan-2-formamide (Compound 125)

Compound 125

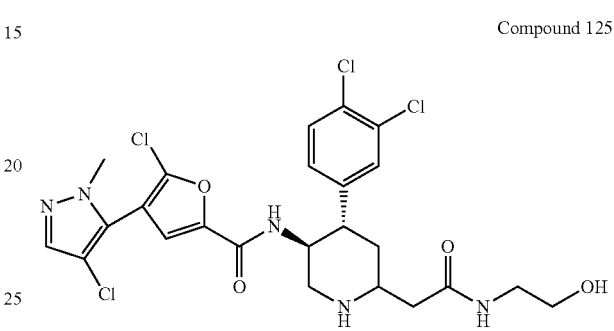

By using 5-chloro-4-(4-chloro-1-methyl-1H-pyrazol-5-yl)furan-2-formic acid and (4S,5S)-2-(2-((2-hydroxyethyl)amido)-2-oxoethyl)-4-(3,4-dichlorophenyl)-5-amidopiperidin-1-tert-butyl formate as raw materials, Compound 125 is prepared and obtained according to the methods as in Example 144, the yield is 21%; ¹H NMR (500 MHz, MeOD) δ 7.57-7.54 (m, 2H), 7.47 (d, J=8.3 Hz, 1H), 7.31-7.28 (m, 2H), 4.48 (td, J=11.1, 4.7 Hz, 1H), 3.99-3.93 (m, 1H), 3.77 (s, 3H), 3.66 (t, J=5.7 Hz, 2H), 3.40-3.36 (m, 2H), 3.33-3.28 (m, 3H), 3.00 (dd, J=15.7, 9.5 Hz, 1H), 2.73 (dd, J=15.7, 5.5 Hz, 1H), 2.24-2.15 (m, 1H), 2.06-2.00 (m, 1H). ESI (M+H)⁺=590.

Example 166. N-((3S,4S)-6-(2-acetaminoethyl)-4-(3,4-difluorophenyl)piperidin-3-yl)-5-chloro-4-(4-chloro-1-methyl-1H-pyrazol-5-yl)furan-2-formamide (Compound 126)

Compound 126

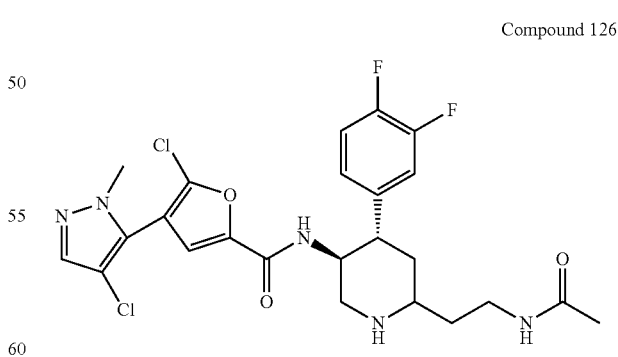

By using 5-chloro-4-(4-chloro-1-methyl-1H-pyrazol-5-yl)furan-2-formic acid and (4S,5S)-2-(2-acetaminoethyl)-4-(3,4-difluorophenyl)-5-amidopiperidine-1-tert-butyl formate as raw materials, Compound 126 is prepared and obtained according to the methods as in Example 144, the yield is 44%; ¹H NMR (500 MHz, DMSO) δ 9.67 (t, J=10.3

Hz, 1H), 9.06 (d, J=11.0 Hz, 1H), 8.80 (d, J=9.2 Hz, 1H), 8.18 (t, J=5.7 Hz, 1H), 7.68 (s, 1H), 7.53 (s, 1H), 7.38 (dd, J=19.2, 8.6 Hz, 1H), 7.31 (dd, J=9.9, 8.2 Hz, 1H), 7.12 (s, 1H), 4.57-4.47 (m, 1H), 3.73 (s, 3H), 3.56 (s, 1H), 3.34-3.27 (m, 1H), 3.26-3.02 (m, 4H), 2.12 (td, J=14.3, 4.4 Hz, 1H), 1.95 (dd, J=23.3, 15.7 Hz, 3H), 1.83 (s, 3H). ESI (M+H)$^+$=540.

Example 167. 5-chloro-4-(4-chloro-1-methyl-1H-pyrazol-5-yl)-N-((3S,4S)-4-(3,4-difluoro phenyl)-6-(2-(methylsulfonamido)ethyl)piperidin-3-yl)furan-2-formamide (Compound 127)

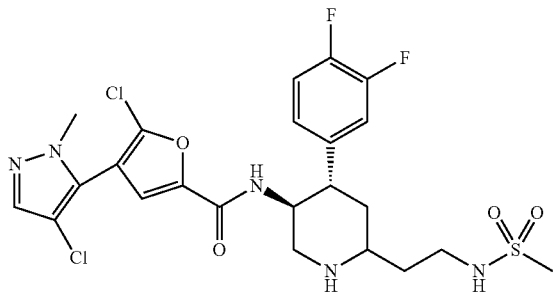

Compound 127

By using 5-chloro-4-(4-chloro-1-methyl-1H-pyrazol-5-yl)furan-2-formic acid and (4S,5S)-2-(2-methylsulfonamidoethyl)-4-(3,4-difluorophenyl)-5-amidopiperidine-1-tert-butyl formate as raw materials, Compound 127 is prepared and obtained according to the methods as in Example 144, the yield is 33%; $^1$H NMR (400 MHz, MeOD) δ 7.44 (s, 1H), 7.24-7.15 (m, 2H), 7.14-7.03 (m, 2H), 4.45 (td, J=11.4, 4.8 Hz, 1H), 3.79 (t, J=12.2 Hz, 1H), 3.65 (s, 3H), 3.46-3.24 (m, 3H), 3.21-3.12 (m, 2H), 2.90 (s, 3H), 2.24-1.98 (m, 4H). ESI (M+H)$^+$=476.

Example 168. 5-chloro-4-(4-chloro-1-methyl-1H-pyrazol-5-yl)-N-((3S,4S)-4-(3,4-difluoro phenyl)-6-(2,3-dihydroxypropyl)piperidin-3-yl)furan-2-formamide (Compound 128)

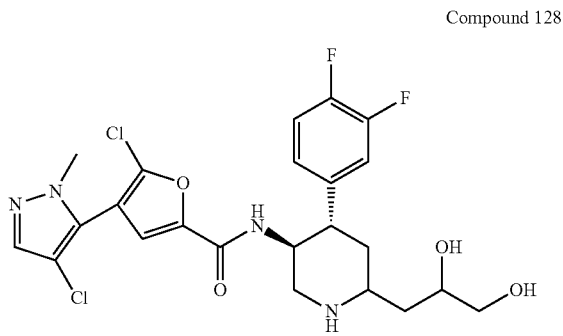 [SMILES: Cn1ncc(Cl)c1-c1cc(C(=O)N[C@@H]2CNC(CC(O)CO)C[C@H]2c2ccc(F)c(F)c2)oc1Cl]

Compound 128

By using 5-chloro-4-(4-chloro-1-methyl-1H-pyrazol-5-yl)furan-2-formic acid and (4S,5S)-2-(2,3-dihydroxypropyl)-4-(3,4-difluorophenyl)-5-nitropiperidine-1-tert-butyl formate as raw materials, Compound 128 is prepared and obtained according to the methods as in Example 144, the yield is 47%; $^1$H NMR (500 MHz, MeOD) δ 7.56 (s, 1H), 7.31 (s, 1H), 7.30-7.25 (m, 1H), 7.25-7.19 (m, 1H), 7.17 (s, 1H), 4.57 (td, J=11.3, 5.1 Hz, 1H), 4.01 (d, J=2.5 Hz, 1H), 3.93-3.88 (m, 1H), 3.77 (s, 3H), 3.68-3.59 (m, 2H), 3.46-3.36 (m, 3H), 2.37-2.31 (m, 1H), 2.27-2.16 (m, 2H), 2.02-1.96 (m, 1H). ESI (M+H)+=529.

Example 169. 5-chloro-4-(4-chloro-1-methyl-1H-pyrazol-5-yl)-N-((3S,4S)-4-(3,4-difluoro phenyl)-6-(2-hydroxyethyl) piperidin-3-yl)furan-2-formamide (Compound 129)

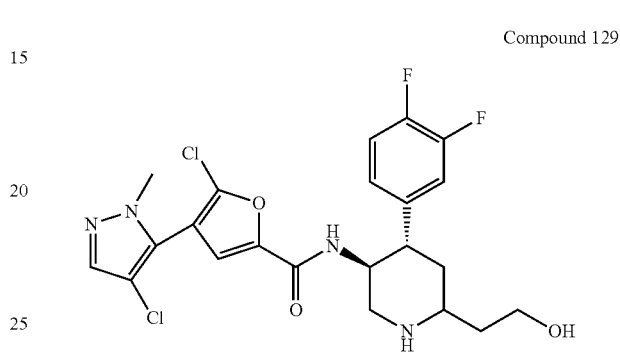

Compound 129

By using 5-chloro-4-(4-chloro-1-methyl-1H-pyrazol-5-yl)furan-2-formic acid and (4S,5S)-2-(2-hydroxyethyl)-4-(3,4-difluorophenyl)-5-amidopiperidine-1-tert-butyl formate as raw materials, Compound 129 is prepared and obtained according to the methods as in Example 144, the yield is 23%; $^1$H NMR (400 MHz, MeOD) δ 7.55 (s, 1H), 7.33-7.08 (m, 4H), 4.27 (td, J=10.5, 4.9 Hz, 1H), 3.84-3.71 (m, 5H), 3.28 (d, J=4.9 Hz, 1H), 3.15 (td, J=11.8, 3.6 Hz, 1H), 3.04-2.87 (m, 2H), 2.16-2.07 (m, 1H), 2.01-1.93 (m, 1H), 1.93-1.77 (m, 2H). ESI (M+H)$^+$=499.

Example 170. 5-chloro-4-(4-chloro-1-methyl-1H-pyrazol-5-yl)-N-((3S,4S)-4-(3,4-dichloro phenyl)-6-propylpiperidin-3-yl)furan-2-formamide (Compound 130)

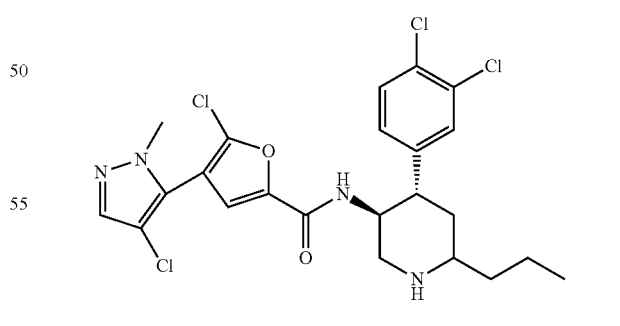

Compound 129

By using 5-chloro-4-(4-chloro-1-methyl-1H-pyrazol-5-yl)furan-2-formic acid and (4S,5S)-2-propyl-4-(3,4-dichlorophenyl)-5-amidopiperidine-1-tert-butyl formate as raw materials, Compound 130 is prepared and obtained according to the methods as in Example 144, the yield is 44%; $^1$H NMR (400 MHz, MeOD) δ 7.67-7.44 (m, 3H), 7.40-7.27 (m, 2H), 4.60-4.53 (m, 1H), 3.89-3.58 (m, 4H), 3.46-3.34

(m, 3H), 2.26-1.98 (m, 3H), 1.86 (dt, J=15.3, 6.0 Hz, 1H), 1.62-1.47 (m, 2H), 1.10 (t, J=7.3 Hz, 3H). ESI (M+H)$^+$=531.

Example 171. 2-((4S,5S)-5-(5-chloro-4-(4-chloro-1-methyl-1H-pyrazol-5-yl)furan-2-formamido)-4-(3,4-difluorophenyl)piperidin-2-yl)ethylacetate (Compound 131)

Compound 131

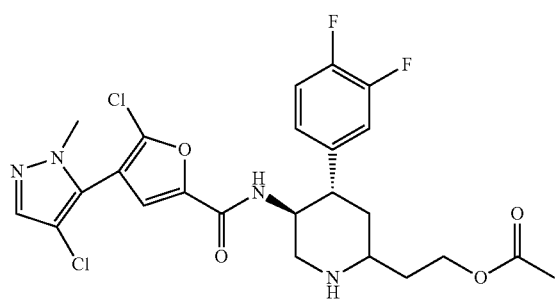

By using 5-chloro-4-(4-chloro-1-methyl-1H-pyrazol-5-yl)furan-2-formic acid and (4S,5S)-2-(2-acetoxylethyl)-4-(3,4-difluorophenyl)-5-amidopiperidine-1-tert-butyl formate as raw materials, Compound 131 is prepared and obtained according to the methods as in Example 144, the yield is 29%; $^1$H NMR (400 MHz, MeOD) δ 7.55 (s, 1H), 7.37-7.08 (m, 4H), 4.44-4.11 (m, 3H), 3.76 (s, 3H), 3.28-3.10 (m, 2H), 3.00 (dd, J=12.8, 4.8 Hz, 1H), 2.95-2.83 (m, 1H), 2.17 (tt, J=13.1, 6.5 Hz, 1H), 2.03 (s, 3H), 2.02-1.91 (m, 2H), 1.90-1.82 (m, 1H). ESI (M+H)$^+$=541.

Example 172. 2-((4S,5S)-5-(5-chloro-4-(4-chloro-1-methyl-1H-pyrazol-5-yl)furan-2-formamido)-4-(3,4-difluorophenyl)piperidin-2-yl)ethyl 2,2,2-trifluoroacetate (Compound 132)

Compound 132

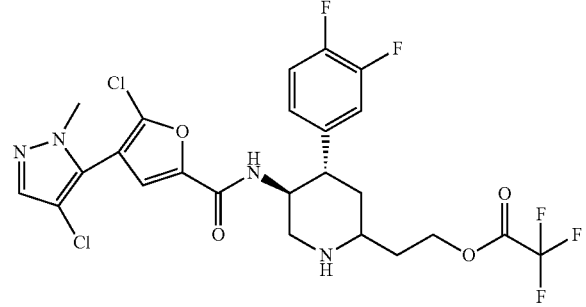

By using 5-chloro-4-(4-chloro-1-methyl-1H-pyrazol-5-yl)furan-2-formic acid and (4S,5S)-2-(2-trifluoroacetoxylethyl)-4-(3,4-difluorophenyl)-5-amidopiperidine-1-tert-butyl formate as raw materials, Compound 132 is prepared and obtained according to the methods as in Example 144, the yield is 21%; ESI (M+H)$^+$=595.

Example 173. 4-(4-chloro-1-methyl-1H-pyrazol-5-yl)-N-((3S,4S)-4-(3,4-difluorophenyl)-6-(2-(methylamido)-2-oxyethyl)piperidin-3-yl)thiophene-2-formamide (Compound 133)

Compound 133

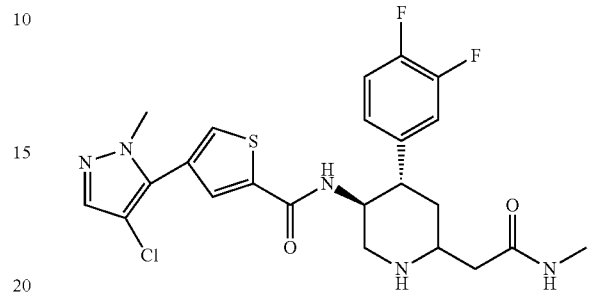

By using 4-(4-chloro-1-methyl-1H-pyrazol-5-yl)thiophene-2-formic acid and Intermediate 7-5 as raw materials, Compound 133 is prepared and obtained according to the methods as in Example 144, the yield is 51%; ESI (M+H)$^+$=508.

Example 174. 5-chloro-4-(4-chloro-1-methyl-1H-pyrazol-5-yl)-N-((3S,4S,5R)-4-(3-fluoro phenyl)-5-propylpiperidin-3-yl)thiophene-2-formamide (Compound 134)

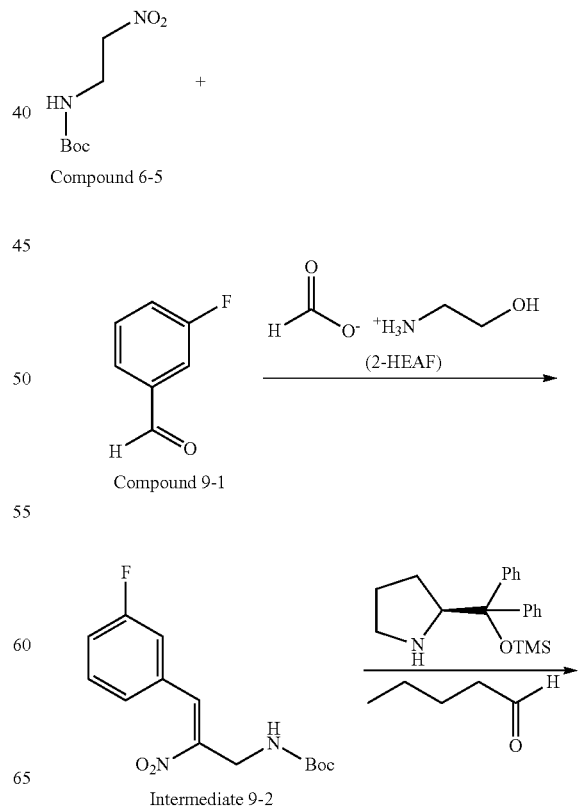

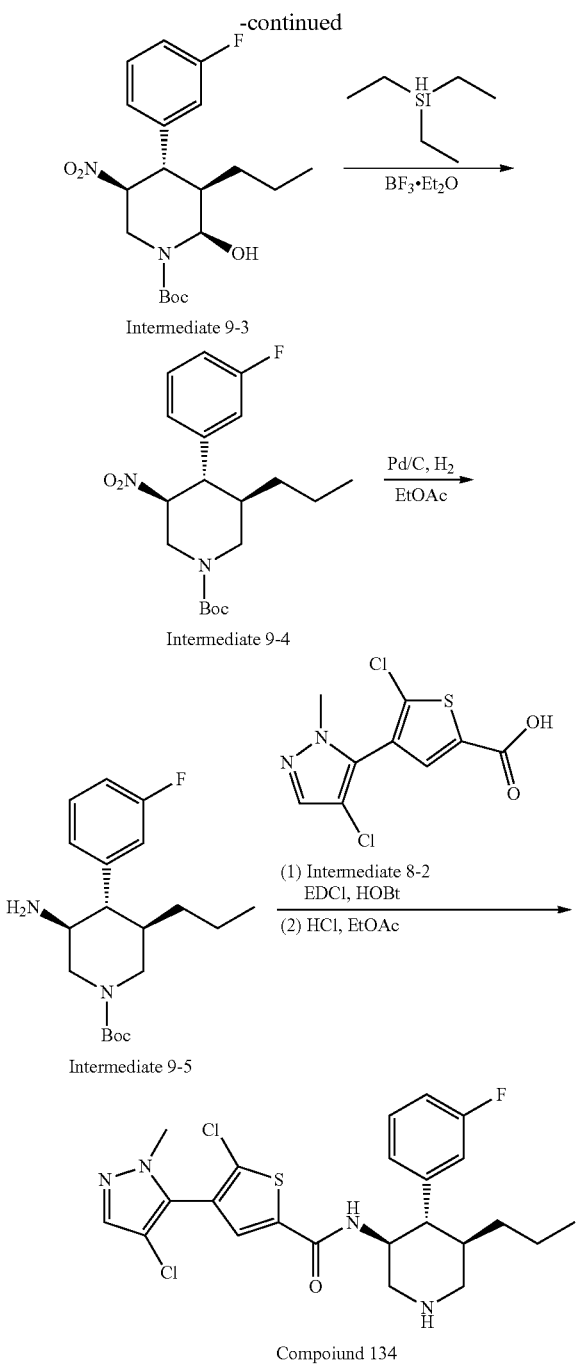

Step 1. Synthesis of (Z)-(3-(3-fluorophenyl)-2-nitroallyl)amino tert-butyl formate (Intermediate 9-2)

Adding Intermediate 1-5 (380 mg, 2 mmol) into 2-HEAF ion solution, slowly dropwise adding m-fluorobenzaldehyde (Intermediate 4-1, 372 mg, 3 mmol) thereto in an ice bath, and reacting overnight at room temperature. After the reaction is completed, adding water for diluting, extracting thereof with ethyl acetate 3 times, merging the layer of ethyl acetate, washing the organic layer with saturated saline solution 3 times, and drying it with anhydrous sodium sulfate. Carrying out column chromatography with ethyl acetate/petroleum ether system, recycling the solvent under reduced pressure, and purifying by column chromatography, 473 mg of light yellow solid (Intermediate 9-2) is obtained and the yield is 80%.

Step 2. Synthesis of (3S, 4S, 5R)-4-(3-fluorophenyl)-3-nitro-5-propylpiperidin-1-tert-butyl formate (Intermediate 9-4)

Dissolving Intermediate 9-2 (592 mg, 2 mmol), ((S)-(−)-α,α-diphenyl-2-pyrrylmethyl) trimethylsilyl ether (33 mg, 0.1 mmol), benzoic acid (25 mg, 0.2 mmol) in water (5 ml), slowly dropwise adding 0.1 ml of n-valeraldehyde under vigorous stirring, and then reacting overnight after the adding is completed. After the reaction is completed, extracting the water layer with ethyl acetate 3 times, merging the layer of ethyl acetate, washing the organic layer with saturated $NaHCO_3$ solution 3 times and with saturated saline solution 3 times, drying it with anhydrous sodium sulfate, and recycling the solvent under reduced pressure, yellow oily matter is obtained (Intermediate 9-3).

Dissolving the oily matter obtained from the previous step (Intermediate 9-3) in anhydrous dichloromethane (5 ml), sequentially slowly dropwise adding triethyl silicane (700 mg, 6 mmol) and aether boron trifluoride (426 mg, 3 mmol) thereto in an ice bath. After the reaction is completed, slowly adding saturated $NaHCO_3$ solution (10 ml), extracting thereof with dichloromethane 3 times, merging the organic layer, washing the organic layer with saturated saline solution 3 times, and drying it with anhydrous sodium sulfate. Recycling the solvent under reduced pressure, primary product is obtained (Intermediate 9-4) and input to the next reaction.

Step 3. Synthesis of (3S, 4S, 5R)-4-(3-fluorophenyl)-3-amido-5-propylpiperidin-1-tert-butyl formate (Intermediate 9-5)

Dissolving above primary product (Intermediate 9-4) in ethyl acetate (10 ml), adding 50 mg of 10% Pd/C thereto, hydrogenating overnight at room temperature, suction filtrating after the reaction is completed, and spin drying the filtrate, 290 mg of oily matter (Intermediate 9-5) is obtained, the yield of three steps is 43%; ESI $(M+H)^+=337$.

Step 4. Synthesis of 5-chloro-4-(4-chloro-1-methyl-1H-pyrazol-5-yl)-N-((3S, 4S, 5R)-4-(3-fluorophenyl)-5-propylpiperidin-3-yl)thiophene-2-formamide (Compound 134)

Dissolving Intermediate 8-2 (95 mg, 0.345 mmol), 1-hydroxybenzotriazole (HOBt) (78.62 mg, 0.517 mmol) and 1-ethyl-(3-dimethylaminopropyl)carbodiimide hydrochloride EDC.HCl (98.8 mg, 0.517 mmol) in anhydrous dichloromethane (4 ml), after stirring for 10 min in an ice bath, adding diisopropylethylamine (0.115 ml, 1.21 mmol), after continue stirring for 15 min in an ice bath, slowly adding dichloromethane solution (4 ml) dissolved with Intermediate 9-5 (118 mg, 0.35 mmol), and stirring overnight at room temperature. After the reaction is completed, pouring the reaction liquid to 15 ml of water, extracting thereof with dichloromethane 3 times, merging the organic phase, washing with saturated sodium chloride twice, drying it with anhydrous sodium sulfate, and spin drying; dissolving the obtained residue to a small amount of acetate ethyl, slowly adding HCl saturated ethyl acetate in an ice bath, spin drying after reacting for 3 h at room temperature, adding saturated $NaHCO_3$ solution thereto, extracting the reaction liquid with ethyl acetate 2 times, merging the organic phase, drying it with anhydrous sodium sulfate, and purifying by column chromatography on silica gel, 100 mg of white powder (Compound 134) is obtained and the yield is 59%; $^1$H NMR (500 MHz, MeOD) δ 7.95 (dd, J=8.3, 1.2 Hz, 1H), 7.75 (d, J=1.2 Hz, 1H), 7.41-6.93 (m, 4H), 4.55 (td, J=11.7, 4.4 Hz, 1H), 3.82 (d, J=6.1 Hz, 3H), 3.68-3.55 (m, 2H), 3.22-3.07 (m, 1H), 2.98-2.81 (m, 2H), 2.31-2.13 (m, 1H), 2.08-2.00 (m, 1H), 1.46-1.15 (m, 4H), 0.80 (dd, J=16.0, 9.1 Hz, 3H). ESI (M+H)$^+$=495.

Example 175. 5-chloro-4-(4-chloro-1-methyl-1H-pyrazol-5-yl)-N-((3S, 4S, 5R)-4-(3-fluorophenyl)-5-methyl piperidin-3-yl)thiophene-2-formamide (Compound 135)

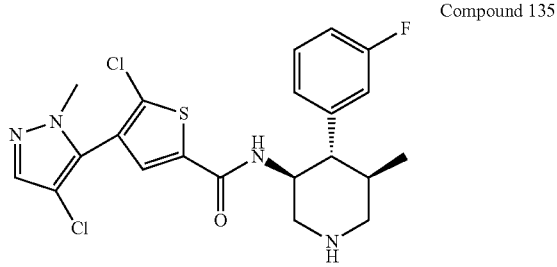 [SMILES: C[C@H]1CNC[C@@H](NC(=O)c2cc(-c3c(Cl)cnn3C)c(Cl)s2)[C@@H]1c1cccc(F)c1]

Compound 135

By using 5-chloro-4-(4-chloro-1-methyl-1H-pyrazol-5-yl)thiophene-2-formic acid and (3S, 4S,5R)-4-(3-fluorophenyl)-3-amido-5-methylpiperidin-1-tert-butyl formate as raw materials, Compound 135 is prepared and obtained according to the methods as in Example 174, and the yield is 61%; $^1$H NMR (500 MHz, MeOD) δ 7.95 (dd, J=8.3, 1.1 Hz, 1H), 7.71 (dd, J=28.5, 1.1 Hz, 1H), 7.37-7.21 (m, 2H), 7.18-6.96 (m, 2H), 4.57 (td, J=11.5, 4.6 Hz, 1H), 3.81 (d, J=6.3 Hz, 3H), 3.69-3.59 (m, 1H), 3.51 (dt, J=23.5, 10.0 Hz, 1H), 3.20-3.07 (m, 1H), 2.92 (t, J=12.5 Hz, 1H), 2.78 (dt, J=28.3, 11.3 Hz, 1H), 2.38-2.20 (m, 1H), 2.10-1.96 (m, 1H), 0.91-0.77 (m, 3H). ESI (M+H)$^+$=467.

Example 176. 5-chloro-4-(4-chloro-1-methyl-1H-pyrazol-5-yl)-N-((3S, 4S, 5R)-4-(3-fluorophenyl)-5-methylpiperidin-3-yl)furan-2-formamide (Compound 136)

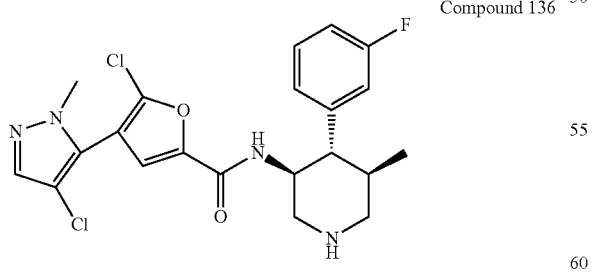

Compound 136

By using 5-chloro-4-(4-chloro-1-methyl-1H-pyrazol-5-yl)furan-2-formic acid and (3S, 4S, 5R)-4-(3-fluorophenyl)-3-amido-5-methylpiperidin-1-tert-butyl formate as raw materials, Compound 136 is prepared and obtained according to the methods as in Example 174, and the yield is 66%; $^1$H NMR (500 MHz, MeOD) δ 7.55 (d, J=1.4 Hz, 1H), 7.40-7.20 (m, 3H), 7.17-6.97 (m, 2H), 4.70-4.59 (m, 1H), 3.75 (d, J=4.0 Hz, 3H), 3.60 (dd, J=12.1, 4.1 Hz, 1H), 3.51 (dt, J=9.9, 4.5 Hz, 1H), 3.12 (td, J=12.1, 5.1 Hz, 1H), 2.91 (t, J=12.5 Hz, 1H), 2.85-2.70 (m, 1H), 2.35-2.21 (m, 1H), 2.04 (d, J=4.4 Hz, 1H), 0.83 (dd, J=9.5, 6.7 Hz, 3H). ESI (M+H)$^+$=451.

Example 177. 5-chloro-4-(4-chloro-1-methyl-1H-pyrazol-5-yl)-N-((3S, 4S, 5R)-4-(3-fluorophenyl)-5-propylpiperidin-3-yl)furan-2-formamide (Compound 137)

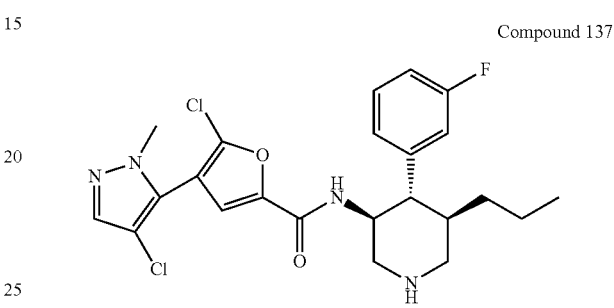

Compound 137

By using 5-chloro-4-(4-chloro-1-methyl-1H-pyrazol-5-yl)furan-2-formic acid and Intermediate 9-5 as raw materials, Compound 137 is prepared and obtained according to the methods as in Example 174, and the yield is 60%; $^1$H NMR (500 MHz, MeOD) δ 7.56 (s, 1H), 7.40-7.29 (m, 1H), 7.24 (s, 1H), 7.19-6.97 (m, 3H), 4.68-4.55 (m, 1H), 3.75 (d, J=4.0 Hz, 3H), 3.69-3.54 (m, 2H), 3.19-3.05 (m, 1H), 2.99-2.81 (m, 2H), 2.28-2.14 (m, 1H), 2.08-1.98 (m, 1H), 1.44-1.15 (m, 4H), 0.79 (dd, J=16.0, 9.0 Hz, 3H). ESI (M+H)$^+$=479.

Example 178. 5-(4-chloro-1-methyl-1H-pyrazol-5-yl)-N-((3S,4S)-4-(3-fluorophenyl) piperidin-3-yl) thiophene-2-formamide (Compound 138)

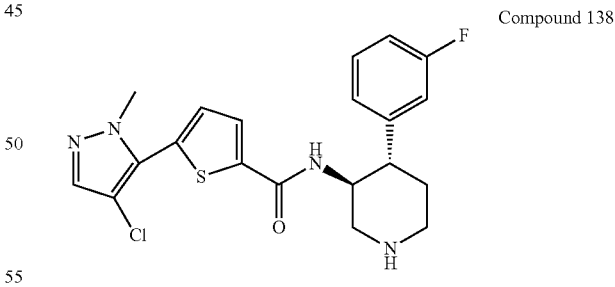

Compound 138

By using 5-(4-chloro-1-methyl-1H-pyrazol-5-yl)thiophene-2-formic acid and (3S,4S)-3-amido-4-(3-fluorophenyl)piperidin-1-tert-butyl formate as raw materials, Compound 138 is prepared and obtained according to the methods as in Example 174, and the yield is 53%; $^1$H NMR (500 MHz, MeOD) δ 7.65 (d, J=3.8 Hz, 1H), 7.55 (s, 1H), 7.37-7.30 (m, 2H), 7.18 (d, J=7.8 Hz, 1H), 7.13 (d, J=10.1 Hz, 1H), 6.98 (m, 1H), 4.60 (m, 1H), 3.89 (s, 3H), 3.67-3.61 (m, 1H), 3.56 (d, J=12.7 Hz, 1H), 3.22 (t, J=13.0 Hz, 2H), 3.15 (t, J=12.0 Hz, 1H), 2.23 (d, J=12.4 Hz, 1H), 2.14-2.04 (m, 1H). ESI (M+H)$^+$=419.

Example 179. 4-chloro-5-(4-chloro-1-methyl-1H-pyrazol-5-yl)-N-((3S, 4S)-4-(3-fluoro phenyl)piperidin-3-yl)thiophene-2-formamide (Compound 139)

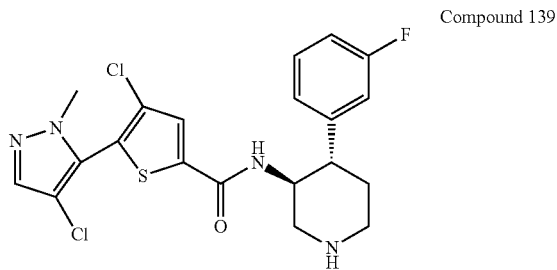 [SMILES: Cn1ncc(Cl)c1-c1sc(C(=O)N[C@@H]2CNCC[C@H]2c2cccc(F)c2)cc1Cl]

Compound 139

By using 4-chloro-5-(4-chloro-1-methyl-1H-pyrazol-5-yl)thiophene-2-formic acid and (3S, 4S)-3-amido-4-(3-fluorophenyl)piperidin-1-tert-butyl formate as raw materials, Compound 139 is prepared and obtained according to the methods as in Example 174, and the yield is 52%; ESI (M+H)$^+$=453.

Example 180. N-((3S, 4S)-4-(3-fluorophenyl)piperidin-3-yl)-5-(1-methyl-4-(pyridinyl-4-yl)-1H-pyrazol-5-yl)thiophene-2-formamide (Compound 140)

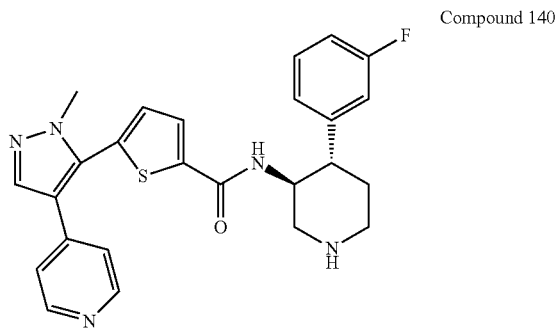 [SMILES: Cn1ncc(-c2ccncc2)c1-c1ccc(C(=O)N[C@@H]2CNCC[C@H]2c2cccc(F)c2)s1]

Compound 140

By using 5-(1-methyl-4-(pyridinyl-4-yl)-1H-pyrazol-5-yl)thiophene-2-formic acid and (3S, 4S)-3-amido-4-(3-fluorophenyl)piperidin-1-tert-butyl formate as raw materials, Compound 140 is prepared and obtained according to the methods as in Example 174, and the yield is 34%; $^1$H NMR (500 MHz, MeOD) δ 8.61 (d, J=6.7 Hz, 2H), 8.29 (s, 1H), 7.85 (d, J=6.7 Hz, 2H), 7.80 (d, J=3.8 Hz, 1H), 7.38-7.33 (m, 2H), 7.22 (d, J=7.7 Hz, 1H), 7.15 (d, J=9.9 Hz, 1H), 7.00 (td, J=8.4, 2.1 Hz, 1H), 4.61 (dt, J=11.6, 5.8 Hz, 1H), 3.83 (s, 3H), 3.63-3.59 (m, 1H), 3.58-3.53 (m, 1H), 3.31-3.12 (m, 3H), 2.22 (d, J=12.4 Hz, 1H), 2.13-2.06 (m, 1H). ESI (M+H)$^+$=462.

Example 181. N-((3S, 4S)-4-(3-fluorophenyl)piperidin-3-yl)-5-(4-(hydroxylmethyl)-1-methyl-1H-pyrazol-5-yl)thiophene-2-formamide (Compound 141)

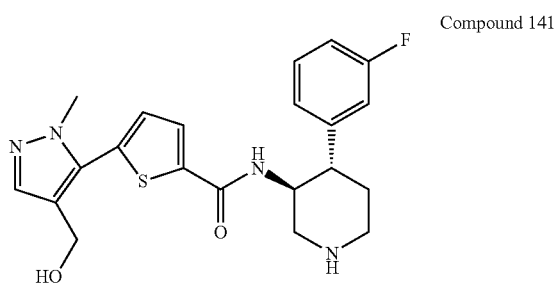 [SMILES: Cn1ncc(CO)c1-c1ccc(C(=O)N[C@@H]2CNCC[C@H]2c2cccc(F)c2)s1]

Compound 141

By using 5-(1-methyl-4-hydroxylmethyl-1H-pyrazol-5-yl)thiophene-2-formic acid and (3S, 4S)-3-amido-4-(3-fluorophenyl)piperidin-1-tert-butyl formate as raw materials, Compound 141 is prepared and obtained according to the methods as in Example 174, and the yield is 39%; $^1$H NMR (500 MHz, MeOD) δ 7.80 (s, 1H), 7.69 (d, J=3.9 Hz, 1H), 7.37-7.30 (m, 2H), 7.20 (d, J=7.7 Hz, 1H), 7.13 (d, J=10.0 Hz, 1H), 6.98 (dd, J=11.8, 5.1 Hz, 1H), 4.61 (td, J=11.6, 4.3 Hz, 1H), 4.29 (s, 2H), 3.94 (s, 3H), 3.66-3.62 (m, 1H), 3.56 (d, J=12.6 Hz, 1H), 3.28-3.12 (m, 3H), 2.22 (d, J=12.9 Hz, 1H), 2.14-2.06 (m, 1H). ESI (M+H)$^+$=415.

Example 182. 5-(5-(((3S, 4S)-4-(3-fluorophenyl)piperidin-3-yl)formamido)thiophene-2-yl)-1-methyl-1H-pyrazol-4-formic acid (Compound 142)

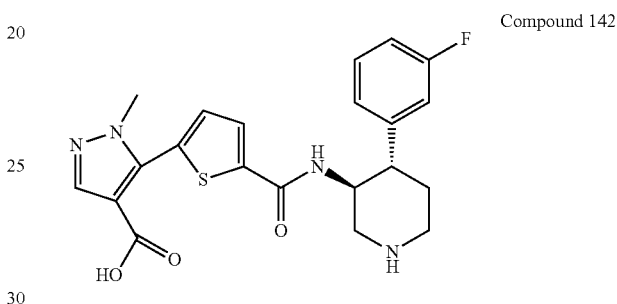

Compound 142

By using 5-(1-methyl-4-methoxycarbonyl-1H-pyrazol-5-yl)thiophene-2-ethyl formate and (3S, 4S)-3-amido-4-(3-fluorophenyl)piperidin-1-tert-butyl formate as raw materials, Compound 142 is prepared and obtained by amide condensation, hydrolysis, deprotection steps and the like according to the methods as in Example 174, the yield is 54%; $^1$H NMR (500 MHz, MeOD) δ 7.96 (s, 1H), 7.63 (d, J=3.1 Hz, 1H), 7.39-7.30 (m, 1H), 7.24 (d, J=3.2 Hz, 1H), 7.21-7.09 (m, 2H), 6.98 (t, J=7.6 Hz, 1H), 4.62 (s, 1H), 3.77 (s, 3H), 3.63 (d, J=7.0 Hz, 1H), 3.54 (t, J=10.0 Hz, 1H), 3.28-3.09 (m, 3H), 2.22 (d, J=14.0 Hz, 1H), 2.08 (d, J=11.8 Hz, 1H). ESI (M+H)$^+$=429.

Example 183. N-((3S, 4S)-4-(3-fluorophenyl)piperidin-3-yl)-5-(4-(1-hydroxyethyl)-1-methyl-1H-pyrazol-5-yl)thiophene-2-formamide (Compound 143)

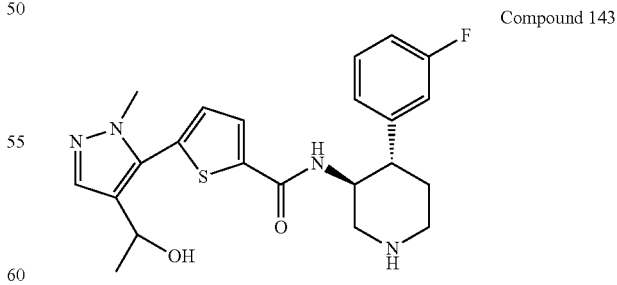

Compound 143

By using 5-(1-methyl-4-(1-hydroxyethyl)-1H-pyrazol-5-yl)thiophene-2-formic acid and (3S, 4S)-3-amido-4-(3-fluorophenyl)piperidin-1-tert-butyl formate as raw materials, Compound 143 is prepared and obtained according to the methods as in Example 174, and the yield is 34%; ESI (M+H)$^+$=429.

Example 184. N-((3S, 4S)-4-(3-fluorophenyl)piperidin-3-yl)-5-(1-methyl-4-vinyl-1H-pyrazol-5-yl)thiophene-2-formamide (Compound 144)

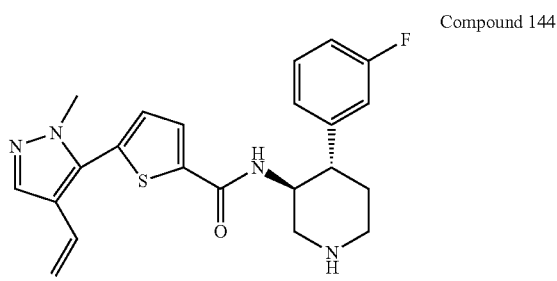 [SMILES: C=Cc1cnn(C)c1-c1ccc(C(=O)N[C@@H]2CNCC[C@H]2c2cccc(F)c2)s1]
Compound 144

By using 5-(1-methyl-4-vinyl-1H-pyrazol-5-yl)thiophene-2-formic acid and (3S,4S)-3-amido-4-(3-fluorophenyl)piperidin-1-tert-butyl formate as raw materials, Compound 144 is prepared and obtained according to the methods as in Example 174, and the yield is 64%; ESI (M+H)$^+$=411.

Example 185. 5-(4-ethyl-1-methyl-1H-pyrazol-5-yl)-N-((3S, 4S)-4-(3-fluorophenyl) piperidin-3-yl) thiophene-2-formamide (Compound 145)

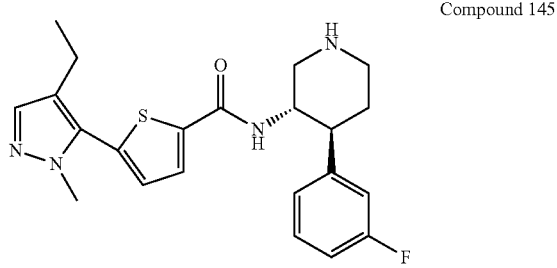 [SMILES: CCc1cnn(C)c1-c1ccc(C(=O)N[C@@H]2CNCC[C@H]2c2cccc(F)c2)s1]
Compound 145

By using 5-(1-methyl-4-ethyl-1H-pyrazol-5-yl)thiophene-2-formic acid and (3S, 4S)-3-amido-4-(3-fluorophenyl)piperidin-1-tert-butyl formate as raw materials, Compound 145 is prepared and obtained according to the methods as in Example 174, and the yield is 62%; $^1$H NMR (500 MHz, MeOD) δ 7.92 (s, 1H), 7.76 (d, J=3.8 Hz, 1H), 7.36-7.29 (m, 2H), 7.21 (d, J=7.7 Hz, 1H), 7.15 (d, J=10.0 Hz, 1H), 6.96 (td, J=8.5, 2.2 Hz, 1H), 4.64 (td, J=11.6, 4.3 Hz, 1H), 3.93 (s, 3H), 3.66-3.62 (m, 1H), 3.57 (d, J=12.6 Hz, 1H), 3.32-3.17 (m, 3H), 2.57-2.50 (m, 2H), 2.25-2.07 (m, 2H), 1.21-1.16 (m, 3H). ESI (M+H)$^+$=413.

Example 186. N-((3S, 4S)-4-(3-fluorophenyl)piperidin-3-yl)-5-(1-methyl-1H-pyrazol-5-yl)thiophene-2-formamide (Compound 146)

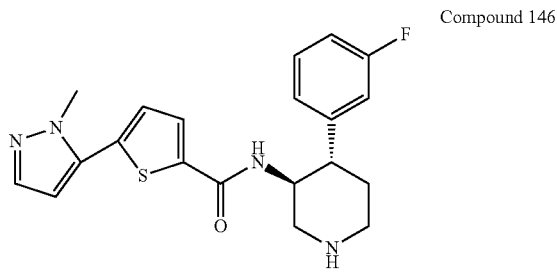 [SMILES: Cn1nccc1-c1ccc(C(=O)N[C@@H]2CNCC[C@H]2c2cccc(F)c2)s1]
Compound 146

By using 5-(1-methyl-1H-pyrazol-5-yl)thiophene-2-formic acid and (3S,4S)-3-amido-4-(3-fluorophenyl)piperidin-1-tert-butyl formate as raw materials, Compound 146 is prepared and obtained according to the methods as in Example 174, and the yield is 54%; $^1$H NMR (500 MHz, MeOD) δ 7.98-7.96 (m, 1H), 7.70 (d, J=4.0 Hz, 1H), 7.42 (d, J=3.9 Hz, 1H), 7.24 (dd, J=14.0, 7.9 Hz, 1H), 7.15 (d, J=7.8 Hz, 1H), 7.09 (dd, J=10.0, 1.9 Hz, 1H), 6.88 (td, J=8.5, 2.3 Hz, 1H), 6.78 (d, J=2.6 Hz, 1H), 4.60 (td, J=11.6, 4.3 Hz, 1H), 4.05 (s, 3H), 3.60-3.57 (m, 1H), 3.51 (d, J=12.7 Hz, 1H), 3.25-3.13 (m, 3H), 2.17-2.04 (m, 2H). ESI (M+H)$^+$=385.

Example 187. 5-(4-bromo-1-methyl-1H-pyrazol-5-yl)-N-((3S,4S)-4-(3-fluorophenyl) piperidin-3-yl) thiophene-2-formamide (Compound 147)

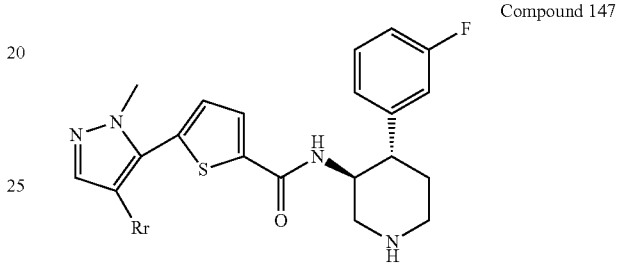
Compound 147

By using 5-(1-methyl-4-bromo-1H-pyrazol-5-yl)thiophene-2-formic acid and (3S,4S)-3-amido-4-(3-fluorophenyl)piperidin-1-tert-butyl formate as raw materials, Compound 147 is prepared and obtained according to the methods as in Example 174, and the yield is 68%; $^1$H NMR (500 MHz, MeOD) δ 7.68 (d, J=3.9 Hz, 1H), 7.56 (s, 1H), 7.35-7.30 (m, 1H), 7.28 (d, J=3.9 Hz, 1H), 7.20 (d, J=7.7 Hz, 1H), 7.14 (d, J=9.9 Hz, 1H), 6.96 (td, J=8.5, 2.2 Hz, 1H), 4.63 (td, J=11.5, 4.1 Hz, 1H), 3.87 (s, 3H), 3.67-3.61 (m, 1H), 3.57 (d, J=12.3 Hz, 1H), 3.30-3.14 (m, 3H), 2.22 (d, J=13.7 Hz, 1H), 2.17-2.06 (m, 1H). ESI (M+H)$^+$=463.

Example 188. N-((3S, 4S)-4-(3,4-difluorophenyl) piperidin-3-yl)-5-(1-methyl-4-phenyl-1H-pyrazol-5-yl)thiophene-2-formamide (Compound 148)

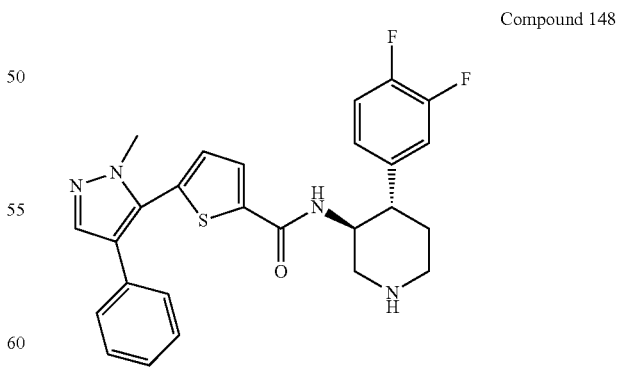
Compound 148

By using 5-(1-methyl-4-phenyl-1H-pyrazol-5-yl)thiophene-2-formic acid and (3S, 4S)-3-amido-4-(3,4-difluorophenyl)piperidin-1-tert-butyl formate as raw materials, Compound 148 is prepared and obtained according to the methods as in Example 174, and the yield is 59%; $^1$H NMR (500 MHz, CDCl₃) δ 7.78 (s, 1H), 7.55 (d, J=3.2 Hz, 1H), 7.19-6.94 (m, 9H), 6.82 (t, J=7.5 Hz, 1H), 4.47 (t, J=9.4 Hz, 1H), 3.71 (s, 3H), 3.46-3.32 (m, 2H), 3.13-2.95 (m, 3H), 2.10-1.91 (m, 2H). ESI (M+H)⁺=479.

Example 189. 4-chloro-5-(4-chloro-1-methyl-1H-pyrazol-5-yl)-N-((3S, 4S)-4-(3-fluoro phenyl)-6-(2-(methylamido)-2-oxoethyl)piperidin-3-yl)thiophene-2-formamide (Compound 149)

Compound 149

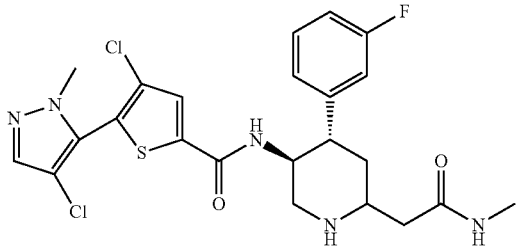

By using 4-chloro-5-(4-chloro-1-methyl-1H-pyrazol-5-yl)thiophene-2-formic acid and (4S, 5S)-4-(3-fluorophenyl)-2-(2-(1-methylamino)-2-oxyethyl)-5-amidopiperidine-1-tert-butyl formate as raw materials, Compound 149 is prepared and obtained according to the methods as in Example 174, and the yield is 46%; ESI (M+H)⁺=524.

Example 190. 5-(4-chloro-1-methyl-1H-pyrazol-5-yl)-N-((3S, 4S, 5R)-4-(3-fluorophenyl)-5-methyl piperidin-3-yl)thiophene-2-formamide (Compound 150)

Compound 150

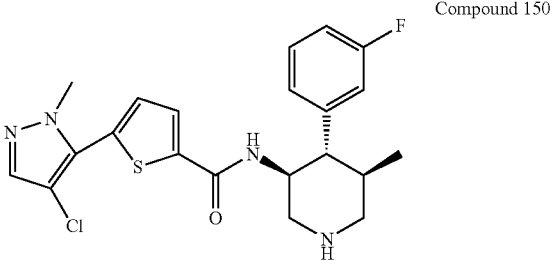 [SMILES: C[C@H]1CNC[C@@H](NC(=O)c2ccc(-c3c(Cl)cnn3C)s2)[C@@H]1c1cccc(F)c1]

By using 5-(4-chloro-1-methyl-1H-pyrazol-5-yl)thiophene-2-formic acid and (3S, 4S, 5R)-4-(3-fluorophenyl)-3-amido-5-methylpiperidin-1-tert-butyl formate as raw materials, Compound 150 is prepared and obtained according to the methods as in Example 174, and the yield is 56%; ¹H NMR (500 MHz, MeOD) δ 7.64-7.52 (m, 2H), 7.39-7.22 (m, 3H), 7.19-6.95 (m, 2H), 4.58 (s, 1H), 3.89 (d, J=3.9 Hz, 3H), 3.62 (d, J=7.0 Hz, 1H), 3.50 (dd, J=14.0, 7.1 Hz, 1H), 3.12 (s, 1H), 2.91 (s, 1H), 2.87-2.70 (m, 1H), 2.28 (s, 1H), 2.03 (d, J=4.5 Hz, 1H), 0.95-0.75 (m, 3H). ESI (M+H)⁺=433.

Example 191. 5-(4-chloro-1-methyl-1H-pyrazol-5-yl)-N-((3S, 4S, 5R)-4-(3-fluorophenyl)-5-propylpiperidin-3-yl)thiophene-2-formamide (Compound 151)

Compound 151

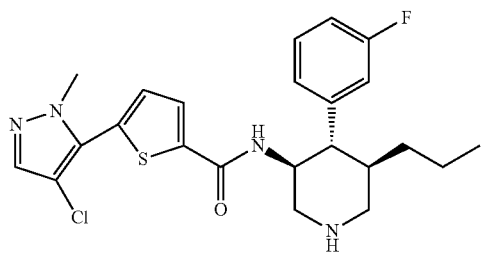

By using 5-(4-chloro-1-methyl-1H-pyrazol-5-yl)thiophene-2-formic acid and Intermediate 9-5 as raw materials, Compound 151 is prepared and obtained according to the methods as in Example 174, and the yield is 71%; ¹H NMR (500 MHz, MeOD) δ 7.59 (d, J=3.9 Hz, 1H), 7.55 (d, J=4.2 Hz, 1H), 7.39-7.30 (m, 2H), 7.18-6.97 (m, 3H), 4.55 (td, J=11.7, 4.5 Hz, 1H), 3.89 (d, J=4.0 Hz, 3H), 3.63 (dd, J=12.5, 4.0 Hz, 2H), 3.11 (t, J=12.1 Hz, 1H), 2.99-2.81 (m, 2H), 2.21 (dd, J=7.6, 3.8 Hz, 1H), 1.49-1.06 (m, 4H), 0.80 (dd, J=15.9, 9.0 Hz, 3H). ESI (M+H)⁺=461.

Example 192. 5-(4-chloro-1-methyl-1H-pyrazol-5-yl)-N-((3S,4S)-4-(3,4-difluorophenyl)-6-(2-(methylamido)-2-oxoethyl)piperidin-3-yl)thiophene-2-formamide (Compound 152)

Compound 152

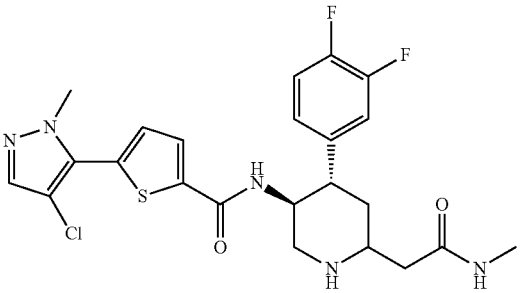

By using 5-(4-chloro-1-methyl-1H-pyrazol-5-yl)thiophene-2-formic acid and Intermediate 7-5 as raw materials, Compound 152 is prepared and obtained according to the methods as in Example 174, and the yield is 69%; ¹H NMR (500 MHz, MeOD) δ 7.71 (d, J=4.0 Hz, 1H), 7.57 (d, J=5.2 Hz, 1H), 7.35 (d, J=3.9 Hz, 1H), 7.34-7.28 (m, 1H), 7.27-7.15 (m, 2H), 4.50 (td, J=11.5, 4.9 Hz, 1H), 4.12 (dd, J=13.1, 6.0 Hz, 1H), 3.91 (s, 3H), 3.53-3.45 (m, 1H), 3.41 (dt, J=19.3, 8.2 Hz, 2H), 3.06 (dd, J=16.3, 10.0 Hz, 1H), 2.81 (d, J=5.7 Hz, 3H), 2.76 (dd, J=16.3, 5.2 Hz, 1H), 2.29-2.19 (m, 1H), 2.09 (d, J=13.2 Hz, 1H). ESI (M+H)⁺=508.

Inhibitory Effects of the Compounds Disclosed in the Present Invention on the Growth of Tumor Cells and Inhibitory Activities Thereof Against Akt1 Enzymes The compound AZD5363 (NCT02208375, NCT02208375, NCT01625286) which enters in clinical phase II studies as a positive control, the inhibitory effects in vitro ($IC_{50}$) of Compounds on common tumor cell strains (Human ovarian cancer cell strain OVCAR-8 and human colon cancer cell strain HCT-116) are determined using MTT assay, meanwhile, the inhibitory activities ($IC_{50}$) thereof against Akt1 enzyme are assessed using commercial Akt1 kit.

Methods and results of pharmacological experiments on antitumor activity of compounds in the present invention are as follows:

First, inhibitory activity on tumor proliferation in vitro is determined and the structure activity relationship is preliminarily studied, in which different solid tumor cell strains are selected for determining the antitumor activities in vitro of the synthesized compounds.

Experimental materials:

Cell strains: Human ovarian cancer cell strain (OVCAR8), colon adenocarcinoma cell strain (HCT-116)

Medium: OVCAR8: RPMI 1640+Fetal Bovine Serum
HCT-116: RPMI 1640+Fetal Bovine Serum Preparing method of medicines: Dissolving the medicine in DMSO to make a 50 mM stock solution, and diluting it according to a certain ratio to obtain 5 different concentrations.

Culture the tumor cell strains in vitro:

Two selected tumor cells OVCAR8 and HCT-116 are incubated at 37° C. in a 5% $CO_2$ incubator, which are subcultured when cells grow up to a density of 70~90% (adherent cells are subcultured after digesting by Duck's EDTA) for later experiments.

Compounds are dissolved and diluted by dimethyl sulfoxide (DMSO), and tumor cells OVCAR8 and HCT-116 are seeded in a 96-well plate at a density of 4000 cells/200 μl/well, 1 μl of the compounds are added to each well with the final concentration of 50 μM, 10 μM, 2 μM, 0.4 μM and 0.08 μM, which is incubated for 72 h at 37° C. in a 5% $CO_2$ incubator with DMSO (1%) as blank control. After incubating for 72 h, MTT with a final concentration of 0.25 mg/mL is added, which is maintained for 4 h at 37° C. in a 5% $CO_2$ incubator, and then the medium is suck dried, 100 μl of DMSO is added to each well, the absorbance (OD value) is determined at 570 nm by enzyme-linked immunometric meter, thus obtained data is used to calculate $IC_{50}$.

The calculating formula of cell inhibitory rate is: cell inhibitory rate %=(the OD value of the control group−the OD value of the medication group)/the OD value of the control group×100%, the half maximal inhibitory concentration ($IC_{50}$) is obtained by Bliss method.

Second, method for determining the inhibitory activities of substituted nitrogen-containing heterocyclic derivatives in the present invention against Akt1 enzyme:

The inhibitory activities of compounds against AKT1/PKBα are determined by using AKT1/PKBα KinEASE™ FP Fluorescein Green Assay (Green fluorescence detection system of Kinase).

Principle adopted by the fluorescence polarization detection of protein kinase B is a competitive reaction: the phosphorylated tracers labeled with fluorescence will compete with unlabeled phosphorylated products produced by reacting with protein kinase B to combine anti-serine antibodies. In a reaction mixture without phosphorylated products, the combination a part of fluorescent tracers and antibodies will lead to a higher polarization value. However, in the reaction mixture containing phosphorylated products, fewer tracers will combine with antibodies (fluorescent tracers are replaced from the antibodies), and signals sent our occur depolarizing. Therefore, the change of polarization is directly related to the activity of protein kinase B in the reaction.

Compounds in the present invention and the positive control AZD5363 are dissolved with dimethyl sulfoxide (DMSO), and are diluted to a concentration of 50 μM. Each of 0.25 μl of compounds with a concentration of 50 μM and the positive control are added to a 384-well plate at room temperature, and each sample is provided with three parallel wells, and then 10 μl of STK Substrate 3 Working Solution, 5 μl of AKT1/PKBα Working Solution, 10 μl of ATP Working Solution are added to each sample respectively, the mixtures are slightly vibrated and shaked for a few minutes. Reaction is carried out just after the adding 10 μl of ATP Working Solution, from this time, reacting for 1 h. After 1 h, 5 μl of STK Stop Mix and 5 μl of STK Antibody Mix are added to each sample respectively to stop the reaction. The samples are maintained for 4 h at room temperature after adding is completed, the polarization values of samples are determined by fluorescence polarization of Microplate Reader (Detection of the signals is valid within 24 h), the inhibitory rate of compounds against the enzyme is calculated by polarization value, and thereby $IC_{50}$ is calculated.

Experiment is set up four control groups at the same time, which are Buffer Control Wells, Tracer Control Wells, No Enzyme Wells and blank control of dimethyl sulfoxide, respectively. Thus obtained data are used to calculate the inhibitory rate (the preparation methods of above various solution required for determining the activities of compounds against enzyme refer to the specification of the kit of AKT1/PKBα KinEASE™ FP Fluorescein Green Assay Catalog #32-021).

TABLE 1

Inhibitory activities of compounds against Akt1 and antitumor proliferative activities thereof against two tumor cell strains

| Compd. | Inhibitory activities against Akt1 ($IC_{50}$, μM) | Antitumor proliferative activities of tumor cell ($IC_{50}$, μM) OVCAR-8 | HCT-116 |
|---|---|---|---|
| AZD5363 | 0.009 | 7.27 | 5.20 |
| Compound 1 | 0.072 | 1.34 | 3.98 |
| Compound 2 | 0.099 | 6.45 | 1.41 |
| Compound 3 | 0.043 | 13.0 | 8.9 |
| Compound 4 | 0.048 | 5.19 | 15.6 |
| Compound 5 | 0.121 | 14.3 | 6.8 |
| Compound 6 | 0.032 | 3.68 | 10.8 |
| Compound 7 | 0.062 | 3.88 | 8.3 |
| Compound 8 | 0.082 | 9.01 | 3.26 |
| Compound 9 | 0.088 | 0.94 | 2.35 |
| Compound 10 | 0.026 | 6.57 | 3.31 |
| Compound 14 | 0.005 | 3.68 | 3.78 |
| Compound 15 | 0.052 | 1.26 | 2.04 |
| Compound 16 | 0.009 | 4.19 | 2.94 |
| Compound 17 | 0.028 | 1.43 | 3.4 |
| Compound 18 | 0.018 | 5.69 | 1.83 |
| Compound 19 | 0.082 | 9.83 | 4.56 |
| Compound 20 | 0.012 | 9.91 | 2.11 |
| Compound 21 | 0.119 | 10.7 | 21.0 |
| Compound 22 | 0.108 | 7.89 | 12.2 |
| Compound 23 | 0.045 | 1.22 | 3.78 |
| Compound 24 | 0.018 | 0.98 | 2.90 |
| Compound 25 | 0.238 | 21.4 | 3.19 |
| Compound 26 | 0.034 | 4.89 | 2.16 |
| Compound 27 | 0.017 | 1.82 | 5.89 |
| Compound 28 | 0.062 | 3.38 | 11.8 |
| Compound 29 | 0.062 | 1.12 | 8.67 |
| Compound 30 | 0.092 | 1.01 | 21.6 |
| Compound 31 | 0.018 | 4.54 | 1.85 |
| Compound 32 | 0.123 | 1.47 | 18.1 |

TABLE 1-continued

Inhibitory activities of compounds against Akt1 and antitumor proliferative activities thereof against two tumor cell strains

| Compd. | Inhibitory activities against Akt1 (IC$_{50}$, μM) | Antitumor proliferative activities of tumor cell (IC$_{50}$, μM) | |
|---|---|---|---|
| | | OVCAR-8 | HCT-116 |
| Compound 35 | 0.120 | 4.61 | 11.5 |
| Compound 36 | 0.105 | 3.38 | 3.28 |
| Compound 37 | 0.052 | 5.36 | 2.24 |
| Compound 38 | 0.409 | 4.69 | 1.94 |
| Compound 39 | 0.058 | 14.3 | 3.45 |
| Compound 40 | 0.118 | 1.69 | 1.56 |
| Compound 41 | 0.452 | 9.43 | 4.06 |
| Compound 42 | 0.092 | 9.71 | 8.11 |
| Compound 43 | 0.342 | 3.58 | 13.8 |
| Compound 44 | 0.672 | 1.88 | 18.3 |
| Compound 45 | 0.812 | 2.01 | 12.6 |
| Compound 46 | 0.348 | 7.94 | 23.8 |
| Compound 47 | 0.216 | 5.57 | 3.11 |
| Compound 51 | 0.085 | 0.68 | 3.11 |
| Compound 52 | 0.072 | 1.06 | 2.05 |
| Compound 53 | 0.029 | 4.69 | 2.66 |
| Compound 54 | 0.678 | 13.3 | 3.14 |
| Compound 55 | 0.048 | 5.79 | 10.8 |
| Compound 56 | 0.362 | 9.53 | 4.51 |
| Compound 57 | 0.082 | 12.91 | 2.50 |
| Compound 58 | 0.052 | 3.68 | 15.8 |
| Compound 59 | 0.142 | 7.88 | 8.33 |
| Compound 60 | 0.972 | 6.01 | 2.27 |
| Compound 61 | 0.188 | 8.44 | 3.85 |
| Compound 62 | 0.626 | 6.67 | 31.1 |
| Compound 64 | 0.256 | 1.62 | 22.6 |
| Compound 66 | 0.345 | 3.48 | 3.22 |
| Compound 67 | 0.272 | 10.6 | 20.4 |
| Compound 68 | 0.679 | 4.19 | 2.84 |
| Compound 69 | 0.323 | 24.3 | 3.04 |
| Compound 70 | 0.087 | 2.69 | 10.3 |
| Compound 71 | 0.116 | 2.61 | 11.1 |
| Compound 72 | 0.006 | 1.34 | 0.92 |
| Compound 73 | 0.007 | 2.45 | 1.21 |
| Compound 74 | 0.014 | 1.30 | 0.42 |
| Compound 75 | 0.013 | 2.19 | 0.99 |
| Compound 76 | 0.021 | 2.54 | 1.56 |
| Compound 77 | 0.018 | 3.68 | 2.81 |
| Compound 78 | 0.006 | 0.76 | 2.03 |
| Compound 79 | 0.019 | 3.77 | 4.08 |
| Compound 80 | 0.001 | 0.94 | 2.51 |
| Compound 81 | 0.018 | 3.57 | 1.10 |
| Compound 82 | 0.016 | 1.15 | 1.56 |
| Compound 83 | 0.010 | 1.32 | 4.09 |
| Compound 84 | 0.009 | 4.44 | 2.10 |
| Compound 85 | 0.021 | 3.07 | 5.56 |
| Compound 86 | 0.014 | 1.26 | 1.47 |
| Compound 87 | 0.010 | 2.43 | 5.63 |
| Compound 88 | 0.008 | 1.07 | 4.21 |
| Compound 89 | 0.011 | 5.69 | 1.02 |
| Compound 90 | 0.014 | 1.83 | 0.69 |
| Compound 91 | 0.005 | 2.91 | 0.34 |
| Compound 92 | 0.016 | 1.07 | 1.25 |
| Compound 93 | 0.008 | 7.89 | 5.82 |
| Compound 94 | 0.007 | 1.22 | 0.89 |
| Compound 95 | 0.017 | 0.98 | 0.95 |
| Compound 96 | 0.009 | 2.41 | 0.78 |
| Compound 97 | 0.008 | 4.89 | 4.14 |
| Compound 98 | 0.004 | 1.82 | 0.92 |
| Compound 99 | 0.007 | 3.38 | 1.21 |
| Compound 100 | 0.009 | 1.12 | 0.42 |
| Compound 101 | 0.007 | 0.43 | 2.11 |
| Compound 102 | 0.008 | 0.34 | 0.80 |
| Compound 103 | 0.005 | 1.11 | 2.81 |
| Compound 104 | 0.003 | 1.71 | 2.43 |
| Compound 105 | 0.051 | 1.94 | 0.56 |
| Compound 106 | 0.002 | 1.02 | 2.51 |
| Compound 107 | 0.014 | 1.01 | 1.08 |
| Compound 108 | 0.009 | 2.04 | 0.57 |
| Compound 109 | 0.009 | 1.30 | 0.78 |
| Compound 110 | 0.011 | 1.21 | 0.89 |
| Compound 111 | 0.004 | 0.07 | 0.49 |
| Compound 112 | 0.002 | 0.33 | 0.84 |
| Compound 113 | 0.003 | 0.14 | 1.72 |
| Compound 114 | 0.014 | 1.56 | 1.10 |
| Compound 115 | 0.0008 | 0.78 | 0.56 |
| Compound 116 | 0.001 | 3.68 | 5.01 |
| Compound 117 | 0.003 | 0.92 | 4.28 |
| Compound 118 | 0.003 | 4.02 | 3.68 |
| Compound 119 | 0.004 | 0.65 | 1.47 |
| Compound 120 | 0.003 | 0.45 | 0.44 |
| Compound 121 | 0.005 | 0.74 | 0.36 |
| Compound 122 | 0.002 | 0.43 | 1.02 |
| Compound 123 | 0.0001 | 0.09 | 0.07 |
| Compound 124 | 0.001 | 0.56 | 0.34 |
| Compound 125 | 0.0001 | 0.12 | 1.25 |
| Compound 126 | 0.0002 | 0.47 | 5.82 |
| Compound 127 | 0.0003 | 0.67 | 0.89 |
| Compound 128 | 0.0005 | 0.92 | 0.95 |
| Compound 129 | 0.0004 | 0.51 | 0.78 |
| Compound 130 | 0.0005 | 1.06 | 4.10 |
| Compound 131 | 0.0008 | 4.69 | 0.92 |
| Compound 132 | 0.002 | 1.33 | 1.21 |
| Compound 133 | 0.003 | 5.79 | 0.42 |
| Compound 134 | 0.0003 | 0.53 | 0.69 |
| Compound 135 | 0.012 | 1.20 | 0.80 |
| Compound 136 | 0.002 | 3.68 | 2.81 |
| Compound 137 | 0.001 | 1.88 | 0.43 |
| Compound 138 | 0.001 | 3.01 | 0.56 |
| Compound 139 | 0.0007 | 1.44 | 2.51 |
| Compound 140 | 0.001 | 6.67 | 1.10 |
| Compound 141 | 0.012 | 1.05 | 6.56 |
| Compound 142 | 0.002 | 1.62 | 3.09 |
| Compound 143 | 0.0007 | 0.04 | 0.08 |
| Compound 144 | 0.002 | 3.48 | 3.68 |
| Compound 145 | 0.004 | 1.06 | 1.47 |
| Compound 146 | 0.007 | 4.19 | 0.44 |
| Compound 147 | 0.009 | 2.43 | 0.36 |
| Compound 148 | 0.005 | 0.67 | 1.23 |
| Compound 149 | 0.007 | 3.21 | 2.56 |
| Compound 150 | 0.003 | 1.19 | 4.43 |
| Compound 151 | 0.001 | 1.52 | 2.5 |
| Compound 152 | 0.0006 | 1.41 | 2.82 |

It can be seen from the activity data in above table, all the tested compounds show significant inhibitory activities against Akt1 kinase, IC$_{50}$ values of most compounds are less than 0.1 μM; IC$_{50}$ values of a part of compounds are less than 0.009 μM, better than or equal to the positive compound AZD5363 (IC$_{50}$=0.009 μM, the compound is a potent Akt1 inhibitor, which is in clinical phase II study for treating human breast cancer, NCT01625286); IC$_{50}$ values of part of compounds can reach to a pmol level, such as: Compound 115 (0.0008 μM), Compound 123 (0.0001 μM), Compound 127 (0.0003 μM) and Compound 134 (0.0003 μM) and the like, which is significantly better than the positive control AZD5363 (0.009 μM). Therefore, compounds in the present invention can be used as a kind of Akt inhibitors with novel structure.

In addition, the majority of tested compounds show potent anti-proliferative activities against both of two tumor cell strains (both of the IC$_{50}$ values are less than 10 μM), IC$_{50}$ values of most compounds to OVCAR-8, HCT-116 tumor cell strains are less than the positive drug AZD5363 (7.27 μM, 5.20 μM), which is better than or equal to the positive compound AZD5363; IC$_{50}$ values of part of compounds can reach to less than 0.1 µM, such as Compound 115 (0.78 µM, 0.56 µM), Compound 123 (0.09 µM, 0.07 µM), Compound 134 (0.53 µM, 0.69 µM), which is significantly better than the positive compound AZD5363. Therefore, compounds involved in the present invention have potent antitumor activities.

In conclusion, substituted nitrogen-containing heterocyclic derivatives involved in the present invention can be used as Akt inhibitors, having a broad applicating prospect for cancer treatment.

What is claimed:
1. A compound of general formula (IV):

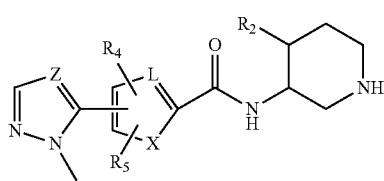

IV and an optical isomer thereof, or a pharmaceutically acceptable salt or a solvate thereof, wherein:
$R_2$ is selected from unsubstituted or substituted aryl, unsubstituted or substituted heterocyclic aryl, unsubstituted or substituted cycloalkyl, unsubstituted or substituted saturated heterocyclic alkyl, unsubstituted or substituted unsaturated heterocyclic alkyl, optionally fused aryl and heterocyclic aryl;
L is selected from CH and N;
$R_4$, $R_5$ are each independently selected from the group consisting of H, halogen, and $C_1$-$C_3$ alkyl;
X is selected from the group consisting of O, S, NH and $NCH_3$;
Z is selected from N and —C($R_g$)—, wherein $R_g$ is selected from the group consisting of H, halogen, and $C_1$-$C_3$ alkyl.

2. The compound according to claim 1, which is characterized in that the compound is selected from the group consisting of:
4-(1-methyl-1H-pyrazol-5-yl)-N-(3,4-trans-4-phenylpiperidin-3-yl)furan-2-formamide;
5-chloro-4-(4-chloro-1-methyl-1H-pyrazol-5-yl)-N-(3,4-trans-4-(4-chlorphenyl)piperidin-3-yl) furan-2-formamide;
5-bromo-4-(1-methyl-1H-1,2,4-triazol-5-yl)-N-(3,4-trans-4-(4-trifluoromethylphenyl)piperidin-3-yl)furan-2-formamide;
5-bromo-3-ethyl-1-methyl-4-(1-methyl-1H-1,2,4-triazol-5-yl)-N-(3,4-trans-4-(3-trifluoromethylphenyl)piperidin-3-yl)-1H-pyrrole-2-formamide;
5-methyl-4-(4-chloro-1-methyl-1H-pyrazol-5-yl)-N-(3,4-trans-4-(3,4-difluorophenyl)piperidin-3-yl)thiophene-2-formamide;
5-methyl-4-(4-bromo-1-methyl-1H-pyrazol-5-yl)-N-(3,4-trans-4-(pyridin-4-yl)piperidin-3-yl)-1H-pyrrole-2-formamide;
4-chloro-5-(1-methyl-1H-1,2,4-triazol-5-yl)-N-(3,4-trans-4-(3-methylphenyl)piperidin-3-yl)furan-2-formamide;
4-chloro-5-(1-methyl-1H-1,2,4-triazol-5-yl)-N-(3,4-trans-4-(4-(1-chloroethyl)phenyl)piperidin-3-yl)thiophene-2-formamide;
5-methyl-4-(4-isopropyl-1-methyl-1H-pyrazol-5-yl)-N-(3,4-trans-4-(quinolin-3-yl)piperidin-3-yl) thiophene-2-formamide;
5-methyl-4-(1-methyl-4-bromo-1H-pyrazol-5-yl)-N-(3,4-trans-4-(3-cyanophenyl)piperidin-3-yl)-1H-pyrrole-2-formamide;
4-chloro-5-(1-methyl-1H-1,2,4-triazol-5-yl)-N-(3,4-trans-4-(3,5-dimethoxyphenyl)piperidin-3-yl) furan-2-formamide;
4-chloro-5-(1-methyl-4-bromo-1H-pyrazol-5-yl)-N-(3,4-trans-4-(1H-pyrrole-2-yl)piperidin-3-yl) furan-2-formamide;
4-methyl-5-(1-methyl-1H-1,2,4-triazol-5-yl)-N-(3,4-trans-4-(1H-indol-2-yl)piperidin-3-yl)furan-2-formamide;
5-ethyl-4-(4-isopropyl-1-methyl-1H-pyrazol-5-yl)-N-(3,4-trans-4-(7-methyl-5,6,7,8-tetrahydroquinolin-3-yl)piperidin-3-yl)thiophene-2-formamide;
5-ethyl-1-methyl-4-(4-chloro-1-methyl-1H-pyrazol-5-yl)-N-(3,4-trans-4-(3-fluorocyclopentane)piperidin-3-yl)-1H-pyrrole-2-formamide;
5-bromo-4-(1,4-dimethyl-1H-pyrazol-5-yl)-N-(3,4-trans-4-(4-methylcyclohexane)piperidin-3-yl)-1H-pyrrole-2-formamide;
5-ethyl-1-methyl-4-(4-ethyl-1-methyl-1H-pyrazol-5-yl)-N-(3,4-trans-4-(piperidin-3-yl)piperidin-3-yl)-1H-pyrrole-2-formamide;
5-chloro-3-methyl-4-(1-methyl-1H-1,2,4-triazol-5-yl)-N-(3,4-trans-4-(5-chloropiperidin)piperidin-3-yl)thiophene-2-formamide;
4-(1-methyl-1H-pyrazol-5-yl)-N-(3,4-trans-4-phenylpiperidin-3-yl)oxazole-2-formamide;
4-(4-chloro-1-methyl-1H-pyrazol-5-yl)-N-(3,4-trans-4-(3,4-difluorophenyl)piperidin-3-yl)-5-methylthiazole-2-formamide;
4-(1-methyl-1H-pyrazol-5-yl)-N-(3,4-trans-4-(3,4-difluorophenyl)piperidin-3-yl)furan-2-formamide;
4-(4-bromo-1-methyl-1H-pyrazol-5-yl)-N-(3,4-trans-4-phenylpiperidin-3-yl)furan-2-formamide;
4-(4-chloro-1-methyl-1H-pyrazol-5-yl)-N-(3,4-trans-4-(4-chlorophenyl)piperidin-3-yl)furan-2-formamide;
4-(4-chloro-1-methyl-1H-pyrazol-5-yl)-N-(3,4-trans-4-(4-trifluoromethylphenyl)piperidin-3-yl) furan-2-formamide;
4-(4-chloro-1-methyl-1H-pyrazol-5-yl)-N-(3,4-trans-4-(3,4-difluorophenyl)piperidin-3-yl)furan-2-formamide;
4-(4-bromo-1-methyl-1H-pyrazol-5-yl)-N-(3,4-trans-4-(4-chlorophenyl)piperidin-3-yl)furan-2-formamide;
4-(4-bromo-1-methyl-1H-pyrazol-5-yl)-N-(3,4-trans-4-(4-trifluoromethylphenyl)piperidin-3-yl) furan-2-formamide;
4-(4-bromo-1-methyl-1H-pyrazol-5-yl)-N-(3,4-trans-4-(3,4-difluorophenyl)piperidin-3-yl)furan-2-formamide;
5-chloro-4-(4-chloro-1-methyl-1H-pyrazol-5-yl)-N-(3,4-trans-4-phenylpiperidin-3-yl)furan-2-formamide;
5-chloro-4-(4-chloro-1-methyl-1H-pyrazol-5-yl)-N-(3,4-trans-4-(4-trifluoromethylphenyl) piperidin-3-yl)furan-2-formamide;
5-chloro-4-(4-chloro-1-methyl-1H-pyrazol-5-yl)-N-(3,4-trans-4-(3,4-difluorophenyl)piperidin-3-yl)furan-2-formamide;
4-(1-methyl-1H-pyrazol-5-yl)-N-(3,4-trans-4-(4-chlorophenyl)piperidin-3-yl)thiophene-2-formamide;
4-(1-methyl-1H-pyrazol-5-yl)-N-(3,4-trans-4-(3,4-difluorophenyl)piperidin-3-yl)thiophene-2-formamide;
4-(4-chloro-1-methyl-1H-pyrazol-5-yl)-N-(3,4-trans-4-phenylpiperidin-3-yl)thiophene-2-formamide;

4-(4-chloro-1-methyl-1H-pyrazol-5-yl)-N-(3,4-trans-4-(4-chlorophenyl)piperidin-3-yl)thiophene-2-formamide;

4-(4-chloro-1-methyl-1H-pyrazol-5-yl)-N-(3,4-trans-4-(3,4-difluorophenyl)piperidin-3-yl) thiophene-2-formamide;

4-(4-bromo-1-methyl-1H-pyrazol-5-yl)-N-(3,4-trans-4-(4-chlorophenyl)piperidin-3-yl) thiophene-2-formamide;

4-(4-bromo-1-methyl-1H-pyrazol-5-yl)-N-(3,4-trans-4-(3,4-difluorophenyl)piperidin-3-yl) thiophene-2-formamide;

5-chloro-4-(4-chloro-1-methyl-1H-pyrazol-5-yl)-N-((3R,4R)-4-(3,4-dichlorophenyl)piperidin-3-yl) furan-2-formamide;

5-chloro-4-(4-chloro-1-methyl-1H-pyrazol-5-yl)-N-((3S,4S)-4-(3,4-dichlorophenyl)piperidin-3-yl)furan-2-formamide;

4-(4-bromo-1-methyl-1H-pyrazol-5-yl)-N-((3R,4R)-4-(3,4-difluorophenyl)piperidin-3-yl) thiophene-2-formamide;

4-(4-bromo-1-methyl-1H-pyrazol-5-yl)-N-((3S,4S)-4-(3,4-difluorophenyl)piperidin-3-yl) thiophene-2-formamide;

5-chloro-4-(4-chloro-1-methyl-1H-pyrazol-5-yl)-N-((3R,4R)-4-(4-trifluoromethylphenyl) piperidin-3-yl)furan-2-formamide;

5-chloro-4-(4-chloro-1-methyl-1H-pyrazol-5-yl)-N-((3S,4S)-4-(4-trifluoromethylphenyl) piperidin-3-yl)furan-2-formamide;

5-(4-chloro-1-methyl-1H-pyrazol-5-yl)-N-((3S,4S)-4-(3-fluorophenyl)piperidin-3-yl)thiophene-2-formamide;

4-chloro-5-(4-chloro-1-methyl-1H-pyrazol-5-yl)-N-((3S,4S)-4-(3-fluorophenyl)piperidin-3-yl) thiophene-2-formamide;

5-(4-ethyl-1-methyl-1H-pyrazol-5-yl)-N-((3S,4S)-4-(3-fluorophenyl)piperidin-3-yl)thiophene-2-formamide;

N-((3S,4S)-4-(3-fluorophenyl)piperidin-3-yl)-5-(1-methyl-1H-pyrazol-5-yl)thiophene-2-formamide;

5-(4-bromo-1-methyl-1H-pyrazol-5-yl)-N-((3S,4S)-4-(3-fluorophenyl)piperidin-3-yl)thiophene-2-formamide;

and an optical isomer thereof, or a pharmaceutically acceptable salt or a solvate thereof.

3. A pharmaceutical composition comprising at least one active ingredient and one or more pharmaceutically acceptable carriers or excipients, wherein one active ingredient is selected from any one or more compounds according to claim 1, an optical isomer of the compound, a pharmaceutically acceptable salt of the compound or the optical isomer thereof, a solvate of the compound or the optical isomer thereof.

4. A method for treating a tumor, the method comprising administering an effective amount of the compound according to claim 1 to a patient in need thereof, wherein the tumor is selected from the group consisting of breast cancer, sarcoma, lung cancer, prostate cancer, colon cancer, rectal cancer, kidney cancer, pancreatic cancer, leukemia, neuroblastoma, glioma, head cancer, neck cancer, thyroid cancer, liver cancer, ovarian cancer and vulvar cancer, cervical cancer, endometrial cancer, testicular cancer, bladder cancer, esophageal cancer, gastric cancer, nasopharyngeal carcinoma, buccal cancer, oral cancer, gastrointestinal stromal tumor, skin cancer and multiple myeloma.

* * * * *